(12) United States Patent
Tachdjian et al.

(10) Patent No.: US 9,138,013 B2
(45) Date of Patent: Sep. 22, 2015

(54) SWEET FLAVOR MODIFIER

(71) Applicant: SENOMYX, INC., San Diego, CA (US)

(72) Inventors: Catherine Tachdjian, San Diego, CA (US); Donald Karanewsky, Escondido, CA (US); Sara Werner, San Diego, CA (US); Vincent Darmohusodo, Encinitas, CA (US); Jeff Yamamoto, San Diego, CA (US)

(73) Assignee: Senomyx, Inc., San Diego, CA (US)

( * ) Notice: Subject to any disclaimer, the term of this patent is extended or adjusted under 35 U.S.C. 154(b) by 0 days.

(21) Appl. No.: 14/449,350

(22) Filed: Aug. 1, 2014

(65) Prior Publication Data

US 2015/0031684 A1    Jan. 29, 2015

Related U.S. Application Data

(60) Division of application No. 14/096,531, filed on Dec. 4, 2013, now Pat. No. 8,877,922, which is a continuation of application No. PCT/US2013/053666, filed on Aug. 5, 2013.

(60) Provisional application No. 61/779,502, filed on Mar. 13, 2013, provisional application No. 61/679,912, filed on Aug. 6, 2012.

(51) Int. Cl.
| | |
|---|---|
| *C07D 417/12* | (2006.01) |
| *C07D 417/14* | (2006.01) |
| *C07D 471/04* | (2006.01) |
| *A23L 1/22* | (2006.01) |
| *A23L 1/236* | (2006.01) |

(52) U.S. Cl.
CPC ............. *A23L 1/22091* (2013.01); *A23L 1/236* (2013.01); *C07D 417/12* (2013.01); *C07D 417/14* (2013.01); *C07D 471/04* (2013.01); *A23V 2002/00* (2013.01)

(58) Field of Classification Search
CPC .. C07D 417/12; C07D 417/14; C07D 471/04; A23L 1/22091
USPC .......................... 514/222.8; 426/535, 532, 72
See application file for complete search history.

(56) References Cited

U.S. PATENT DOCUMENTS

| | | | |
|---|---|---|---|
| 3,278,532 A | 10/1966 | Houlihan | |
| 3,843,804 A | 10/1974 | Evers et al. | |
| 3,845,770 A | 11/1974 | Theeuwes et al. | |
| 3,857,972 A | 12/1974 | Evers et al. | |
| 3,916,899 A | 11/1975 | Theeuwes et al. | |
| 3,957,783 A | 5/1976 | Hirohashi et al. | |
| 3,960,860 A | 6/1976 | Katz et al. | |
| 4,146,716 A | 3/1979 | Cox et al. | |
| 4,196,207 A | 4/1980 | Webber et al. | |
| 4,377,580 A | 3/1983 | Ueda et al. | |
| 4,765,539 A | 8/1988 | Noakes et al. | |
| 5,112,598 A | 5/1992 | Biesalski | |
| 5,380,541 A | 1/1995 | Beyts et al. | |
| 5,504,095 A | 4/1996 | Nakane et al. | |
| 5,556,611 A | 9/1996 | Biesalski | |
| 5,698,155 A | 12/1997 | Grosswald et al. | |
| 5,801,180 A | 9/1998 | Takase et al. | |
| 5,950,619 A | 9/1999 | van der Linden et al. | |
| 5,954,047 A | 9/1999 | Armer et al. | |
| 5,970,974 A | 10/1999 | van der Linden et al. | |
| 5,990,117 A | 11/1999 | Pamukcu et al. | |
| 6,046,206 A | 4/2000 | Pamukcu et al. | |
| 6,316,454 B1 | 11/2001 | Uckun et al. | |
| 7,105,650 B2 | 9/2006 | Adler | |
| 7,915,410 B2 | 3/2011 | Johnson et al. | |
| 7,928,111 B2 | 4/2011 | Tachdjian et al. | |
| 8,541,421 B2 | 9/2013 | Tachdjian et al. | |
| 8,633,186 B2 | 1/2014 | Tachdjian et al. | |
| 2003/0008344 A1 | 1/2003 | Adler et al. | |
| 2003/0054448 A1 | 3/2003 | Adler et al. | |
| 2003/0232407 A1 | 12/2003 | Zoller et al. | |
| 2004/0127435 A1 | 7/2004 | Carson et al. | |
| 2005/0032158 A1 | 2/2005 | Adler et al. | |
| 2006/0045953 A1 | 3/2006 | Tachdjian et al. | |
| 2006/0134693 A1 | 6/2006 | Servant et al. | |
| 2006/0135552 A1 | 6/2006 | Malherbe et al. | |
| 2007/0104709 A1 | 5/2007 | Li et al. | |
| 2008/0306053 A1 | 12/2008 | Tachdjian et al. | |
| 2008/0306093 A1 | 12/2008 | Servant et al. | |
| 2011/0224155 A1 | 9/2011 | Tachdjian et al. | |
| 2011/0230502 A1 | 9/2011 | Tachdjian et al. | |

FOREIGN PATENT DOCUMENTS

| | | |
|---|---|---|
| DE | 22 58 403 A1 | 6/1973 |
| EP | 0530994 A1 | 3/1993 |
| RU | 2241436 C2 | 12/2004 |

(Continued)

OTHER PUBLICATIONS

Albrecht et al., "Synthesis of 1,2,6-Thiadiazine 1,1-Dioxides via Isoxazolylsulfamides," J. Org. Chem. 44:4191-4194 (1979).

Alderman, "A Review of Cellulose Ethers in Hydrophilic Matrices for Oral Controlled-Release Dosage Forms," Int. J. Pharm. Tech. & Prod. Mfr. 5(3):1-9 (1984).

Bamba et al., "Release mechanisms in Gelforming Sustained Release Preparations," Int. J. Pharm. 2:307-315 (1979).

Bandurco et al., "Synthesis and Cardiotonic Activity of a Series of Substituted 4-Alkyl-2(1H)-quinazolinones," J. Med. Chem. 30:1421-1426 (1987).

Belikov V.G., Farmatsevticheskaya khimiya, M., Visshaya shkola, 1993, pp. 43-47.

Bellur et al., "Synthesis of 4-(3-hydroxyalkyl)pyrimidines by ring transformation reactions of 2-alkylidenetetrahydrofurans with amidines," Tetrahedron 62:5426-5434 (2006).

(Continued)

*Primary Examiner* — Kahsay Habte
(74) *Attorney, Agent, or Firm* — Knobbe Martens Olson & Bear LLP

(57) ABSTRACT

The present invention includes compounds having structural formula (I), or salts or solvates thereof. These compounds are useful as sweet flavor modifiers. The present invention also includes compositions comprising the present compounds and methods of modulating the sweet taste of compositions.

31 Claims, No Drawings

(56) References Cited

FOREIGN PATENT DOCUMENTS

| | | |
|---|---|---|
| WO | WO 03/001876 A2 | 1/2003 |
| WO | WO 03/004992 A2 | 1/2003 |
| WO | WO 03/022214 A2 | 3/2003 |
| WO | WO 03/051878 A1 | 6/2003 |
| WO | WO 03/055866 A1 | 7/2003 |
| WO | WO 2005/015158 A2 | 2/2005 |
| WO | WO 2005/116069 A2 | 12/2005 |
| WO | WO 2006/076102 A2 | 7/2006 |
| WO | WO 2006/084184 A2 | 8/2006 |
| WO | WO 2006/113422 A2 | 10/2006 |
| WO | WO 2006/113432 A2 | 10/2006 |
| WO | WO 2007/004709 A1 | 1/2007 |
| WO | WO 2007/047988 A2 | 4/2007 |
| WO | WO 2007/071963 A2 | 6/2007 |
| WO | WO 2008/003378 A1 | 1/2008 |
| WO | WO 2008/154221 A2 | 12/2008 |
| WO | WO 2012/021837 A2 | 2/2012 |
| WO | WO 2012/054526 A2 | 4/2012 |

OTHER PUBLICATIONS

Berge et al., "Pharmaceutical Salts," J. Pharm. Sci. 66(1):1-19 (1977).
Bhattacharya et al., "Thieno[3',2' :4,5][1]benzothieno[2,3-d] pyrimidine derivatives: synthesis and conformation," J. Chem. Soc. Perkin Trans. 1, 1994, 6: 689-693.
Blackburn et al., "Identification and characterization of aminopiperidinequinolones and quinazolinones as MCHr1 antagonists," Bioorg. & Med. Chem. Lett. 16:2621-2627 (2006).
Boarland et al., "Monosubstituted Pyrimidines, and the Action of Thiourea on Chloropyrimidines," J. Chem. Soc. 1218-1221 (1951).
Brown, et al., "Evolution of a Series of Peptidoleukotriene Antagonists: Synthesis and Structure-Activity Relationships of 1,6-Disubstituted Indoles and Indazoles," J. Med. Chem. 33:1771-1781 (1990).
Buck et al., "A Novel Multigene Family May Encode Odorant Receptors: A Molecular Basis for Odor Recognition," Cell 65(1):175-187 (1991).
Campillo et al., "A study of peculiar tautomerism of pyrido[2,3-c][1,2,6]thiadiazine 2,2-dioxide system," J. Mol. Struct. 678:83-89 (2004).
Campillo et al., "A Novel Tetracyclic System Containing the 1,2,6-Thiadiazine Ring: Synthesis, Structural Assignment and Tautomeric Studies," Heterocycles, 1998, 48(3): 1833-1840.
Chandrashekar et al., "T2Rs Function as Bitter Taste Receptors," Cell 100:703-711 (2000).
Cheng et al., "Potential Purine Antagonists. XII. Synthesis of 1-Alkyl(aryl)-4,6-disubstituted Pyrazolo[3,4-d]pyrimidines" Journal of Organic Chemistry, Jun. 1, 1958 23(1):852-861.
Chien et al., "Nucleosides XI. Synthesis and Antiviral Evaluation of 5'-Alkylthio-5'-deoxy Quinazolinone Nucleoside Derivatives as S-Adenosyl-L-homocysteine Analogs," Chem. Pharm. Bull. 52(12):1422-1426 (2004).
Clauß et al., "Cycloadditionen von Halogensulfonylisocyanaten an Acetylene," Tetrahedron Lett. 2:119-122 (1970).
Corbett et al., "Novel 2,2-Dioxide-4,4-disubstituted-1,3-H-2,1,3-benzothiadiazines as Non-Nucleside Reverse Transcriptase Inhibitors," Bioorg. Med. Chem. Lett. 10:193-195 (2000).
Da Settimo et al.,"Naphtho[1,2-d]isothiazole Acetic Acid Derivatives as a Novel Class of Selective Aldose Reductase Inhibitors," J. Med. Chem. 48:6897-6907 (2005).
Dominguez et al., "Efficient synthesis of 4,4-disubstituted-3,4-dihydro-1H-2,1,3-benzothiadiazine 2,2-dioxides," Tetrahedron Lett. 41:9825-9828 (2000).
Dorwald, "Side Reactions in Organic Synthesis: A Guide to Successful Synthesis Design," Weinheim: Wiley-VCH Verlag Gmbh & o. KGaA, 2005, ISBN: 3-527-31021-5.
During et al., "Controlled Release of Dopamine from a Polymeric Brain Implant: In Vivo Characterization," Ann. Neurol. 25:351-356 (1989).

Elmegeed et al., "Novel synthesizes aminosteroidal heterocycles intervention for inhibiting iron-induced oxidative stress," Eur. J. Med. Chem. 40:1283-1294 (2005).
El-Sherbeny et al., "Novel Pyridothienopyrimidine and Pyridothienothiazine Derivatives as Potential Antiviral and Antitumor Agents," Med. Chem. Res. 10:122-135 (2000).
Etter et al., "An Enolized Sulfonamide Formed by Strong Hydrogen Bonding to Triphenylphosphine Oxide," J. Org. Chem. 51:5405-5408 (1986).
European Search Opinion based on EP Application No. 08770047.2, mailed on Sep. 14, 2009.
European Search Report, EP Appl. No. 12175764.5, 16 pages (Feb. 22, 2013).
Francis et al., "Anxiolytic Properties of Certain Annelated [1,2,4]Triazolo[1,5-c]pyrimidin-5(6H)-ones," J. Med. Chem. 34:2899-2906 (1991).
Frauli et al., "Amino-Pyrrolidine Tricarboxylic Acids Give New Insight into Group III Metabotropic Glutamate Receptor Activation Mechanism," Mol. Pharmacol. 71:704-712 (2007).
Garcia-Munoz et al., "Synthesis of Purine-Like Ring Systems Derived From 1,2,6-Thiadiazine 1,1-Dioxide," J. Heterocyclic Chem. 13:793-796 (1976).
Goya and Martinez, "Synthesis and Cytostatic Screening of an SO2 Analogue of Doridosine," Arch. Pharm. (Weinheim) 321:99-101 (1988).
Goya and Paez, "Pteridine Analogues; Synthesis and Physico-Chemical Properties of 7-Oxopyrazino [2,3-c][1,2,6] thiadiazine 2,2-Dioxides," Liebigs Ann. Chem., 121-124 (1988).
Goya et al., "Aminopyrido [2,3-c] [1,2,6] Thiadiazine 2,2-Dioxides: Synthesis and Physico-chemical Properties," Chemica Scripta, 26:607-611 (1986).
Goya et al., "Fused 1,2,6-Thiadiazines: Tetrahydrobenzo[b]thieno[2,3-c] [1,2,6]thiadiazine 2,2-Dioxides," Arch. Pharm. (Weinheim) 317:777-781 (1984).
Goya et al., "N-Glucosyl-5-Amino-4-Carbamoyl- and 4-Ethoxycarbonylimidazoles as Potential Precursors of 4-Oxoimidazo[4,5-c]-1,2,6-thiadiazine 2,2-Dioxides," Heterocycles 24:3451-3458 (1986).
Goya et al., "Synthesis of 2S-Dioxo Isosteres of Purine and Pyrimidine Nucleosides IV. Selective Glycosylation of 4-Amino-5H-Imidazo [4,5-c] -1,2,6-Thiadiazine 2,2-Dioxide," Nucleosides & Nucleotides, 6(3), 631-642 (1987).
Goya et al., CAPLUS Accession No. 1987:18628, 2 pages, abstract of ES 531159 A1 (1985).
Hauser et al., "Synthesis of 5-Phenyl-4,6-Dimethyl-2-Pyrimidol and Derivatives from the Cyclization of Urea with 3-Phenyl-2,4-Pentanedione," J. Org. Chem. 18:588-593 (1953).
Hirayama et al., "The Discovery of YM-60828: A Potent, Selective and Orally-Bioavailable Factor Xa Inhibito," Bioorg. & Med. Chem. 10:1509-1523 (2002).
Hirohashi et al. "Nuclear magnetic resonance studies of bicyclic thiophene derivatives. I ring current effects of the benzene ring on the H.alpha. and H.beta. signals of the thiophene ring in benzoylthiophene, thienopyrimidine, and thienodiazepine derivatives" Bulletin of The Chemical Society of Japan, 48(1), 147-156 (1975).
Hirota et al., "Synthesis and Biological Evaluation of 2,8-Disubstituted 9-Benzyladenines: Discovery of 8-Mercaptoadenines as Potent Interferon-Inducers," Bioorg. Med. Chem. 11:2715-2722 (2003).
Hoon et al., Putative Mammalian Taste Receptors: A Class of Taste-Specific GPCRs with Distinct Topographic Selectivity. Cell 96:541-551 (1991).
Howard et al., "Intracerebral drug delivery in rats with lesion-induced memory deficits," J. Neurosurg. 71:105-112 (1989).
Hu et al., "Organic Reactions in Ionic Liquids: Gewald Synthesis of 2-Aminothiophenes Catalyzed by Ethylenediammonium Diacetate," Synthetic Communication 34:3801-3806 (2004).
International Search Report, 5 pages, PCT Appl. No. PCT/US2008/065650 (mailed Nov. 20, 2008).
Jordan, "Tamoxifen: A Most Unlikely Pioneering Medicine," Nature Reviews: Drug Discovery 2003, vol. 2, pp. 205-213.

(56) References Cited

OTHER PUBLICATIONS

Jung et al., "Discovery of Novel and Potent thiazoloquinazolines as Selective Aurora A and B Kinase Inhibitors," J. Med. Chem. 49:955-970 (2006).

Kamal et al., "Cyclization of 2-(Carbamoyloxy)- and 2-(Sulfamoyloxy)benzoates Mediated by Liver Microsomes," J. Org. Chem. 53:4112-4114 (1988).

Kamal et al., "Enzymatic Cyclization of 2-(Carbamoyloxy)Benzoates, 2-(Sulfamoyloxy)-Benzoates and 2-(Carbamoyloxy)benzopenones with Yeast and Lipase," Heterocycles 29:1391-1397 (1989).

Kanbe et al., "Discovery of thiochroman derivatives bearing a carboxy-containing side chain as orally active pure antiestrogens," Bioorg. & Med. Chem. Lett. 16:4090-4094 (2006).

Kanuma et al., "Lead optimization of 4-(dimethylamino)quinazolines, potent and selective antagonists for the melanin-concentrating hormone receptor 1," Bioorg. & Med. Chem. Lett. 15:3853-3856 (2005).

Keith, "Synthesis and Reduction of some 1H-2,1,3-Benzothiadiazin-4(3H)one 2,2-Dioxides," J. Heterocyclic Chem., 15:1521-1523 (1978).

Khabnadideh et al., "Design, synthesis and evaluation of 2,4-diaminoquinazolines as inhibitors of trypanosomal and leishmanial dihydrofolate reductase," Bioorg. Med. Chem. 13:2637-2649 (2005).

Klinger et al., "Inhibition of Carbonic Anhydrase-II by Sulfamate and Sulfamide Groups: An Investigation Involving Direct Thermodynamic Binding Measurements," J. Med. Chem. 49:3496-3500 (2006).

Kyte et al., "A Simple Method for Displaying the Hydropathic Character of a Protein," J. Mol. Biol. 157:105-132(1982).

Langer et al., "Chemical and Physical Structure of Polymers as Carriers for Controlled Release of Bioactive Agents: A Review," J. Macromol. Sci. Rev. Macromol Chem. 23:61-126 (1983).

Langer, "New Methods of Drug Delivery," Science 249:1527-1533 (1990).

Lee et al., "Acetonitrile-Mediated Synthesis of 2,4-Dichloroquinoline from 2-Ethynyl-aniline and 2,4-Dichloroquinazoline from Anthranilonitrile," Synlett, 2006 No. 1:65-68 (2006).

Leistner et al., "Eine einfache Synthese von 2-Alhylthio-4-amino-thieno[2,3-d]pyrimidinen," Arch. Pharm. (Weinheim) 322:227-230 (1989).

Levy et al., "Inhibition of Calcification of Bioprosthetic Heart Valves by Local Controlled-Release Diphosphonate," Science 228:190-192 (1985).

Li et al., "Human receptors for sweet and umami taste," Proc. Natl. Acad. Sci. USA 99:4692-4696 (2002).

Linkies et al., "Ein neues Verfahren zur Herstellung von 6-Methyl-1,2,3-oxathiazin-4(3H)-on-2,2-dioxid Kaliumsalz (Acesulfam-K)," Synthesis 405-406 (1990).

Liu et al., "Discovery of a new class of 4-anilinopyrimidines as potent c-Jun N-terminal kinase inhibitors: Synthesis and SAR studies," Bioorg. & Med. Chem. Lett. 17:668-672 (2007).

Martinez et al., "Benzothiadiazine Dioxide Dibenzyl Derivatives as Potent Human Cytomegalovirus Inhibitors: Synthesis and Comparative Molecular Field Analysis," J. Med. Chem., 43:3218-3225 (2000).

Meyer, Jr. and Skibo, "Synthesis of Fused [1,2,6]Thiadiazine 1,1-Dioxides as Potential Transition-State Analogue Inhibitors of Xanthine Oxidase and Guanase," J. Med. Chem. 22(8):944-948 (1979).

Naganawa et al., "Further optimization of sulfonamide analogs as EP1 receptor antagonists: Synthesis and evaluation of bioisosteres for the carboxylic acid group," Bioorg. Med. Chem. 14:7121-7137 (2006).

Nie et al., "Distinct Contributions of T1R2 and T1R3 Taste Receptor Subunits to the Detection of Sweet Stimuli," Curr. Biol. 15(21):1948-1952 (2005).

Office Action, U.S. Appl. No. 11/760,592, 13 pages (mailed Jan. 7, 2010).

Office Action, U.S. Appl. No. 11/760,592, 19 pages (mailed Oct. 7, 2010).

Office Action, U.S. Appl. No. 11/760,592, 26 pages (mailed Jan. 16, 2014).

Office Action, U.S. Appl. No. 11/836,074, 11 pages (mailed Sep. 29, 2009).

Office Action, U.S. Appl. No. 11/836,074, 13 pages (mailed Oct. 30, 2008).

Office Action, U.S. Appl. No. 11/836,074, 18 pages (mailed Jun. 10, 2009).

Office Action, U.S. Appl. No. 11/836,074, 18 pages (mailed Jun. 23, 2008).

Office Action, U.S. Appl. No. 11/836,074, 7 pages (mailed Nov. 8, 2010).

Office Action, U.S. Appl. No. 12/663,634, 9 pages (mailed Feb. 6, 2013).

Office Action, U.S. Appl. No. 12/663,634, 8 pages (mailed Apr. 12, 2013).

Office Action, U.S. Appl. No. 12/663,634, 8 pages (mailed Jun. 14, 2013).

Office Action, U.S. Appl. No. 12/663,634, 7 pages (mailed Jul. 19, 2013).

Office Action for U.S. Appl. No. 13/051,586, mailed Jun. 21, 2012.

Office Action for U.S. Appl. No. 13/051,586, mailed Feb. 27, 2013.

Pal et al., "Synthesis and Cyclooxygenase-2 (COX-2) Inhibiting Properties of 1,5-Diarylpyrazoles Possessing N-Substitution on the Sulfonamide (-SO2NH2) Moiety," Letters in Drug Design & Discovery 2:329-340 (2005).

Partial European Search Report, EP appl. No. 12175761.1, 7 pages (Feb. 27, 2013).

Petersen et al., "Synthesis of Heterocycles Containing Two Cytosine or Two Guanine Base-Pairing Sites. Novel Tectons for Self-Assembly," Bioorg. Med Chem. 4:1107-1112 (1996).

Rad-Moghadam et al., "One-pot Three-component Synthesis of 2-Substituted 4-Aminoquinazolines," J. Heterocyclic Chem. 43:913-916 (2006).

Rasmussen et al., "The Electrophilic Addition of Chlorosulfonyl Isocyanate to Ketones. A Convenient Synthesis of Oxazines, Oxathiazines, and Uracils," J. Org. Chem. 38:2114-2115 (1973).

Reddy et al., "An Efficient Synthesis of 3,4-Dihydro-4-Imino-2(1H)-Quinazolinones," Synthetic Commun. 18:525-530 (1988).

Robinson et al., "Sulfonamide Ligands Attained through Opening of Saccharin Derivatives," Eur. J. Org. Chem. 19:4483-4489 (2006).

Rodriguez-Hahn et al., "A Study of the Thorpe-Ziegler Reaction in Very Mild Conditions," Synthetic Commun. 14:967-972 (1984).

Rosowsky and Modest, "Quinazolines. III. Synthesis of 1,3-Diaminobenzo[f]quinazoline and Related Compounds," J. Org. Chem. 31:2607-2613 (1966).

Roy et al., "Auto-Redox Reaction: Tin(II) Chloride-Mediated One-Step Reductive Cyclization Leading to the Synthesis of Novel Biheterocyclic 5,6-Dihydro-quinazolino[4,3-b]quinazolin-8-ones with Three-Point Diversity," J. Org. Chem. 71:382-385 (2006).

Saudek et al., "A Preliminary Trial of the Programmable Implantable Medication System for Insulin Delivery," N. Engl. J Med. 321:574-579 (1989).

Seijas et al., "Microwave enhanced synthesis of 4-aminoquinazolines," Tetrahedron Lett. 41:2215-2217 (2000).

Sharma et al., "Synthesis and QSAR studies on 5-[2-(2-methylprop 1-enyl)-1H benzimidazol-1yl]-4,6-diphenyl-pyrimidin-2-(5H)-thione derivatives as antibacterial agents," Eur. J. Med. Chem. 41:833-840 (2006).

Silve et al., "Delineating a Ca2+ Binding Pocket within the Venus Flytrap Module of the Human Calcium Sensing Receptor," The Journal of Biological Chemistry, Nov. 2005, vol. 280, pp. 37917-37923.

Srivastava et al., "Solid Phase Synthesis of Structurally Diverse Pyrimido[4,5-d] Pyrimidines for the Potential Use in Combinatorial Chemistry," Bioorg. Med. Chem. Lett. 9:965-966 (1999).

Supplementary European Search Report based on EP Application No. 08770047.2, mailed on Sep. 14, 2009.

Tripathi et al., "Reaction of Flavanones with Chlorosulphonyl Isocyanate," Indian J. Chem. Sect. B 26B:1082-1083 (1987).

(56) References Cited

OTHER PUBLICATIONS

Uehling et al., "Biarylaniline Phenethanolamines as Potent and Selective β3 Adrenergic Receptor Agonists," J. Med. Chem. 49:2758-2771 (2006).

Verma et al., "Osmotically Controlled Oral Drug Delivery," Drug Dev. Ind. Pharm. 26:695-708 (2000).

Verschoyle et al., "Pharmacokinetics of Isotretinoin (ISO) in Rats Following Oral Dosing or Aerosol Inhalation," British J. Cancer 80, Suppl. 2:96 Abstract No. P269 (1999).

Vippagunta et al., "Crystalline solids," Adv. Drug Deliv. Rev. 48:3-26 (2001).

Wilson et al., "Synthesis of 5-deazaflavin derivatives and their activation of p53 in cells," Bioorg. & Med. Chem. 15:77-86 (2007).

Wilson, "Traceless Solid-Phase Synthesis of 2,4-Diaminoquinazolines," Org. Lett. 3:585-588 (2000).

Winkler et al., "Synthesis and microbial transformation of β-amino nitriles," Tetrahedron 61:4249-4260 (2005).

Wright, "The Reaction of Sulfamide with α- and β-Diketones. The Preparation of 1,2,5-thiadiazole 1,1-Dioxides and 1,2,6-Thiadiazine 1,1-Dioxides," J. Org. Chem. 29:1905-1909 (1964).

Wright, "The Synthesis of 2,1,3-Benzothiadiazine 2,2-Dioxides and 1,2,3-Benzoxathiazine 2,2-Dioxides," Journal of Organic Chemistry 30(11):3960-3962 (1965).

Written Opinion of the International Searching Authority,19 pages, PCT Appl. No. PCT/US2008/065650 (mailed Nov. 20, 2008).

Xu et al., "Oxidative cyclization of N-alkyl-o-methyl-arenesulfonamides to biologically important saccharin derivatives," Tetrahedron 62:7902-7910 (2006).

Xu et al., "Purine and Pyrididine Nucleotides Inhibit a Noninactivating K1 Current and Depolarize Adrenal Cortical Cells through a G Protein-coupled Receptor," Molecular Pharmacology, 1999, vol. 55, pp. 364-376.

Yamada et al., "Discovery of Novel and Potent Small-Molecule inhibitors of NO and Cytokine Production as Antisepsis Agents: Synthesis and Biological Activity of Alkyl 6-(N-Substituted sulfamoyl)cyclohex-1-ene-1-carboxylate," J. Med. Chem. 48:7457-7467 (2005).

Yoshizawa et al., "Efficient solvent-free Thrope reaction," Green Chem. 4:68-70 (2002).

Zunszain et al., "Search for the pharmacophore in prazosin for Transport-P," Bioorg. & Med. Chem. 13:3681-3689 (2005).

International Search Report for PCT/US2013/053666, Dec. 9, 2013.

Written Opinion for PCT/US2013/053666, Dec. 6, 2013.

SWEET FLAVOR MODIFIER

CROSS-REFERENCE TO RELATED APPLICATIONS

This application is a divisional of U.S. application Ser. No. 14/096,531, filed Dec. 4, 2013, which is a continuation of PCT/US2013/053666, filed Aug. 5, 2013, which claims the benefit of priority to U.S. Provisional Application No. 61/779,502, filed on Mar. 13, 2013, and U.S. Provisional Application No. 61/679,912, filed on Aug. 6, 2012, the contents of each of which are hereby incorporated by reference in their entireties for all purposes.

FIELD OF THE INVENTION

The invention relates to compounds suitable for modifying receptors and their ligands associated with chemosensory or chemosensory related sensation or reaction.

BACKGROUND OF THE INVENTION

The taste system provides sensory information about the chemical composition of the external world. Taste transduction is one of the most sophisticated forms of chemical-triggered sensation in animals. Signaling of taste is found throughout the animal kingdom, from simple metazoans to the most complex of vertebrates. Mammals are believed to have five basic taste modalities: sweet, bitter, sour, salty, and umami (the taste of monosodium glutamate, a.k.a. savory taste).

Obesity, diabetes, and cardiovascular disease are health concerns on the rise globally, but are growing at alarming rates in the United States. Sugar and calories are key components that can be limited to render a positive nutritional effect on health. High-intensity sweeteners can provide the sweetness of sugar, with various taste qualities. Because they are many times sweeter than sugar, much less of the sweetener is required to replace the sugar.

High-intensity sweeteners have a wide range of chemically distinct structures and hence possess varying properties, such as, without limitation, odor, flavor, mouthfeel, and aftertaste. These properties, particularly flavor and aftertaste, are well known to vary over the time of tasting, such that each temporal profile is sweetener-specific (Tunaley, A., "Perceptual Characteristics of Sweeteners", Progress in Sweeteners, T. H. Grenby, Ed. Elsevier Applied Science, 1989).

Sweeteners such as saccharin and 6-methyl-1,2,3-oxathiazin-4(3H)-one-2,2-dioxide potassium salt (acesulfame potassium) are commonly characterized as having bitter and/or metallic aftertastes. Products prepared with 2,4-dihydroxybenzoic acid are claimed to display reduced undesirable aftertastes associated with sweeteners, and do so at concentrations below those concentrations at which their own tastes are perceptible. Also, high intensity sweeteners such as sucralose and aspartame are reported to have sweetness delivery problems, i.e., delayed onset and lingering of sweetness (S. G. Wiet, et al., J. Food Sci., 58(3):599-602, 666 (1993)).

It has been reported that an extra-cellular domain, e.g., the Venus flytrap domain of a chemosensory receptor, especially one or more interacting sites within the Venus flytrap domain, is a suitable target for compounds or other entities to modulate the chemosensory receptor and/or its ligands. Certain compounds have been reported to be modulators of the chemosensory receptors in T1R family and/or their ligands and are described in the four patent applications listed below.

(1) U.S. patent application Ser. No. 11/760,592, entitled "Modulation of Chemosensory Receptors and Ligands Associated Therewith", filed Jun. 8, 2007; (2) U.S. Pat. No. 7,928,111, entitled "Modulation of Chemosensory Receptors and Ligands Associated Therewith", issued Apr. 19, 2011: and (3) International Application No. PCT/US2008/065650, entitled "Modulation of Chemosensory Receptors and Ligands Associated Therewith", filed Jun. 3, 2008. The content of these applications are herein incorporated by reference in their entirety for all purposes.

There is a need in the art to develop novel and inventive compounds suitable for modifying receptors and/or their ligands associated with chemosensory or chemosensory related sensation or reaction.

SUMMARY OF THE INVENTION

In one embodiment, the present invention provides a compound having structural Formula (I):

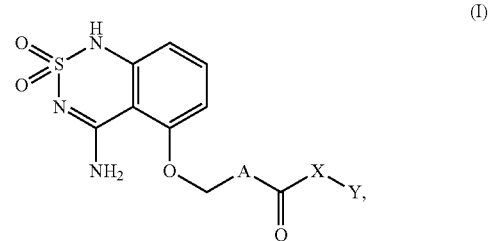

(I)

or a salt or solvate thereof: wherein

A is an optionally substituted four to eight-membered azacyclic ring;

X is a covalent bond or —$NR^1$—;

$R^1$ is hydrogen or C1 to C6 alkyl; and

Y is alkyl, substituted alkyl, heteroalkyl, substituted heteroalkyl, carbocyclyl, substituted carbocyclyl, heterocyclyl, substituted heterocyclyl, aryl, substituted aryl, heteroaryl, substituted heteroaryl, aralkyl, substituted aralkyl, heteroarylalkyl, or substituted heteroarylalkyl.

In another embodiment, the present invention provides an ingestible composition comprising a compound of the present invention; and optionally an ingestibly acceptable excipient.

In another embodiment, the present invention provides a method of increasing the sweet taste of an ingestible composition comprising contacting the ingestible composition thereof with a compound of the present invention to form a modified ingestible composition. In the method, the present compound can be a chemosensory receptor modifier, a chemosensory receptor ligand modifier, or both, i.e., a partial chemosensory receptor modifier and partial chemosensory receptor ligand modifier. For example, the present compound can be a sweet receptor agonist, or a sweet modulator, or a partial sweet receptor agonist and partial sweet modulator.

In another embodiment, the present invention provides a sweet modulating composition, comprising a compound of the present invention in an amount effective to provide sweetening in combination with a first amount of sweetener, wherein the sweetening is more than the sweetening provided by the first amount of sweetener without the compound.

In another embodiment, the present invention provides a flavoring concentrate formulation comprising i) as flavor modifying ingredient, a compound of the present invention; ii) a carrier; and iii) optionally at least one adjuvant.

In another embodiment, the present invention provides a method of treating a condition, disease, or disorder associated with a chemosensory receptor comprising administering to a subject in need of such treatment an therapeutically effective amount of a compound of the present invention, or a salt, solvate, and/or prodrug thereof.

DETAILED DESCRIPTION OF THE INVENTION

These and other embodiments, advantages, and features of the present invention are provided in the sections below. Unless defined otherwise, all technical and scientific terms used herein have the same meaning as commonly understood by one of ordinary skill in the art to which this invention belongs.

Definitions

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. The term "alkyl" includes "cycloalkyl" as defined herein below. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl." and "alkynyl" are used. In some embodiments, an alkyl group comprises from 1 to 20 carbon atoms ($C_1$-$C_{20}$ alkyl). In other embodiments, an alkyl group comprises from 1 to 12 carbon atoms ($C_1$-$C_{12}$ alkyl). In still other embodiments, an alkyl group comprises from 1 to 6 carbon atoms ($C_1$-$C_6$ alkyl). It is noted that when an alkyl group is further connected to another atom, it becomes an "alkylene" group. In other words, the term "alkylene" refers to a divalent alkyl. For example, —$CH_2CH_3$ is an ethyl, while —$CH_2CH_2$— is an ethylene. That is, "Alkylene," by itself or as part of another substituent, refers to a saturated or unsaturated, branched, straight-chain or cyclic divalent hydrocarbon radical derived by the removal of two hydrogen atoms from a single carbon atom or two different carbon atoms of a parent alkane, alkene or alkyne. The term "alkylene" includes "cycloalkylene" as defined herein below. The term "alkylene" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanylene," "alkenylene," and "alkynylene" are used. In some embodiments, an alkylene group comprises from 1 to 20 carbon atoms ($C_1$-$C_{20}$ alkylene). In other embodiments, an alkylene group comprises from 1 to 12 carbon atoms ($C_1$-$C_{12}$ alkylene). In still other embodiments, an alkylene group comprises from 1 to 6 carbon atoms ($C_1$-$C_6$ alkylene).

"Alkanyl," by itself or as part of another substituent, refers to a saturated branched, straight-chain or cyclic alkyl radical derived by the removal of one hydrogen atom from a single carbon atom of a parent alkane. The term "alkanyl" includes "cycloakanyl" as defined herein below. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The term "alkenyl" includes "cycloalkenyl" as defined herein below. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkoxy," by itself or as part of another substituent, refers to a radical of the formula —O—$R^{199}$, where $R^{199}$ is alkyl or substituted alkyl as defined herein.

"Acyl" by itself or as part of another substituent refers to a radical —$C(O)R^{200}$, where $R^{200}$ is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmethylcarbonyl, benzoyl, benzylcarbonyl and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). i.e., 6- to 20-membered aryl ring. In other embodiments, an aryl group comprises from 6 to 15 carbon atoms ($C_6$-$C_{15}$ aryl), i.e., 6- to 15-membered aryl ring. In still other embodiments, an aryl group comprises from 6 to 15 carbon atoms ($C_6$-$C_{10}$ aryl), i.e., 6- to 10-membered aryl ring.

"Arylalkyl" or "aralkyl" by itself or as part of another substituent, refers to an acyclic alkyl group in which one of the hydrogen atoms bonded to a carbon atom, typically a terminal or sp$^3$ carbon atom, is replaced with an aryl group as, as defined herein. That is, an arylalkyl or aralkyl group is composed of an aryl group connected to an alkylene group which is further attached to other portion of a molecule. The alkylene group in the arylalkyl or aralkyl group can be an alkylene having 1 to 12 carbon atoms, or 1 to 6 carbon atoms, or 1 to 3 carbon atoms. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkanyl, alkenyl or alkynyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkanyl, alkenyl or alkynyl moiety of the arylalkyl group is ($C_1$-$C_5$) alkyl and the aryl moiety is ($C_6$-$C_{10}$) aryl.

"Cycloalkyl," or "Carbocyclyl," by itself or as part of another substituent, refers to a saturated or unsaturated cyclic alkyl radical, as defined herein. Similarly, "Cycloalkylene," or "Carbocyclylene," by itself or as part of another substituent, refers to a saturated or unsaturated cyclic alkylene radical, as defined herein. Where a specific level of saturation is intended, the nomenclature "cycloalkanyl", "cycloalkenyl", or "cycloalkynyl" is used. Typical cycloalkyl groups include, but are not limited to, groups derived from cyclopropane, cyclobutane, cyclopentane, cyclohexane, and the like. In some embodiments, the cycloalkyl group comprises from 3 to 10 ring atoms ($C_3$-$C_{10}$ cycloalkyl). In other embodiments, the cycloalkyl group comprises from 3 to 7 ring atoms ($C_3$-$C_7$ cycloalkyl). The cycloalkyl may be further substituted by one or more heteroatoms including, but not limited to, N, P, O, S, and Si, which attach to the carbon atoms of the cycloalkyl via monovalent or multivalent bond.

"Heteroalkyl," "Heteroalkanyl," "Heteroalkenyl" and "Heteroalkynyl," by themselves or as part of other substituents, refer to alkyl, alkanyl, alkenyl and alkynyl groups, respectively, in which one or more of the carbon atoms (and optionally any associated hydrogen atoms), are each, independently of one another, replaced with the same or different heteroatoms or heteroatomic groups. Similarly, "Heteroalkylene," "Heteroalkanylene," "Heteroalkenylene" and "Heteroalkynylene," by themselves or as part of other substituents, refer to alkylene, alkanylene, alkenylene and alkynyenel groups, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, —NR$^{201}$R$^{202}$—, =N—N=, —N=N—, —N=N—NR$^{203}$R$^{204}$, —PR$^{205}$—, —P(O)$_2$—, —POR$^{206}$—, —O—P(O)$_2$—, —SO—, —SO$_2$—, —SnR$^{207}$R$^{208}$— and the like, where R$^{201}$, R$^{202}$, R$^{203}$, R$^{204}$, R$^{205}$, R$^{206}$, R$^{207}$ and R$^{208}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Cycloheteroalkyl." or "Heterocyclyl," by itself or as part of another substituent, refers to a saturated or unsaturated cyclic alkyl radical in which one or more carbon atoms (and optionally any associated hydrogen atoms) are independently replaced with the same or different heteroatom. Similarly, "Cycloheteroalkylene," or "Heterocyclylene," by itself or as part of another substituent, refers to a saturated or unsaturated cyclic alkylene radical in which one or more carbon atoms (and optionally any associated hydrogen atoms) are independently replaced with the same or different heteroatom. The cycloheteroalkyl may be further substituted by one or more heteroatoms including, but not limited to, N, P, O, S, and Si, which attach to the carbon atoms of the cycloheteroalkyl via monovalent or multivalent bond. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidone, quinuclidine, and the like. In some embodiments, the cycloheteroalkyl group comprises from 3 to 10 ring atoms (3-10 membered cycloheteroalkyl). In other embodiments, the cycloalkyl group comprise from 5 to 7 ring atoms (5-7 membered cycloheteroalkyl). A cycloheteroalkyl group may be substituted at a heteroatom, for example, a nitrogen atom, with a ($C_1$-$C_6$) alkyl group. As specific examples, N-methyl-imidazolidinyl, N-methyl-morpholinyl, N-methyl-piperazinyl, N-methyl-piperidinyl, N-methyl-pyrazolidinyl and N-methyl-pyrrolidinyl are included within the definition of "cycloheteroalkyl." A cycloheteroalkyl group may be attached to the remainder of the molecule via a ring carbon atom or a ring heteroatom.

In one embodiment, heterocyclyl includes "azacyclyl" which denotes a heterocycle having one or more nitrogen atoms in the ring. An azacyclyl may also contain additional other heteroatom(s), such as oxygen and sulfur. An azacyclyl may be a four, five, six, seven, or eight-membered ring having one or more nitrogen atoms, such as azetidine, imidazolidine, morpholine, piperazine, piperidine, pyrazolidine, pyrrolidone, diazepane, azepane, diazocane, and azocane.

"Compounds" refers to compounds encompassed by structural formulae disclosed herein, such as (I), (Ia), (Ib), (Ic), (Id), and (Ie) and includes any specific compounds within these formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The term "tautomer" as used herein refers to isomers that change into one another with great ease so that they can exist together in equilibrium. In general, compounds may be hydrated, solvated or N-oxides. Certain compounds may exist in multiple crystalline or amorphous forms. In general, all physical forms are equivalent for the uses contemplated herein and are intended to be within the scope of the present invention. Further, it should be understood, when partial structures of the compounds are illustrated, that brackets indicate the point of attachment of the partial structure to the rest of the molecule.

"Halo," by itself or as part of another substituent refers to a radical —F, —Cl, —Br or —I.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. That is, a heteroarylalkyl group is composed of a heteroaryl group connected to an alkylene group which is further attached to other portion of a molecule. The alkylene group in the heteroarylalkyl group can be an alkylene having 1 to 12 carbon atoms, or 1 to 6 carbon atoms, or 1 to 3 carbon atoms. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanylene, alkenylene or alkynylene moiety of the heteroarylalkyl is ($C_1$-$C_6$) alkylene and the heteroaryl moiety is a 5-15-membered heteroaryl. In other embodiments, the heteroarylalkyl is a 6-13 membered heteroarylalkyl, e.g., the alkanylene, alkenylene or alkynylene moiety is ($C_1$-$C_3$) alkylene and the heteroaryl moiety is a 5-10 membered heteroaryl.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$ ed. 1991) and Harrison et al., "Compendium of Synthetic Organic Methods". Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid. 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Solvate" means a compound formed by solvation (the combination of solvent molecules with molecules or ions of the solute), or an aggregate that consists of a solute ion or molecule, i.e., a compound of the present invention, with one or more solvent molecules. When water is the solvent, the corresponding solvate is "hydrate".

"N-oxide", also known as amine oxide or amine-N-oxide, means a compound that derives from a compound of the present invention via oxidation of an amine group of the compound of the present invention. An N-oxide typically contains the functional group $R_3N^+$—$O^-$ (sometimes written as $R_3N$=O or $R_3N{\rightarrow}O$).

"Substituted," when used to modify a specified group or radical, means that one or more hydrogen atoms of the specified group or radical are each, independently of one another, replaced with the same or different substituent(s). The term "optionally substituted" means substitued or nonsubstituted. For example, an optionally substituted azacyclic ring means the azacyclic ring can be substituted or nonsubstituted. Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R_b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl. As another specific example, a substituted alkyl is meant to include -alkylene-O-alkyl, -alkylene-heteroaryl, -alkylene-cycloheteroalkyl, -alkylene-C(O)$OR^b$, -alkylene-C(O)$NR^bR^b$, and —$CH_2$—$CH_2$—C(O)—$CH_3$. The one or more substituent groups, taken together with the atoms to which they are bonded, may form a cyclic ring including cycloalkyl and cycloheteroalkyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups from the above lists useful for substituting other specified groups or atoms will be apparent to those of skill in the art.

The above-referenced substituents as represented by chemical formulas are also readily recognized by their chemical names known to one skilled in the art. For example, those substituents include alkyl, heteroalkyl, halo, hydroxyl, alkoxy, amino, alkylamino, cyano, nitro, haloalkyl, carboxylic acid, amide, ester, acyl, thiol, alkylthio, sulfonamide, and etc.

The substituents used to substitute a specified group can be further substituted, typically with one or more of the same or different groups selected from the various groups specified above.

"Treating" or "treatment" of any condition, disease or disorder refers to ameliorating the condition, disease or disorder (i.e., arresting or reducing the development of the condition, disease or disorder or at least one of the clinical symptoms thereof). In other embodiments "treating" or "treatment" refers to ameliorating at least one physical parameter, which may not be discernible by the patient. In yet other embodiments, "treating" or "treatment" refers to inhibiting the condition, disease or disorder, either physically, (e.g. stabilization of a discernible symptom), physiologically, (e.g., stabilization of a physical parameter) or both. In yet other embodiments, "treating" or "treatment" refers to delaying the onset of the condition, disease or disorder.

"Therapeutically effective amount" means the amount of the present compound that, when administered to a patient for treating a condition, disease or disorder, is sufficient to effect such treatment for the condition, disease or disorder. The "therapeutically effective amount" will vary depending on the compound, the condition, disease or disorder and its severity and the age, weight, etc., of the patient to be treated. In one embodiment, the therapeutically effective amount is different from the taste modulating amount, such as a sweet receptor modulating amount, a sweet receptor ligand modulating amount, a sweet flavor modulating amount, or a sweet flavoring agent amount.

"Vehicle" refers to a diluent, adjuvant, excipient or carrier with which a compound is administered.

As used herein, an "ingestible composition" includes any substance that, either alone or together with another substance, can be taken by mouth whether intended for consumption or not. The ingestible composition includes both "food or beverage products" and "non-edible products". By "Food or beverage products", it is meant any edible product intended for consumption by humans or animals, including solids, semi-solids, or liquids (e.g. beverages). The term "non-edible products" or "noncomestible composition" includes any product or composition that can be taken by humans or animals for purposes other than consumption or as food or beverage. For example, the non-edible product or noncomestible composition includes supplements, nutraceuticals, functional food products (e.g., any fresh or processed food claimed to have a health-promoting and/or disease-preventing properties beyond the basic nutritional function of supplying nutrients), pharmaceutical and over the counter medications, oral care products such as dentifrices and mouthwashes, cosmetic products such as sweetened lip balms and other personal care products that may or may not contain any sweetener.

A "ingestibly acceptable carrier or excipient" is a medium and/or composition that is used to prepare a desired dispersed dosage form of the inventive compound, in order to administer the inventive compound in a dispersed/diluted form, so that the biological effectiveness of the inventive compound is maximized. The medium and/or composition may be in any form depending on the intended use of a product, e.g., solid, semi-solid, liquid, paste, gel, lotion, cream, foamy material, suspension, solution, or any combinations thereof (such as a liquid containing solid contents). Ingestibly acceptable carriers includes many common food ingredients, such as water at neutral, acidic, or basic pH, fruit or vegetable juices, vinegar, marinades, beer, wine, natural water/fat emulsions such as milk or condensed milk, edible oils and shortenings, fatty acids and their alkyl esters, low molecular weight oligomers of propylene glycol, glyceryl esters of fatty acids, and dispersions or emulsions of such hydrophobic substances in aqueous media, salts such as sodium chloride, wheat flours, solvents such as ethanol, solid edible diluents such as vegetable powders or flours, or other liquid vehicles; dispersion or suspension aids; surface active agents; isotonic agents; thickening or emulsifying agents, preservatives; solid binders; lubricants and the like.

According to the present invention, a chemosensory receptor can be any receptor associated with chemosensory sensation or chemosensory ligand triggered signal transduction, e.g., via taste receptors or taste related receptors expressed in taste bud or internal organs of the body, such as gastrointestinal tract, etc. In one embodiment, a chemosensory receptor is a receptor that belongs to the 7-transmembrane receptor superfamily or G protein-coupled receptors (GPCRs). In another embodiment, a chemosensory receptor is a receptor carrying out signal transduction via one or more G proteins.

In yet another embodiment, a chemosensory receptor is a receptor that belongs to family C or class C of GPCRs. In yet another embodiment, a chemosensory receptor is a receptor that belongs to the T1R family. In yet another embodiment, a chemosensory receptor is a receptor of T1R1, T1R2, T1R3, or their equivalences or variances or a combination thereof. In still another embodiment, a chemosensory receptor is a hetero-dimer of T1R2 and T1R3, or their equivalences or variances.

An "modulator" herein refers to a compound, or an ingestibly acceptable salt or solvate thereof, that modulates (increases) the activation of a particular receptor, preferably the chemosensory, e.g. T1R2/T1R3 receptor. Herein such modulators will enhance the activation of a chemosensory receptor by its ligand. Typically the "modulator" will be specific to a particular ligand, i.e., it will not enhance the activation of a chemosensory receptor by chemosensory ligands other than the particular chemosensory ligand or ligands closely related thereto. Some modulators, at its ligand enhancing concentration, do not result in activation of the particular receptor by themselves. That is, the ligand enhancing concentrations of these modulators are concentration levels of the modulators that increase or enhance the activation of a particular receptor by a ligand without substantially activating the particular receptor by the modulators themselves. In some embodiments, certain modulators, when used at a concentration higher than the ligand enhancing concentration, can also activate a particular receptor by themselves in addition to modulating (e.g., increase or enhancement) the activation of the receptor. For example, certain modulators, when used at a concentration higher than the ligand enhancing concentration, can be sweeteners (i.e., sweet flavoring agent/entity) as well. In other embodiments, certain modulators can activate a particular receptor by themselves in addition to modulating (e.g., increase or enhancement) the activation of the receptor simultaneously at the same concentration. In other words, certain modulators are also sweeteners (i.e., sweet flavoring agent/entity) at the same time.

A "flavor" herein refers to the perception of taste in a subject, which include sweet, sour, salty, bitter and umami. The subject may be a human or an animal.

A "flavoring agent" herein refers to a compound or the ingestibly acceptable salt or solvate thereof that induces a flavor or taste in an animal or a human. The flavoring agent can be natural, semi-synthetic, or synthetic.

A "flavor modifier" or "flavor modifying agent" herein refers to a compound or the ingestibly acceptable salt or solvate thereof that modifies, including potentiating and/or inducing, the tastes of a flavoring agent in an animal or a human.

A "flavor modulator" herein refers to a compound or ingestibly acceptable salt thereof that modulates (potentiates) and/or multiplies the tastes of a flavoring agent, or an ingestible composition comprising the flavoring agent.

A "sweet flavor" refers to the sweet taste typically induced by sugar, such as fructose, in an animal or a human.

A "sweet flavoring agent", "sweet flavor entity", "sweetener", or "sweet compound" herein refers to a compound or ingestibly acceptable salt thereof that elicits a detectable sweet flavor in a subject, e.g. fructose or a compound that activates a T1R2/T1R3 receptor in vitro. The subject may be a human or an animal.

A "sweet flavor modifier" or "sweet flavor modifying agent" herein refers to a compound or ingestibly acceptable salt or solvate thereof that modifies, including potentiating, inducing, or blocking, the sweet taste of a sweet flavoring agents in an animal or a human. The sweet flavor modifier includes both sweet flavor modulator and sweet flavoring agent.

A "sweet flavor modulator" or "sweet flavor modulating agent" herein refers to an modulator of a sweet flavor wherein the term modulator is the same as defined above.

A "sweet receptor activating compound" or "sweet receptor agonist" herein refers to a compound that activates a sweet receptor, such as a T1R2/T1R3 receptor. One example of a sweet receptor activating compound is a sweetener, such as fructose.

A "sweet receptor modulating compound" herein refers to a compound that modulates (activates, block, or enhances/reduces activation of) a sweet receptor such as a T1R2/T1R3 receptor. For example, a sweet receptor modulating compound may potentiate the effect of a sweet receptor activating compound, e.g., fructose.

The present sweet receptor modulating compound, at its ligand enhancing concentration of use, may or may not result in activation of the particular receptor by themselves. Some of the sweet receptor modulating compounds or sweet flavor modulators, can also activate a particular receptor by themselves in addition to modulating (increase) the activation of the receptor. For example, some of the sweet receptor modulating compounds or sweet flavor modulators can also activate a sweet receptor, such as a T1R2/T1R3 receptor, acting as the receptor agonists.

A "sweet flavor modulating amount" herein refers to an amount of a compound of Formula (I) that is sufficient to modulate sweet taste in an ingestible composition, or a precursor thereof, sufficiently to be perceived by a human subject. In many embodiments of the invention, at least about 0.001 ppm of the present compound would need to be present in order for most human subjects to perceive a modulation of the sweet flavor of an ingestible composition comprising the present compound. A broad range of concentration that would typically be employed in order to economically provide a desirable degree of sweet flavor modulation can be from about 0.001 ppm to 100 ppm, or a narrow range from about 0.1 ppm to about 10 ppm. Alternative ranges of sweet flavor modulating amounts can be from about 0.01 ppm to about 30 ppm, from about 0.05 ppm to about 15 ppm, from about 0.1 ppm to about 5 ppm, or from about 0.1 ppm to about 3 ppm. In some embodiments, sweet flavor modulating amount is the amout corresponding to ligand enhancing concentration(s) of a sweet flavor modulators of the present invention.

A "sweet receptor modulating amount" herein refers to an amount of a compound that is sufficient to modulate (activate, enhance or block) a sweet taste receptor protein. In many embodiments of the invention, a sweet receptor modulating amount is at least about 10 nM, or at least about 100 nM (i.e. about 0.1 µM), or at least about 1 µM, or at least about 10 µM. A "T1R2T1R3 receptor modulating or activating amount" is an amount of compound that is sufficient to modulate or activate a T1R2/T1R3 receptor. A "sweet receptor" is a taste receptor that can be modulated by a sweet compound. Preferably a sweet receptor is a G protein coupled receptor, and more preferably the sweet receptor is a T1R2/T1R3 receptor.

Compounds

In one embodiment, the present invention provides a compound having structural Formula (I):

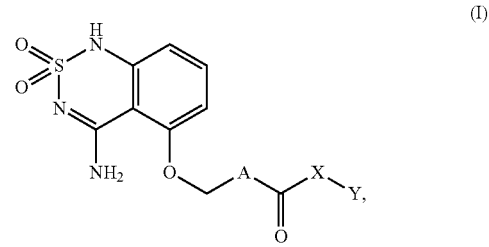

or a salt or solvate thereof; wherein

A is an optionally substituted four, five, six, seven, or eight-membered azacyclic ring;

X is a covalent bond or —NR¹—;

R¹ is hydrogen or C1 to C6 alkyl; and

Y is alkyl, substituted alkyl, heteroalkyl, substituted heteroalkyl, carbocyclyl, substituted carbocyclyl, heterocyclyl, substituted heterocyclyl, aryl, substituted aryl, heteroaryl, substituted heteroaryl, aralkyl, substituted aralkyl, heteroarylalkyl, or substituted heteroarylalkyl.

In one embodiment of the present invention, Formula (I) does not include the following compounds:

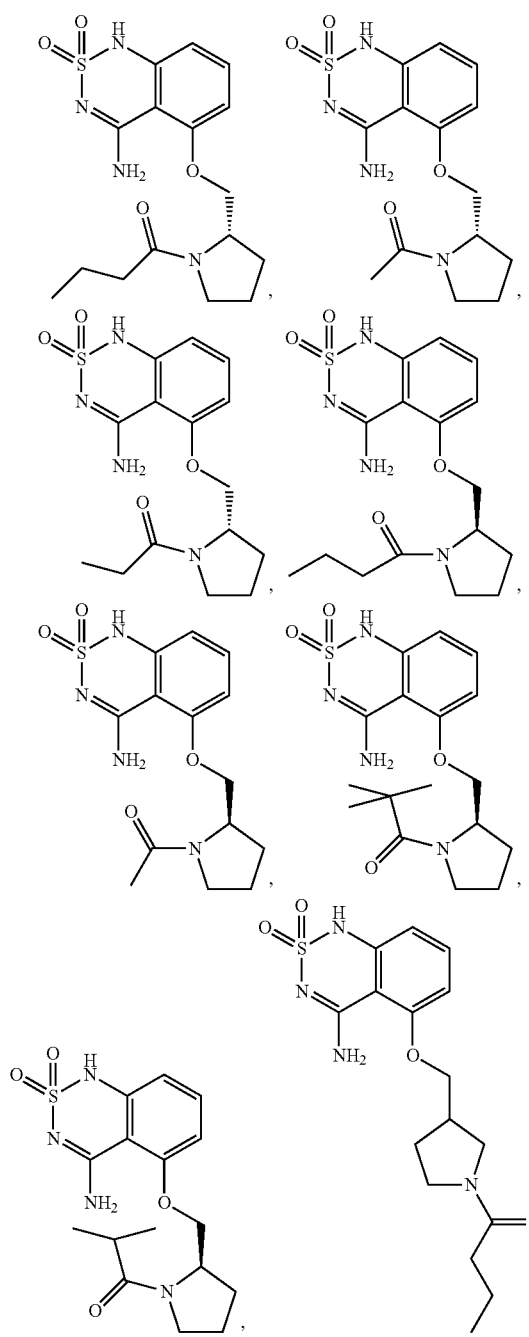

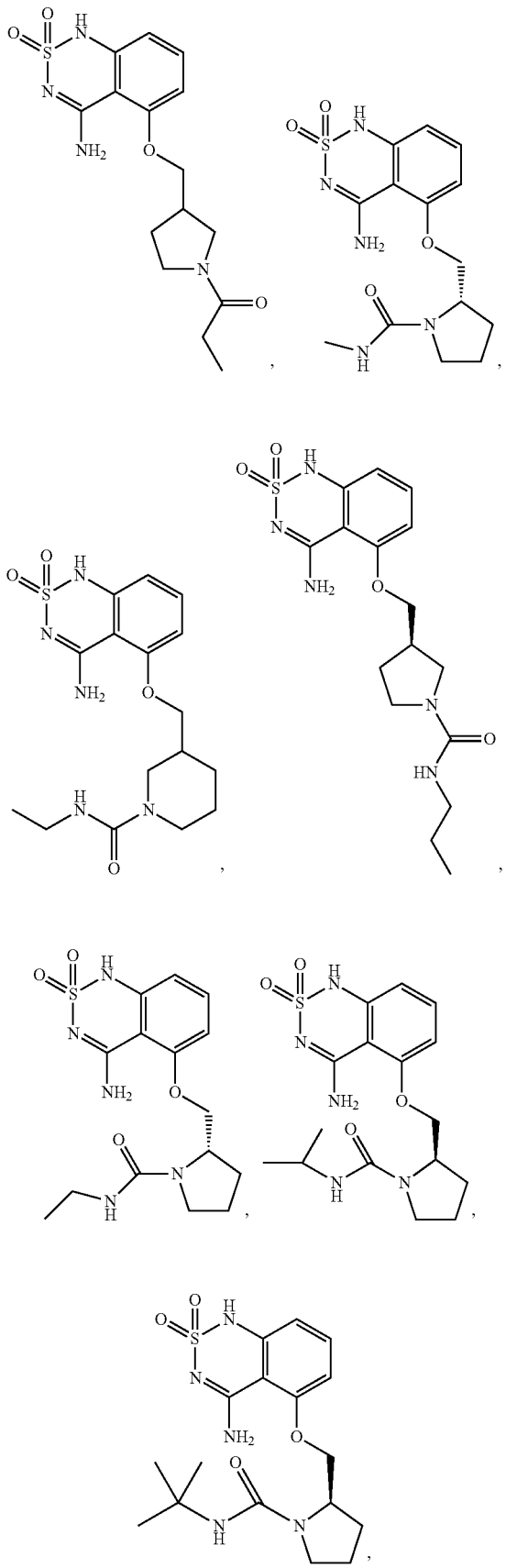

-continued

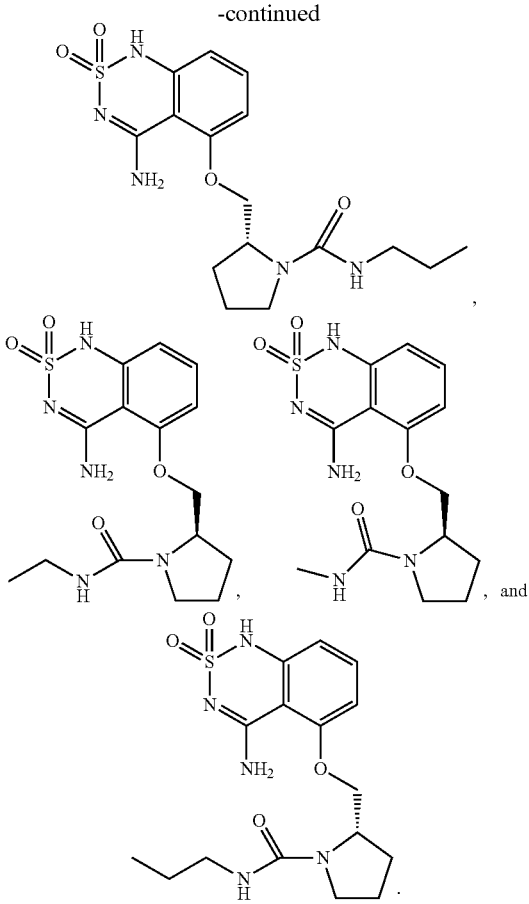

In one embodiment of Formula (I), X is NH.

In one embodiment of Formula (I), X is a covalent bond.

In one embodiment of Formula (I), A is an optionally substituted five, six, or seven-membered azacyclic ring. In one embodiment of Formula (I), A is an optionally substituted six-membered azacyclic ring. In one embodiment of Formula (I). A is an optionally substituted piperidine.

In one embodiment of Formula (I), the compound can be represented by structural Formula (Ia):

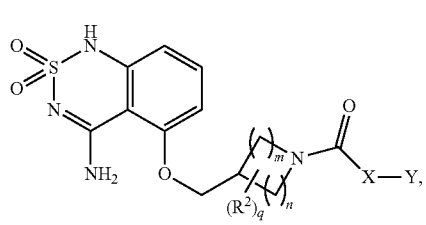

wherein, m is 1, 2, 3, 4, 5, or 6;

n is 0, 1, 2, or 3; with the proviso that m+n is more than 1 and less than 7:

q is 0, 1, 2, 3, 4, 5, or 6; with the proviso that q is less than m+n;

X is a covalent bond or —NR$^1$—;

R$^1$ is hydrogen or C1 to C6 alkyl;

Y is alkyl, substituted alkyl, heteroalkyl, substituted heteroalkyl, carbocyclyl, substituted carbocyclyl, heterocyclyl, substituted heterocyclyl, aryl, substituted aryl, heteroaryl, substituted heteroaryl, aralkyl, substituted aralkyl, heteroarylalkyl, or substituted heteroarylalkyl; and each R$^2$ is independently selected from the group consisting of alkyl, heteroalkyl, halo, hydroxyl, alkoxy, amino, alkylamino, cyano, nitro, haloalkyl, carboxylic acid, amide, ester, acyl, thiol, alkylthio, and sulfonamide.

In one embodiment of Formula (Ia), X is NH.

In one embodiment of Formula (Ia), X is a covalent bond.

In one embodiment of Formula (Ia), m is 1, 2, 3, or 4; and n is 0, 1, or 2.

In one embodiment of Formula (Ia), q is 1, 2, or 3.

In one embodiment of Formula (Ia), q is 0.

In one embodiment of Formula (Ia), m is 4, and n is 0; or m is 3, and n is 1; or m and n are both 2.

In one embodiment of Formula (Ia), the compound can be represented by structural Formula (Ib):

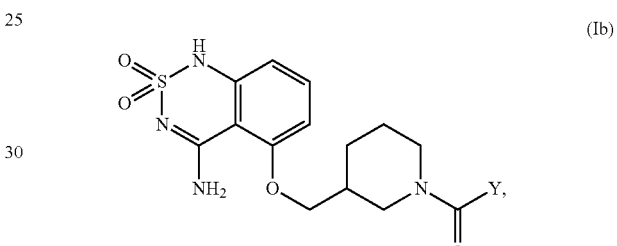

wherein,

Y is alkyl, substituted alkyl, heteroalkyl, substituted heteroalkyl, carbocyclyl, substituted carbocyclyl, heterocyclyl, substituted heterocyclyl, aryl, substituted aryl, heteroaryl, substituted heteroaryl, aralkyl, substituted aralkyl, heteroarylalkyl, or substituted heteroarylalkyl.

In one embodiment of Formula (Ia), the compound can be represented by structural Formula (Ic):

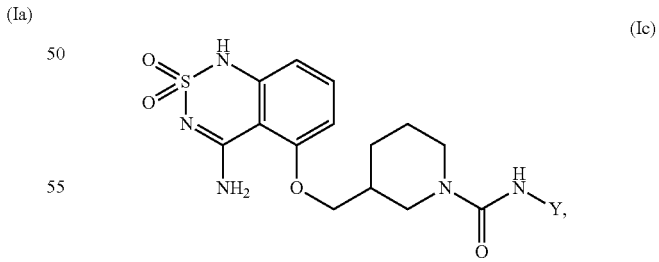

wherein,

Y is alkyl, substituted alkyl, heteroalkyl, substituted heteroalkyl, carbocyclyl, substituted carbocyclyl, heterocyclyl, substituted heterocyclyl, aryl, substituted aryl, heteroaryl, substituted heteroaryl, aralkyl, substituted aralkyl, heteroarylalkyl, or substituted heteroarylalkyl.

In one embodiment of Formula (Ia), the compound can be represented by structural

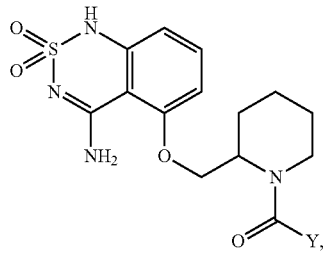

(Id)

wherein,

Y is alkyl, substituted alkyl, heteroalkyl, substituted heteroalkyl, carbocyclyl, substituted carbocyclyl, heterocyclyl, substituted heterocyclyl, aryl, substituted aryl, heteroaryl, substituted heteroaryl, aralkyl, substituted aralkyl, heteroarylalkyl, or substituted heteroarylalkyl.

In one embodiment of Formula (Ia), the compound can be represented by structural Formula (Ie):

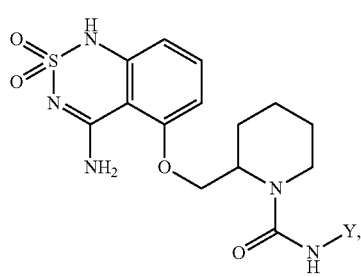

(Ie)

wherein,

Y is alkyl, substituted alkyl, heteroalkyl, substituted heteroalkyl, carbocyclyl, substituted carbocyclyl, heterocyclyl, substituted heterocyclyl, aryl, substituted aryl, heteroaryl, substituted heteroaryl, aralkyl, substituted aralkyl, heteroarylalkyl, or substituted heteroarylalkyl.

In one embodiment of Formula (Ib), (Ic), (Id), or (Ie), Y is C1 to C12 alkyl, substituted C1 to C12 alkyl, C1 to C12 heteroalkyl, or substituted C1 to C12 heteroalkyl.

In one embodiment of Formula (Ib), (Ic), (Id), or (Ie), Y is three to ten-membered carbocyclyl, substituted three to ten-membered carbocyclyl, three to ten-membered heterocyclyl, or substituted three to ten-membered heterocyclyl.

In one embodiment of Formula (Ib), (Ic), (Id), or (Ie), Y is six to fifteen-membered aryl, substituted six to fifteen-membered aryl, five to ten-membered heteroaryl, five to ten-membered substituted heteroaryl, In one embodiment of Formula (Ib), (Ic), (Id), or (Ie), Y is —(C1 to C3 alkylene)-aryl or —(C1 to C3 alkylene)-substituted aryl.

In one embodiment of Formula (Ib), (Ic), (Id), or (Ie), Y is —(C1 to C3 alkylene)-heteroaryl or —(C1 to C3 alkylene)-substituted heteroaryl.

In one embodiment of Formula (Ic) or (Ie), Y is C1 to C12 alkyl, substituted C1 to C12 alkyl, five or six-membered heteroaryl, substituted five or six-membered heteroaryl, —(C1 to C3 alkylene)-(five or six-membered heteroaryl), or —(C1 to C3 alkylene)-(substituted five or six-membered heteroaryl). In any of these preceding embodiments, the heteroaryl is pyrrole, pyridine, pyrimidine, pyridazine, or pyrazine, each of which is optionally substituted. In any of these preceding embodiments, the heteroaryl is an optionally substituted pyridine.

In one embodiment of Formula (Ib) or (Id), Y is C1 to C12 alkyl, substituted C1 to C12 alkyl, C1 to C12 heteroalkyl, or substituted C1 to C12 heteroalkyl. In any of these preceding embodiments, the optionally substituted C1 to C12 alkyl or C1 to C12 heteroalkyl may be straight or branched.

In one embodiment of Formula (Ib) or (Id), Y is three, four, five, six, or seven-membered cycloalkyl, substituted three, four, five, six, or seven-membered cycloalkyl, five, six, or seven-membered heterocyclyl, or substituted five, six, or seven-membered heterocyclyl. In any of these preceding embodiments, the cycloalkyl is cyclopropyl, cyclobutyl, cyclopentyl, cyclohexyl, or cycloheptyl, each of which is optionally substituted. In any of these preceding embodiments, the heterocyclcyl is tetrahydrofuran or tetrahydropyran, each of which is optionally substituted.

In one embodiment of Formula (Ib) or (Id), Y is phenyl or substituted phenyl.

In one embodiment of Formula (Ib) or (Id), Y is an optionally substituted five or six-membered monocyclic heteroaryl, or an optionally substituted ten to twelve-membered bicyclic heteroaryl. In any of these preceding embodiments, the heteroaryl is selected from the group consisting of pyrrole, pyridine, pyrimidine, pyridazine, pyrazine, pyridine N-oxide, quinoline, imidazopyridine, and pyrazolopyridine, each of which is optionally substituted.

In one embodiment of Formula (Ib) or (Id), Y is —CH$_2$-phenyl or —C(CH$_3$)$_2$— substituted phenyl.

In one embodiment of Formula (Ib) or (Id), Y is —CH$_2$-heteroaryl or —C(CH$_3$)$_2$— substituted heteroaryl. In any of these preceding embodiments, the heteroaryl is pyrrole, pyridine, pyrimidine, pyridazine, or pyrazine, each of which is optionally substituted. In any of these preceding embodiments, the heteroaryl is optionally substituted pyridine.

In certain specific embodiments of Formula (I), the compound is selected from the group consisting of

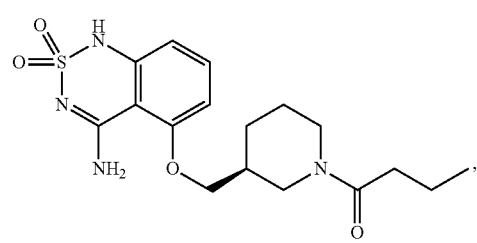

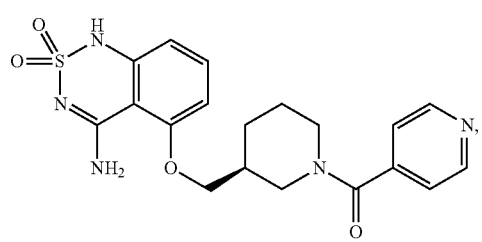

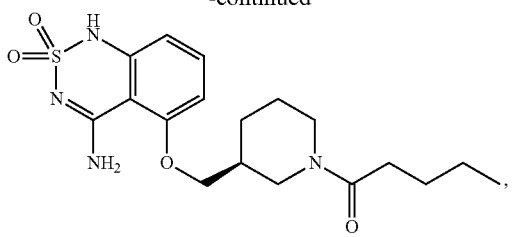
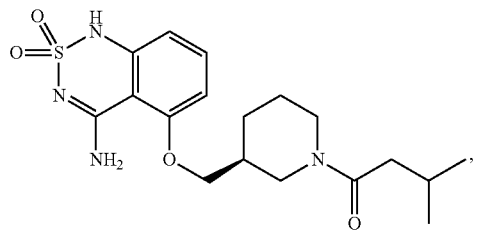
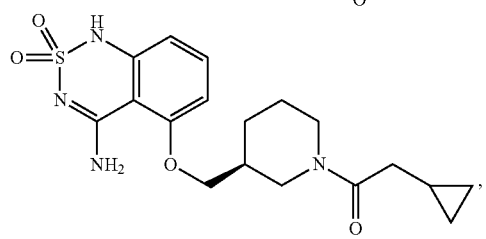
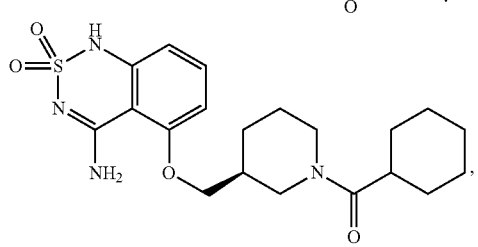
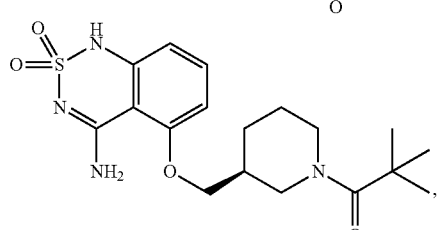
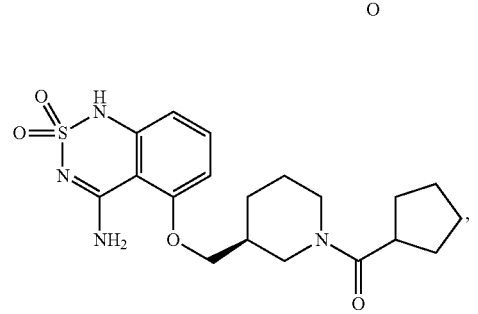
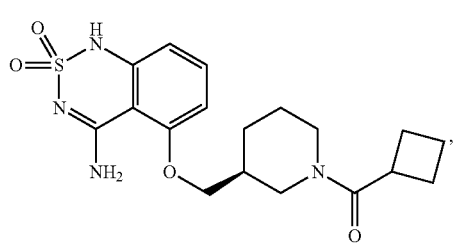
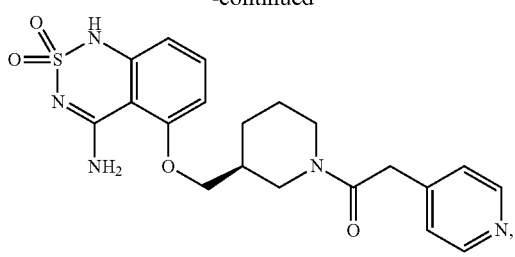
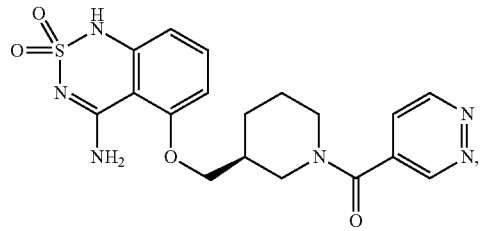
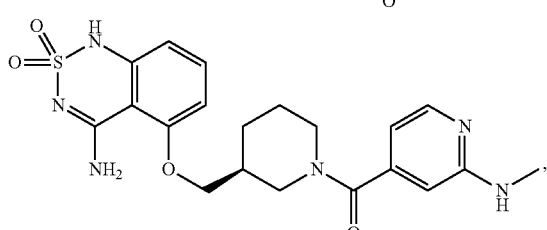
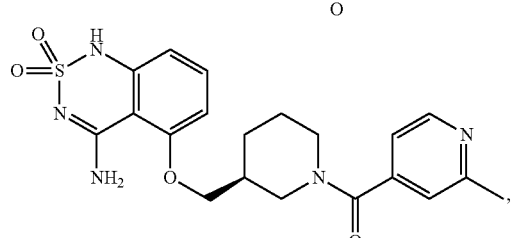
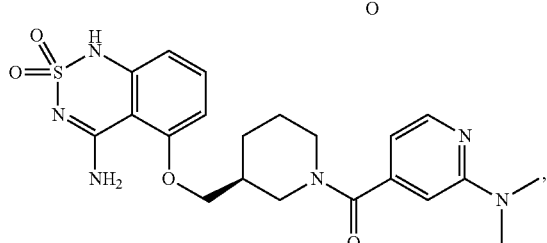
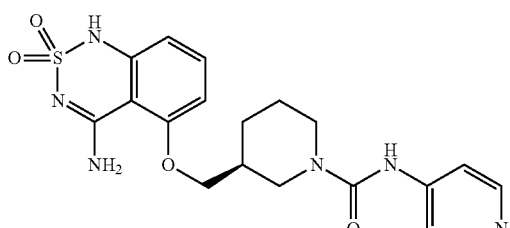
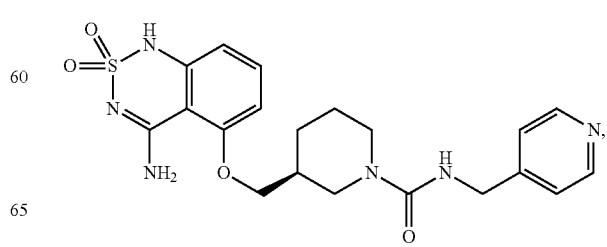

-continued
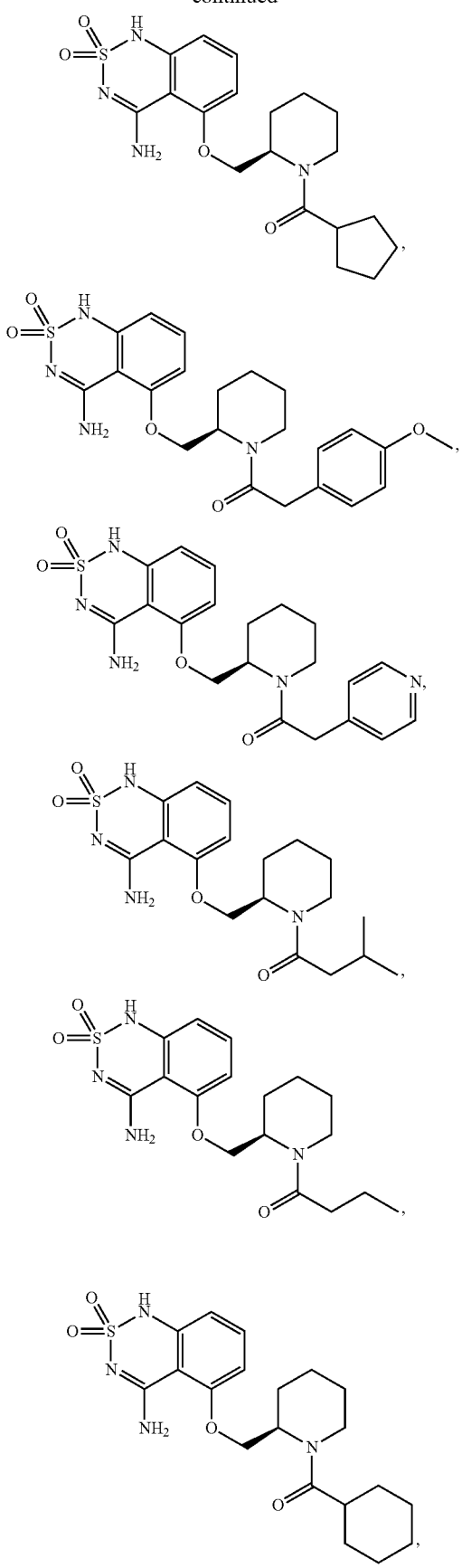
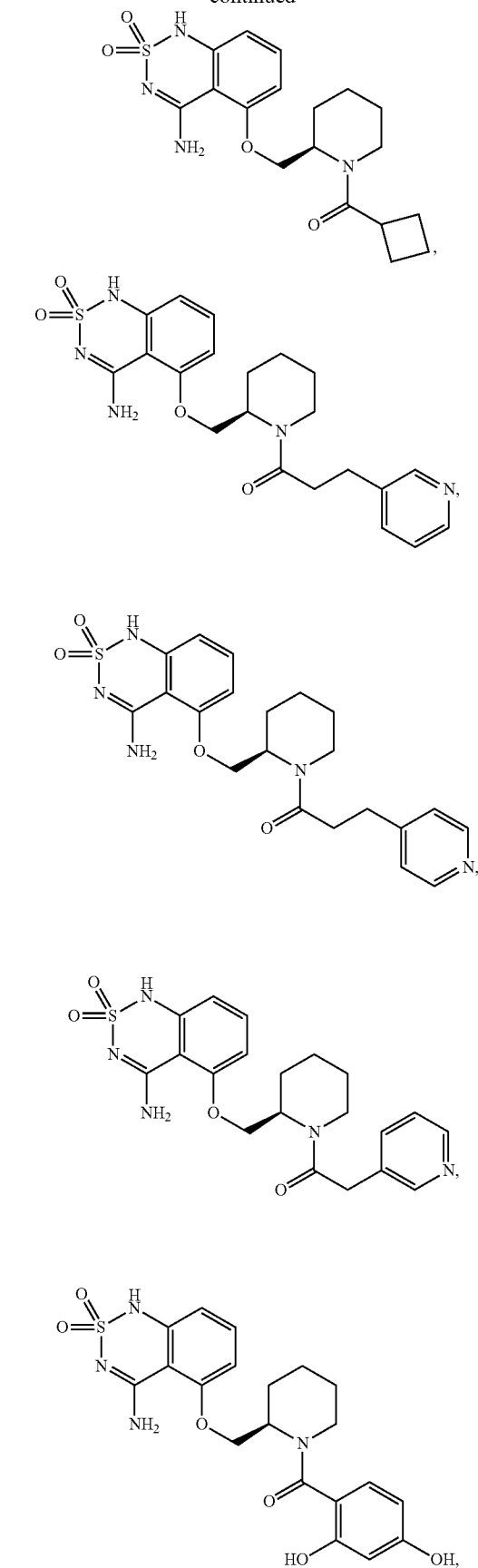

23
-continued
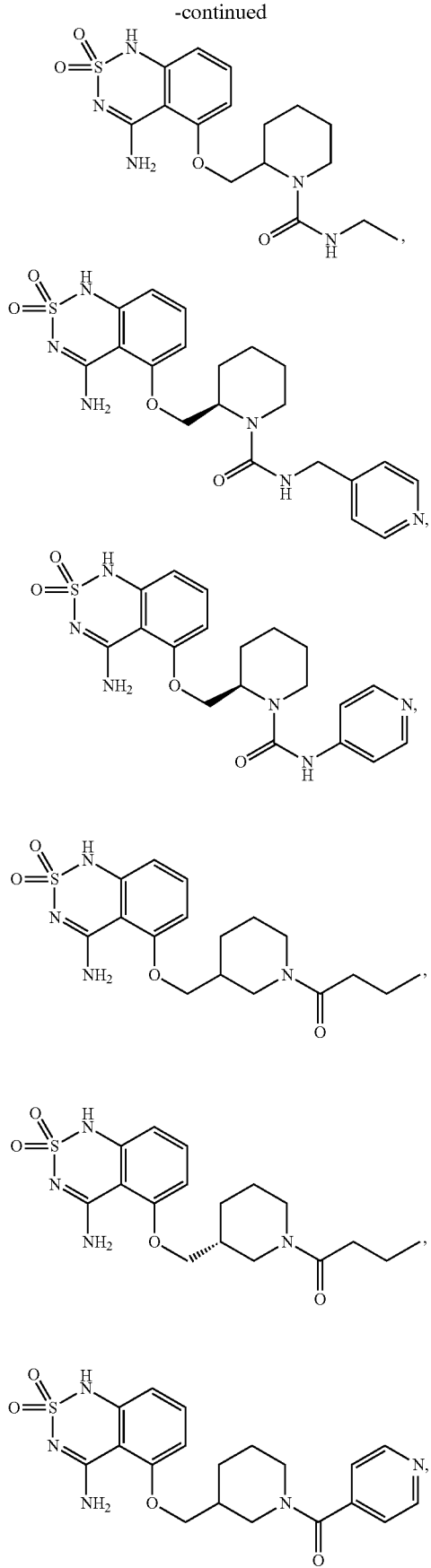
24
-continued
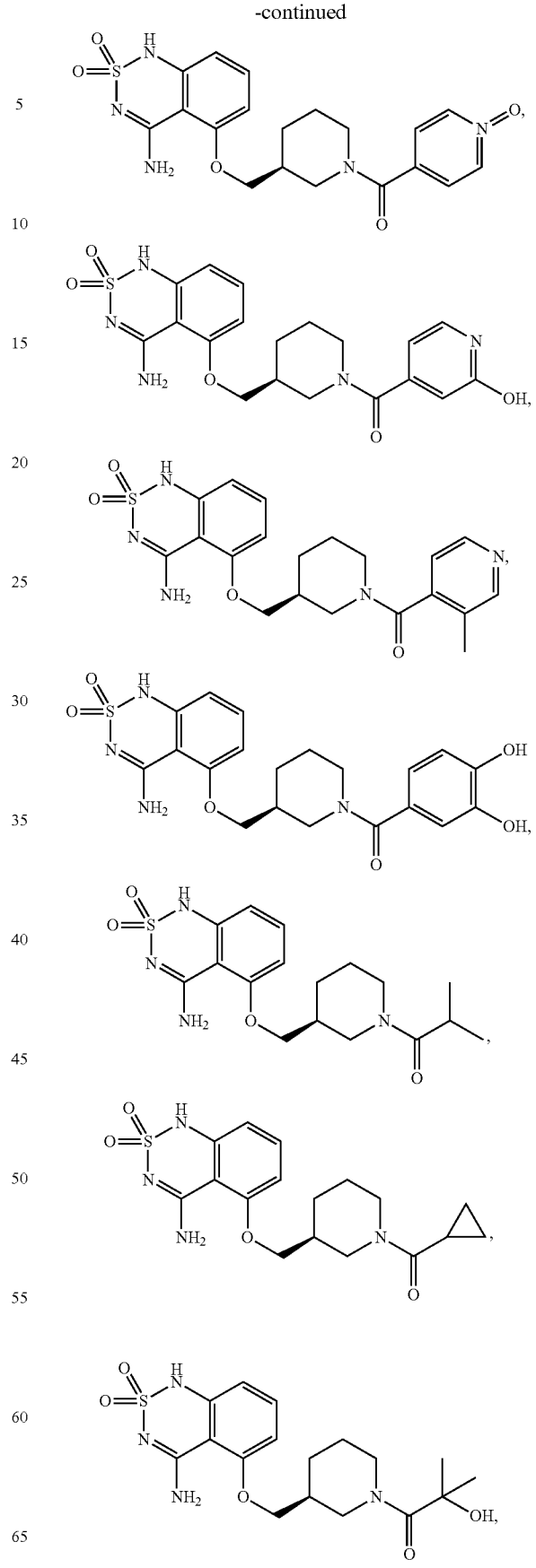

25
-continued
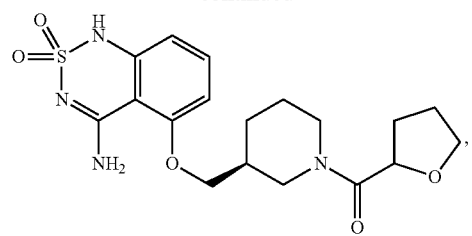
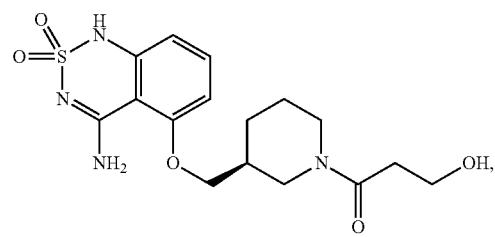
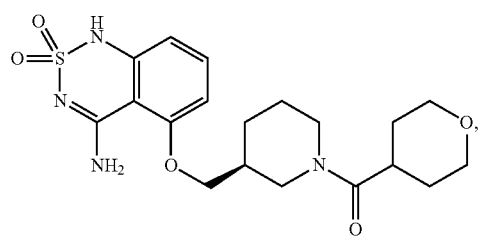
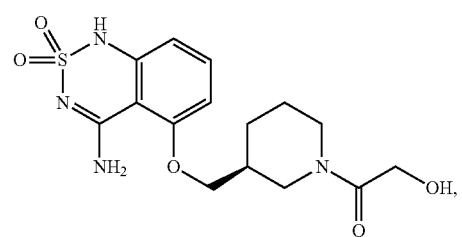
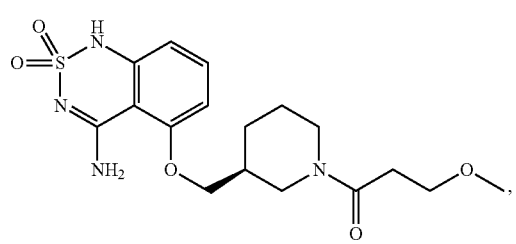
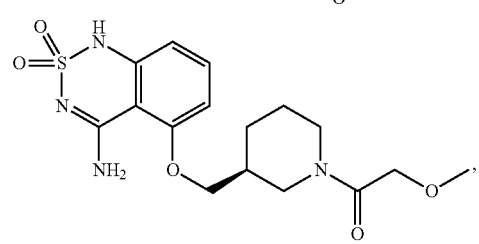
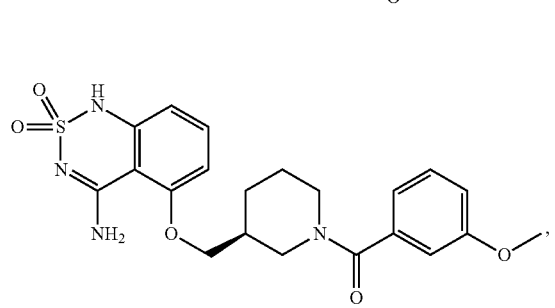
26
-continued
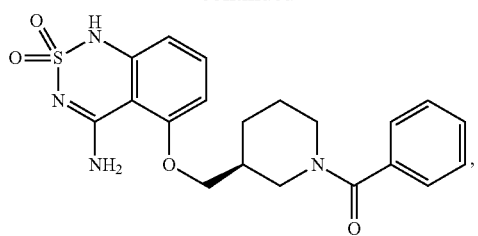
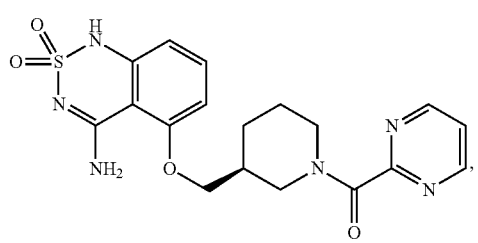
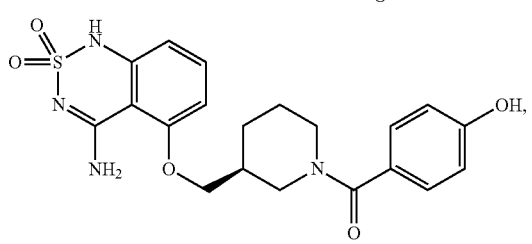
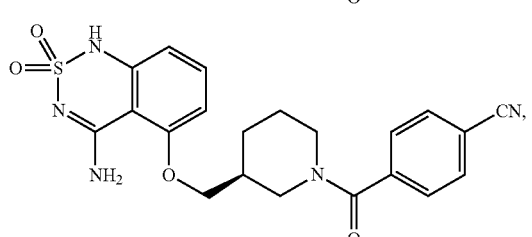
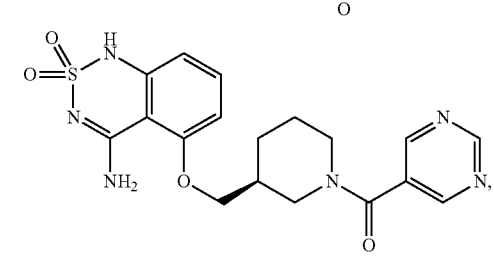
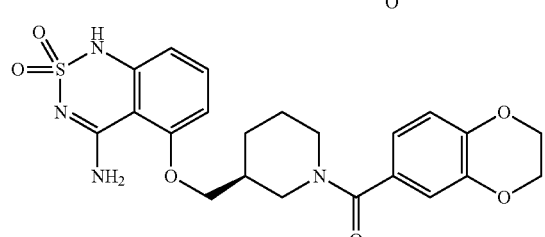
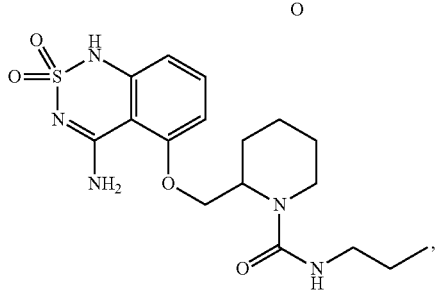

27
-continued
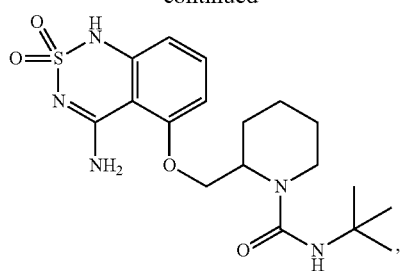
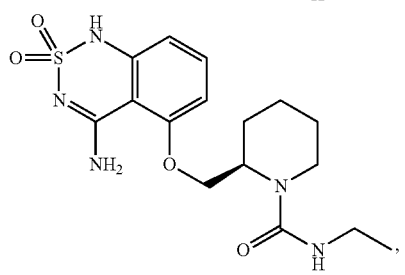
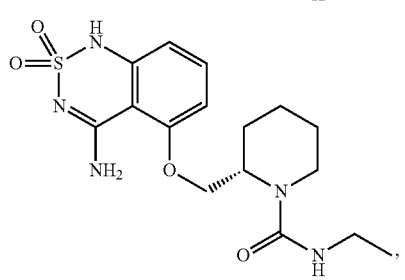
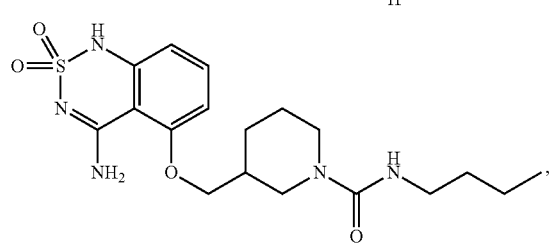
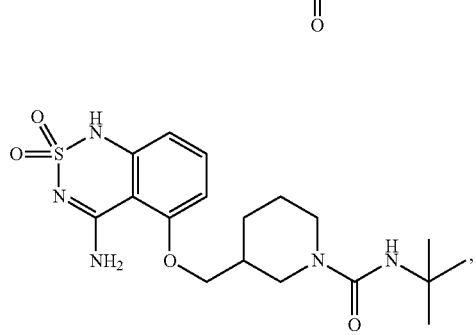
28
-continued
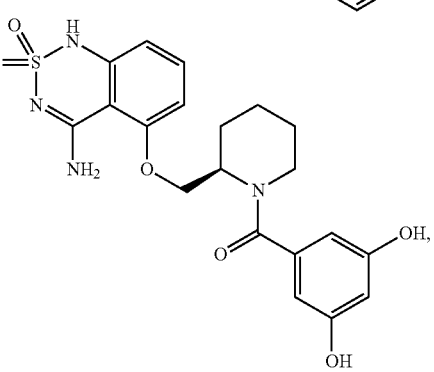
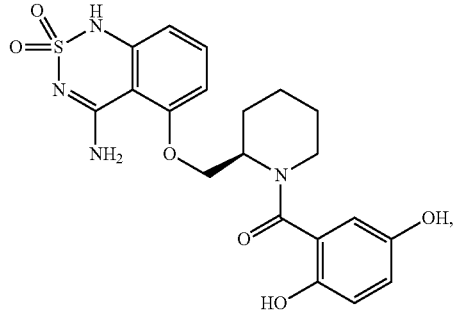
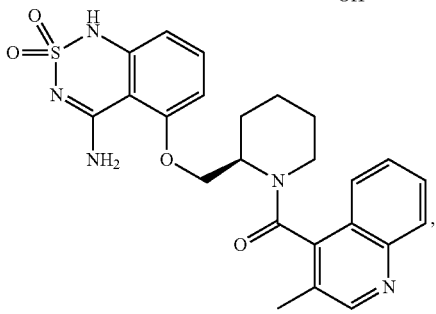

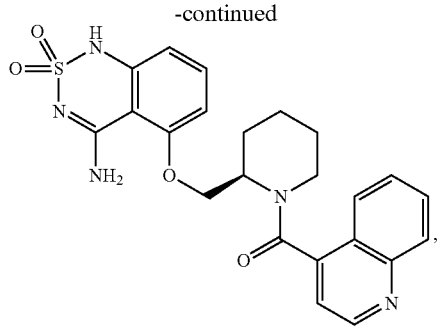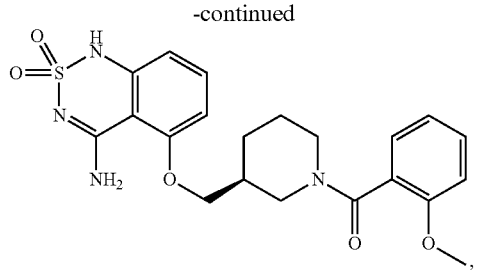

31
-continued
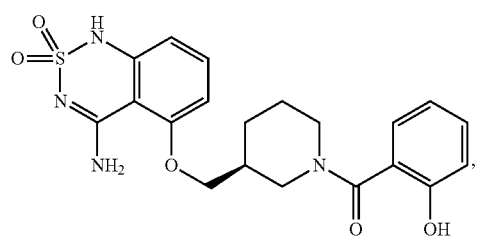
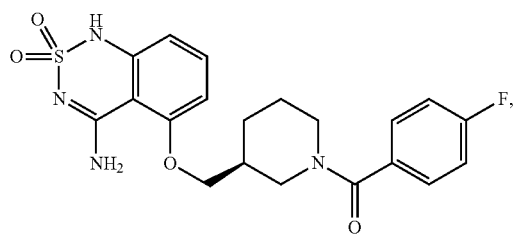
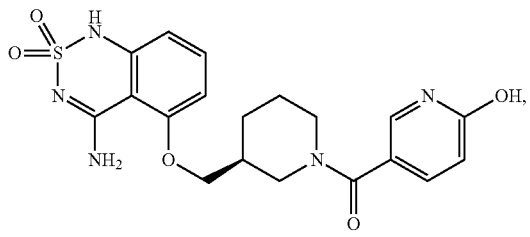
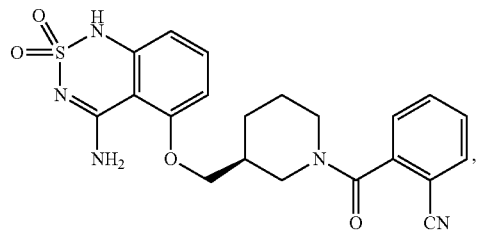
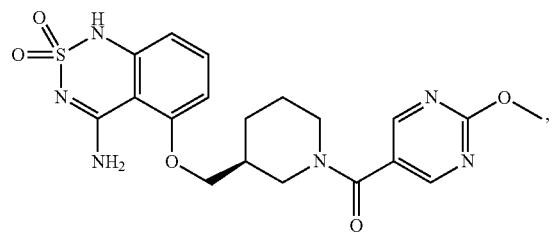
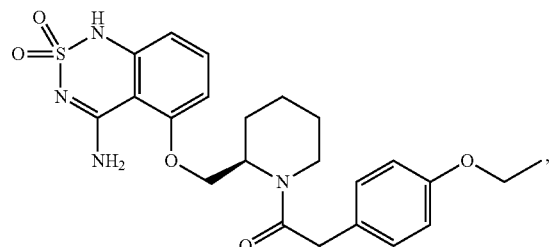
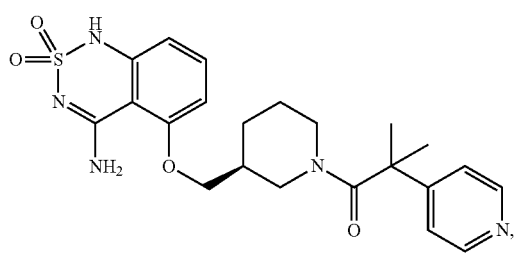
32
-continued
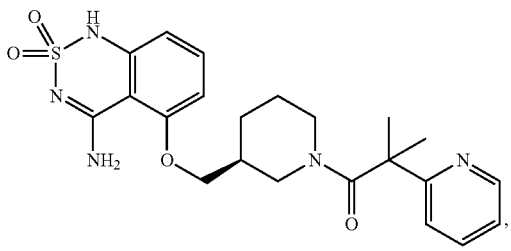
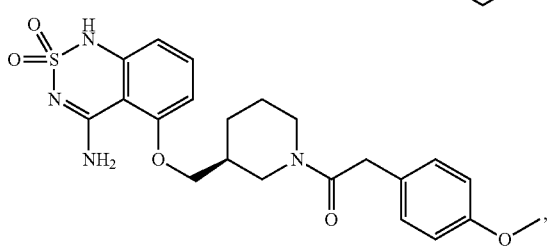
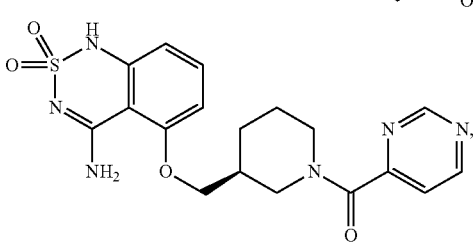
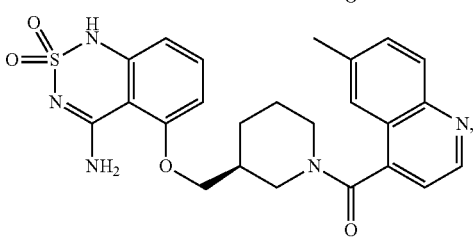
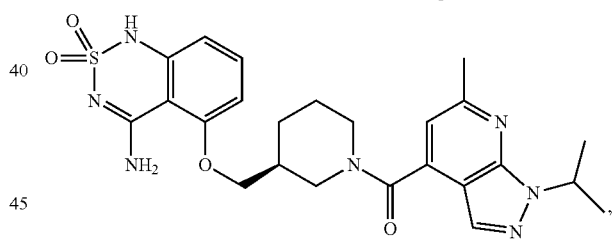
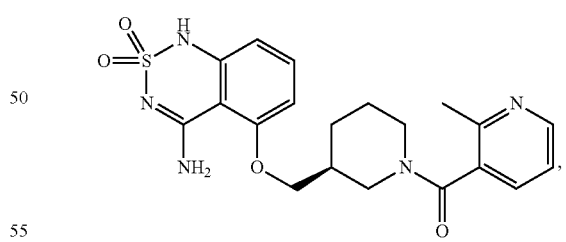
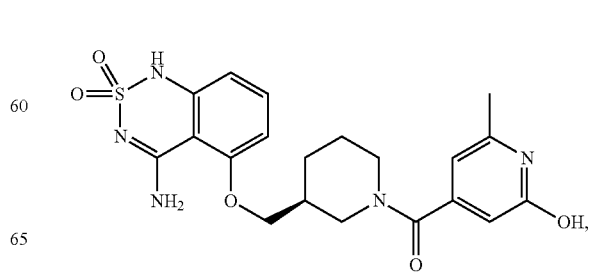

-continued
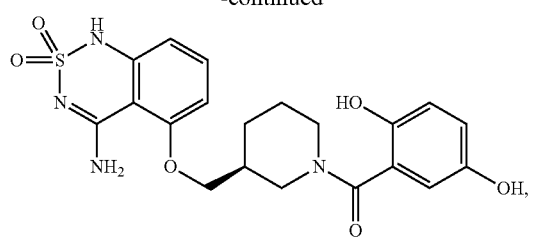
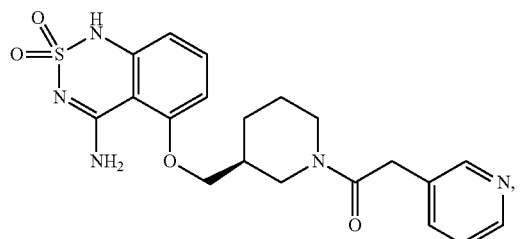
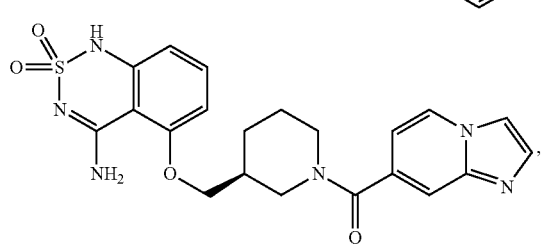
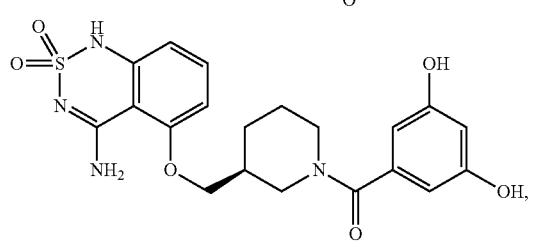
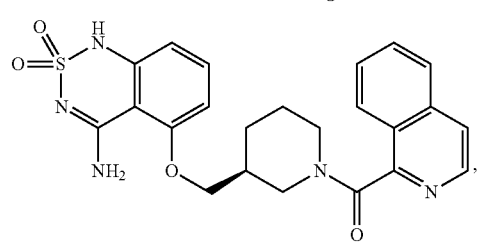
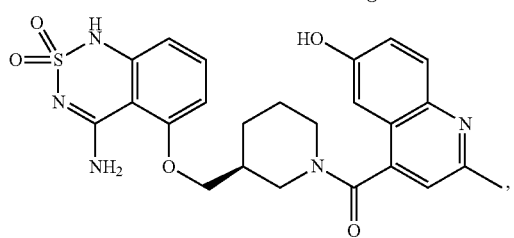
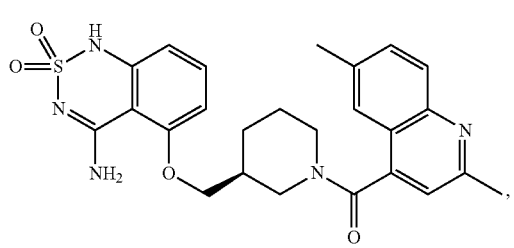
-continued
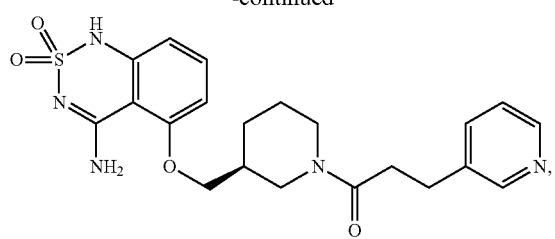
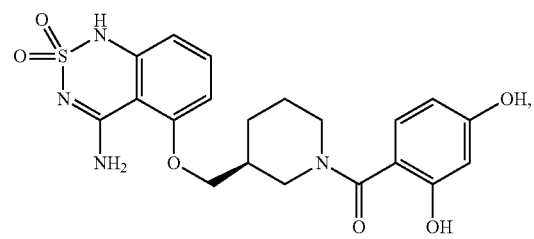
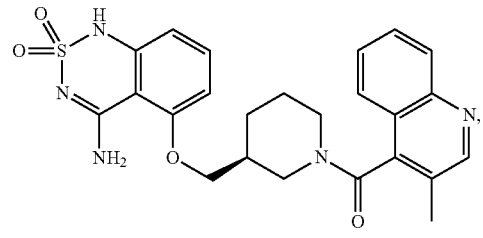
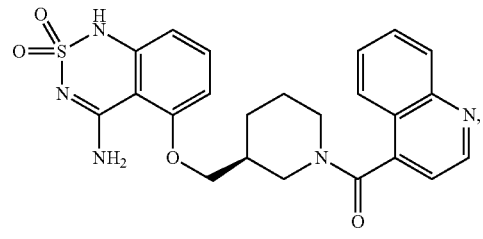
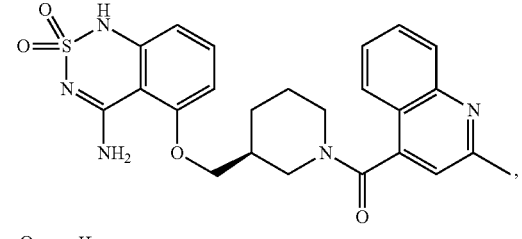
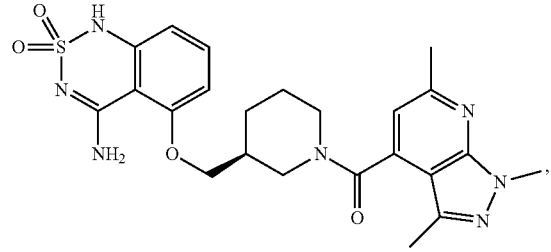
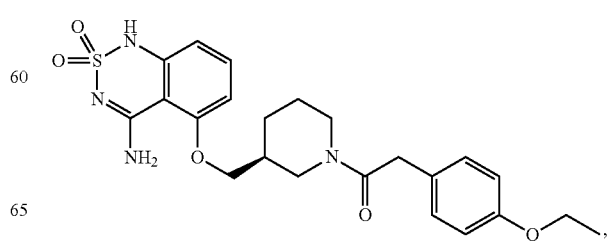

35
-continued
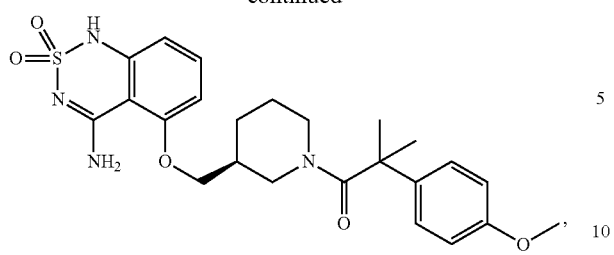
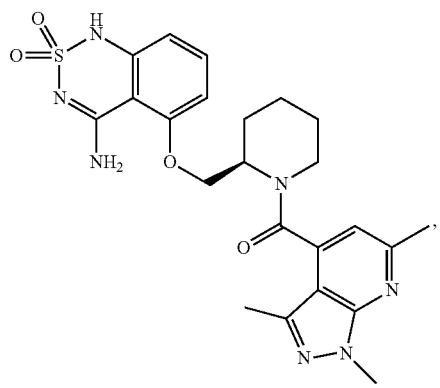
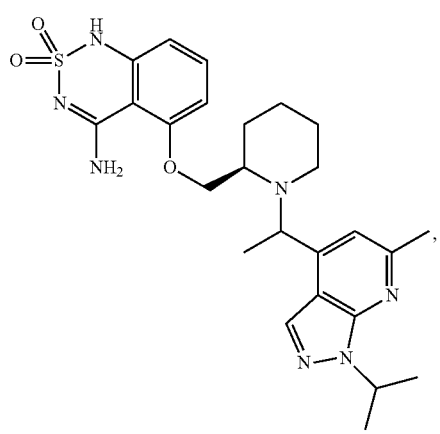
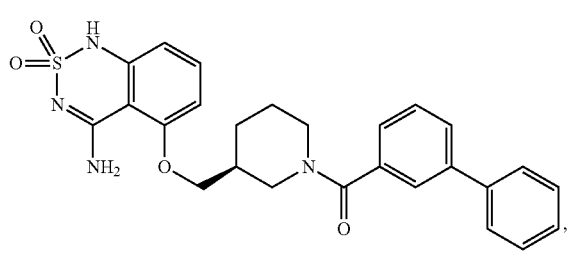
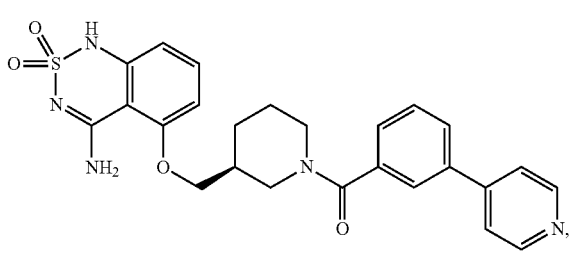
36
-continued
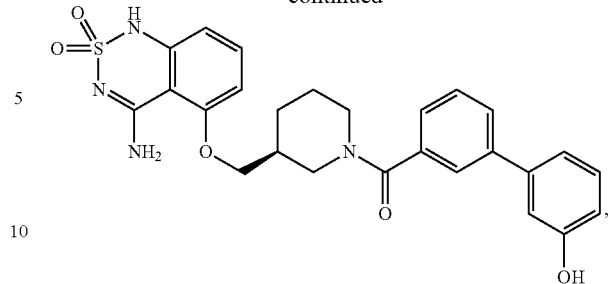
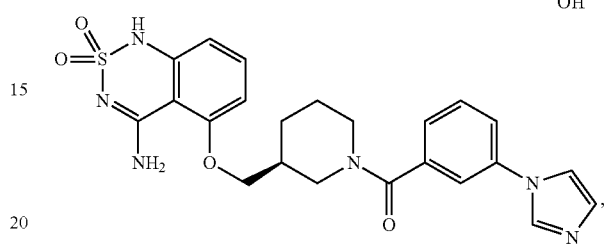
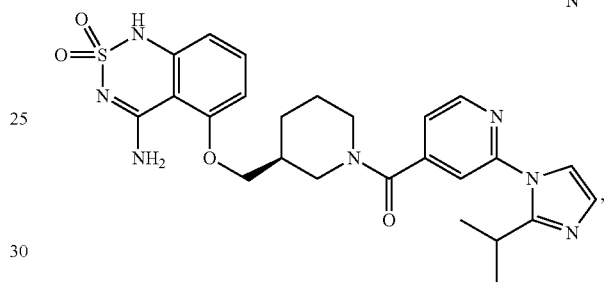
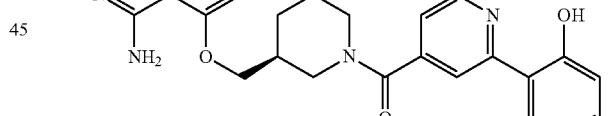
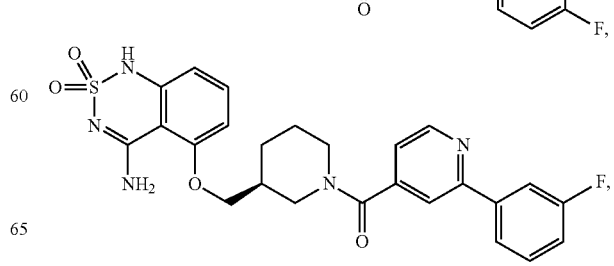

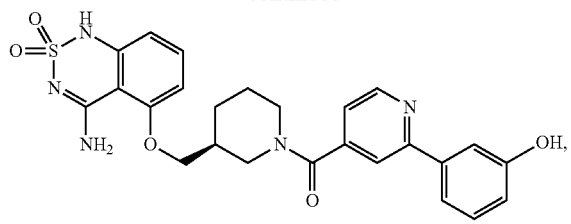
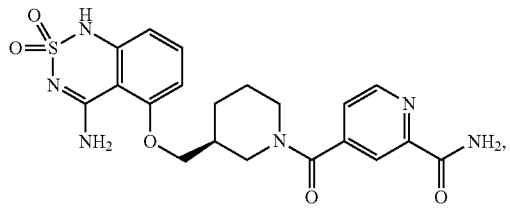
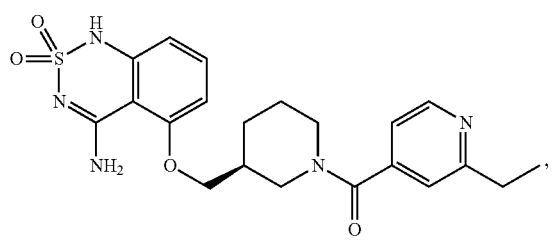
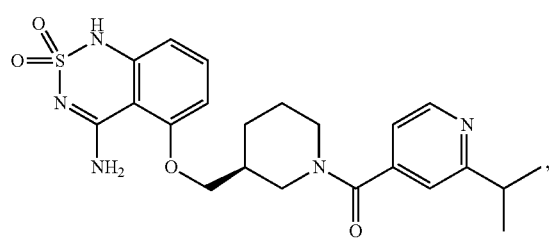
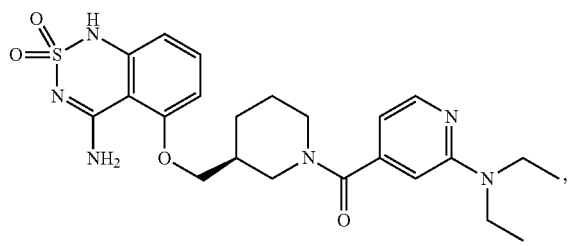
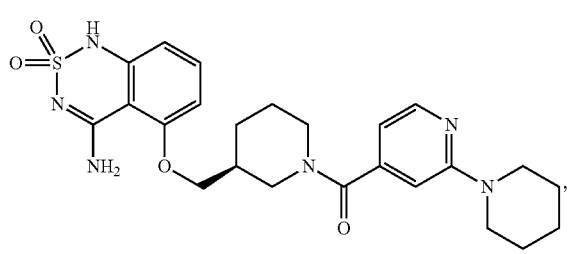
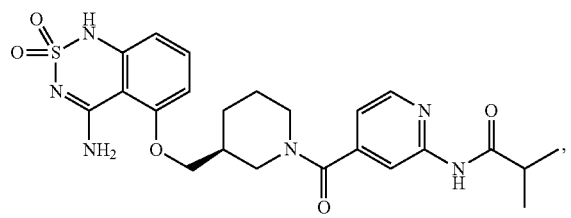

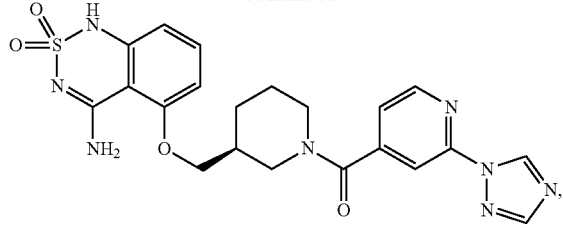
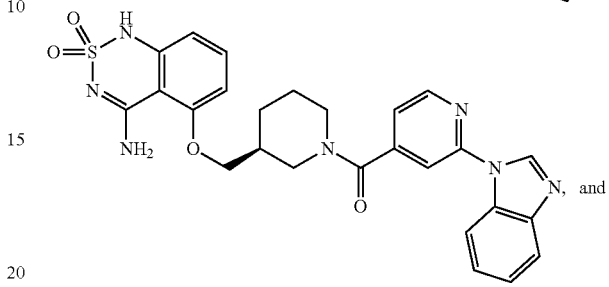
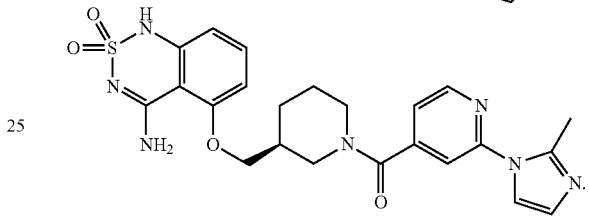

Compositions

The present compounds can be used for one or more methods of the present invention, e.g., modifying receptors and their ligands associated with chemosensory or chemosensory related sensation or reaction. According to the present invention, a method of modulating a chemosensory receptor and/or its ligand includes modulating the activity, structure, function, expression, and/or modification of a chemosensory receptor as well as modulating, treating, or taking prophylactic measure of a condition, e.g., physiological or pathological condition, associated with a chemosensory receptor. In general, a physiological or pathological condition associated with a chemosensory receptor includes a condition, disease, or disorder associated with the chemosensory receptor and/or its ligand, e.g., gastrointestinal disorders, metabolic disorders, functional gastrointestinal disorders, etc. In one embodiment, the method includes increasing or potentiating sweet flavor. In another embodiment, the method includes modulating a sweet receptor and/or its ligand expressed in a place of the body other than the taste buds, such as an internal organ. In general, the compounds of the present invention, individually or in combination, can be provided in a composition, such as, e.g., an ingestible composition. In one embodiment, the present compound can impart a more sugar-like temporal profile and/or flavor profile to a sweetener composition by combining one or more present compound with one or more sweetener in the sweetener composition. In another embodiment, the present compound can increase or potentiate the sweet taste of a composition by contacting the composition thereof with one or more present compound to form a modified composition. In another embodiment, the present compound can be in a composition that modulates the sweet receptors and/or their ligands expressed in the body other than in the taste buds.

The compounds of Formula (I), (Ia), (Ib), (Ic), (Id), (Ie), and its various subgenuses and species, and their salts and/or solvates, should preferably be comestibly acceptable, e.g., deemed suitable for consumption in food or drink from the perspective of giving unmodified comestible compositions an improved and/or pleasing sweet taste, and would not be significantly toxic or causes unpleasant or undesirable pharmacological or toxicological effects on an animal or human at the typical concentrations they are employed as flavoring agents for the comestible compositions.

One of the methods of demonstrating that a flavorant compound is comestibly acceptable is to have the compound tested and/or evaluated by an Expert Panel of the Flavor and Extract Manufacturers Association (FEMA) and declared as to be "Generally Recognized As Safe" ("GRAS"). The FEMA/GRAS evaluation process for flavorant compounds is complex but well known to those of ordinary skill in the food product preparation arts, as is discussed by Smith, et al. in an article entitled "GRAS Flavoring Substances 21," Food Technology, 57(5), pgs 46-59, May 2003, the entire contents of which are hereby incorporated herein by reference. In addition to the FEMA expert panel, an independent, qualified panel of experts in pertinent scientific disciplines may be formed by the manufacturer to evaluate the safety of a specific compound for GRAS status. This process is known as a "self determination of GRAS status." Another method of demonstrating that a flavorant compound is comestibly acceptable is to obtain favorable review by the WHO/FAO Joint Expert Committee on Food Additives, or JECFA. There are also other evaluation methods, such as independent review by the regulatory agency, which are generally known to those of ordinary skill in the food product preparation arts.

In one embodiment, the compounds of the present invention can be used at its ligand enhancing concentrations, e.g., very low concentrations on the order of a few parts per million, in combination with one or more known sweeteners, natural or artificial, so as to reduce the concentration of the known sweetener required to prepare an ingestible composition having the desired degree of sweetness.

In one embodiment of the present invention, the present compounds can potentiate, i.e. intensify or multiply, the sweetness of a sweetener under a broad range of pH. e.g., from lower pH to neutral pH. The lower and neutral pH includes, but is not limited to, a pH from about 2.1 to about 8.5; from about 2.3 to about 8.0; from about 2.5 to about 7.5; and from about 2.6 to about 7.3. In one embodiment, the present compounds can potentiate, i.e., intensify or multiply, the sweetness of a sweetener in a pH range from about 2.8 to about 7.1. In certain embodiments, the present compounds can potentiate the perceived sweetness of a fixed concentration of a sweetener in taste tests at a compound concentration of about 50 µM, 40 µM, 30 µM, 20 µM, or 10 µM at both low to neutral pH value. In certain embodiments, the potentiating factor of the present compounds at the lower pH is substantially similar to the potentiating factor of the compounds at neutral pH. Such consistent sweet potentiating property under a broad range of pH render the present compounds good candidates for a broad use in a wide variety of foods and beverages.

Commonly used known or artificial sweeteners for use in such combinations of sweeteners include but are not limited to the common saccharide sweeteners, e.g., sucrose, fructose, glucose, and sweetener compositions comprising natural sugars, such as corn syrup (including high fructose corm syrup) or other syrups or sweetener concentrates derived from natural fruit and vegetable sources, semi-synthetic "sugar alcohol" sweeteners such as erythritol, isomalt, lactitol, mannitol, sorbitol, xylitol, maltodextrin, and the like, and artificial sweeteners such as aspartame, saccharin, acesulfame-K, cyclamate, sucralose, and alitame. Sweeteners also include cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet Stevia-based glycosides, carrelame and other guanidine-based sweeteners, etc. The term "sweeteners" also includes combinations of sweeteners as disclosed herein.

In one embodiment, the present compound is added to a noncomestible composition or non-edible product, such as supplements, nutraceuticals, functional food products (e.g. any fresh or processed food claimed to have a health-promoting and/or disease-preventing properties beyond the basic nutritional function of supplying nutrients), pharmaceutical product, over the counter (OTC) product, oral care product, cosmetic products such as sweetened lip balms, and other personal care products.

In general, over the counter (OTC) product and oral care product generally refer to product for household and/or personal use which may be sold without a prescription and/or without a visit to a medical professional. Examples of the OTC products include, but are not limited to Vitamins and dietary supplements; Topical analgesics and/or anesthetic; Cough, cold and allergy remedies; Antihistamines and/or allergy remedies; and combinations thereof. Vitamins and dietary supplements include, but are not limited to vitamins, dietary supplements, tonics/bottled nutritive drinks, child-specific vitamins, dietary supplements, any other products of or relating to or providing nutrition, and combinations thereof. Topical analgesics and/or anesthetic include any topical creams/ointments/gels used to alleviate superficial or deep-seated aches and pains, e.g. muscle pain; teething gel; patches with analgesic ingredient; and combinations thereof. Cough, cold and allergy remedies include, but are not limited to decongestants, cough remedies, pharyngeal preparations, medicated confectionery, antihistamines and child-specific cough, cold and allergy remedies; and combination products. Antihistamines and/or allergy remedies include, but are not limited to any systemic treatments for hay fever, nasal allergies, insect bites and stings. Examples of oral care product include, but are not limited to mouth cleaning strips, toothpaste, toothbrushes, mouthwashes/dental rinses, denture care, mouth fresheners at-home teeth whiteners, dentifrices, and dental floss.

In another embodiment, the present compounds are added to food or beverage products or formulations. Examples of food and beverage products or formulations include, but are not limited to sweet coatings, frostings, or glazes for comestible products or any entity included in the Soup category, the Dried Processed Food category, the Beverage category, the Ready Meal category, the Canned or Preserved Food category, the Frozen Processed Food category, the Chilled Processed Food category, the Snack Food category, the Baked Goods category, the Confectionary category, the Dairy Product category, the Ice Cream category, the Meal Replacement category, the Pasta and Noodle category, and the Sauces, Dressings, Condiments category, the Baby Food category, and/or the Spreads category.

In general, the Soup category refers to canned/preserved, dehydrated, instant, chilled, UHT and frozen soup. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consommé) to sauces (cream or cheese-based soups).

The Dehydrated and Culinary Food Category usually means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

The Beverage category usually means beverages, beverage mixes and concentrates, including but not limited to, carbonated and non-carbonated beverages, alcoholic and non-alcoholic beverages, ready to drink beverages, liquid concentrate formulations for preparing beverages such as sodas, and dry powdered beverage precursor mixes. The Beverage category also includes the alcoholic drinks, the soft drinks, sports drinks, isotonic beverages, and hot drinks. The alcoholic drinks include, but are not limited to beer, cider/perry, FABs, wine, and spirits. The soft drinks include, but are not limited to carbonates, such as colas and non-cola carbonates; fruit juice, such as juice, nectars, juice drinks and fruit flavored drinks; bottled water, which includes sparkling water, spring water and purifieditable water; functional drinks, which can be carbonated or still and include sport, energy or elixir drinks; concentrates, such as liquid and powder concentrates in ready to drink measure. The drinks, either hot or cold, include, but are not limited to coffee or ice coffee, such as fresh, instant, and combined coffee; tea or ice tea, such as black, green, white, oolong, and flavored tea; and other drinks including flavor-, malt- or plant-based powders, granules, blocks or tablets mixed with milk or water.

The Snack Food category generally refers to any food that can be a light informal meal including, but not limited to Sweet and savory snacks and snack bars. Examples of snack food include, but are not limited to fruit snacks, chips/crisps, extruded snacks, tortilla/corn chips, popcorn, pretzels, nuts and other sweet and savory snacks. Examples of snack bars include, but are not limited to granola/muesli bars, breakfast bars, energy bars, fruit bars and other snack bars.

The Baked Goods category generally refers to any edible product the process of preparing which involves exposure to heat or excessive sunlight. Examples of baked goods include, but are not limited to bread, buns, cookies, muffins, cereal, toaster pastries, pastries, waffles, tortillas, biscuits, pies, bagels, tarts, quiches, cake, any baked foods, and any combination thereof.

The Ice Cream category generally refers to frozen dessert containing cream and sugar and flavoring. Examples of ice cream include, but are not limited to: impulse ice cream; take-home ice cream; frozen yoghurt and artisanal ice cream; soy, oat, bean (e.g. red bean and mung bean), and rice-based ice creams.

The Confectionary category generally refers to edible product that is sweet to the taste. Examples of confectionary include, but are not limited to candies, gelatins, chocolate confectionery, sugar confectionery, gum, and the likes and any combination products.

The Meal Replacement category generally refers to any food intended to replace the normal meals, particularly for people having health or fitness concerns. Examples of meal replacement include, but are not limited to slimming products and convalescence products.

The Ready Meal category generally refers to any food that can be served as meal without extensive preparation or processing. The ready meal includes products that have had recipe "skills" added to them by the manufacturer, resulting in a high degree of readiness, completion and convenience. Examples of ready meal include, but are not limited to cannedpreserved, frozen, dried, chilled ready meals; dinner mixes; frozen pizza; chilled pizza; and prepared salads.

The Pasta and Noodle category includes any pastas and/or noodles including, but not limited to canned, dried and chilled/fresh pasta; and plain, instant, chilled, frozen and snack noodles.

The Canned/Preserved Food category includes, but is not limited to canned/preserved meat and meat products, fish/seafood, vegetables, tomatoes, beans, fruit, ready meals, soup, pasta, and other canned/preserved foods.

The Frozen Processed Food category includes, but is not limited to frozen processed red meat, processed poultry, processed fish/seafood, processed vegetables, meat substitutes, processed potatoes, bakery products, desserts, ready meals, pizza, soup, noodles, and other frozen food.

The Dried Processed Food category includes, but is not limited to rice, dessert mixes, dried ready meals, dehydrated soup, instant soup, dried pasta, plain noodles, and instant noodles.

The Chill Processed Food category includes, but is not limited to chilled processed meats, processed fish/seafood products, lunch kits, fresh cut fruits, ready meals, pizza, prepared salads, soup, fresh pasta and noodles.

The Sauces, Dressings and Condiments category includes, but is not limited to tomato pastes and purees, bouillon/stock cubes, herbs and spices, monosodium glutamate (MSG), table sauces, soy based sauces, pasta sauces, wet/cooking sauces, dry sauces/powder mixes, ketchup, mayonnaise, mustard, salad dressings, vinaigrettes, dips, pickled products, and other sauces, dressings and condiments.

The Baby Food category includes, but is note limited to milk- or soybean-based formula; and prepared, dried and other baby food.

The Spreads category includes, but is not limited to jams and preserves, honey, chocolate spreads, nut based spreads, and yeast based spreads.

The Dairy Product category generally refers to edible product produced from mammal's milk. Examples of dairy product include, but are not limited to drinking milk products, cheese, yoghurt and sour milk drinks, and other dairy products.

Additional examples for comestible composition, particularly food and beverage products or formulations, are provided as follows. Exemplary comestible compositions include one or more confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorice, other sugar confectionery, gum, chewing gum, sugarized gum, sugar-free gum, functional gum, bubble gum, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, rte cereals, family breakfast cereals, flakes, muesli, other cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners, powder milk, flavored powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavored fromage frais and quark, savory fromage frais and quark, sweet and savory snacks, fruit snacks, chips/crisps, extruded snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, hot soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads. Exemplary comestible compositions also include confectioneries, bakery products, ice creams, dairy products, sweet and savory snacks, snack bars, meal replacement products, ready meals, soups, pastas, noodles, canned foods, frozen foods, dried foods, chilled foods, oils and fats, baby foods, or spreads or a mixture thereof. Exemplary comestible compositions also include breakfast cereals, sweet beverages or solid or liquid concentrate compositions for preparing beverages, ideally so as to enable the reduction in concentration of previously known saccharide sweeteners, or artificial sweeteners.

Typically at least a sweet receptor modulating amount, a sweet receptor ligand modulating amount, a sweet flavor modulating amount, a sweet flavoring agent amount, or a therapeutically effective amount of one or more of the present compounds will be added to the ingestible composition, optionally in the presence of known sweeteners, e.g., so that the sweet flavor modified ingestible composition has an increased sweet taste as compared to the ingestible composition prepared without the compounds of the present invention, as judged by human beings or animals in general, or in the case of formulations testing, as judged by a majority of a panel of at least eight human taste testers, via procedures commonly known in the field.

The concentration of sweet flavoring agent needed to modulate or improve the flavor of the ingestible composition will of course depend on many variables, including the specific type of the ingestible composition and its various other ingredients, especially the presence of other known sweet flavoring agents and the concentrations thereof, the natural genetic variability and individual preferences and health conditions of various human beings tasting the compositions, and the subjective effect of the particular compound on the taste of such chemosensory compounds.

One application of the present compounds is for modulating (inducing, potentiating, or inhibiting) the sweet taste or other taste properties of other natural or synthetic sweet tastants, and ingestable compositions made therefrom. In one embodiment, the compounds of the present invention is used or provided in its ligand enhancing concentration(s). For example, a broad but also low range of concentrations of the compounds or entities of the present invention would typically be required, i.e., from about 0.001 ppm to 100 ppm, or narrower alternative ranges from about 0.1 ppm to about 10 ppm, from about 0.01 ppm to about 30 ppm, from about 0.05 ppm to about 10 ppm, from about 0.01 ppm to about 5 ppm, or from about 0.02 ppm to about 2 ppm, or from about 0.01 ppm to about 1 ppm.

In one embodiment, the present invention provides a sweet modulating composition. The sweet modulating composition comprises a compound of the present invention in an amount effective to provide sweetening, e.g., sweet flavor modulating amount in combination with a first amount of sweetener, wherein the sweetening is more than the sweetening provided by the first amount of sweetener without the compound.

In one embodiment, the present invention provides an ingestible composition which comprises the sweet modulating composition of the present invention. In certain embodiments, the present ingestible composition is in the form of a food or beverage product, a pharmaceutical composition, a nutritional product, a dietary supplement, over-the-counter medication, or oral care product.

In one embodiment, the present invention provides a sweetener replacement composition which comprises one or more compounds of the present invention in an amount effective to provide sweetening, e.g., at a concentration higher than their ligand enhancing concentration in the absence of a sweetener. e.g., sucrose other than the present compound(s).

According to another aspect of the invention, the compounds of the present invention are provided in a flavoring concentrate formulation, e.g., suitable for subsequent processing to produce a ready-to-use (i.e., ready-to-serve) product. By "a flavoring concentrate formulation", it is meant a formulation which should be reconstituted with one or more diluting medium to become a ready-to-use composition. The term "ready-to-use composition" is used herein interchangeably with "ingestible composition", which denotes any substance that, either alone or together with another substance, can be taken by mouth whether intended for consumption or not. In one embodiment, the ready-to-use composition includes a composition that can be directly consumed by a human or animal. The flavoring concentrate formulation is typically used by mixing with or diluted by one or more diluting medium, e.g. any consumable or ingestible ingredient or product, to impart or modify one or more flavors to the diluting medium. Such a use process is often referred to as reconstitution. The reconstitution can be conducted in a household setting or an industrial setting. For example, a frozen fruit juice concentrate can be reconstituted with water or other aqueous medium by a consumer in a kitchen to obtain the ready-to-use fruit juice beverage. In another example, a soft drink syrup concentrate can be reconstituted with water or other aqueous medium by a manufacture in large industrial scales to produce the ready-to-use soft drinks. Since the flavoring concentrate formulation has the flavoring agent or flavor modifying agent in a concentration higher than the ready-to-use composition, the flavoring concentrate formulation is typically not suitable for being consumed directly without reconstitution. There are many benefits of using and producing a flavoring concentrate formulation. For example, one benefit is the reduction in weight and volume for transportation as the flavoring concentrate formulation can be reconstituted at the time of usage by the addition of suitable solvent, solid or liquid.

In one embodiment, the flavoring concentrate formulation comprises i) as flavor modifying ingredient, a compound of the present invention; ii) a carrier: and iii) optionally at least one adjuvant. The term "as flavor modifying ingredient" denotes that the compound of the present invention acts as a flavoring agent or a flavor modifying agent (such as a flavor modulator) in the formulation. The term "carrier" denotes a usually inactive accessory substance, such as solvents, binders, or other inert medium, which is used in combination with the present compound and one or more optional adjuvants to form the formulation. For example, water or starch can be a carrier for a flavoring concentrate formulation. In some embodiments, the carrier is the same as the diluting medium for reconstituting the flavoring concentrate formulation; and in other embodiments, the carrier is different from the diluting medium. The term "carrier" as used herein includes, but is not limited to, ingestibly acceptable carrier.

The term "adjuvant" denotes an additive which supplements, stabilizes, maintains, or enhances the intended function or effectiveness of the active ingredient, such as the compound of the present invention. In one embodiment, the at least one adjuvant comprises one or more flavoring agents. The flavoring agent may be of any flavor known to one skilled in the art or consumers, such as the flavor of chocolate, coffee, tea, mocha, French vanilla, peanut butter, chai, or combinations thereof. In another embodiment, the at least one adjuvant comprises one or more sweeteners. The one or more sweeteners can be any of the sweeteners described in this application. In another embodiment, the at least one adjuvant comprises one or more ingredients selected from the group consisting of a emulsifier, a stabilizer, an antimicrobial preservative, an antioxidant, vitamins, minerals, fats, starches, protein concentrates and isolates, salts, and combinations thereof. Examples of emulsifiers, stabilizers, antimicrobial preservatives, antioxidants, vitamins, minerals, fats, starches, protein concentrates and isolates, and salts are described in U.S. Pat. No. 6,468,576, the contents of which are hereby incorporated by reference in its entirety for all purposes.

In one embodiment, the present flavoring concentrate formulation can be in a form selected from the group consisting of liquid including solution and suspension, solid, foamy material, paste, gel, cream, and a combination thereof, such as a liquid containing certain amount of solid contents. In one embodiment, the flavoring concentrate formulation is in form of a liquid including aqueous-based and nonaqueous-based. The present flavoring concentrate formulation can be carbonated or non-carbonated.

The flavoring concentrate formulation may further comprise a freezing point depressant, nucleating agent, or both as the at least one adjuvant. The freezing point depressant is a ingestibly acceptable compound or agent which can depress the freezing point of a liquid or solvent to which the compound or agent is added. That is, a liquid or solution containing the freezing point depressant has a lower freezing point than the liquid or solvent without the freezing point depressant. In addition to depress the onset freezing point, the freezing point depressant may also lower the water activity of the flavoring concentrate formulation. The examples of the freezing point depressant include, but are not limited to, carbohydrates, oils, ethyl alcohol, polyol, e.g., glycerol, and combinations thereof. The nucleating agent denotes a ingestibly acceptable compound or agent which is able to facilitate nucleation. The presence of nucleating agent in the flavoring concentrate formulation can improve the mouthfeel of the frozen slushes of a frozen slush and to help maintain the physical properties and performance of the slush at freezing temperatures by increasing the number of desirable ice crystallization centers. Examples of nucleating agents include, but are not limited to, calcium silicate, calcium carbonate, titanium dioxide, and combinations thereof.

In one embodiment, the flavoring concentrate formulation is formulated to have a low water activity for extended shelf life. Water activity is the ratio of the vapor pressure of water in a formulation to the vapor pressure of pure water at the same temperature. In one embodiment, the flavoring concentrate formulation has a water activity of less than about 0.85. In another embodiment, the flavoring concentrate formulation has a water activity of less than about 0.80. In another embodiment, the flavoring concentrate formulation has a water activity of less than about 0.75.

In one embodiment, the flavoring concentrate formulation has the present compound in a concentration that is at least 2 times of the concentration of the compound in a ready-to-use composition. In one embodiment, the flavoring concentrate formulation has the present compound in a concentration that is at least 5 times of the concentration of the compound in a ready-to-use composition. In one embodiment, the flavoring concentrate formulation has the present compound in a concentration that is at least 10 times of the concentration of the compound in a ready-to-use composition. In one embodiment, the flavoring concentrate formulation has the present compound in a concentration that is at least 15 times of the concentration of the compound in a ready-to-use composition. In one embodiment, the flavoring concentrate formulation has the present compound in a concentration that is at least 20 times of the concentration of the compound in a ready-to-use composition. In one embodiment, the flavoring concentrate formulation has the present compound in a concentration that is at least 30 times of the concentration of the compound in a ready-to-use composition. In one embodiment, the flavoring concentrate formulation has the present compound in a concentration that is at least 40 times of the concentration of the compound in a ready-to-use composition. In one embodiment, the flavoring concentrate formulation has the present compound in a concentration that is at least 50 times of the concentration of the compound in a ready-to-use composition. In one embodiment, the flavoring concentrate formulation has the present compound in a concentration that is at least 60 times of the concentration of the compound in a ready-to-use composition. In one embodiment, the flavoring concentrate formulation has the present compound in a concentration that is up to 100 times of the concentration of the compound in a ready-to-use composition.

Therapeutic Utilities

In one aspect of the present invention, the present compounds can be used for therapeutic purpose. That is, the present compounds can be used in methods for modulating a chemosensory receptor and/or its ligand to achieve therapeutic effect. For example, the present method includes modulating a chemosensory receptor and/or its ligand expressed in the body other than in the taste buds.

In one embodiment, the method of the present invention, e.g., modulating a chemosensory receptor and/or its ligand includes modulating the expression, secretion, and/or functional level of TI R expressing cells associated with hormone, peptide, enzyme production. In one example, the method of the present invention includes modulating the level of glucose, e.g., inhibitors of a chemosensory receptor such as T1R2 can be used to decrease glucose level (e.g., glucose absorption) in a subject. In another example, the method of the present invention includes modulating the level of incretins, e.g., agonist of a chemosensory receptor such as T1R2 can be used to increase glucagon-like peptide 1 (GLP-1) and thus increase the production of insulin. In yet another example, the method of the present invention includes modulating the expression, secretion, and/or activity level of hormones or peptides produced by T1R expressing cells or gastrointestinal hormone producing cells, e.g., ligands for 5HT receptors (e.g., serotonin), incretins (e.g., GLP-1 and glucose-dependent insulinotropic polypeptide (GIP)), gastrin, secretin, pepsin, cholecystokinin, amylase, ghrelin, leptin, somatostatin, etc. In still another example, the method of the present invention includes modulating the pathways associated with hormones, peptides, and/or enzymes secreted by TiR expressing cells.

In another embodiment, the method of the present invention, e.g., modulating a chemosensory receptor and/or its ligand includes modulating the activity of T1R (e.g., T1R1, T1R2, or T1R3) expressing cells, e.g., liver cells (e.g., hepatocytes, endothelial cells, Kupffer cells. Stellate cells, epithelial cells of bile duct, etc.), heart cells (e.g., endothelial, cardiac, and smooth muscle cells, etc.), pancreatic cells (e.g., alpha cell, beta cell, delta cell, neurosecretory PP cell, D1 cell, etc.), cells in the nipple (e.g., ductal epithelial cells, etc.), stomach cells (e.g., mucous cells, parietal cells, chief cells, G cells, P/D1 cells), intestinal cells (e.g., enteroendocrine cells, brush cells, etc.), salivary gland cells (e.g., Seromucous cells, mucous cells, myoepithelial cells, intercalated duct cell, striated duct cell, etc.), L cells (e.g., expressing GLP-1, etc.), enterochromaffin cells (e.g., expressing serotonin), enterochromaffin-like cells, G cells (e.g., expressing gastrin). D cells (delta cells, e.g., expressing somatostatin), I cells (e.g., expressing cholescystokinin (CCK), K cells (e.g., expressing gastric inhibitory polypeptide), P/D1 cells (e.g., expressing ghrelin), chief cells (e.g., expressing pepsin), and S cells (e.g., expressing secretin). In one example, the method of the present invention includes increasing the expression level of T1R in T1R expressing cells. In another example, the method of the present invention includes increasing the secretion level of T1R expressing cells.

In yet another embodiment, the method of the present invention, e.g., modulating a chemosensory receptor and/or its ligand includes modulation, treatment, and/or prophylactic measure of a condition associated with the gastrointestinal system including without any limitation conditions associated with esophageal motility (e.g., cricopharyngeal achalasia, globus hystericus, achalasia, diffuse esophageal spasm and related motor disorders, scleroderma involving the esophagus, etc.), inflammatory disorders (e.g., gastroesophageal reflux and esophagitis, infectious esophagitis, etc.), peptic ulcer, duodenal ulcer, gastric ulcer, gastrinoma, stress ulcers and erosions, drug-associated ulcers and erosions, gastritis, esophageal cancer, tumors of the stomach, disorders of absorption (e.g., absorption of specific nutrients such as carbohydrate, protein, amino acid, fat, cholesterol and fat-soluble vitamins, water and sodium, calcium, iron, water-soluble vitamins, etc.), disorders of malabsorption, defects in mucosal function (e.g. inflammatory or infiltrative disorders, biochemical or genetic abnormalities, endocrine and metabolic disorders, protein-losing enteropathy, etc.), autoimmune diseases of the digestive tract (e.g., celiac disease. Crohn's disease, ulcerative colitis, etc.), irritable bowel syndrome, inflammatory bowel disease, complications of inflammatory bowel disease, extraintestinal manifestations of inflammatory bowel disease, disorders of intestinal motility, vascular disorders of the intestine, anorectal disorders (e.g., hemorrhoids, anal inflammation, etc.), colorectal cancer, tumors of the small intestine, cancers of the anus, derangements of hepatic metabolism, hyperbilirubinemia, hepatitis, alcoholic liver disease and cirrhosis, biliary cirrhosis, neoplasms of the liver, infiltrative and metabolic diseases affecting the liver (e.g., fatty liver, reye's syndrome, diabetic glycogenosis, glycogen storage disease, Wilson's disease, hemochromatosis), diseases of the gallbladder and bile ducts, disorders of the pancreas (e.g., pancreatitis, pancreatic exocrine insufficiency, pancreatic cancer, etc.), endocrine tumors of the gastrointestinal tract and pancreas, etc.

In still another embodiment, the method of the present invention, e.g., modulating a chemosensory receptor and/or its ligand includes modulation, treatment, and/or prophylactic measure of a condition associated with metabolic disorders, e.g., appetite, body weight, food or liquid intake or a subject's reaction to food or liquid intake, or state of satiety or a subject's perception of a state of satiety, nutrition intake and regulation, (e.g., protein-energy malnutrition, physiologic impariements associated with protein-energy malnutrition, etc.), obesity, secondary obesity (e.g., hypothyroidism, Cushing's disease, insulinoma, hypothalamic disorders, etc.), eating disorders (e.g., anorexia nervosa, bulimia, etc.), vitamin deficiency and excess, insulin metabolism, diabetes (type I and type II) and complications thereof (e.g., circulatory abnormalities, retinopathy, diabetic nephropathy, diabetic neuropathy, diabetic foot ulcers, etc.), glucose metabolism, fat metabolism, hypoglycemia, hyperglycermia, hyperlipoproteinemias, etc.

In still yet another embodiment, the method of the present invention, e.g. modulating a chemosensory receptor and/or its ligand includes modulation, treatment, and/or prophylactic measure of a condition associated with functional gastrointestinal disorders, e.g., in the absence of any particular pathological condition such as peptic ulcer and cancer, a subject has abdominal dyspepsia, e.g., feeling of abdominal distention, nausea, vomiting, abdominal pain, anorexia, reflux of gastric acid, or abnormal bowel movement (constipation, diarrhea and the like), optionally based on the retention of contents in gastrointestinal tract, especially in stomach. In one example, functional gastrointestinal disorders include a condition without any organic disease of the gastrointestinal tract, but with one or more reproducible gastrointestinal symptoms that affect the quality of life of a subject, e.g., human.

Exemplary functional gastrointestinal disorders include, without any limitation, functional dyspepsia, gastroesophageal reflux condition, diabetic gastroparesis, reflux esophagitis, postoperative gastrointestinal dysfunction and the like, nausea, vomiting, sickly feeling, heartburn, feeling of abdominal distention, heavy stomach, belching, chest writhing, chest pain, gastric discomfort, anorexia, dysphagia, reflux of gastric acid, abdominal pain, constipation, diarrhea, breathlessness, feeling of smothering, low incentive or energy level, pharyngeal obstruction, feeling of foreign substance, easy fatigability, stiff neck, myotonia, mouth dryness (dry mouth, thirst, etc.) tachypnea, burning sensation in the gastricintestinal tract, cold sensation of extremities, difficulty in concentration, impatience, sleep disorder, headache, general malaise, palpitation, night sweat, anxiety, dizziness, vertigo, hot flash, excess sweating, depression, etc.

In still yet another embodiment, the method of the present invention, e.g., modulating a chemosensory receptor and/or its ligand includes increasing or promoting digestion, absorption, blood nutrient level, and/or motility of gastrointestinal tract in a subject, e.g., promotion of gastric emptying (e.g., clearance of stomach contents), reduction of abdominal distention in the early postprandial period, improvement of anorexia, etc. In general, such promotion can be achieved either directly or via increasing the secretion of a regulatory entity, e.g., hormones, etc.

In still yet another embodiment, the method of the present invention, e.g., modulating a chemosensory receptor and/or its ligand includes increasing one or more gastrointestinal functions of a subject, e.g., to improve the quality of life or healthy state of a subject.

In one embodiment, the present invention provides a pharmaceutical composition containing a therapeutically effective amount of one or more compounds of the present invention, or a salt, solvate, and/or prodrug thereof, optionally with a suitable amount of a pharmaceutically acceptable vehicle. In another embodiment, the pharmaceutical composition comprises a therapeutically effective amount of one or more compounds of the present invention, or a salt, solvate, and/or prodrug thereof; and a suitable amount of a pharmaceutically acceptable vehicle so as to provide the form for proper administration to a patient.

In one embodiment, when administered to a patient, the compounds of the present invention and the optional pharmaceutically acceptable vehicles are sterile. In one embodiment, water is a preferred vehicle when a compound of the present invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, lubricating and coloring agents may be used.

Pharmaceutical compositions comprising a compound of the present invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the present invention into preparations which can be used pharmaceutically. Proper formulation is dependent upon the route of administration chosen.

The present pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In some embodiments, the pharmaceutically acceptable vehicle is a capsule (see e.g., Grosswald et al., U.S. Pat. No. 5,698,155). Other examples of suitable pharmaceutical vehicles have been described in the art (see Remington: The Science and Practice of Pharmacy. Philadelphia College of Pharmacy and Science, $20^{th}$ Edition, 2000).

For topical administration a compound of the present invention may be formulated as solutions, gels, ointments, creams, suspensions, etc. as is well-known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration. Systemic formulations may be made in combination with a further active agent that improves mucociliary clearance of airway mucus or reduces mucous viscosity. These active agents include, but are not limited to, sodium channel blockers, antibiotics, N-acetyl cysteine, homocysteine and phospholipids.

In some embodiments, the compounds of the present invention are formulated in accordance with routine procedures as a pharmaceutical composition adapted for intravenous administration to human beings. Typically, compounds of the present invention for intravenous administration are solutions in sterile isotonic aqueous buffer. For injection, a compound of the present invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. When necessary, the pharmaceutical compositions may also include a solubilizing agent.

Pharmaceutical compositions for intravenous administration may optionally include a local anesthetic such as lignocaine to ease pain at the site of the injection. Generally, the ingredients are supplied either separately or mixed together in unit dosage form, for example, as a lyophilized powder or water free concentrate in a hermetically sealed container such as an ampoule or sachette indicating the quantity of active agent. When the compound of the present invention is administered by infusion, it can be dispensed, for example, with an infusion bottle containing sterile pharmaceutical grade water or saline. When the compound of the present invention is administered by injection, an ampoule of sterile water for injection or saline can be provided so that the ingredients may be mixed prior to administration.

For transmucosal administration, penetrants appropriate to the barrier to be permeated are used in the formulation. Such penetrants are generally known in the art.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optionally agents, for example, sweetening agents such as fructose, aspartame or saccharin; flavoring agents such as peppermint, oil of wintergreen, or cherry coloring agents and preserving agents, to provide a pharmaceutically palatable preparation.

Moreover, where in tablet or pill form, the pharmaceutical compositions may be coated to delay disintegration and absorption in the gastrointestinal tract, thereby providing a sustained action over an extended period of time. Selectively permeable membranes surrounding an osmotically active driving compound are also suitable for orally administered compounds of the present invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5.0 mM to about 50.0 mM) etc. Additionally, flavoring agents, preservatives, coloring agents, bile salts, acylcarnitines and the like may be added.

For buccal administration, the pharmaceutical compositions may take the form of tablets, lozenges, etc. formulated in conventional manner.

Liquid drug formulations suitable for use with nebulizers and liquid spray devices and EHD aerosol devices will typically include a compound of the present invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611).

A compound of the present invention may also be formulated in rectal or vaginal pharmaceutical compositions such as suppositories or retention enemas, e.g., containing conventional suppository bases such as cocoa butter or other glycerides.

In addition to the formulations described previously, a compound of the present invention may also be formulated as a depot preparation. Such long acting formulations may be administered by implantation (for example, subcutaneously or intramuscularly) or by intramuscular injection. Thus, for example, a compound of the present invention may be formulated with suitable polymeric or hydrophobic materials (for example, as an emulsion in an acceptable oil) or ion exchange resins, or as sparingly soluble derivatives, for example, as a sparingly soluble salt.

A compound of the present invention, and/or pharmaceutical composition thereof, will generally be used in an amount effective to achieve the intended purpose. For use to treat or prevent diseases or disorders the compounds of the present invention and/or pharmaceutical compositions thereof, are administered or applied in a therapeutically effective amount.

The amount of a compound of the present invention that will be effective in the treatment of a particular disorder or condition disclosed herein will depend on the nature of the disorder or condition and can be determined by standard clinical techniques known in the art. In addition, in vitro or in vivo assays may optionally be employed to help identify optimal dosage ranges. The amount of a compound of the present invention administered will, of course, be dependent on, among other factors, the subject being treated, the weight of the subject, the severity of the affliction, the manner of administration and the judgment of the prescribing physician.

For example, the dosage may be delivered in a pharmaceutical composition by a single administration, by multiple applications or controlled release. In some embodiment, the compounds of the present invention are delivered by oral sustained release administration. Dosing may be repeated intermittently, may be provided alone or in combination with other drugs and may continue as long as required for effective treatment of the disease state or disorder.

Suitable dosage ranges for oral administration depend on potency, but are generally between about 0.001 mg to about 200 mg of a compound of the present invention per kilogram body weight. Dosage ranges may be readily determined by methods known to the artisan of ordinary skill the art.

Suitable dosage ranges for intravenous (i.v.) administration are about 0.01 mg to about 100 mg per kilogram body weight. Suitable dosage ranges for intranasal administration are generally about 0.01 mg/kg body weight to about 1 mg/kg body weight. Suppositories generally contain about 0.01 milligram to about 50 milligrams of a compound of the present invention per kilogram body weight and comprise active ingredient in the range of about 0.5% to about 10% by weight. Recommended dosages for intradermal, intramuscular, intraperitoneal, subcutaneous, epidural, sublingual or intracerebral administration are in the range of about 0.001 mg to about 200 mg per kilogram of body weight. Effective doses may be extrapolated from dose-response curves derived from in vitro or animal model test systems. Such animal models and systems are well-known in the art.

In one embodiment, a therapeutically effective dose of a compound of the present invention described herein will provide therapeutic benefit without causing substantial toxicity. Toxicity of compounds of the present invention may be determined using standard pharmaceutical procedures and may be readily ascertained by the skilled artisan. The dose ratio between toxic and therapeutic effect is the therapeutic index. A compound of the present invention will preferably exhibit particularly high therapeutic indices in treating disease and disorders. The dosage of a compound of the present invention described herein will preferably be within a range of circulating concentrations that include an effective dose with little or no toxicity.

In certain embodiments of the present invention, the compounds of the present invention and/or pharmaceutical compositions thereof can be used in combination therapy with at least one other agent. The compound of the present invention and/or pharmaceutical composition thereof and the other agent can act additively or, more preferably, synergistically. In some embodiments, a compound of the present invention and/or pharmaceutical composition thereof is administered concurrently with the administration of another agent, which may be part of the same pharmaceutical composition as the compound of the present invention or a different pharmaceutical composition. In other embodiments, a pharmaceutical composition of the present invention is administered prior or subsequent to administration of another agent.

Preparations

The starting materials used in preparing the compounds of the invention, i.e. the various structural subclasses and species of the compounds of the synthetic precursors of the present compounds of Formula (I), are often known compounds, or can be synthesized by known methods described in the literature, or are commercially available from various sources well known to those of ordinary skill in the art, such as for example. Sigma-Aldrich Corporation of St. Louis, Mo. USA and their subsidiaries Fluka and Riedel-de Haen, at their various other worldwide offices, and other well known chemical suppliers such as Fisher Scientific. TCI America of Philadelphia, Pa., ChemDiv of San Diego, Calif., Chembridge of San Diego, Calif. Asinex of Moscow, Russia, SPECS/BIOSPECS of the Netherlands, Maybridge of Cornwall, England, Acros, TimTec of Russia, Comgenex of South San Francisco, Calif., and ASDI Biosciences of Newark, Del.

It is recognized that the skilled artisan in the art of organic chemistry can readily carry out the synthesis of many starting materials and subsequent manipulations without further direction, that is, it is well within the scope and practice of the skilled artisan to carry out many desired manipulations. These include reduction of carbonyl compounds to their corresponding alcohols, oxidations, acylations, aromatic substitutions, both electrophilic and nucleophilic, etherifications, esterification, saponification, nitrations, hydrogenations, reductive animation and the like. These manipulations are discussed in standard texts such as March's Advanced Organic Chemistry (3d Edition, 1985, Wiley-Interscience, New York), Feiser and Feiser's Reagents for Organic Synthesis, and in the various volumes and editions o'iMethoden der Organischen Chemie (Houben-Weyl), and the like. Many general methods for preparation of starting materials comprising variously substituted heterocyclic, hetereoaryl, and aryl rings (the precursors of Ar, hAr[1], and/or hAr[2]) can be found in Methoden der Organischen Chemie (Houben-Weyl), whose various volumes and editions are available from Georg Thieme Verlag, Stuttgart. The entire disclosures of the treatises recited above are hereby incorporated by reference in their entireties for their teachings regarding methods for synthesizing organic compounds and their precursors.

The skilled artisan will also readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts, Protecting Groups in Organic Synthesis, 3[r] Ed., John Wiley & Sons (1999).

Some exemplary synthetic methods which can be used for preparing the present compounds or the intermediates thereof can be found in WO 2010/014666, entitled "Processes and Intermediates for Making Sweet Taste Enhancers" and published on Feb. 4, 2010.

EXAMPLES

Having now generally described the invention, the same will be more readily understood by reference to the following examples, which are provided by way of illustration and are not intended as limiting. It is understood that various modifications and changes can be made to the herein disclosed exemplary embodiments without departing from the spirit and scope of the invention.

Example 1

(S)-1-(3-(((4-amino-2,2-dioxido-1H-benzo[c][1,2,6]thiadiazin-5-yl)oxy)methyl)piperidin-1-yl)butan-1-one

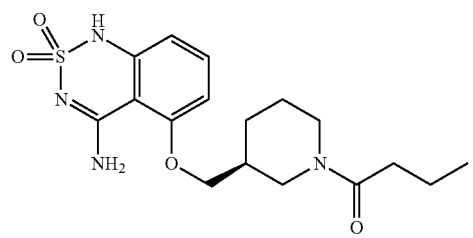

To a stirred solution of (S)-2-sulfamoylamino-6-((1-butyrylpiperidin-3-yl)methoxy)benzonitrile (Example 1a, 9.5 g. 24.97 mmol) in EtOH (65 mL) was added at room temperature aq.NaOH (2.0 N, 37 mL. 74.91 mmol). The reaction mixture was refluxed for 4 hrs then cooled to 0° C. and neutralized carefully with 2N HCl. The precipitate was collected by filtration, re-crystallized from EtOH/H$_2$O, and dried under vacuum to give the title compound as a white solid (6 g) in 63% yield. $^1$H NMR (400 MHz, DMSO-d$_6$,) δ 0.82-0.86 (m, 3H), 1.30-1.51 (m, 4H), 1.65 (m, 1H), 1.82 (m, 1H), 2.01-2.21 (m, 2H), 2.22-2.27 (m, 2H), 2.71-3.12 (m, 2H), 3.63-3.86 (m, 1H), 4.03 (m, 2H), 4.12 (m, 1H), 6.60 (m, 1H), 6.75 (t, J=8.0 Hz, 1H), 7.43-7.45 (m, 1H), 7.77 (d, J=20 Hz, 1H), 8.36 (m, 1H), 10.91 (s, 1H). MS 381 (MH$^+$). Elem. Anal. Calcd.: C, 53.67%; H, 6.36%; N, 14.73%. Found: C, 53.64%; H, 6.63%; N, 14.73%

Example 1a (S)-2-sulfamoylamino-6-((1-butyrylpiperidin-3-yl)methoxy)benzonitrile

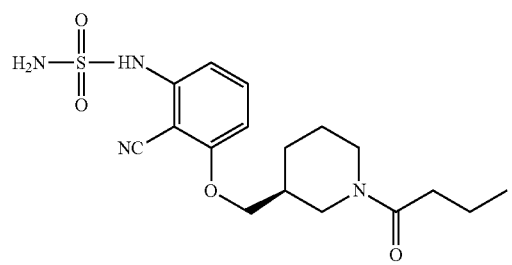 [SMILES: CCCC(=O)N1CCC[C@H](COc2cccc(NS(N)(=O)=O)c2C#N)C1]

To a solution of (S)-2-amino-6-((1-butyrylpiperidin-3-yl) methoxy)benzonitrile (Example 1b, 9.2 g, 30.53 mmol) in DMA (60 mL) was added sulfamoyl chloride (Example 1f, 10.54 g, 91.58 mmol) at room temperature under nitrogen. The reaction mixture was stirred at room temperature under nitrogen overnight then concentrated under reduced pressure, diluted with EtOAc, successively washed with NaHCO$_3$, water and brine, dried over Na$_2$SO$_4$, filtered and the solvent was removed under reduced pressure to give the title compound as colorless gel (9.5 g) in 82% yield. MS 381 (MH$^+$).

Example 1b (S)-2-amino-6-((1-butyrylpiperidin-3-yl)methoxy) benzonitrile

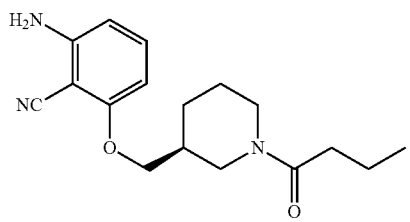

To a solution of (S)-2-((1-butyrylpiperidin-3-yl)methoxy)- 6-nitrobenzonitrile (Example 1c, 9.92 g, 32.92 mmol) in acetic acid (60 mL) and THF (60 mL), was added iron powder (5.5 g. 98.76 mmol) at room temperature. The reaction mixture was heated to 70° C. and stirred for 1 hour then cooled to room temperature, diluted with EtOAc, filtered through Celite. The filtrate was concentrated under reduced pressure and then re-dissolved in EtOAc, washed with NaHCO$_3$, water and brine, dried over MgSO$_4$, filtered and evaporated. The residue was crystallized from DCM/EtOAc, to give the title compound as off white solid (9.92 g, 93% for 2 steps). MS 302 (MH$^+$).

Example 1c (S)-2-((1-butyrylpiperidin-3-yl)methoxy)-6-nitrobenzonitrile

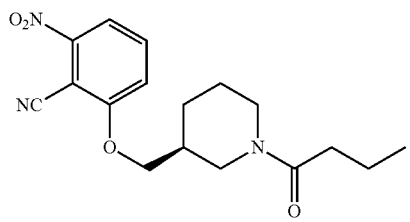 [SMILES: CCCC(=O)N1CCC[C@H](COc2cccc([N+](=O)[O-])c2C#N)C1]

To a suspension of (S)-2-nitro-6-(piperidin-3-ylmethoxy) benzonitrile hydrochloride (Example 1d, 9.8 g, 32.92 mmol) in CH$_2$Cl$_2$ (550 mL) and DMF (50 mL) was added triethylamine (9.2 mL, 65.84 mmol). After being stirred at room temperature for 5 min., a solution of butyric acid (3.33 mL, 36.21 mmol), EDCI (6.94 g, 36.21 mmol) and HOBt (4.89 g, 36.21 mmol) in DCM (50 mL) was added, and the reaction mixture was then stirred at room temperature overnight. The resulting mixture was diluted with CH$_2$Cl$_2$, washed with 0.5 N HCl, water, NaHCO$_3$ and brine, dried over MgSO$_4$, filtered and evaporated to give the crude product as a light brown gel, used as this in the next step. MS 332 (MH$^+$).

Example 1d (S)-2-nitro-6-(piperidin-3-ylmethoxy)benzonitrile hydrochloride

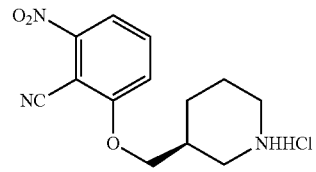

To a solution of (S)-tert-butyl 3-((2-cyano-3-nitrophenoxy)methyl)piperidine-1-carboxylate (Example 1e, 41.74 g) in dioxane (115 mL) cooled to 0° C. in an ice bath was added a solution of 4N HCl in dioxane (70 mL, 280 mmol). The reaction mixture was stirred at room temperature overnight then evaporated under reduced pressure. Et$_2$O (700 mL) was added to the residue and the suspension was refluxed for one hour. The solid was collected by filtration and dried under high vacuum to afford (S)-2-nitro-6-(piperidin-3-ylmethoxy) benzonitrile hydrochloride as a pale peach solid (24.64 g, 89% yield over two steps). $^1$H NMR (400 MHz, DMSO-d$_6$) δ 1.47-1.30 (m, 1H). 1.77-1.62 (m, 1H), 1.84 (t, J=12.4 Hz, 2H), 2.32 (d, J=9.4 Hz, 1H), 2.87-2.68 (m, 2H), 3.27-3.16 (m, 2H), 4.15 (dd, J=9.7, 7.2 Hz, 1H), 4.25 (dd, J=9.7, 5.4 Hz, 1H), 7.72 (dd, J=7.6, 1.9 Hz, 1H), 7.96-7.86 (m, 2H), 9.20-8.89 (m, 2H). MS 262 (MH$^+$).

Example 1e (S)-tert-butyl 3-((2-cyano-3-nitrophenoxy)methyl) piperidine-1-carboxylate

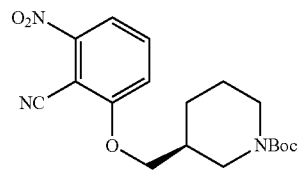 [SMILES: CC(C)(C)OC(=O)N1CCC[C@H](COc2cccc([N+](=O)[O-])c2C#N)C1]

To a 2 L 3-neck round bottom flask outfitted with an addition funnel and thermometer were added anhydrous THF (700 mL) and NaH (60 wt %, 3.90 g, 97.5 mmol). The suspension was cooled in an isopropanol/dry ice bath until the internal temperature was about −20° C. (S)-tert-butyl 3-(hydroxymethyl)piperidine-1-carboxylate (20.0 g, 92.9 mmol) dissolved in anhydrous THF (300 mL) was added dropwise via the addition funnel maintaining the internal temperature between −20° C. to −15° C. Once the addition was complete, the reaction was stirred for 45 minutes at a temperature between 0° C. to 10° C. The reaction was then cooled to −70° C. and a solution of 2,6-dinitrobenzonitrile (19.9 g, 103 mmol) in anhydrous DMF (200 mL) was added dropwise via the addition funnel. The reaction was allowed to warm up gradually to room temperature overnight and THF was removed under reduced pressure. The remaining solution was cooled in an ice bath and treated with a cooled saturated NH$_4$Cl solution (200 mL). The resulting mixture was diluted with EtOAc and successively washed with water and brine. The organic layer was dried over Na₂SO₄, filtered and evaporated under reduced pressure to afford crude (S)-tert-butyl 3-((2-cyano-3-nitrophenoxy)methyl)piperidine-1-carboxylate (41.74 g) as an orange solid. MS 262 (MH⁺-Boc). This material was used without purification in the next step.

Example 1f

Sulfamoyl Chloride

To a solution of chlorosulfonyl isocyanate (65.2 g, 461 mmol) in dichloromethane (100 mL) at 0° C., was added dropwise a solution of formic acid (17.4 mL, 461 mmol) in dichloromethane (100 mL). The mixture was stirred at 0° C. for 1 h, warmed to room temperature and stirred for 18 h. The mixture was then cooled to −78° C., stirred for 2 hours and the bulk of the solvent was decanted off. The resulting solid was dried under vacuum to provide sulfamoyl chloride (48 g, 90%) as a white solid.

Example 2

(S)-1-(3-(((4-amino-2,2-dioxido-1H-benzo[c][1,2,6]thiadiazin-5-yl)oxy)methyl)piperidin-1-yl)-2-cyclopropylethan one

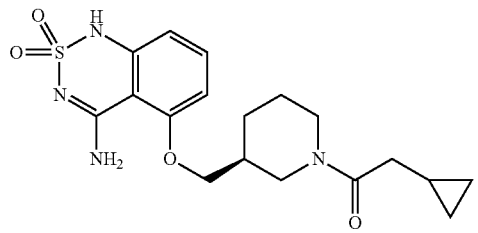 [SMILES: NC1=NS(=O)(=O)Nc2cccc(OC[C@H]3CCCN(C(=O)CC4CC4)C3)c21]

To a solution of (S)-4-amino-5(piperidine-3-ylmethoxy)-1H-benzo[c][1,2,6]thiadiazin 2,2-dioxide hydrochloride (Example 2a, 694 mg, 2.0 mmol) in H₂O/ACN (5 mL, 1:1) was added triethylamine (228 uL, 2.0 mmol). After stirring at room temperature for 5 min a solution of 2-cyclopropylacetic acid (200 mg, 2.0 mmol), HOBt (272 mg. 2.0 mmol), and EDCI-HCl (382 mg. 2.0 mmol) in H₂O/ACN (5 mL, 1:1) was added to the mixture. An additional equivalent of triethylamine (228 uL, 2.0 mmol) was added and the reaction mixture was stirred at room temperature overnight. The product crashed out of solution and is collected by vacuum filtration. The compound was purified via preparative RP HPLC (10 to 90% EtOH in water) then diluted with 10 mL water and 200 mg of NaHCO₃ was added. The solution was heated at 90° C. for 20 minutes until all the compound was dissolved then cooled to 0° C. and neutralized with 1N HCl solution. The product precipitated out and was collected by filtration and dried to provide the title compound (410 mg, 52.3%). ¹H NMR (DMSO-d₆, 400 MHz, 80° C.): 0.12 (br s, 2H), 0.44 (m, 2H), 0.96 (br s, 1H), 1.42 (m, 2H), 1.70 (m, 1H), 1.88 (m, 1H), 1.98 (br s, 1H), 2.09 (m, 1H), 2.26 (br s, 2H), 2.91 (m, 2H), 3.67 (br s, 0.5H), 3.85 (br s, 0.5H), 4.09 (m, 3H), 6.65 (d, J=8.4 Hz, 1H), 6.71 (d, J=8.4 Hz, 1H), 7.46 (t, J=8.4 Hz, 1H), 7.75 (br s, 1H), 8.16 (br s, 1H), 10.79 (s, 1H). M+H=393.

Example 2a (S)-4-amino-5-(piperidin-3-ylmethoxy)-1H-benzo[c][1,2,6]thiadiazine 2,2-dioxide hydrochloride

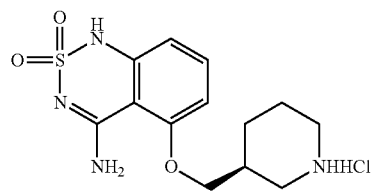

A solution of (S)-tert-butyl-3-(((4-amino-2,2-dioxido-1H-benzo[c][1,2,6]thiadiazin-5-yl)oxy)methyl)piperidine-1-carboxylate (Example 2b, 7.0 g, 17.1 mmol) in conc. HCl:MeOH (1:1, 170 mL) was stirred at room temperature for 4 hours. The precipitate was collected by vacuum filtration, and dried to provide the desired product (3.75 g, 63.2%) as a white solid. ¹H NMR (DMSO-d₆, 400 MHz): δ 1.29 (m, 1H), 1.65 (m, 1H), 1.82 (m, 2H), 2.37 (m, 1H), 2.75 (m, 2H), 3.20 (d, J=8.0 Hz, 1H), 3.27 (d, J=11.2 Hz, 1H), 4.10 (d, J=6.0 Hz, 3H), 6.27 (d, J=8.4 Hz, 1H), 6.75 (d, J=8.4 Hz, 1H), 7.45 (t, J=8.4 Hz, 1H), 7.68 (s, 1H), 8.35 (br s, 1H), 8.74 (m, 1H), 9.05 (m, 1H), 10.98 (s, 1H). MS 311 (MH⁺).

Example 2b (S)-tert-butyl 3-(((4-amino-2,2-dioxido-1H-benzo[c][1,2,6]thiadiazin-5-yl)oxy)methyl)piperidine-1-carboxylate

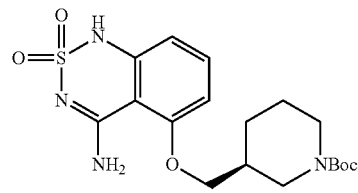 [SMILES: CC(C)(C)OC(=O)N1CCC[C@H](COc2cccc3c2C(N)=NS(=O)(=O)N3)C1]

To a solution of (S)-tert-butyl 3-((3-amino-2-cyanophenoxy)methyl)piperidine-1-carboxylate (Example 2c, 11.0 g, 33.2 mmol) in DMA (100 mL) was added pyridine (13.4 mL, 166 mmol) and sulfamoyl chloride (7.64 g, 66.4 mmol) in small portions. The mixture was stirred at room temperature under nitrogen for 1 hour until the reaction was complete according to LCMS. Saturated NaHCO₃ was added until the mixture was neutral and the solution was extracted with EtOAc (3×). The combined organics were dried over Na₂SO₄ and concentrated. The residue was diluted with EtOH (100 mL) and NaOH (66.4 mL, 132.8 mmol, 2M solution) was added and the solution was heated to 80° C. for 3 hours. The reaction mixture was then allowed to cool to room temperature. The solution was further cool to 0° C. and neutralized with 2N HCl. Water was added and the desired product crashed out. The product was then filtered off and dried to yield the title compound (7.0 g, 51.4%). (M+H)-Boc=311.

Example 2c (S)-tert-butyl 3-((3-amino-2-cyanophenoxy)methyl)piperidine-1-carboxylate

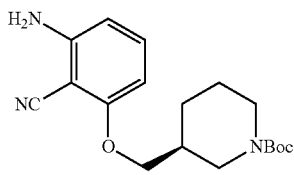

To a solution of (S)-tert-butyl 3-((2-cyano-3-nitrophenoxy)methyl)piperidine-1-carboxylate (Example 1e, 13 g, 36 mmol) in EtOAc (200 mL) was added Pd/C (3.82 g. 3.6 mmol 10% solution) and the mixture was stirred at room temperature under $H_2$ for 6 hours until the reaction was complete. The mixture was filtered and concentrated. The residue was purified by chromatography on silica gel (EtOAc/hexanes) to yield the title compound (11 g, 92.3%). (M+H)−Boc=232.

Example 3

(S)-(3-(((4-amino-2,2-dioxido-1H-benzo[c][1,2,6]thiadiazin-5-yl)oxy)methyl)piperidin-1-yl)(pyridin-4-yl)methanone

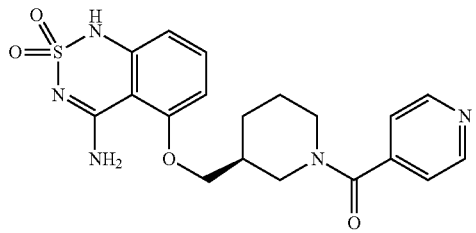 [SMILES: NC1=NS(=O)(=O)Nc2cccc(OC[C@H]3CCCN(C(=O)c4ccncc4)C3)c21]

Prepared as in Example 2 from (S)-5-(piperidin-3-ylmethoxy)-1H-benzo[c][1,2,6]thiadiazin-4-amine-2,2-dioxide hydrochloride (Example 2a) and isonicotinic acid (55% yield). M.p.: >250° C. $^1$H NMR (400 MHz, DMSO-$d_6$) δ 1.41-1.89 (m, 4H), 2.22 (m, 1H), 2.92-3.09 (m, 2H), 3.36-3.55 (m, 1H), 3.91-3.99 (m, 1H), 4.12-4.31 (m, 2H), 6.57-6.80 (m, 2H), 7.28-7.46 (m, 3H), 7.51, 7.81 (s, 1H), 8.16, 8.40 (s, 1H), 8.61-8.65 (m, 2H), 10.95 (s, 1H). MS 416 (MH$^+$).

Example 4

(S)-1-(3-(((4-amino-2,2-dioxido-1H-benzo[c][1,2,6]thiadiazin-5-yl)oxy)methyl)piperidin-1-yl)pentan-1-one

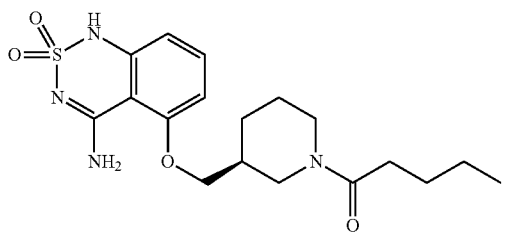

Prepared as in Example 2 from (S)-5-(piperidin-3-ylmethoxy)-1H-benzo[c][1,2,6]thiadiazin-4-amine-2,2-dioxide hydrochloride (Example 2a) and pentanoic acid (74.6% yield). $^1$H NMR (DMSO-$d_6$, 400 MHz, 80° C.): 0.85 (t, 3H, J=7.0 Hz), 1.28 (sext, 2H, J=7.0 Hz), 1.40 (m, 2H), 1.47 (pent, 2H, J=7.3 Hz), 1.68 (m, 1H), 1.87 (m, 1H), 2.06 (m, 1H), 2.27 (t, 2H, J=7.3 Hz), 2.93 (m, 2H), 3.93 (m, 1H), 4.08 (m, 3H), 6.64 (d, 1H, J=8.0 Hz), 6.74 (d, 1H, J=8.3 Hz), 7.43 (t, 1H, J=8.3 Hz), 7.78 (br s, 1H), 7.99 (br s, 1H), 10.69 (s, 1H). M+H=395.

Example 5

(S)-1-(3-(((4-amino-2,2-dioxido-1H-benzo[c][1,2,6]thiadiazin-5-yl)oxy)methyl)piperidin-1-yl)-3-methylbutan-1-one

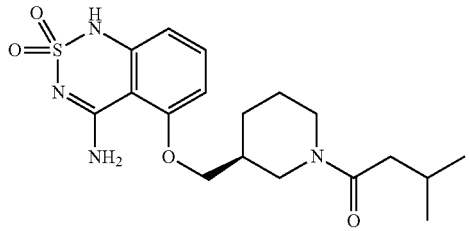

To a stirred solution of (S)-2-sulfamoylamino-6-((1-(3-methylbutanoyl)piperidin-3-yl)methoxy)benzonitrile (Example 5a, 19.5 g. 49.4 mmol) in EtOH (130 mL) was added 2N NaOH solution (84 mL) at room temperature. The reaction mixture was then heated at 65° C. until LC/MS confirmed that the starting material was consumed approximately 18 hours. The mixture was concentrated to remove ethanol, diluted with water (500 mL) and washed with ethyl acetate (50 mL×2). Ethanol (100 mL) was added to the aqueous phase and the mixture was acidified with 1M aq. HCl solution until pH=3. The precipitate that formed was collected by vacuum filtration to give a white solid that was further suspended in Ethanol (300 mL) and the solution was heated to reflux for 1 hr then cooled to 0° C. The precipitate was collected and dried under vacuum to give the title compound as an off-white solid (17.7 g, 82% yield). This material was combined with several other batches synthesized following the same procedure. A suspension of the combined batches (73.6 g, 186.57 mmol) in water (1500 mL) was treated with a solution of NaHCO$_3$ (39.18 g, 466.43 mmol, 2.5 equivalents) in water (500 mL) and heated to 98° C. for 12 hrs until complete dissolution. The hot solution was then filtered to remove undissolved fine particles and the filtrate was cooled to room temperature and treated dropwise with 0.3M HCl until neutral pH, followed by 2M HCl until pH 3 and the solution was further stirred for 30 minutes. The precipitate that formed was collected by vacuum filtration, washed with water, and dried under vacuum to afford the title compound as an off-white powder (72.44 g). $^1$H NMR (400 MHz, DMSO-$d_6$, 80° C.) δ 0.89 (d, 6H, J=4.0 Hz), 1.37-1.47 (m, 2H), 1.67-1.72 (m, 1H), 1.86-1.91 (m, 1H), 1.94-2.19 (m, 4H), 2.96 (br. s, 2H), 3.55-4.14 (m, 4H), 6.66 (d, 1H, J=4.0 Hz), 6.75 (d, 1H, J=8.0 Hz), 7.45 (t, 1H, J=8.0 Hz), 7.78 (br. s, 1H) 8.00 (br. s, 1H), 10.69 (s, 1H). MS 395 (MH⁺). Mp 237-238.

Example 5a (S)-2-sulfamoylamino-6-((1-(3-methylbutanoyl)piperidin-3-yl)methoxy)benzonitrile

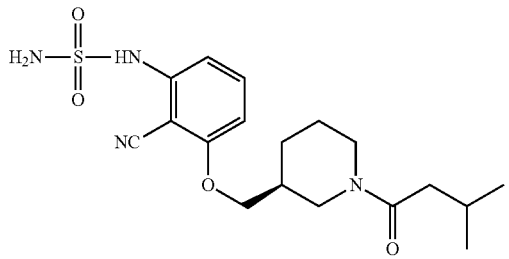 [SMILES: CC(C)CC(=O)N1CCC[C@H](COc2cccc(NS(N)(=O)=O)c2C#N)C1]

To a stirred solution of (S)-2-amino-6-((1-(3-methylbutanoyl)piperidin-3-yl)methoxy)benzonitrile (example 5b, 54.55 g, 172.95 mmol) in DMA (110 mL) cooled to 0° C. in an ice bath was added sulfamoyl chloride (55 g, 476 mmol) in two portions (20 g and 35 g). The reaction mixture was stirred for 30 minutes at 0° C. under N₂, then at room temperature for 4 hours. The reaction mixture was poured slowly into rapidly stirred cold water (2 L) to provide a milky solution. An additional 800 mL of water was added in several portions to precipitate the desired product (at this point the milky solution has become clear). The precipitate was collected by decantation of the water and was suspended in ethyl acetate (500 mL) then rapidly stirred until it became a fine white solid. The solid material was collected by vacuum filtration and dried under vacuum to give (S)-2-sulfamoylamino-6-((1-(3-methylbutanoyl)piperidin-3-yl)methoxy)benzonitrile as a white solid (59.25 g, 150.2 mmol) in 87% yield. MS 395 (MH⁺)

Example 5b (S)-2-amino-6-((1-(3-methylbutanoyl)piperidin-3-yl)methoxy)benzonitrile

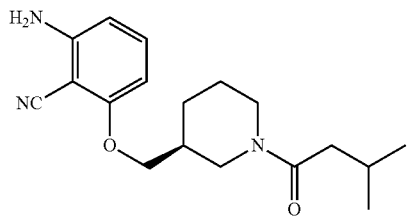

To a solution of (S)-2-((1-(3-methylbutanoyl)piperidin-3-yl)methoxy)-6-nitrobenzonitrile (Example 5c, 43.26 g, ~18.0 mmol) in glacial acetic acid (35 mL) cooled to 0° C. in an ice bath was added iron powder (2.02 g, 36.1 mmol). The solution was stirred under a N₂ balloon at 0° C. for 10 minutes then at room temperature overnight and filtered through a bed of Celite, rinsing well with EtOAc. The EtOAc solution was then washed successively with 2N Na₂CO₃, water, and brine, dried over Na₂SO₄, filtered and concentrated to give the crude product as an orange oil. The residue was purified by silica gel chromatography using a 0-60% EtOAc/Hexanes gradient followed by crystallization from EOAc/Hexane to afford the title compound a a pale yellow solid (27.01 g, 85.63 mmol, 71% over two steps). ¹H NMR (400 MHz, DMSO-d₆) 20° C.) δ 0.79-0.92 (3×d, J=6.4 Hz, 6H), 1.19-1.46 (m, 2H), 1.51-2.01 (m, 4H), 2.03-2.25 (m, 2H), 2.57 (dd, J=10.4, 12.8 Hz, 0.3H), 2.75-2.88 (m, 0.6H), 2.92-3.10 (m, 1H), 3.65-4.08 (m, 3.6H), 4.27-4.40 (dm, 0.3H), 5.98 & 6.00 (s & s, 2H), 6.18 (pseudo t, J=8.4 & 9.2 Hz, 1H), 6.32 (pseudo d, J=8.4 Hz, 1H), 7.11-7.21 (m, 1H). MS 316 (MH⁺).

Alternatively (S)-2-amino-6-((1-(3-methylbutanoyl)piperidin-3-yl)methoxy) benzonitrile (Example 5b) can be prepared as follow:

A solution of (S)-1-(3-(hydroxymethyl)piperidin-1-yl)-3-methylbutan-1-one (Example 5d) (42 g, 210.75 mmol, 1.2 eq.) in anhydrous THF (300 mL) was added dropwise at 0° C. to a suspension of NaH (60% in mineral oil, 8.43 g, 273.97 mmol, 1.63 eq.) in anhydrous THF (600 mL). The mixture was warmed up to about 25° C. and stirred for 1 h while keeping the temperature below 25° C. A solution of 2-amino-6-fluorobenzonitrile (22.95 g, 168.6 mmol, 1 eq.) in THF (300 mL) was added dropwise. The reaction was heated slowly to reflux and stirred overnight. The mixture was cooled down to room temperature, concentrated to about 400 mL of residual material. Saturated ammonium chloride (200 mL) was added. After stirring vigorously for 15 minutes, EtOAc (800 mL) was added and stirring continued for additional 30 minutes. The organic phase was washed subsequently with water, brine and dried over Na₂SO₄. The solvent was removed under vacuum and the residue was chromatographed on silica gel (Hex/EtOAc to provide the desired product (44.6 g, 141.40 mmol, 83.87%). 1H NMR (400 MHz, DMSO-d₆, 20° C.) δ 0.79-0.92 (3×d, J=6.4 Hz/each, 6H), 1.19-1.46 (m, 2H), 1.51-2.01 (m, 4H), 2.03-2.25 (m, 2H), 2.57 (dd, J=10.4, 12.8 Hz, 0.3H), 2.75-2.88 (m, 0.6H), 2.92-3.10 (m, 1H), 3.65-4.08 (m, 3.6H), 4.27-4.40 (dm, 0.3H), 5.98 & 6.00 (s & s, 2H), 6.18 (pseudo t, J=8.4 & 9.2 Hz, 1H), 6.32 (pseudo d, J=8.4 Hz, 1H), 7.11-7.21 (m, 1H). MS 316 (MH⁺)

Example 5c (S)-2-((1-(3-methylbutanoyl)piperidin-3-yl)methoxy)-6-nitrobenzonitrile

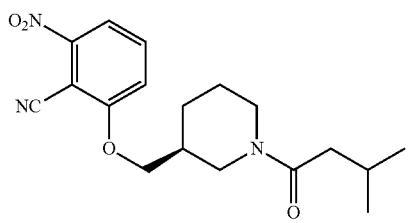 [SMILES: CC(C)CC(=O)N1CCC[C@H](COc2cccc([N+](=O)[O-])c2C#N)C1]

To a suspension of (S)-2-nitro-6-(piperidin-3-ylmethoxy) benzonitrile hydrochloride (Example 1d, 35.84 g, 120.41 mmol) in DCM (600 mL) cooled to 0° C. in an ice bath was added triethylamine (42 mL, 300.94 mmol) followed by dropwise addition of isovaleryl chloride (2.77 mL, 132.35 mmol). The reaction mixture was stirred under N₂ for 30 minutes at 0° C., then at room temperature overnight. The solution was diluted with DCM and successively washed with 10% citric acid, saturated NaHCO₃ solution, water, brine, dried over Na$_2$SO$_4$, filtered and concentrated to afford crude (S)-2-((1-(3-methylbutanoyl)piperidin-3-yl)methoxy)-6-nitrobenzonitrile as a golden brown oil (43.26 g). MS 346 (MH$^+$). This material was used without purification in the next step.

Example 5d (S)-1-(3-(hydroxymethyl)piperidin-1-yl)-3-methylbutan-1-one

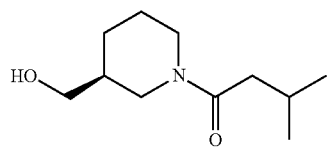

(S)-piperidin-3-ylmethanol hydrochloride (10 g, 65.95 mmol) in water (25 mL) was treated dropwise at 0° C. with a solution of NaOH (13.2 g, 330 mmol, 5 eq.) in water (25 mL). The mixture was stirred for 15 min and a solution of isovaleryl chloride (15.90 g, 131.9 mmol, 2 eq.) in anhydrous THF (25 mL) was added dropwise while stirring vigorously. After 30 minutes at 0° C. the reaction was slowly warmed up to room temperature and stirred overnight. Et$_2$O (500 mL) was added to the reaction mixture with vigorous stirring. The organic layer was separated and washed with brine, dried over Na$_2$SO$_4$ and concentrated to give a residue that was purified by chromatography on silica (Hex/EtOAc 0-100 to yield the desired compound as a colorless oil (16.27 g, 82.62 mmol, 94%). 1H NMR (400 MHz, DMSO-d6, 20° C.) δ 0.88 (pseudo d, J=6.4 Hz, 6H), 1.06-1.75 (m, 5H), 1.88-2.05 (m, 1H), 2.07-2.23 (m, 2H), 2.30 (dd, J=10.8, 12.8 Hz, 0.5H), 2.64 (ddd, J=3.2, 10.8, 13.2 Hz, 0.5H), 2.78 (dd, J=10.4, 13.2 Hz, 0.5H), 2.93 (ddd, J=2.4, 11.6, 13.6 Hz, 0.5H), 3.14-3.35 (m, 2H), 3.70-3.85 (m, 1H), 4.08-4.18 (dm, 0.5H), 4.31-4.40 (dm, 0.5H), 4.49 (t, J=5.2 Hz, 0.5H), 4.58 (t, J=5.2 Hz, 0.5H). MS 200 (MH$^+$).

Alternatively (S)-1-(3-(hydroxymethyl)piperidin-1-yl)-3-methylbutan-1-one (Example 5d) can be prepared as follow:

A solution of (S)-ethyl 1-(3-methylbutanoyl)piperidine-3-carboxylate (Example 5e, 37.4 g, 154.97 mmol) in anhydrous THF (200 mL) was cooled down to 0° C. and treated with LiCl (17 g, 401.04 mmol). After stirring for 5 min, NaBH$_4$ (15 g, 396.50 mmol) was added at the same temperature. The reaction was cooled down further to −20 C and anhydrous ethanol (400 mL) was added dropwise. The reaction was kept on the cooling bath, allowed to warm up slowly to room temperature and stirred overnight. Ethanol (100 mL) was added and the reaction was treated portionwise with saturated aqueous citric acid solution (600 mL) and stirred for another 30 min. Volatiles were removed under vacuum to give a thick colorless material. Water (100 mL) and DCM (800 mL) were added to the residue and the mixture was stirred vigorously for 15 minutes. The phases were separated and the aqueous phase was further extracted with DCM (2×800 mL). The combined organic extract was washed with brine and dried over Na$_2$SO$_4$. The solvent was removed under vacuum to give a colorless residue that was purified by chromatography on silica gel (3 eluent: Hex/EtOAc 0-100) to yield the clean product (29.65 g, 148.79 mmol, 96%).

Example 5e (S)-ethyl 1-(3-methylbutanoyl)piperidine-3-carboxylate

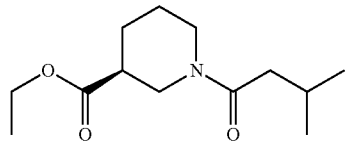 [SMILES: CCOC(=O)[C@H]1CCCN(C(=O)CC(C)C)C1]

Ethyl (S)-Piperidine-3-carboxylate (25 g, 159.02 mmol) in anhydrous DCM (500 mL) was cooled down to 0° C. and treated with Et$_3$N. A solution of isovaleryl chloride (23.27 mL, 190.08 mmol, 1.2 eq.) in anhydrous DCM (200 mL) was added dropwise at 0° C. The resulting reaction mixture was kept on the cooling bath and allowed to warm up slowly to room temperature. After 6 hrs the reaction was washed subsequently with aqueous HCl solution (2M), saturated NaHCO$_3$, brine, dried over Na$_2$SO$_4$, filtered, concentrated under vacuum and purified by filtration over a short silica gel column using EtOAc as solvent. The solvent was removed under vacuum to yield the desired product as pale yellow oil (37.4 g, 154.97 mmol, 97.5%) that was used in the next step without further purification. 1H NMR (400 MHz, DMSO-d6, 20° C.) δ 0.88 (pseudo d, J=6.4 Hz, 6H), 1.13-1.23 (m, 3H), 1.26-1.45 (m, 1H), 1.47-1.75 (m, 2H), 1.82-2.03 (m, 2H), 2.10-2.28 (m, 2H), 2.28-2.39 (m, 0.5H), 2.45-2.56 (m, 0.5H), 2.84 (dd, J=10.0, 12.8 Hz, 0.5H), 2.97-3.11 (m, 1H), 3.38 (dd, J=8.8, 13.6 Hz, 0.5H), 3.63-3.83 (m, 1.5H), 4.00-4.14 (m, 2H), 4.26-4.36 (dm, 0.5H). MS 242 (MH).

Example 6

(S)-(3-(((4-amino-2,2-dioxido-1H-benzo[c][1,2,6]thiadiazin-5-yl)oxy)methyl)piperidin-1-yl)(cyclohexyl)methanone

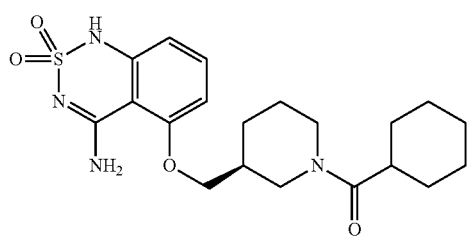

Prepared as in Example 2 from cyclohaxanecarboxylic acid and (S)-4-amino-5-(piperidin-3-ylmethoxy)-1H-benzo[c][1,2,6]thiadiazine 2,2-dioxide hydrochloride (Example 2a) in 25% yield. $^1$H NMR (DMSO-d$_6$, 400 MHz, 80° C.): 1.07-1.50 (m, 7H), 1.51-1.77 (m, 5H), 1.88 (m, 2H), 2.08 (m, 2H), 2.95 (br m, 2H), 3.88 (br m, 2H), 4.09 (m, 2H), 6.65 (d, 1H, 8.4 Hz), 6.76 (d, 1H, 8.0 Hz), 7.45 (t, 1H, 8.4 Hz), 7.75 (br s, 1H), 8.14 (br s, 1H), 10.78 (s, 1H). M+H=421.

Example 7

(S)-1-(3-(((4-amino-2,2-dioxido-1H-benzo[c][1,2,6]thiadiazin-5-yl)oxy)methyl)piperidin-1-yl)-2,2-dimethylpropan-1-one

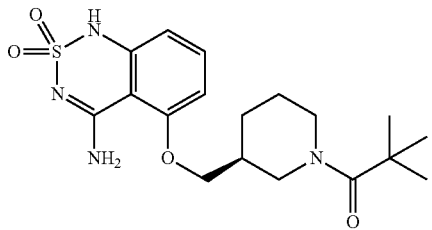 [SMILES: CC(C)(C)C(=O)N1CCC[C@H](COc2cccc3c2C(N)=NS(=O)(=O)N3)C1]

Pivalic acid (71 mg, 0.692 mmol), 1H-benzo[d][1,2,3]triazol-1-ol (117 mg, 0.865 mmol), and 1-(3-Dimethylaminopropyl)-3-ethyl carbodiimide HCl (166 mg, 10.8 mmol) were placed into a 20 mL microwave flask and diluted with anhydrous CAN (12 mL) then a solution of (S)-4-amino-5-(piperidin-3-ylmethoxy)-1H-benzo[c][1,2,6]thiadiazine 2,2-dioxide hydrochloride (Example 2a, 200 mg, 0.577 mmol) and TEA (320 uL, 2.30 mmol) in DMF (2 mL) was added. The mixture was heated with stirring in the microwave at 130° C. for 1 hour then cooled to room temperature, transferred to 250 mL round bottom flask and concentrated via rotary evaporation. The residue was purified via preparative RP HPLC (10 to 90% ACN in water). The pure fractions were collected and dried then diluted with water (6 mL) and NaHCO₃ (100 mg) was added and the solution heated to 90° C. for 15 minutes until the entire compound dissolved. The solution was then cooled to 0° C. and neutralized with 1N HCl solution. The precipitate was collected and dried to provide the title compound (110 mg, 48%). $^1$H NMR (DMSO-d$_6$, 400 MHz, 80° C.): 1.15 (s, 9H), 1.35 (m, 2H), 1.68 (br s, 1H), 1.85 (br s, 1H), 2.05 (br s, 1H), 2.83 (br s, 2H), 2.16 (br s, 2H), 4.06 (d, J=8 Hz, 2H), 4.12 (d, J=12 Hz, 1H), 4.20 (d, J=16 Hz, 1H), 6.60 (d, J=8 Hz, 1H), 6.76 (d, J=8 Hz, 1H), 7.44 (t, J=8 Hz, 1H), 7.78 (s, 1H), 8.37 (s, 1H), 10.93 (s, 1H). M+H=395.

Example 8

(S)-(3-(((4-amino-2,2-dioxido-1H-benzo[c][1,2,6]thiadiazin-5-yl)oxy)methyl)piperidin-1-yl)(cyclopentyl)methanone

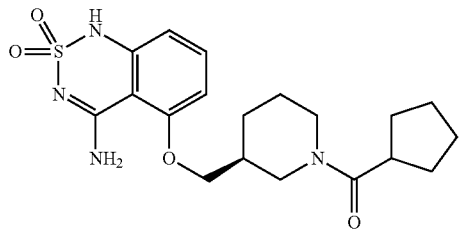

To a solution of (S)-3-(((4-amino-2,2-dioxido-1H-benzo[c][1,2,6]thiadiazin-5-yl)oxy)methyl)piperidinium hydrochloride (Example 2a, 528 mg, 1.52 mmol) in H₂O:THF (20 mL, 2:1), was added NaHCO₃ (640 mg, 7.60 mmol). Upon complete dissolution of the NaHCO₃, cyclopentanecarbonyl chloride (945 uL, 7.60 mmol) was added dropwise. The reaction was stirred at room temperature overnight. The precipitate was collected by vacuum filtration and purified by preparative HPLC (10-90% acetonitrile in water). The pure fractions were combined, concentrated then dissolved in a solution of NaHCO₃ (250 mg in 10 mL water). After complete dissolution, the mixture was cooled in an ice bath and neutralized with 1N HCl. The resulting white solid was collected by vacuum filtration to provide the desired product (322 mg, 52%) as a white solid. $^1$H NMR (DMSO-d$_6$, 400 MHz, 80° C.): 1.43 (m, 2H), 1.51-1.80 (m, 10H), 1.90 (m, 1H), 2.09 (m, 1H), 2.96 (m, 2H), 4.01 (br m, 2H), 4.12 (d, J=6.4 Hz, 2H), 6.67 (d, J=7.8 Hz, 1H), 6.77 (d, J=8.3 Hz, 1H), 7.46 (t, J=8.3 Hz, 1H), 7.92 (br s, 2H), 10.70 (br s, 1H). MS=407 (MH⁺).

Example 9

(S)-(3-(((4-amino-2,2-dioxido-1H-benzo[c][1,2,6]thiadiazin-5-yl)oxy)methyl)piperidin-1-yl)(cyclobutyl)methanone

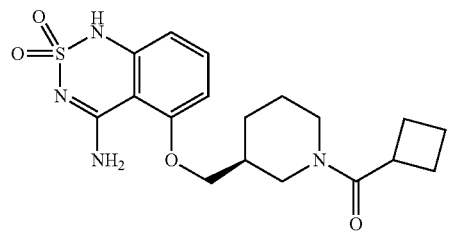 [SMILES: NC1=NS(=O)(=O)Nc2cccc(OC[C@H]3CCCN(C(=O)C4CCC4)C3)c21]

Prepared as in Example 8 from (S)-4-amino-5-(piperidin-3-ylmethoxy)-1H-benzo[c][1,2,6]thiadiazine 2,2-dioxide hydrochloride (Example 2a) and cyclobutanecarboxylic acid (Yield: 43.4%). $^1$H NMR (DMSO-d$_6$, 400 MHz, 60° C.): 1.35 (m, 2H), 1.62-1.80 (m, 2H), 1.82-1.98 (m, 2H), 2.00-2.23 (m, 5H), 2.76 (br s, 0.5H), 2.88 (br s, 1H), 3.07 (br s, 0.5H), 3.30 (m, 1H), 3.54 (br s, 0.5H), 3.70 (br s, 3H), 4.09 (d, J=6.8 Hz, 2H), 4.14 (m, 1H), 6.73 (d, J=8.0 Hz, 1H), 6.77 (d, J=7.6 Hz, 1H), 7.46 (t, J=8.0 Hz, 1H), 7.74 (br s, 1H), 8.20 (br s, 1H), 10.79 (s, 1H). M+H=393.

Example 10

(S)-1-(3-(((4-amino-2,2-dioxido-1H-benzo[c][1,2,6]thiadiazin-5-yl)oxy)methyl)piperidin-1-yl)-2-(pyridin-4-yl)ethanone

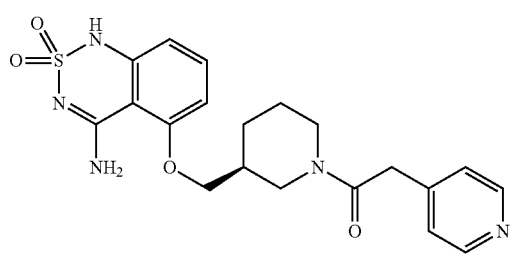 [SMILES: NC1=NS(=O)(=O)Nc2cccc(OC[C@H]3CCCN(C(=O)Cc4ccncc4)C3)c21]

Prepared as in Example 2 from (S)-4-amino-5-(piperidin-3-ylmethoxy)-1H-benzo[c][1,2,6]thiadiazine 2,2-dioxide hydrochloride (Example 2a) and 2-(pyridin-4-yl)acetic acid (Yield: 34.9%). ¹H NMR (400 MHz, DMSO-d$_6$, 80° C.) δ : 1.35 (m, 2H), 1.68 (br s, 1H), 1.79 (br s, 1H), 1.89 (br s, 1H), 2.09 (br s, 2H), 3.55-3.91 (m, 3H), 4.01 (br s, 3H), 6.57 (d, J=8.0 Hz, 1H), 6.65 (d, J=8.4 Hz, 1H), 7.11 (d, J=8.0 Hz, 2H), 7.36 (t, J=8.4 Hz, 1H), 7.74 (br s, 2H), 8.55 (d, 2H, 8.4 Hz), 10.54 (br s, 1H). MS 430 (MH⁺).

Example 11

(S)-(3-(((4-amino-2,2-dioxido-1H-benzo[c][1,2,6]thiadiazin-5-yl)oxy)methyl)piperidin-1-yl)(pyridazin-4-yl)methanone

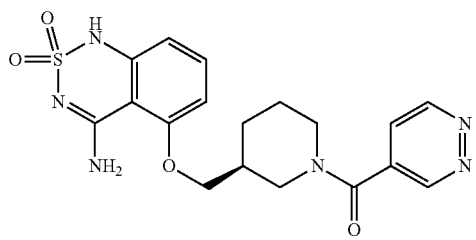 [SMILES: NC1=NS(=O)(=O)Nc2cccc(OC[C@H]3CCCN(C(=O)c4ccnnc4)C3)c21]

Prepared as in Example 2 from (S)-4-amino-5-(piperidin-3-ylmethoxy)-1H-benzo[c][1,2,6]thiadiazine 2,2-dioxide hydrochloride (Example 2a) and pyridazine-4-carboxylic acid (yield: 40.8%). ¹H NMR (400 MHz, DMSO-d$_6$, 80° C.) δ: 1.41 (m, 2H), 1.68 (br s, 1H), 1.87 (br s, 1H), 1.98 (br s, 1H), 2.16 (br s, 2H), 3.65-4.00 (br s, 1H), 4.08 (br s, 3H), 6.65 (d, J=8.0 Hz, 1H), 6.73 (d, J=8.4 Hz, 1H), 7.43 (t, J=8.4 Hz, 1H), 7.86 (br s, 2H), 8.12 (d, J=8.0 Hz, 1H), 9.49 (d, J=8.0 Hz, 1H,), 9.82 (s, 1H), 10.69 (br s, 1H). MS 417 (MH⁺).

Example 12

(S-(3-(((4-amino-2,2-dioxido-1H-benzo[c][1,2,6]thiadiazin-5-yl)oxy)methyl)piperidin-1-yl)(2-(methylamino)pyridin-4-yl)methanone

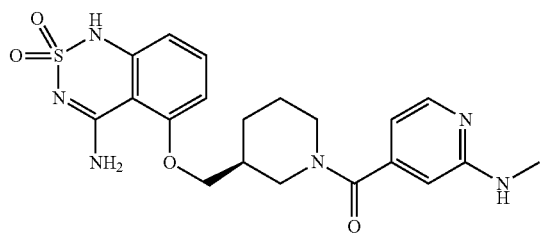 [SMILES: CNc1cc(C(=O)N2CCC[C@H](COc3cccc4c3C(N)=NS(=O)(=O)N4)C2)ccn1]

Prepared as in Example 2 from (S)-4-amino-5-(piperidin-3-ylmethoxy)-1H-benzo[c][1,2,6]thiadiazine 2,2-dioxide hydrochloride (Example 2a) and 2-(methylamino)isonicotinic acid. (Yield: 44%). ¹H NMR (400 MHz, DMSO-d$_6$, 60° C.) δ 1.45 (br m, 2H), 1.68 (br m, 1H), 1.91 (br m, 1H), 2.15 (br m, 1H), 2.77 (d, J=7.6 Hz, 3H), 3.02 (br m, 1H), 1.97 (br m, 1H), 2.13 (br m, 2H), 2.80 (br m, 2H), 3.19 (br m, 1H), 3.30-4.09 (br m, 4H), 6.34 (br m, 1H), 6.38 (br m, 1H), 6.64 (d, J=8.4 Hz, 1H), 6.74 (m, 1H), 7.42 (t, J=8.4 Hz, 1H), 7.73 (br s, 2H), 8.01 (m, 1H), 10.70 (br s, 1H). MS 445 (MH⁺).

Example 13

(S)-(3-(((4-amino-2,2-dioxido-1H-benzo[c][1,2,6]thiadiazin-5-yl)oxy)methyl)piperidin-1-yl)(2-methylpyridin-4-yl)methanone

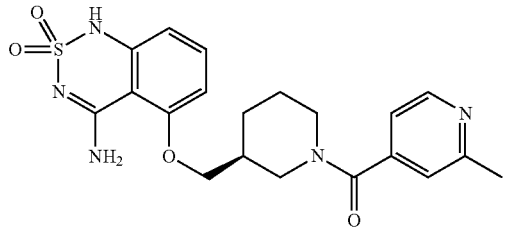 [SMILES: Cc1cc(C(=O)N2CCC[C@H](COc3cccc4c3C(N)=NS(=O)(=O)N4)C2)ccn1]

Prepared as in Example 2 from (S)-4-amino-5-(piperidin-3-ylmethoxy)-1H-benzo[c][1,2,6]thiadiazine 2,2-dioxide hydrochloride (Example 2a) and 2-methylisonicotinic acid (Yield: 15%). ¹H NMR (400 MHz, DMSO-d$_6$, 60° C.) δ 1.48 (br m, 2H), 1.70 (br m, 1H), 1.90 (br m, 1H), 2.16 (br m, 1H), 3.02 (br m, 2H), 3.30-4.09 (br m, 4H), 6.57 (d, J=6.4 Hz, 1H), 6.62 (m, 1H), 7.10 (m, 1H), 7.16 (s, 1H), 7.35 (t, J=8.4 Hz, 1H), 7.53 s, 1H), 8.48 (d, J=4.8 Hz, 1H), 10.56 (s, 1H). MS 430 (MH⁺).

Example 14

(S)-(3-(((4-amino-2,2-dioxido-1H-benzo[c][1,2,6]thiadiazin-5-yl)oxy)methyl)piperidin-1-yl)(2-(dimethylamino)pyridin-4-yl)methanone

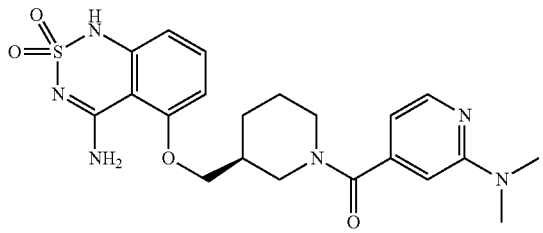 [SMILES: CN(C)c1cc(C(=O)N2CCC[C@H](COc3cccc4c3C(N)=NS(=O)(=O)N4)C2)ccn1]

Prepared as in Example 2 from (S)-4-amino-5-(piperidin-3-ylmethoxy)-1H-benzo[c][1,2,6]thiadiazine 2,2-dioxide hydrochloride (Example 2a) and 2-(dimethylamino)isonicotinic acid (8%). ¹H NMR (400 MHz, DMSO-d$_6$, 60° C.) δ 1.45 (br m, 2H), 1.68 (br m, 1H), 1.90 (br m, 1H), 2.16 (br m, 2H), 3.00 (s, 6H), 3.30-4.09 (br m, 4H), 6.44 (d, J=5.6 Hz, 1H), 6.47 (s, 1H), 6.61 (d, J=8.4 Hz, 1H), 6.69 (d, J=6.8 Hz, 1H), 7.39 (t, J=8.0 Hz, 1H), 7.67 (br s, 2H), 10.67 (br s, 1H). MS 459 (MH⁺)

Example 15

(R)-1-(2-(((4-amino-2,2-dioxido-1H-benzo[c][1,2,6]thiadiazin-5-yl)oxy)methyl)piperidin-1-yl)-3-methylbutan-1-one

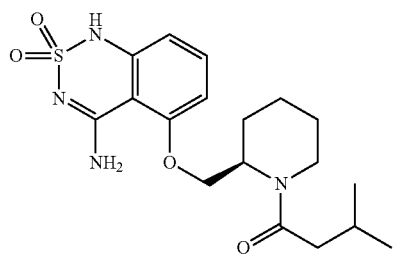 [SMILES: CC(C)CC(=O)N1CCCC[C@@H]1COc1cccc2c1C(N)=NS(=O)(=O)N2]

To a solution of (R)-4-amino-5-(piperidin-2-ylmethoxy)-1H-benzo[c][1,2,6]thiadiazine 2,2-dioxide hydrochloride (Example 15a, 500 mg, 1.44 mmol) in DMF (12 mL) was added triethylamine (399 uL, 2.88 mmol), 3-methylbutanoic acid (159 uL, 1.44 mmol), EDCI-HCl (276 mg, 1.44 mmol), and HOBt (220 mg, 1.44 mmol). The reaction mixture was stirred at room temperature, under nitrogen for 18 hrs, then was filtered and purified by HPLC (10-90% acetonitrile in water). The pure fractions were combined, concentrated and crystallized from ethanol and water to give the title compound as a white solid (73 mg. 13% yield). $^1$H NMR (400 MHz, DMSO-$d_6$, 80° C.) δ 0.89 (d, J=6.8 Hz, 6H), 1.37 (m, 1H), 1.51-1.70 (m, 4H), 1.78 (d, J=12.8 Hz, 1H), 2.01 (m, 1H), 2.13-2.27 (m, 2H), 3.02 (br s, 1H), 3.89 (br s, 1H), 4.18 (br s, 1H), 4.48 (t, J=9.2 Hz, 1H), 5.02 (br s, 1H), 6.63 (d, J=8.0 Hz, 1H), 6.83 (d, J=8.8 Hz, 1H), 7.42 (t, J=8.4 Hz, 1H), 7.82 (br s, 2H), 10.63 (s, 1H). MS 395 (MH$^+$).

Example 15a (R)-2-(((4-amino-2,2-dioxido-1H-benzo[c][1,2,6]thiadiazin-5-yl)oxy)methyl)piperidinium hydrochloride

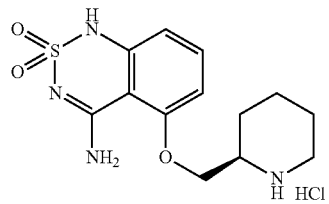 [SMILES: NC1=NS(=O)(=O)Nc2cccc(OC[C@H]3CCCCN3)c21 ; Cl]

To a solution of (R)-tert-butyl-2-(((4-amino-2,2-dioxido-1H-benzo[c][1,2,6]thiadiazin-5-yl)oxy)methyl)piperidine-1-carboxylate (Example 15b, 10.7 g, 26.1 mmol) in ethanol (175 mL) was added HCl in ethanol (104 mL, 2.5M, 261 mmol). The reaction stirred at 60° C. under nitrogen for 4 hours. The compound was collected by filtration as an off white solid (7.70 g. 85% yield for three steps). $^1$H NMR (400 MHz, DMSO-$d_6$) δ 1.03-1.90 (br m, 6H), 2.89 (br t, J=2.8 Hz, 1H), 3.27 (br m, 1H), 3.61 (br m, 1H), 4.27-4.40 (br m, 2H), 6.67 (d, J=7.6 Hz, 1H), 6.80 (d, J=8.8 Hz, 1H), 7.46 (t, J=8.0 Hz, 1H), 7.79 (br s, 1H), 8.35 (br s, 1H), 9.26 (br s, 2H), 10.97 (br s, 1H). MS 311 (MH$^+$).

Example 15b (R)-tert-butyl-2-(((4-amino-2,2-dioxido-1H-benzo[c][1,2,6]thiadiazin-5-yl)oxy)methyl)piperidine-1-carboxylate

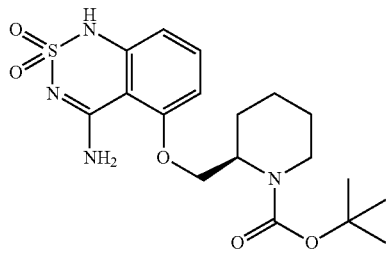 [SMILES: CC(C)(C)OC(=O)N1CCCC[C@@H]1COc1cccc2c1C(N)=NS(=O)(=O)N2]

To a solution of (R)-tert-butyl-2-((2-cyano-3-(sulfamoylamino)phenoxy)methyl)piperidine-1-carboxylate (Example 15c, 10.7 g, 26.1 mmol) in ethanol (130 mL) was added aqueous NaOH (2N, 130 mL, 26.1 mmol). The solution was refluxed for 18 hours under nitrogen. After cooling to room temperature, the solution was cooled to 0° C. and neutralized with 1N HCl. The mixture was partially concentrated and the product was collected by filtration to afford (R)-tert-butyl 2-(((4-amino-2,2-dioxido-1H-benzo[c][1,2,6]thiadiazin-5-yl)oxy)methyl)piperidine-1-carboxylate, which was used immediately in the next step. MS 311 (MH$^+$-boc).

Example 15c (R)-tert-butyl-2-((2-cyano-3-(sulfamoylamino)phenoxy)methyl)piperidine-1-carboxylate

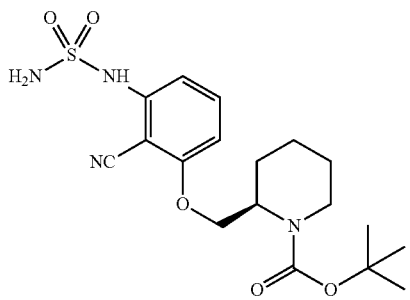 [SMILES: CC(C)(C)OC(=O)N1CCCC[C@@H]1COc1cccc(NS(N)(=O)=O)c1C#N]

To a solution of (R)-tert-butyl-2-((3-amino-2-cyanophenoxy)methyl)piperidine-1-carboxylate (Example 15d, 8.65 g. 26.1 mmol) in dimethyl acetamide (48 mL) were added pyridine (8.44 mL, 104 mmol) and sulfamoyl chloride (6.03 g. 52.2 mmol). The reaction mixture was stirred at room temperature for 1 hour, neutralized with saturated aqueous NaHCO$_3$ solution and extracted with ethyl acetate. The extract was dried over anhydrous Na$_2$SO$_4$, filtered, and concentrated to give the title compound as a clear oil, which was used immediately in the next step. MS 311 (MH$^+$-boc).

Example 15d (R)-tert-butyl-2-((3-amino-2-cyanophenoxy)methyl)piperidine-1-carboxylate

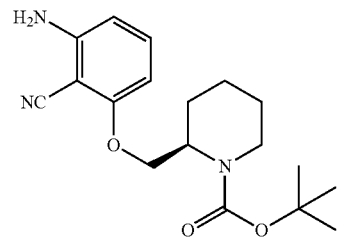

To a solution of (R)-tert-butyl-2-((2-cyano-3-nitrophenoxy)methyl)piperidine-1-carboxylate (Example 15e, 10.8 g, 29.85 mmol) in ethyl acetate (86 mL) was added 10% Pd/C (1.08 g, 3 mmol). H$_2$ was added by balloon, and the mixture was stirred for 48 hours at room temperature. Upon completion, the mixture was filtered through a pad of celite, and the solvent was removed in vacuo. The residue was recrystallized from ethyl acetate/hexanes to afford (R)-tert-butyl-2-((3-amino-2-cyanophenoxy)methyl)piperidine-1-carboxylate (8.65 g, 88%) as an off white solid. MS 323 (MH+-boc).

Example 15e (R)-tert-butyl-2-((2-cyano-3-nitrophenoxy)methyl)piperidine-1-carboxylate

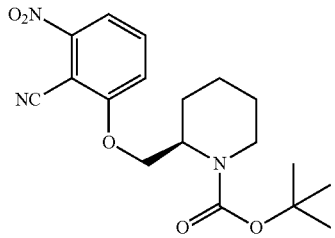 [SMILES: CC(C)(C)OC(=O)N1CCCC[C@@H]1COc1cccc([N+](=O)[O-])c1C#N]

To a solution of (R)-tert-butyl-2-(hydroxymethyl)piperidine-1-carboxylate (Example 15f, 7.10 g, 33.0 mmol) and 2,6-dinitrobenzonitrile (6.37 g, 33.0 mmol) in THF (142 mL) cooled to −78° C., was added NaH (60% dispersion in oil, 1.45 g. 36.3 mmol). The reaction was allowed to warm to room temperature and stirring was continued for 18 hours. Upon completion, the reaction was cooled to 0° C. and quenched with water. The mixture was extracted with ethyl acetate, and the organic extracts were combined and dried over anhydrous Na$_2$SO$_4$, filtered, and concentrated. The residue was recrystallized from ethyl acetate/hexanes to afford (R)-tert-butyl-2-((2-cyano-3-nitrophenoxy)methyl)piperidine-1-carboxylate (10.8 g, 91%) as a yellow solid. MS 282 (MH+-boc).

Example 15f (R)-tert-butyl-2-(hydroxymethyl)piperidine-1-carboxylate

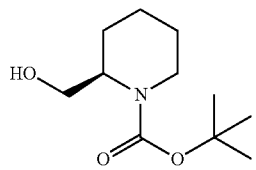

A solution of (R)-1-(tert-butoxycarbonyl)piperidine-2-carboxylic acid (Example 15 g. 18.5 g, 80.7 mmol) in anhydrous THF (44.4 mL) was cooled to 0° C. BH$_3$Me$_2$S (44.4 mL, 88.8 mmol) was added drop wise over 15 minutes. After complete addition, the mixture was allowed to warm to room temperature, and stirring was continued for 18 hours. The mixture was quenched with water, and extracted with ethyl acetate. The organic extract was dried over anhydrous Na$_2$SO$_4$, filtered, and concentrated. The resulting residue was flash chromatographed on silica gel (35% ethyl acetate in hexanes) to provide (R)-tert-butyl-2-(hydroxymethyl)piperidine-1-carboxylate as a white solid (14.2 g, 82%). MS116 (MH+-boc)

Example 15

(R)-1-(tert-butoxycarbonyl)piperidine-2-carboxylic acid

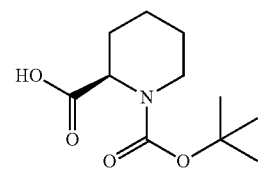 [SMILES: CC(C)(C)OC(=O)N1CCCC[C@@H]1C(=O)O]

To a suspension of (R)-piperidine-2-carboxylic acid (12.5 g, 96.8 mmol) in water (88 mL) and 1,4-dioxane (133 mL), were added di-tert-butyl dicarbonate (23.2 g, 106 mmol) and triethylamine (13.5 mL, 96.8 mmol). The solution was stirred at room temperature for 20 hours. The mixture was concentrated in vacuo, diluted with ethyl acetate (200 mL) and washed with 5% aqueous HCl. The organic phase was separated, dried over anhydrous Na$_2$SO$_4$, filtered, and concentrated to afford the compound as a white solid (18.5 g, 83%). MS130 (MH+-boc).

Example 16

(R)-1-(2-((4-amino-2,2-dioxido-1H-benzo[c][1,2,6]thiadiazin-5-yl)oxy)methyl)piperidin-1-yl)butan-1-one

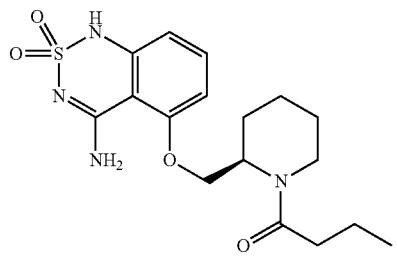 [SMILES: CCCC(=O)N1CCCC[C@@H]1COc1cccc2c1C(N)=NS(=O)(=O)N2]

To a solution of (R)-2-amino-6-((1-butyrylpiperidin-2-yl)methoxy)benzonitrile (Example 16a, 1.0 g, 3.32 mmol) in DMA (15.0 mL) was added sulfamoyl chloride (2.68 g, 23.21 mmol) at room temperature under nitrogen. The reaction mixture was then stirred at room temperature under nitrogen for 2 hrs and the solution was diluted with EtOAc, washed with water, brine, and dried over Na$_2$SO$_4$. The solvent was removed under reduced pressure and the residue was purified by Biotage SP-1 (40s column) eluting with EtOAc/iHexane (10%-70%). The intermediate was dissolved in EtOH (25.0 mL) and aq.NaOH (2.0 N, 5.0 mL) was added at room temperature. The reaction mixture was then refluxed overnight then cooled to 0° C. and neutralized carefully with 1 N HCl. The precipitate was collected by filtration and was recrystallized with 20% water/EtOH to provide the title compound as a white solid (730 mg, 58% yield). $^1$H NMR (400 MHz, DMSO-d$_6$, room temperature) δ 0.86 (t, J=7.6 Hz, 3H), 1.35-1.76 (m, 8H), 2.28-2.32 (m, 2H), 3.14 (t, J=13.6 Hz, 1H), 3.74

(d, J=14 Hz, 1H), 4.07-4.11 (m, 1H), 4.25-4.38 (m, isomer), 4.50 (t, J=10 Hz, 1H), 5.16 (t, J=4.4 Hz, 1H), 6.59 (d, J=8.0 Hz, 1H), 6.84 (d, J=8.0 Hz. 1H), 7.44 (t, J=8.0 Hz, 1H), 7.68 (s, isomer), 7.77 (s, 1H), 8.23 (s, 1H), 8.36 (s, isomer), 10.89 (s, 1H). $^1$H NMR (400 MHz, DMSO-d$_6$, 80° C.) δ 0.88 (t, J=7.6 Hz, 3H), 1.35-1.40 (m, 1H), 1.49-1.67 (m, 7H), 1.77 (d, J=11.6 Hz, 1H), 2.27-2.32 (m, 2H), 3.85-3.90 (m, 1H), 4.18-4.20 (m, 1H), 4.07-4.11 (m, 1H), 4.46 (t, J=10 Hz, 1H), 5.00-5.03 (m, 1H), 6.63 (d, J=8.4 Hz, 1H), 6.82 (d, J=7.6 Hz, 1H), 7.42 (t, J=8.0 Hz, 1H), 7.81 (s, 2H), 10.64 (s, 1H). MS 381 (MH$^+$).

Example 16a (R)-2-amino-6-((1-butyrylpiperidin-2-yl)methoxy)benzonitrile

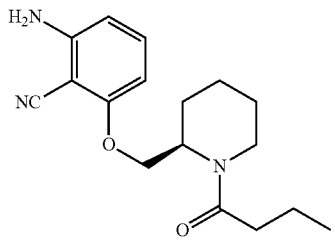

To a solution of (R)-2-((1-butyrylpiperidin-2-yl)methoxy)-6-nitrobenzonitrile (Example 16b, 1.5 g, 4.53 mmol) in ethanol (40 mL) was added 10% Pd/C (300 mg). The reaction mixture was charged with hydrogen balloon at room temperature overnight then then filtered through celite and concentrated under reduced pressure. The residue was purified by Biotage SP-1 (40s column) eluting with EtOAc/Hexane (10%-70%) to give the desired product as an oil (1.1 g. 81%). $^1$H NMR (400 MHz, DMSO-d$_6$) δ 0.86 (t, J=7.2 Hz, 3H), 1.46-1.65 (m, 7H), 1.77-1.85 (m, 1H), 2.24-2.30 (m, 1H), 2.38-2.42 (m, 1H), 2.56-2.63 (m, 0.5H), 3.1-3.16 (m, 0.5H), 3.71-3.74 (m, 0.3H), 3.92-3.98 (m, 1H), y 2H), 7.15-7.19 (m, 1H). MS 302 (MH$^+$).

Example 16b (R)-2-((1-butyrylpiperidin-2-yl)methoxy)-6-nitrobenzonitrile

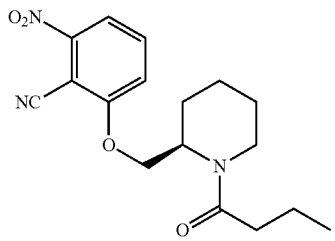 [SMILES: CCCC(=O)N1CCCC[C@@H]1COc1cccc([N+](=O)[O-])c1C#N]

To a solution of (R)-2-((2-cyano-3-nitrophenoxy)methyl)piperidin-1-ium 2,2,2-trifluoroacetate (Example 16c, 2.26 g, 6.03 mmol) in anhydrous DCM (50 mL) was added triethylamine (4.2 mL, 30.1 mmol) at room temperature. The reaction mixture was cooled down to 0° C. and butyryl chloride (0.95 mL, 9.05 mmol) was added and the solution stirred at room temperature overnight. The solvent was then removed under reduced pressure and the residue was diluted with EtOAc (150 mL), the organic layer was washed successively with water, brine and dried over Na$_2$SO$_4$, filtered and evaporated. The residue was purified by Biotage SP-1 (40s column) eluting with EtOAc/Hexane (10%-70%) to give the desired product (1.5 g. 75%). MS 332 (MH$^+$).

Example 16c (R)-2-((2-cyano-3-nitrophenoxy)methyl)piperidin-1-ium 2,2,2-trifluoroacetate

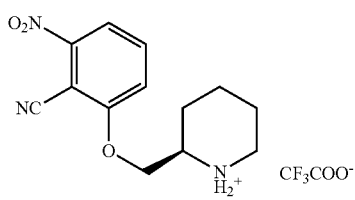

To a solution of (R)-tert-butyl 2-((2-cyano-3-nitrophenoxy)methyl)piperidine-1-carboxylate (Example 15e, 2.18 g, 6.03 mmol) in anhydrous DCM (65 mL) was added trifluoroacetic acid (7.91 mL) at room temperature. The reaction mixture was stirred at room temperature for over 1 hour. The solvent was removed under reduced pressure and the residue was dried under the vacuum to give the title product which could be used for the next step reaction without further purification. MS 262 (MH$^+$).

Example 17

(R)-(2-((4-amino-2,2-dioxido-1H-benzo[c][1,2,6]thiadiazin-5-yl)oxy)methyl)piperidin-1-yl)(cyclohexyl)methanone

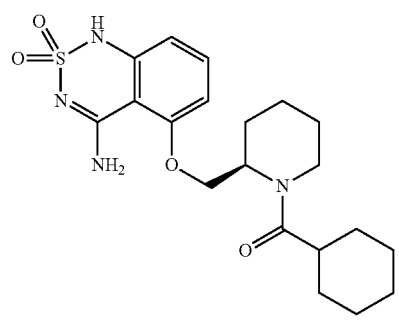 [SMILES: NC1=NS(=O)(=O)Nc2cccc(OC[C@H]3CCCCN3C(=O)C3CCCCC3)c21]

Prepared as in example 15 from (R)-4-amino-5-(piperidin-2-ylmethoxy)-1H-benzo[c][1,2,6]thiadiazine 2,2-dioxide hydrochloride (Example 15a) and cyclohexanecarboxylic acid (Yiel: 23%). $^1$H NMR (400 MHz, DMSO-d$_6$. 80° C.) δ 1.80-1.20 (m, 17H), 2.55-2.52 (m, 1H), 4.00-3.90 (m, 1H), 4.20-4.16 (m, 1H), 4.51-4.20 (m, 1H), 5.04-5.00 (m, 1H), 6.63 (d, J=8.4 Hz, 1H), 6.83 (d, J=8.4 Hz, 1H), 7.42 (t, J=8.4 Hz, 1H), 7.80 (br s, 2H), 10.5 (br s, 1H). MS 421 (MH⁺).

Example 18

(R)-(2-(((4-amino-2,2-dioxido-1H-benzo[c][1,2,6]thiadiazin-5-yl)oxy)methyl)piperidin-1-yl)(cyclobutyl)methanone

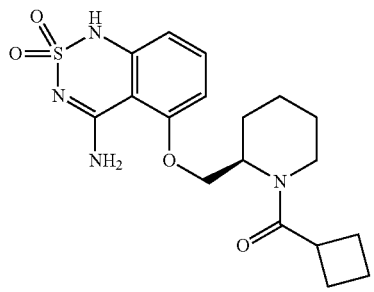 [SMILES: NC1=NS(=O)(=O)Nc2cccc(OC[C@H]3CCCCN3C(=O)C3CCC3)c21]

Prepared as in example 15 from (R)-4-amino-5-(piperidin-2-ylmethoxy)-1H-benzo[c][1,2,6]thiadiazine 2,2-dioxide hydrochloride (Example 15a) and cyclobutanecarboxylic acid (yield: 25%). ¹H NMR (400 MHz, DMSO-d₆, 80° C.) δ 1.67-1.35 (m, 6H), 1.94-1.85 (m, 2H), 2.16-2.10 (m, 3H), 2.33-2.24 (m, 2H), 3.40-3.30 (m, 1H), 3.68-3.60 (m, 1H), 4.21-4.20 (m, 1H), 4.50-4.20 (m, 1H), 5.11-5.00 (m, 1H), 6.65 (d, J=8.4 Hz, 1H), 6.85 (d, J=8.4 Hz. 1H), 7.44 (t, J=8.4 Hz, 1H), 7.81 (br s, 2H), 10.6 (br s, 1H), MS 393 (MH⁺).

Example 19

(R)-1-(2-(((4-amino-2,2-dioxido-1H-benzo[c][1,2,6]thiadiazin-5-yl)oxy)methyl)piperidin-1-yl)-2-(4-methoxyphenyl)ethanone

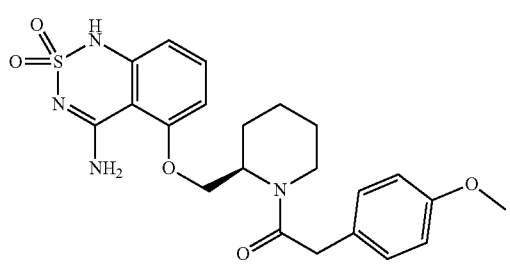 [SMILES: COc1ccc(CC(=O)N2CCCC[C@@H]2COc2cccc3c2C(N)=NS(=O)(=O)N3)cc1]

Prepared as in Example 8 from (R)-2-(((4-amino-2,2-dioxido-1H-benzo[c][1,2,6]thiadiazin-5-yl)oxy)methyl)piperidinium hydrochloride (Example 15a) and 2-(4-methoxyphenyl)acetyl chloride in 14% yield. ¹H NMR (DMSO-d₆, 400 MHz, 80° C.): 1.15-1.29 (m, 1H), 1.44-1.65 (m, 4H), 1.70-1.78 (m, 1H), 3.01 (m, 1H), 3.66 (s, 2H), 3.70 (s, 3H), 3.90 (br s, 1H), 4.19 (br s, 1H), 4.43 (t, J=12 Hz, 1H), 5.03 (br s, 1H), 5.64 (d, J=8 Hz, 1H), 6.80 (t, J=8 Hz, 3H), 7.13 (d, J=8 Hz, 2H), 7.41 (t, J=8 Hz, 1H), 7.81 (br s, 2H), 10.63 (s, 1H). M+H=459.

Example 20

(R)-(2-(((4-amino-2,2-dioxido-1H-benzo[c][1,2,6]thiadiazin-5-yl)oxy)methyl)piperidin-1-yl)(2,4-dihydroxyphenyl)methanone

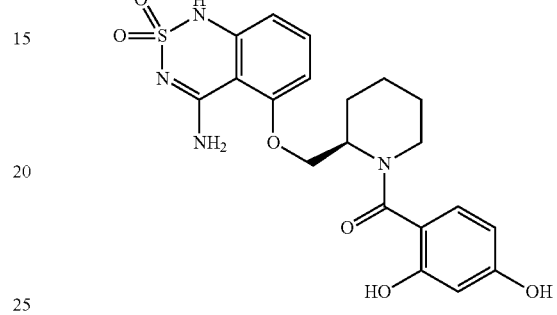

Prepared as in Example 15 from (R)-4-amino-5-(piperidin-2-ylmethoxy)-1H-benzo[c][1,2,6]thiadiazine 2,2-dioxide hydrochloride (Example 15a) and 2,4-dihydroxybenzoic acid (yield: 10%) as a white solid. ¹H NMR (400 MHz, DMSO-d₆ 80° C.) δ 1.81-1.51 (m, 6H), 3.71-3.70 (m, 1H), 4.30-4.26 (m, 2H), 4.60-4.52 (m, 1H), 5.02-5.00 (m, 1H), 6.23 (dd, J=2.4, 8.4 Hz, 1H), 6.30 (d, J=2.4 Hz, 1H), 6.65 (d, J=8.4 Hz, 1H), 6.80 (d, J=8.4 Hz, 1H), 6.91 (d, J=8.4 Hz, 1H), 7.42 (t, J=8.0 Hz, 1H), 7.90 (br s, 2H), 9.24 (br s, 1H), 9.40 (br s, 1H), 10.6 (br s, 1H). MS 447 (MH⁺).

Example 21

(R)-1-(2-(((4-amino-2,2-dioxido-1H-benzo[c][1,2,6]thiadiazin-5-yl)oxy)methyl)piperidin-1-yl)-3-(pyridin-3-yl)propan-1-one

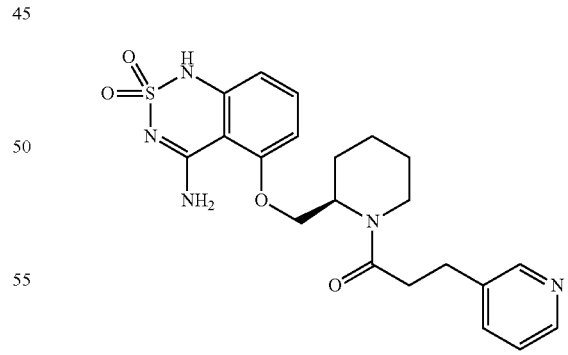

Prepared as in Example 15 from 3-(pyridine-3-yl)propanoic acid and (R)-4-amino-5-(piperidin-2-ylmethoxy)-1H-benzo[c][1,2,6]thiadiazine 2,2-dioxide hydrochloride (Example 15a) in 27.1% yield. ¹H NMR (DMSO-d₆, 400 MHz, 60° C.): 1.20-1.40 (m, 1H), 1.45-1.67 (m, 4H), 1.74 (m, 1H), 2.68 (m, 2H), 2.86 (m, 2H), 3.17 (s, 1H), 3.76 (br s, 1H), 4.17 (br s, 1H), 4.45 (t, J=9.6 Hz, 1H), 5.13 (br s, 1H), 6.63 (d, J=8.0 Hz, 1H), 6.82 (d, J=8.0 Hz, 1H), 7.24 (m, 1H), 7.43 (t, J=8.0 Hz, 1H), 7.64 (m, 1H), 7.74 (br s, 1H), 8.07 (br s, 1H), 8.36 (m, 1H), 8.46 (s, 1H), 10.74 (s, 1H). (444 MH⁺).

Example 22

(R)-1-(2-((4-amino-2,2-dioxido-1H-benzo[c][1,2,6]thiadiazin-5-yl)oxy)methyl)piperidin-1-yl)-3-(pyridin-4-yl)propan-1-one

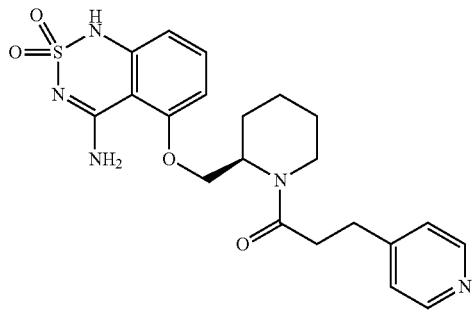 [SMILES: NC1=NS(=O)(=O)Nc2cccc(OC[C@H]3CCCCN3C(=O)CCc3ccncc3)c21]

Prepared as in Example 15 from (R)-2-(((4-amino-2,2-dioxido-1H-benzo[c][1,2,6]thiadiazin-5-yl)oxy)methyl)piperidinium hydrochloride (Example 15a) in 23% yield. $^1$H NMR (DMSO-$d_6$, 400 MHz, 80° C.): 1.34 (m, 1H), 1.59 (m, 4H), 1.76 (m, 1H), 2.67 (br t, J=7.3 Hz, 2H), 2.86 (t, J=7.3 Hz, 2H), 3.01 (m, 1H), 3.87 (br s, 1H), 4.20 (m, 1H), 4.46 (t, J=10.0 Hz, 1H), 5.02 (br s, 1H), 6.64 (dd, J=8.2, 0.8 Hz, 1H), 6.82 (dd, J=8.2, 0.8 Hz, 1H), 7.22 (d, J=5.1 Hz, 2H), 7.43 (t, J=8.3 Hz, 1H), 7.76 (br s, 1H), 7.91 (br s, 1H), 8.40 (m, 2H), 10.65 (s, 1H). MS 444 (MH⁺).

Example 23

(R)-1-(2-((4-amino-2,2-dioxido-1H-benzo[c][1,2,6]thiadiazin-5-yl)oxy)methyl)piperidin-1-yl)-2-(pyridin-3-yl)ethanone

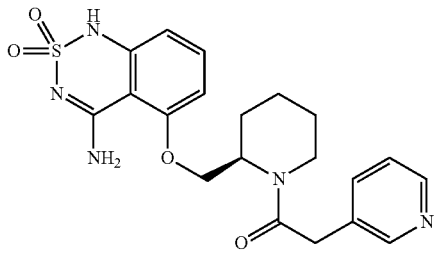 [SMILES: NC1=NS(=O)(=O)Nc2cccc(OC[C@H]3CCCCN3C(=O)Cc3cccnc3)c21]

Prepared as in Example 15 from 2-(pyridine-3-yl)acetic and (R)-4-amino-5-(piperidin-2-ylmethoxy)-1H-benzo[c][1,2,6]thiadiazine-2,2-dioxide hydrochloride (Example 15a) in 40% yield. $^1$H NMR (400 MHz, DMSO-$d_6$, 80° C.) δ 1.31 (br m, 1H), 1.60 (br m, 3H), 1.77 (br m, 2H), 3.04 (br m, 1H), 3.77 (s, 2H), 3.95 (br s, 1H), 4.23 (br s, 1H), 4.49 (m, 1H), 5.02 (br s, 1H), 6.64 (d, J=8.4 Hz, 1H), 6.83 (d, J=8.8 Hz, 1H), 7.26 (m, 1H), 7.43 (t, J=8.4 Hz, 1H), 7.60 (d, J=8.0 Hz, 1H), 7.82 (br s, 1H), 8.39 (m, 1H), 8.43 (m, 1H), 10.66 (s, 1H). MS 430 (MH⁺).

Example 24

(R)-2-(((4-amino-2,2-dioxido-1H-benzo[c][1,2,6]thiadiazin-5-yl)oxy)methyl)piperidin-1-yl)(cyclopentyl)methanone

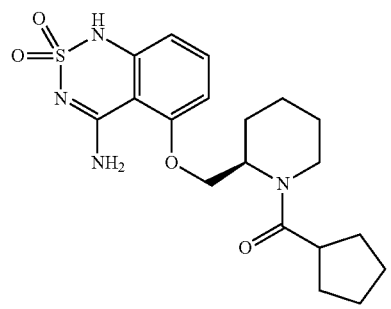 [SMILES: NC1=NS(=O)(=O)Nc2cccc(OC[C@H]3CCCCN3C(=O)C3CCCC3)c21]

Prepared as in Example 15 from (R)-2-(((4-amino-2,2-dioxido-1H-benzo[c][1,2,6]thiadiazin-5-yl)oxy)methyl)piperidinium hydrochloride (Example 15a) and cyclopentyl carboxylic acid in 25% yield. $^1$H NMR (DMSO-$d_6$, 400 MHz, 80° C.): 1.40 (m, 1H), 1.53 (m, 2H), 1.63 (m, 8H), 1.77 (m, 4H), 3.00 (m, 1H), 3.97 (br m, 1H), 4.20 (m, 1H), 4.50 (t, J=8.0 Hz, 1H), 5.06 (br s, 1H), 6.67 (d, J=8.0 Hz, 1H), 6.84 (d, J=8.0 Hz, 1H), 7.43 (t, J=8.0 Hz, 1H), 7.80 (br s, 2H), 10.6 (br s, 1H). MS=407 (MH⁺).

Example 25

(R)-1-(2-(((4-amino-2,2-dioxido-1H-benzo[c][1,2,6]thiadiazin-5-yl)oxy)methyl)piperidin-1-yl)-2-(pyridin-4-yl)ethanone

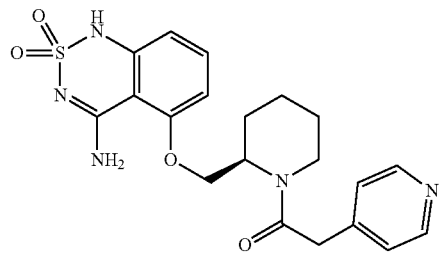 [SMILES: NC1=NS(=O)(=O)Nc2cccc(OC[C@H]3CCCCN3C(=O)Cc3ccncc3)c21]

Prepared as in Example 15 from (R)-2-(((4-amino-2,2-dioxido-1H-benzo[c][1,2,6]thiadiazin-5-yl)oxy)methyl)piperidinium hydrochloride (Example 15a) and 2-(pyridin-4-yl)acetic acid in 27% yield. $^1$H NMR (DMSO-$d_6$, 400 MHz, 80° C.): 1.21-1.37 (m, 1H), 1.48-1.70 (m, 4H), 1.71-1.82 (m, 1H), 3.01 (m, 1H), 3.78 (br s, 3H), 4.22 (br s, 1H), 4.43 (t, J=8 Hz, 1H), 5.05 (br s, 1H), 6.64 (d, J=8 Hz, 1H), 6.82 (d, J=8 Hz, 1H), 7.21 (d, J=8 Hz, 2H), 7.42 (t, J=8 Hz, 1H), 7.82 (br s, 2H), 8.43 (d, J=8 Hz, 2H), 10.67 (s, 1H). M+H=430.

Example 26

2-(((4-amino-2,2-dioxido-1H-benzo[c][1,2,6]thiadiazin-5-yl)oxy)methyl)-N-ethylpiperidine-1-carboxamide

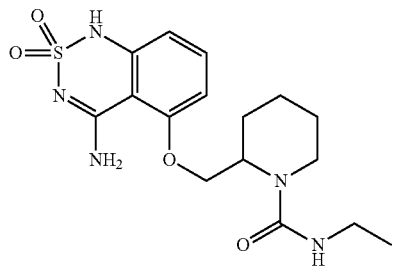

To a solution of 2-((2-cyano-3-(sulfamoylamino)phenoxy) methyl)-N-ethylpiperidine-1-carboxamide (Example 26a, 0.6 g. 1.57 mmol) in EtOH (10 mL) was added NaOH 2M (1.57 mL, 1.57 mmol) and the reaction mixture was heated at 100° C. for 2 h. The solution was then evaporated to dryness. The residue was diluted with water (7.0 mL), and 10% AcOH (3.5 mL, 3.5 mmol) was added at 0° C. to provide a white precipitate which was filtered and washed with cold water and further purified by Biotage purification system (120 g Silicycle column, DCM:THF=4:1 as eluent) to give the title compound (0.318 g, 53%). MS 382 (MH⁺).

Example 26a ((2-cyano-3-(sulfamoylamino)phenoxy)methyl)-N-ethylpiperidine-1-carboxamide

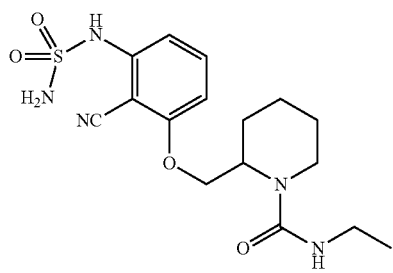 [SMILES: CCNC(=O)N1CCCCC1COc1cccc(NS(N)(=O)=O)c1C#N]

To a solution of 2-((3-amino-2-cyanophenoxy)methyl)-N-ethylpiperidine-1-carboxamide (Example 26b. 0.407 g, 1.35 mmol) in DMA (5 mL) was added sulfamoyl chloride (0.234 mg, 2.02 mmol) and the reaction mixture was stirred vigorously at r.t. for 2 h, then extracted with H₂O/EtOAc. The combined organic phases were washed with brine, dried over MgSO₄, filtered and evaporated. The residue was purified by Biotage purification system (120 g Silicycle column, DCM: THF=4:1 as eluent) to provide the desired product (0.606 g, 90%). MS 382 (MH⁺).

Example 26b 2-((3-amino-2-cyanophenoxy)methyl)-N-ethylpiperidine-1-carboxamide

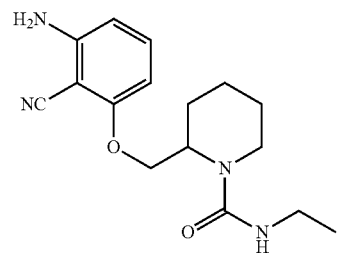 [SMILES: CCNC(=O)N1CCCCC1COc1cccc([N+](=O)[O-])c1C#N]

To a solution of 2-((2-cyano-3-nitrophenoxy)methyl)-N-ethylpiperidine-1-carboxamide (Example 26c, 0.458 g, 1.46 mmol) in EtOH (20 mL) was added cyclohexene (0.74 mL, 7.3 mmol) and catalytic amount of 10% Pd/C (0.146 mg). Reaction mixture was heated at 100° C. for 40 minutes, then filtered through Cellite, washed with EtOH (100 mL) and evaporated to give 2-((3-amino-2-cyanophenoxy)methyl)-N-ethylpiperidine-1-carboxamide (0.407 g. 92%) which was used in to next step without further purification. MS 303 (MH⁺).

Example 26c 2-((2-cyano-3-nitrophenoxy)methyl)-N-ethylpiperidine-1-carboxamide

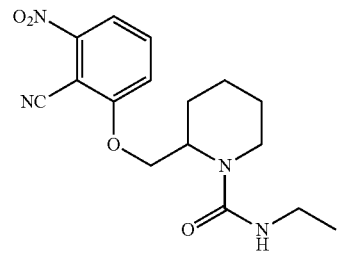

To a solution of 2-nitro-6-(piperidin-2-ylmethoxy)benzonitrile hydrochloride (Example 26d, 0.5 g, 1.68 mmol) in THF were added triethylamine (0.514 mL, 3.7 mmol) and ethylisocyanate (0.2 mL, 2.52 mmol) and the reaction mixture was stirred at room temperature under nitrogen for 3 hours. The solution was then diluted with water and extracted with EtOAc, the combined organic phases were washed with brine, dried over MgSO₄, filtered and evaporated to give 2-((2-cyano-3-nitrophenoxy)methyl)-N-ethylpiperidine-1-carboxamide (0.485 g, 87%) which was used in the next step without further purification. MS 333 (MH⁺).

Example 26d

2-nitro-6-(piperidin-2-ylmethoxy)benzonitrile hydrochloride

To a solution of tert-butyl 2-((2-cyano-3-nitrophenoxy)methyl)piperidine-1-carboxylate (Example 26e, 1.02 g, 2.83 mmol) in EtOH (20 mL) was added HCl 1.25N in EtOH (11.3 mL, 14.13 mmol) and the reaction mixture was stirred at 80° C. under nitrogen for 1 hour. After cooling to room temperature, the reaction mixture was concentrated in vacuum. The oily residue was washed with Hexane:DCM (1:4) and the solvent concentrated in vacuum to give 2-nitro-6-(piperidin-2-ylmethoxy)benzonitrile hydrochloride (0.982 g. 116%). MS 262 (MH$^+$).

Example 26e tert-Butyl 2-((2-cyano-3-nitrophenoxy)methyl)piperidine-1-carboxylate

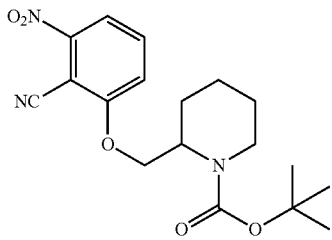

To a solution of tert-butyl 2-(hydroxymethyl)piperidine-1-carboxylate (0.86 g, 4 mmol) in dry THF (30 mL) was added at −20° C. NaH (0.32 g, 8 mmol) and the mixture was stirred 10 min at −20° C. and then 20 min at room temperature. The reaction mixture was then cooled to −20° C. and 2,6-dinitrobenzonitrile (0.772 g, 4 mmol) in dry THF (10 mL) and DMF (1 mL) was added dropwise over 15 min period. The solution was stirred under nitrogen at room temperature for 18 hours, diluted with water and extracted with EtOAc, the combined organic phases were washed with brine, dried over MgSO$_4$, filtered and evaporated. The residue was purified by Biotage purification system (120 g Silicycle column, Hexane:EtOAc=3:2 as eluent) to give tert-butyl 2-((2-cyano-3-nitrophenoxy)methyl)piperidine-1-carboxylate (1.02 g, 70.6%). MS 262 [M+H-Boc]$^+$.

Example 27

(R)-2-(((4-amino-2,2-dioxido-1H-benzo[c][1,2,6]thiadiazin-5-yl)oxy)methyl)-N-(pyridin-4-ylmethyl)piperidine-1-carboxamide

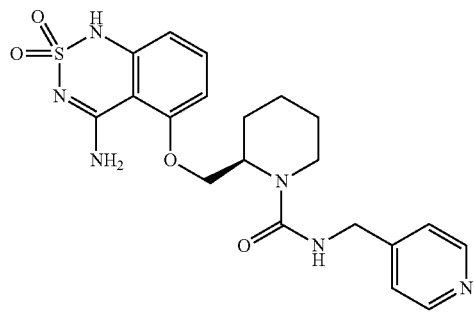 [SMILES: NC1=NS(=O)(=O)Nc2cccc(OC[C@H]3CCCCN3C(=O)NCc3ccncc3)c21]

Prepared as in Example 26 from (R)-2-((2-cyano-3-(sulfamoylamino)phenoxy)methyl)-N-(pyridin-4-ylmethyl)piperidine-1-carboxamide (Example 27a). Yield 28% as an off-white solid. $^1$H NMR (400 MHz, DMSO-d$_6$) δ: 1.35 (m, 1H), 1.59 (m, 4H), 1.77 (m, 1H), 3.86 (m, 1H), 4.03 (dd, J=7.6, 5.2 Hz, 1H), 4.16 (t, J=7.6 Hz, 1H), 4.24 (dd, J=13.2, 4.4 Hz, 1H), 4.34 (dd, 1H, J=10.4, 4.4 Hz), 4.71 (m, 1H), 6.05 (d, J=6.0 Hz, 1H), 6.19 (dd, J=6.8, 0.8 Hz, 1H), 6.93 (t, J=8.0 Hz, 1H), 7.16 (t, J=4.4 Hz, 1H), 7.24 (m, 2H), 8.47 (m, 2H). MS 445 (MH$^+$).

Example 27a

(R)-2-((2-cyano-3-(sulfamoylamino)phenoxy)methyl)-N-(pyridin-4-ylmethyl)piperidine-1-carboxamide

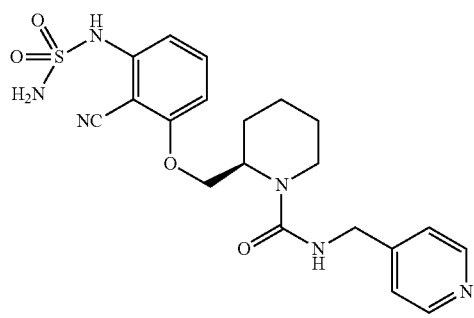 [SMILES: N#Cc1c(NS(N)(=O)=O)cccc1OC[C@H]1CCCCN1C(=O)NCc1ccncc1]

Prepared as in Example 26a from (R)-2-((3-amino-2-cyanophenoxy)methyl)-N-(pyridin-4-ylmethyl)piperidine-1-carboxamide (Example 27b). Yield: 48% as a white solid. MS 445 (MH$^+$).

Example 27b

(R)-2-((3-amino-2-cyanophenoxy)methyl)-N-(pyridin-4-ylmethyl)piperidine-1-carboxamide

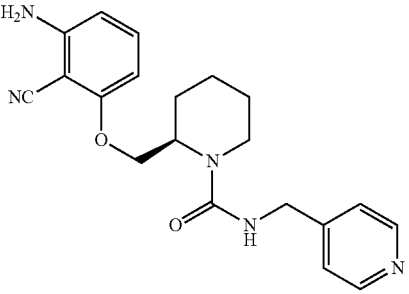 [SMILES: N#Cc1c(OC[C@H]2CCCCN2C(=O)NCc2ccncc2)cccc1[N+](=O)[O-]]

To a solution of (R)-2-((2-cyano-3-nitrophenoxy)methyl)-N-(pyridin-4-ylmethyl)piperidine-1-carboxamide (Example 27c, 365 mg, 0.98 mmol) in THF/acetic acid (20 mL, 1:1), was added iron powder (164 mg, 2.94 mmol). The reaction was heated to reflux over 15 min under nitrogen, and stirred at reflux for 30 min. Upon completion, the reaction was cooled to room temperature, concentrated, diluted with ethyl acetate and successively washed a saturated solution of $NaHCO_3$, dried over $Na_2SO_4$, filtered, concentrated and flash chromatographed (0-10% methanol in dichloromethane) to provide the desired product (141 mg, 40%). MS=366 ($MH^+$).

Example 27c (R)-2-((2-cyano-3-nitrophenoxy)methyl)-N-(pyridin-4-ylmethyl)piperidine-1-carboxamide

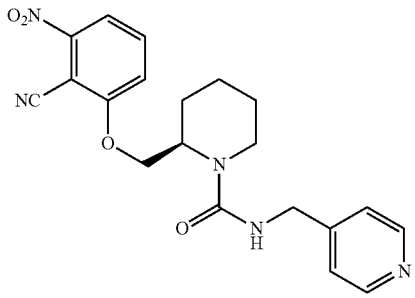

To a solution of (R)-2-((2-cyano-3-nitrophenoxy)methyl)piperidinium 2,2,2-trifluoroacetate (Example 16c, 1.12 g, 2.99 mmol) in dichloromethane (5 mL), was added triethylamine (420 uL, 3.01 mmol). To that mixture was added a suspension of 4-nitrophenyl pyridin-4-ylmethylcarbamate (Example 27d, 980 mg, 3.59 mmol) in dichloromethane (5 mL), followed by triethylamine (420 uL, 3.01 mmol). After stirring for 23 h at room temperature, additional portions of 4-nitrophenyl pyridin-4-ylmethylcarbamate (980 mg, 3.59 mmol) and triethylamine (420 uL, 3.01 mmol) were added, and the resulting reaction mixture was stirred for 1 h. at which time it was poured into water, and washed successively with saturated aqueous $NaHCO_3$ water and brine, dried over $MgSO_4$, filtered, concentrated and purified by flash chromatography (0-100% ethyl acetate in hexanes followed by 0-10% methanol in dichloromethane) to provide (R)-2-((2-cyano-3-nitrophenoxy)methyl)-N-(pyridin-4-ylmethyl)piperidine-1-carboxamide (365 mg, 32%). MS=396 ($MH^+$).

Example 27d 4-nitrophenyl pyridin-4-ylmethylcarbamate

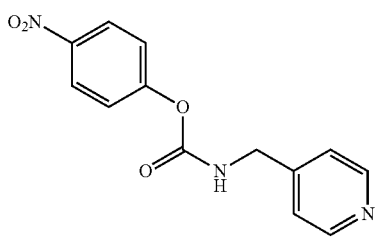 [SMILES: O=C(NCc1ccncc1)Oc1ccc([N+](=O)[O-])cc1]

A solution of pyridin-4-ylmethanamine (505 uL, 5 mmol) and p-nitrophenyl chloroformate (1.0 g, 5 mmol) in dichloromethane (20 mL) was stirred at room temperature for 5 h. Upon completion, the product was collected by vacuum filtration, washed with dichloromethane and purified by preparative HPLC (10-90% acetonitrile in water) to provide 4-nitrophenyl pyridin-4-ylmethylcarbamate as a white solid. MS=274 ($MH^+$).

Example 28

(R)-2-(((4-amino-2,2-dioxido-1H-benzo[c][1,2,6]thiadiazin-5-yl)oxy)methyl)-N-(pyridin-4-yl)piperidine-1-carboxamide

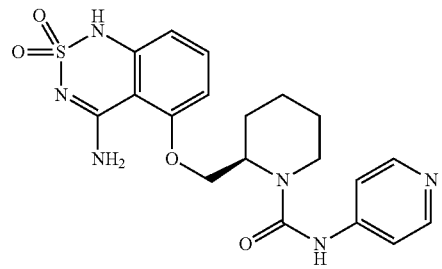 [SMILES: NC1=NS(=O)(=O)Nc2cccc(OC[C@H]3CCCCN3C(=O)Nc3ccncc3)c21]

To a solution of (S)-4-amino-5-(piperidin-3-ylmethoxy)-1H-benzo[c][1,2,6]thiadiazine 2,2-dioxide hydrochloride (Example 15a, 346 mg, 1.0 mmol) and 4-nitrophenyl pyridin-4-ylcarbamate (Example 28a, 518 mg, 2.0 mmol) in DMF (10 mL) was added potassium carbonate (414 mg, 3.0 mmol) and the reaction mixture was stirred at room temperature for 2 hours. The compound was purified via preparative RP HPLC (10 to 90% acetonitrile in water to provide the desired product (120 mg, 28%). $^1$H NMR (DMSO-$d_6$, 400 MHz): 1.47 (m, 1H), 1.65 (m, 4H), 1.80 (m, 1H), 3.12 (t, 1H, J=12.0 Hz), 4.03 (m, 1H), 4.17 (m, 1H), 4.61 (t, 1H, J=10.4 Hz), 4.93 (br s, 1H), 6.61 (d, 1H, J=8.4), 6.89 (d, 1H, J=8.4), 7.48 (m, 3H), 7.99 (br s, 1H), 8.30 (d, 2H, J=5.6 Hz), 8.35 (br s, 1H), 8.92 (s, 1H), 10.94 (s, 1H). M+H=431.

Example 28a 4-nitrophenyl pyridin-4-ylcarbamate

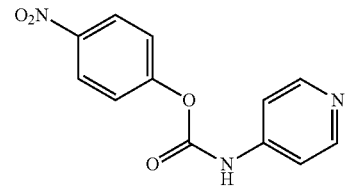 [SMILES: O=C(Nc1ccncc1)Oc1ccc([N+](=O)[O-])cc1]

Prepared as Example 27d from pyridin-4-amine and p-nitrophenyl chloroformate to provide the compound as an off white solid. MS=260 ($MH^+$).

Example 29

(S)-3-(((4-amino-2,2-dioxido-1H-benzo[c][1,2,6]thiadiazin-5-yl)oxy)methyl)-N-(pyridin-4-ylmethyl)piperidine-1-carboxamide

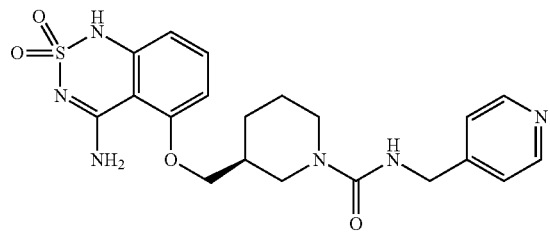 [SMILES: NC1=NS(=O)(=O)Nc2cccc(OC[C@H]3CCCN(C(=O)NCc4ccncc4)C3)c21]

A solution of 4-nitrophenyl (pyridin-4-ylmethyl)carbamate (Example 27d, 27.3 mg, 100 umol), (S)-3-(((4-amino-2,2-dioxido-1H-benzo[c][1,2,6]thiadiazin-5-yl)oxy)methyl)piperidinium hydrochloride (Example 2a, 34.6 mg, 0.10 mmol) and $K_2CO_3$ in DMF (1 mL) was stirred at room temperature overnight. The resulting mixture was filtered and purified by preparative HPLC (10-90% acetonitrile in water) to provide the title product as a white solid. MS=445 (MH$^+$).

Example 30

(S)-3-(((4-amino-2,2-dioxido-1H-benzo[c][1,2,6]thiadiazin-5-yl)oxy)methyl)-N-(pyridin-4-yl)piperidine-1-carboxamide

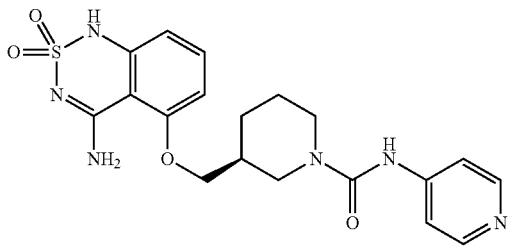 [SMILES: NC1=NS(=O)(=O)Nc2cccc(OC[C@H]3CCCN(C(=O)Nc4ccncc4)C3)c21]

Prepared as in Example 29 from 4-nitrophenyl pyridin-4-ylcarbamate (Example 28a) and (S)-3-(((4-amino-2,2-dioxido-1H-benzo[c][1,2,6]thiadiazin-5-yl)oxy)methyl)piperidinium hydrochloride (Example 2a). MS=431 (MH$^+$).

Example 31

(S)-1-(3-(((4-amino-2,2-dioxido-1H-benzo[c][1,2,6]thiadiazin-5-yl)oxy)methyl)piperidin-1-yl)-2-(pyrimidin-2-yl)ethanone

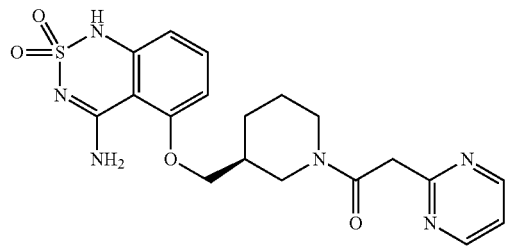 [SMILES: NC1=NS(=O)(=O)Nc2cccc(OC[C@H]3CCCN(C(=O)Cc4ncccn4)C3)c21]

Prepared as in Example 2 from (S)-5-(piperidin-3-ylmethoxy)-1H-benzo[c][1,2,6]thiadiazin-4-amine-2,2-dioxide hydrochloride (Example 2a) and 2-(pyrimidin-2-yl)acetic acid (Example 31a) (10% yield). $^1$H NMR (400 MHz, DMSO-d$_6$) δ 1.31-1.47 (m, 2H), 1.57-1.76 (m, 1H), 1.85 (m, 1H), 2.00 (d, 1H, J=7.9 Hz), 2.03-2.25 (m, 1H), 3.00 (m, 1H), 3.69-4.22 (m, 6H), 6.56 (m, 1H), 6.65 (m, 1H), 7.32 (t, 1H, J=4.9 Hz), 7.39 (t, 1H, J=4.9 Hz), 7.53-7.84 (m, 2H), 8.70 (d, 1H, J=4.9 Hz), 8.76 (d, 1H, J=4.9 Hz), 10.98 (br s, 1H). MS 431 (MH$^+$).

Example 31a 2-(pyrimidin-2-yl)acetic acid

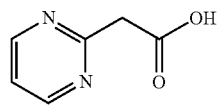

To a solution of ethyl 2-(pyrimidin-2-yl)acetate (Example 31b, 410 mg. 2.47 mmol) in ethanol (5 mL) was added 2N NaOH (2 mL) at room temperature under nitrogen. The reaction mixture was stirred at room temperature under nitrogen for 72 hours, then concentrated under reduced pressure. The residue was triturated with ethanol and concentrated under reduced pressure to give the title compound, which was carried onto the next step without further purification. MS139 (MH$^+$).

Example 31b ethyl 2-(pyrimidin-2-yl)acetate

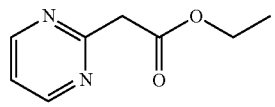

To a solution of diethylmalonate (6.65 mL. 43.65 mmol) in DMF (30 mL) at −78° C. was added NaH (1.76 g, 52.38 mmol, 60% dispersion in mineral oil). The reaction was stirred for 10 min at −78° C., warmed to room temperature and 2-chloropyrimidine (1.0 g, 8.73 mmol) in DMF (3 mL) was added. The reaction mixture was heated to 80° C. for 72 hours, then to 120° C. for 18 hours, and upon completion was cooled to room temperature. The solution was quenched by addition of 1N HCl, neutralized with saturated aqueous NaHCO$_3$ and extracted with EtOAc (3×). The combined organics were dried over Na$_2$SO$_4$, filtered, concentrated and purified by flash chromatography on silica gel (0-100% EtOAc in hexanes) to give the title compound as a yellow-orange oil (1.34 g, 92%). MS167 (MH$^+$).

Example 32

(R)-1-(2-(((4-amino-2,2-dioxido-1H-benzo[c][1,2,6]thiadiazin-5-yl)oxy)methyl)piperidin-1-yl)-2-(pyrimidin-2-yl)ethanone

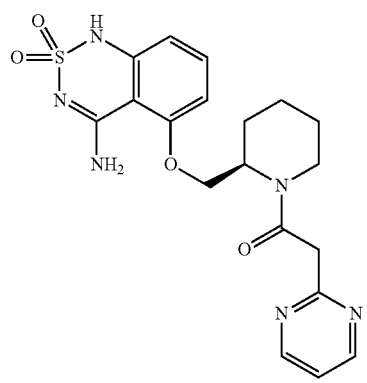 [SMILES: NC1=NS(=O)(=O)Nc2cccc(OC[C@H]3CCCCN3C(=O)Cc3ncccn3)c21]

Prepared as in Example 15 from (R-2-(((4-amino-2,2-dioxido-1H-benzo[c][1,2,6]thiadiazin-5-yl)oxy)methyl)piperidinium hydrochloride (Example 15a) and 2-(pyrimidin-2-yl)acetic acid (Example 31a) (36% yield). $^1$H NMR (400 MHz, DMSO-d$_6$) δ 1.25 (m, 1H), 1.47-1.67 (m, 4H), 1.76 (m, 1H), 3.16 (t, 1H, J=12.6 Hz), 2.77-4.20 (m, 3H), 4.27-4.72 (m, 2H), 5.13 (m, 1H), 6.57 (d, 1H, J=8.2 Hz), 6.78 (br d, 1H, J=7.6 Hz), 7.35 (t, 1H, J=5.0 Hz), 7.40 (br t, 1H, J=8.2 Hz), 7.71 (br s, 1H), 7.91 (br s, 1H), 8.71 (m, 2H), 10.90 (br s, 1H). MS 431 (MH$^+$).

Example 33

(R)-1-(2-(((4-amino-2,2-dioxido-1H-benzo[c][1,2,6]thiadiazin-5-yl)oxy)methyl)piperidin-1-yl)-2-(pyrimidin-4-yl)ethanone

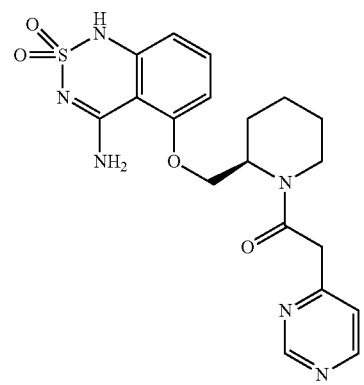 [SMILES: NC1=NS(=O)(=O)Nc2cccc(OC[C@H]3CCCCN3C(=O)Cc3ccncn3)c21]

Prepared as in Example 15 from (R-2-(((4-amino-2,2-dioxido-1H-benzo[c][1,2,6]thiadiazin-5-yl)oxy)methyl)piperidinium hydrochloride (Example 15a) and 2-(pyrimidin-4-yl)acetic acid (Example 33a) (44% yield). $^1$H NMR (400 MHz, DMSO-d$_6$) δ 1.35 (m, 1H), 1.54-1.68 (m, 4H), 1.79 (m, 1H), 3.21 (t, 1H, J=12.3 Hz), 3.84 (m, 1H), 3.98 (m, 2H), 4.16 (dd, 1H, J=10.0, 4.6 Hz), 4.29-4.75 (m, 1H), 5.16 (m, 1H), 6.60 (d, 1H, J=8.6 Hz), 6.81 (br d, 1H, J=7.9 Hz), 7.43 (d, 1H, J=11.0 Hz), 7.45 (d, 1H, J=8.3 Hz), 7.72 (br s, 1H), 8.07 (br s, 1H), 8.70 (d, 1H, J=5.0 Hz), 9.08 (m, 1H), 10.91 (br s, 1H). MS 431 (MH$^+$).

Example 33a 2-(pyrimidin-4-yl)acetic acid

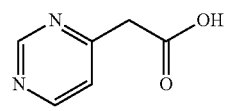

To a solution of ethyl 2-(pyrimidin-4-yl)acetate (Example 33b, 450 mg. 2.71 mmol) in ethanol (5 mL) was added 2N NaOH (2 mL) at room temperature under nitrogen. The reaction mixture was stirred at room temperature under nitrogen for 24 hours, concentrated under reduced pressure and suspended in ethanol. The solid was removed by vacuum filtration, and the filtrate was concentrated under reduced pressure, triturated with ethanol, concentrated again and carried onto the next step without further purification. MS139 (MH$^+$).

Example 33b ethyl 2-(pyrimidin-4-yl)acetate

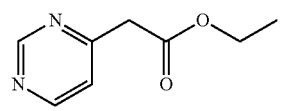

To a flask containing LiHMDS (32 mL, 31.89 mmol, 1.0 M in THF) at −70° C., was slowly added 4-methylpyrimidine (1.0 g, 10.63 mmol). After 5 min of stirring at −70° C. diethylcarbonate (1.93 mL, 15.95 mmol) was added, the reaction was slowly warmed to room temperature and stirred for 4 days. The reaction mixture was quenched by addition of 1 N HCl, neutralized with saturated aqueous NaHCO$_3$ and extracted with EtOAc (3×). The combined organics were dried over Na$_2$SO$_4$, filtered, concentrated under reduced pressure and purified by flash chromatography on silica gel (0-100% EtOAc in hexanes) to give the title compound as a yellow oil (1.38 g, 78%). MS 167 (MH$^+$).

Example 34

(R)-1-3-(((4-amino-2,2-dioxido-1H-benzo[c][1,2,6]thiadiazin-5-yl)oxy)methyl)piperidin-1-yl)-3-methylbutan-1-one

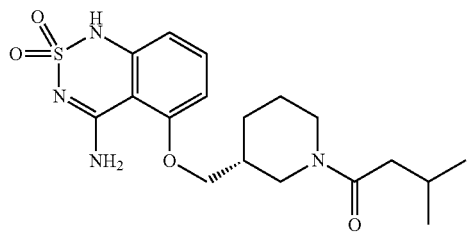

Prepared as in Example 5 from (R)-2-sulfamoylamino-6-((1-(3-methylbutanoyl)piperidin-3-yl)methoxy)benzonitrile (Example 34a) (54% yield). $^1$H NMR (400 MHz, DMSO-$d_6$, 80° C.) δ 0.89 (d, 6H, J=4.0 Hz), 1.41 (m, 2H), 1.69 (m, 1H), 1.88 (m, 1H), 1.98 (m, 1H), 2.07 (m, 1H), 2.17 (m, 2H), 2.96 (br. S, 2H), 3.55-4.14 (m, 4H), 6.66 (d, 1H, J=8.2 Hz), 6.75 (d, 1H, J=8.2 Hz), 7.44 (t, 1H, J=8.2 Hz), 7.75 (br. s, 1H) 8.00 (br. s, 1H), 10.69 (s, 1H). MS 395 (MH$^+$).

Example 34a (R)-2-sulfamoylamino-6-((1-(3-methylbutanoyl)piperidin-3-yl)methoxy)benzonitrile

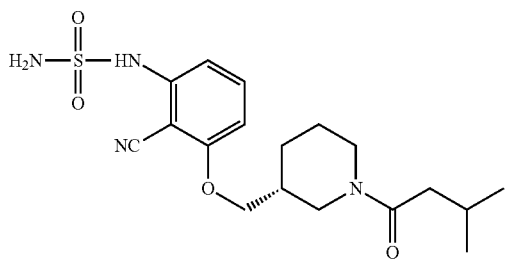 [SMILES: CC(C)CC(=O)N1CCC[C@@H](COc2cccc(NS(N)(=O)=O)c2C#N)C1]

Prepared as in Example 5a from (R)-2-amino-6-((1-(3-methylbutanoyl)piperidin-3-yl)methoxy)benzonitrile (Example 34b). MS 395 (MH$^+$).

Example 34b (R)-2-amino-6-((1-(3-methylbutanoyl)piperidin-3-yl)methoxy)benzonitrile

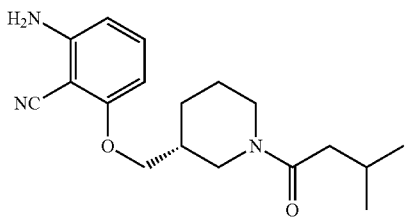 [SMILES: CC(C)CC(=O)N1CCC[C@@H](COc2cccc(N)c2C#N)C1]

To a solution of (R)-1-(3-(hydroxymethyl)piperidin-1-yl)-3-methylbutan-1-one (Example 34c) (145 mg, 0.73 mmol) in THF (15 mL) was added NaH (44 mg, 1.09 mmol, 60% dispersion in mineral oil) at 0° C. The reaction was warmed to room temperature and stirred for 15 minutes, at which time 2-amino-6-fluorobenzonitrile (109 mg, 0.80 mmol) was added. The mixture was heated at 80° C. overnight, quenched with water, concentrated under reduced pressure to remove THF and extracted with EtOAc (3×). The combined extracts were dried over Na$_2$SO$_4$, filtered, concentrated under reduced pressure and purified by flash chromatography on silica gel (EtOAc/hexanes). The residue was further purified by chiral HPLC (normal phase, ethanol/isopropanol/methanol/hexanes) to give the title compound as a white solid (96 mg, 41%). MS 316 (MH$^+$).

Example 34c (R)-1-(3-(hydroxymethyl)piperidin-1-yl)-3-methylbutan-1-one

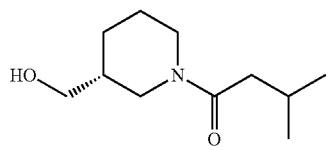

To a solution of (R)-1-(3-methylbutanoyl)piperidine-3-carboxylic acid (Example 34d) (2.52 g, 11.84 mmol) in THF (20 mL) at 0° C., was added BH$_3$Me$_2$S (1.2 mL, 13.0 mmol) dropwise over 15 minutes. The reaction was warmed to room temperature and stirred overnight, cooled to 0° C., quenched with water, concentrated under reduced pressure to remove THF and extracted with EtOAc. The combined extracts were washed with saturated aqueous NaHCO$_3$, dried over Na$_2$SO$_4$, filtered, concentrated under reduced pressure and purified by flash chromatography on silica gel (EtOAc/hexanes) to give the title compound (184 mg, 6%). MS 200 (MH$^+$).

Example 34d (R)-1-(3-methylbutanoyl)piperidine-3-carboxylic acid

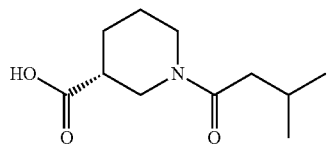

To a solution of (R)-piperidine-3-carboxylic acid (2.0 g, 15.48 mmol) in water (40 mL) and THF (20 mL) were added NaHCO$_3$ (3.30 g, 38.70 mmol) and 3-methylbutanoyl chloride (2.8 mL, 23.2 mmol) at room temperature. The reaction was stirred overnight, concentrated under reduced pressure, diluted with water (50 mL) and extracted with EtOAc (1×). The aqueous layer was acidified with 1N HCl, extracted with EtOAc (3×) and the combined extracts were dried over Na$_2$SO$_4$, filtered and concentrated under reduced pressure to give the title compound (2.53 g, 76%). MS 214 (MH$^+$).

Example 35

(R)-(2-(((4-amino-2,2-dioxido-1H-benzo[c][1,2,6]thiadiazin-5-yl)oxy)methyl)piperidin-1-yl)(pyridin-4-yl)methanone

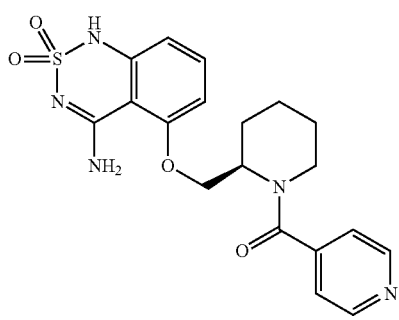 [SMILES: NC1=NS(=O)(=O)Nc2cccc(OC[C@H]3CCCCN3C(=O)c3ccncc3)c21]

Prepared as in Example 15 from (R-2-(((4-amino-2,2-dioxido-1H-benzo[c][1,2,6]thiadiazin-5-yl)oxy)methyl)piperidinium hydrochloride (Example 15a) and isonicotinic acid (26% yield). $^1$H NMR (400 MHz, DMSO-d$_6$, 80° C.) δ 1.48 (m, 1H), 1.58-1.87 (m, 5H), 3.19 (br t, 1H, J=12.4 Hz), 3.19 (br s, 1H), 4.30 (m, 1H), 4.64 (t, 1H, J=8.8 Hz), 4.99 (br s, 1H), 6.64 (d, 1H, J=8.8 Hz), 6.80 (br s, 1H), 7.28 (dd, 2H, J=6.4 Hz), 7.40 (t, 1H, J=8.0 Hz), 7.86 (br s, 2H), 8.60 (dd, 2H, J=5.2 Hz), 10.66 (br s, 1H). MS 416 (MH$^+$).

Example 36

(R)-1-(2-(((4-amino-2,2-dioxido-1H-benzo[c][1,2,6]thiadiazin-5-yl)oxy)methyl)piperidin-1-yl)-2-(pyridin-4-yl)ethanone

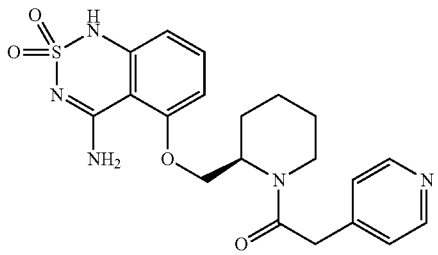 [SMILES: NC1=NS(=O)(=O)Nc2cccc(OC[C@H]3CCCCN3C(=O)Cc3ccncc3)c21]

Prepared as in Example 15 from (R)-2-(((4-amino-2,2-dioxido-1H-benzo[c][1,2,6]thiadiazin-5-yl)oxy)methyl)piperidinium hydrochloride (Example 15a) and 2-(pyridin-4-yl)acetic acid (26% yield). $^1$H NMR (400 MHz, DMSO-d$_6$, 80° C.) δ 1.20-1.33 (m, 1H), 1.49-1.65 (m, 4H), 1.72-1.79 (m, 1H), 3.01 (m, 1H), 3.90 (br s, 3H), 4.22 (br s, 1H), 4.45 (t, 1H, J=8.0 Hz), 5.06 (br s, 1H), 6.64 (d, 1H, J=8.0 Hz), 6.82 (d, 1H, J=8.0 Hz), 7.19 (ddd, 1H, J=8.0, 4.8, 0.8 Hz), 7.27 (d, 1H, J=8.0 Hz), 7.42 (t, 1H, J=8.0 Hz), 7.67 (dt, 1H, J=8.0, 2.0 Hz), 7.80 (br s, 2H), 8.43 (dq, 1H, J=8.0 Hz, 0.8 Hz), 10.65 (s, 1H). MS 430 (MH$^+$).

Example 37

(R)-(2-(((4-amino-2,2-dioxido-1H-benzo[c][1,2,6]thiadiazin-5-yl)oxy)methyl)piperidin-1-yl)(2-hydroxy-6-methylpyridin-4-yl)methanone

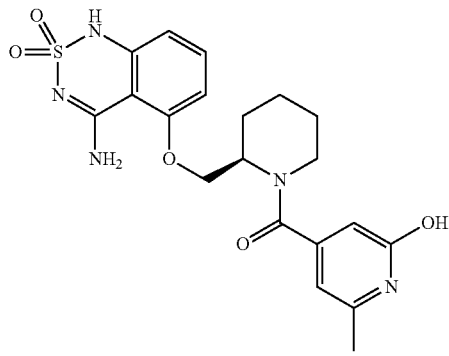 [SMILES: Cc1cc(C(=O)N2CCCC[C@@H]2COc2cccc3c2C(N)=NS(=O)(=O)N3)cc(O)n1]

Prepared as in Example 15 from (R)-2-(((4-amino-2,2-dioxido-1H-benzo[c][1,2,6]thiadiazin-5-yl)oxy)methyl)piperidinium hydrochloride (Example 15a) and 2-hydroxy-6-methylisonicotinic acid. $^1$H NMR (400 MHz, DMSO-d$_6$) δ 1.42 (m, 1H), 1.54-1.72 (m, 5H), 1.80 (m, 1H), 2.16 (s, 3H), 3.21 (m, 1H), 3.44 (m, 1H), 4.19 (dd, 1H, J=10.3, 4.2 Hz), 4.37 (m, 1H), 4.61 (t, 1H, J=10.0 Hz), 5.14 (m, 1H), 5.88 (s, 1H), 6.02 (s, 1H), 6.61 (d, 1H, J=8.4 Hz), 6.86 (d, 1H, J=8.4 Hz), 7.44 (t, 1H, J=8.4 Hz), 7.75 (br s, 1H), 8.34 (br s, 1H), 10.92 (s, 1H). MS 446 (MH$^+$).

Example 38

(R)-(2-(((4-amino-2,2-dioxido-1H-benzo[c][1,2,6]thiadiazin-5-yl)oxy)methyl)piperidin-1-yl)(2,6-dimethylquinolin-4-yl)methanone

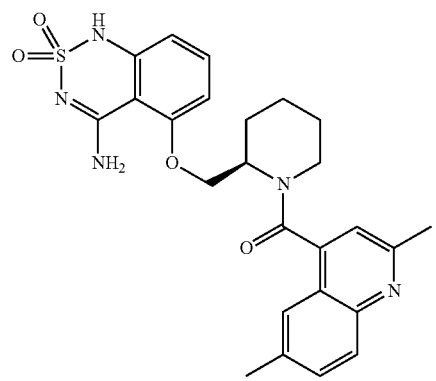 [SMILES: Cc1ccc2nc(C)cc(C(=O)N3CCCC[C@@H]3COc3cccc4c3C(N)=NS(=O)(=O)N4)c2c1]

Prepared as in Example 15 from (R)-2-(((4-amino-2,2-dioxido-1H-benzo[c][1,2,6]thiadiazin-5-yl)oxy)methyl)piperidinium hydrochloride (Example 15a) and 2,6-dimethylquinoline-4-carboxylic acid. $^1$H NMR (400 MHz, DMSO-d$_6$) δ 1.12-1.53 (m, 2H), 1.58-1.84 (m, 4H), 1.98 (s, 3H), 2.64 (s, 3H), 3.02 (m, 1H), 3.19 (m, 1H), 4.18 (dd, 1H, J=9.9, 3.1 Hz), 4.95 (t, 1H, J=10.2 Hz), 5.45 (m, 1H), 6.66 (m, 1H), 7.01 (d, 1H, J=8.2 Hz), 7.27 (s, 1H), 7.38 (s, 1H), 7.46-7.61 (m, 2H), 7.81 (d, 1H, J=8.6 Hz), 7.98 (br s, 1H), 8.26 (br s, 1H), 10.94 (s, 1H). MS 494 (MH$^+$).

Example 39

(R)-2-(((4-amino-2,2-dioxido-1H-benzo[c][1,2,6]thiadiazin-5-yl)oxy)methyl)piperidin-1-yl)(2-(methylamino)pyridin-4-yl)methanone

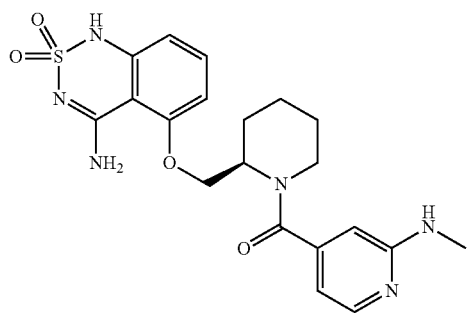 [SMILES: CNc1cc(C(=O)N2CCCC[C@@H]2COc2cccc3c2C(N)=NS(=O)(=O)N3)ccn1]

Prepared as in Example 15 from (R)-2-(((4-amino-2,2-dioxido-1H-benzo[c][1,2,6]thiadiazin-5-yl)oxy)methyl)piperidinium hydrochloride (Example 15a) and 2-(methylamino)isonicotinic acid. $^1$H NMR (400 MHz, DMSO-d$_6$) δ

1.41 (m, 1H), 1.52-1.74 (m, 4H), 1.83 (m, 1H), 2.74 (d, 3H, J=4.6 Hz,), 3.19 (m, 1H), 3.40 (m, 1H), 4.19 (dd, 1H, J=9.9, 3.6 Hz,), 4.65 (t, 1H, J=10.1 Hz,), 5.20 (m, 1H), 6.30 (s, 1H), 6.61 (m, 2H), 6.88 (d, 1H, J=8.5 Hz), 7.46 (t, 1H, J=8.6 Hz,), 7.83 (br s, 1H), 8.01 (d, 1H, J=5.4 Hz,), 8.30 (br s, 1H), 10.93 (s, 1H). MS 445 (MH⁺).

Example 40

(R)-(2-(((4-amino-2,2-dioxido-1H-benzo[c][1,2,6]thiadiazin-5-yl)oxy)methyl)piperidin-1-yl)(2-hydroxypyridin-4-yl)methanone

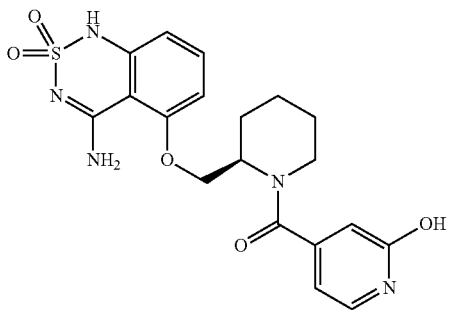 [SMILES: NC1=NS(=O)(=O)Nc2cccc(OC[C@H]3CCCCN3C(=O)c3ccnc(O)c3)c21]

Prepared as in Example 15 from (R)-2-(((4-amino-2,2-dioxido-1H-benzo[c][1,2,6]thiadiazin-5-yl)oxy)methyl)piperidinium hydrochloride (Example 15a) and 2-hydroxyisonicotinic acid. ¹H NMR (400 MHz, DMSO-d₆) δ 1.41 (m, 1H), 1.52-1.74 (m, 4H), 1.81 (m, 1H), 3.22 (m, 1H), 3.43 (m, 1H), 4.19 (dd, 1H, J=10.1, 3.8 Hz), 4.62 (t, 1H, J=10.5 Hz) 5.16 (m, 1H), 6.06 (d, 1H, J=7.0 Hz), 6.23 (s, 1H), 6.61 (d, 1H, J=8.0 Hz,), 6.87 (d, 1H, J=8.7 Hz), 7.45 (m, 2H), 7.75 (br s, 1H), 8.36 (br s, 1H), 10.92 (s, 1H), 11.73 (br s, 1H). MS 432 (MH⁺).

Example 41

(R)-(2-(((4-amino-2,2-dioxido-1H-benzo[c][1,2,6]thiadiazin-5-yl)oxy)methyl)piperidin-1-yl)(3-hydroxypyridin-4-yl)methan one

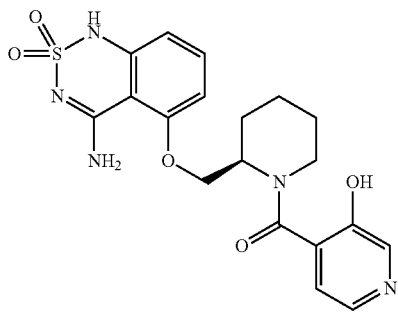 [SMILES: NC1=NS(=O)(=O)Nc2cccc(OC[C@H]3CCCCN3C(=O)c3ccncc3O)c21]

Prepared as in Example 15 from (R)-2-(((4-amino-2,2-dioxido-1H-benzo[c][1,2,6]thiadiazin-5-yl)oxy)methyl)piperidinium hydrochloride (Example 15a) and 3-hydroxyisonicotinic acid. ¹H NMR (400 MHz, DMSO-d₆) δ 1.45 (m, 1H), 1.52-1.74 (m, 4H), 1.84 (m, 1H), 3.19 (m, 2H), 4.18 (dd, 1H, J=10.2, 4.0 Hz), 4.64 (t, 1H, J=10.0 Hz), 5.25 (m, 1H), 6.61 (d, 1H, J=8.2 Hz), 6.87 (d, 1H, J=8.2 Hz), 7.08 (d, 1H, J=5.5 Hz), 7.46 (t, 1H, J=8.2 Hz), 7.84 (br s, 1H), 8.07 (d, 1H, J=5.5 Hz), 8.19 (s, 1H), 8.29 (br s, 1H), 10.28 (s, 1H), 10.9 (br s, 1H). MS 432 (MH⁺).

Example 42

(R)-(2-(((4-amino-2,2-dioxido-1H-benzo[c][1,2,6]thiadiazin-5-yl)oxy)methyl)piperidin-1-yl)(6-methylquinolin-4-yl)methanone

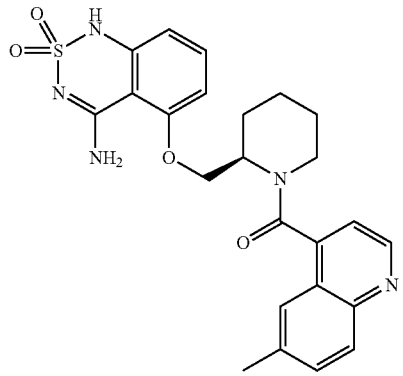 [SMILES: Cc1ccc2nccc(C(=O)N3CCCC[C@@H]3COc3cccc4c3C(N)=NS(=O)(=O)N4)c2c1]

Prepared as in Example 15 from (R)-2-(((4-amino-2,2-dioxido-1H-benzo[c][1,2,6]thiadiazin-5-yl)oxy)methyl)piperidinium hydrochloride (Example 15a) and 6-methylquinoline-4-carboxylic acid. ¹H NMR (400 MHz, DMSO-d₆) δ 1.34-1.53 (m, 2H), 1.59-1.86 (m, 4H), 2.01 (s, 3H), 3.01 (m, 1H), 3.20 (m, 1H), 4.19 (dd, 1H, J=10.1, 3.2 Hz), 4.95 (t, 1H, J=10.6 Hz), 5.46 (m, 1H), 6.67 (d, 1H, J=8.1 Hz), 7.01 (d, 1H, J=8.3 Hz,), 7.34 (s, 1H), 7.48-7.56 (m, 2H), 7.60-7.68 (m, 1H), 7.92 (d, 1H, J=8.7 Hz), 7.99 (br s, 1H), 8.27 (br s, 1H), 8.87 (d, 1H, J=4.4 Hz), 10.94 (s, 1H). MS 480 (MH⁺).

Example 43

(R)-2-(((4-amino-2,2-dioxido-1H-benzo[c][1,2,6]thiadiazin-5-yl)oxy)methyl)piperidin-1-yl)(2-methylpyridin-3-yl)methanone

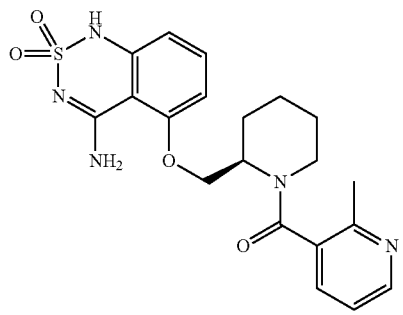 [SMILES: Cc1ncccc1C(=O)N1CCCC[C@@H]1COc1cccc2c1C(N)=NS(=O)(=O)N2]

Prepared as in Example 15 from (R)-2-(((4-amino-2,2-dioxido-1H-benzo[c][1,2,6]thiadiazin-5-yl)oxy)methyl)piperidinium hydrochloride (Example 15a) and 2-methylnicotinic acid. ¹H NMR (400 MHz, DMSO-d₆) δ 1.35 (m, 1H), 1.48-1.81 (m, 4H), 1.86 (m, 1H), 2.24 (s, 3H), 3.12 (m, 1H), 3.24 (m, 1H), 4.16 (m, 1H), 4.77 (t, 1H, J=9.8 Hz), 5.32 (m, 1H), 6.62 (d, 1H, J=8.0 Hz), 6.90 (d, 1H, J=8.3 Hz), 7.27 (m, 1H), 7.47 (t, 1H, J=8.3 Hz), 7.66 (m, 1H), 7.93 (br s, 1H), 8.31 (br s, 1H), 8.47 (dd, 1H, J=5.1, 1.7 Hz), 10.92 (s, 1H). MS 430 (MH⁺).

Example 44

(R)-(2-(((4-amino-2,2-dioxido-1H-benzo[c][1,2,6]thiadiazin-5-yl)oxy)methyl)piperidin-1-yl)(pyridazin-4-yl)methanone

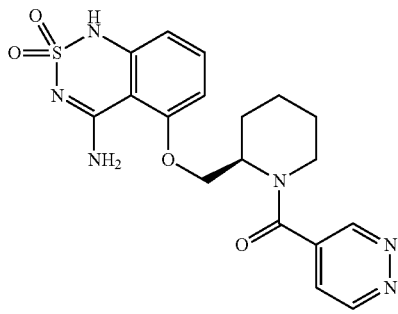 [SMILES: NC1=NS(=O)(=O)Nc2cccc(OC[C@H]3CCCCN3C(=O)c3ccnnc3)c21]

Prepared as in Example 15 from (R)-2-(((4-amino-2,2-dioxido-1H-benzo[c][1,2,6]thiadiazin-5-yl)oxy)methyl)piperidinium hydrochloride (Example 15a) and pyridazine-4-carboxylic acid. $^1$H NMR (400 MHz, DMSO-d$_6$) δ 1.46-1.89 (m, 6H), 2.24 (s, 3H), 3.28 (m, 2H), 4.26 (m, 1H), 4.64 (t, 1H, J=10.1 Hz), 5.29 (m, 1H), 6.62 (d, 1H, J=8.2 Hz), 6.87 (d, 1H, J=8.2 Hz), 7.46 (t, 1H, J=8.2 Hz), 7.69 (dd, 1H, J=5.0, 1.8 Hz), 7.77 (br s, 1H), 8.37 (br s, 1H), 9.26 (m, 1H), 9.35 (d, 1H, J=5.0 Hz), 10.94 (s, 1H). MS 417 (MH⁺).

Example 45

(R)-(2-(((4-amino-2,2-dioxido-1H-benzo[c][1,2,6]thiadiazin-5-yl)oxy)methyl)piperidin-1-yl)(isoquinolin-1-yl)methanone

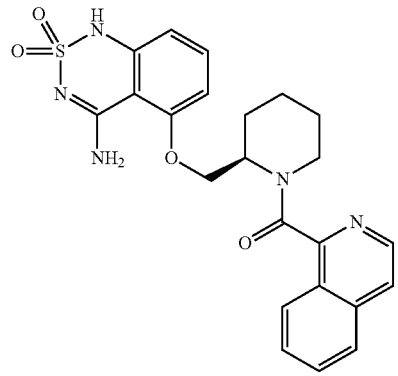 [SMILES: NC1=NS(=O)(=O)Nc2cccc(OC[C@H]3CCCCN3C(=O)c3nccc4ccccc34)c21]

Prepared as in Example 15 from (R)-2-(((4-amino-2,2-dioxido-1H-benzo[c][1,2,6]thiadiazin-5-yl)oxy)methyl)piperidinium hydrochloride (Example 15a) and isoquinoline-1-carboxylic acid. $^1$H NMR (400 MHz, DMSO-d$_6$) δ 1.33 (m, 1H), 1.47 (m, 1H), 1.56-1.74 (m, 2H), 1.81 (m, 1H), 1.93 (m, 1H), 3.00 (m, 1H), 3.21 (m, 1H), 4.26 (dd, 1H, J=10.1, 3.7 Hz), 4.82 (t, 1H, J=10.1 Hz,), 5.45 (m, 1H), 6.66 (d, 1H, J=8.0 Hz,), 6.95 (d, 1H, J=8.5 Hz,), 7.50 (t, 1H, J=8.5 Hz,), 7.61 (m, 1H), 7.74-7.90 (m, 3H), 7.97 (br s, 1H), 8.02 (d, 1H, J=8.0 Hz), 8.28 (br s, 1H), 8.49 (d, 1H, J=5.8 Hz,), 10.94 (s, 1H). MS 466 (MH⁺).

Example 46

(R)-(2-(((4-amino-2,2-dioxido-1H-benzo[c][1,2,6]thiadiazin-5-yl)oxy)methyl)piperidin-1-yl)(2-methylpyridin-4-yl)methanone

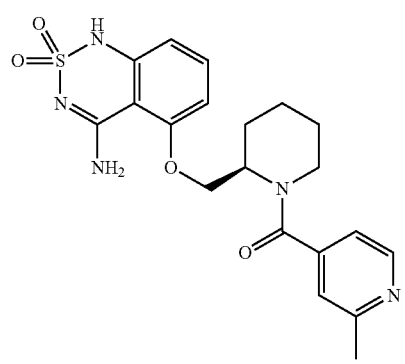 [SMILES: Cc1cc(C(=O)N2CCCC[C@@H]2COc2cccc3c2C(N)=NS(=O)(=O)N3)ccn1]

Prepared as in Example 15 from (R)-2-(((4-amino-2,2-dioxido-1H-benzo[c][1,2,6]thiadiazin-5-yl)oxy)methyl)piperidinium hydrochloride (Example 15a) and 2-methylisonicotinic acid. $^1$H NMR (400 MHz, CD$_3$OD) δ 1.51-2.00 (m, 6H), 2.57 (s, 3H), 3.27 (m, 1H), 3.45 (m, 1H), 4.28 (m, 1H), 4.73 (t, 1H, J=10.5 Hz), 5.42 (m, 1H), 6.66 (d, 1H, J=8.1 Hz), 6.87 (d, 1H, J=8.1 Hz,), 7.22 (m, 1H), 7.26 (s, 1H), 7.48 (t, 1H, J=8.6 Hz), 8.50 (d, 1H, J=4.8 Hz). MS 430 (MH⁺).

Example 47

(S)-1-(2-(((4-amino-2,2-dioxido-1H-benzo[c][1,2,6]thiadiazin-5-yl)oxy)methyl)piperidin-1-yl)-3-methylbutan-1-one

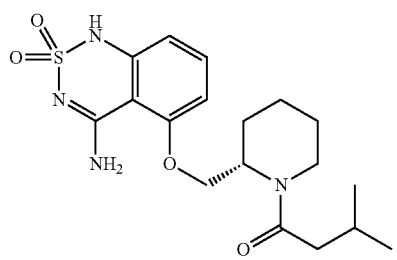 [SMILES: CC(C)CC(=O)N1CCCC[C@H]1COc1cccc2c1C(N)=NS(=O)(=O)N2]

Prepared as in Example 5 from (S)-2-sulfamoylamino-6-((1-(3-methylbutanoyl)piperidin-2-yl)methoxy)benzonitrile (Example 47a) (41% yield). $^1$H NMR (400 MHz, DMSO-d$_6$) δ 0.86 (d, 3H, J=6.9 Hz), 0.88 (d, 3H, J=6.9 Hz), 1.35 (m, 1H), 1.46-1.68 (m, 4H), 1.75 (m, 1H), 1.99 (sept, 1H, J=6.9 Hz), 2.22 (d, 2H, J=6.8 Hz), 3.15 (m, 1H), 3.78 (m, 1H), 4.08 (dd, 1H, J=10.1, 4.1 Hz), 4.53 (t, 1H, J=9.9 Hz), 5.17 (m, 1H), 6.59

(d, 1H, J=8.2 Hz), 6.84 (d, 1H, J=8.2 Hz), 7.44 (t, 1H, J=8.7 Hz), 7.81 (br. s, 1H) 8.22 (br. s, 1H), 10.88 (s, 1H). MS 395 (MH+).

Example 47a (S)-2-sulfamoylamino-6-((1-(3-methylbutanoyl)piperidin-2-yl)methoxy)benzonitrile

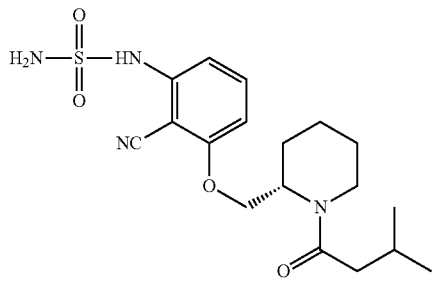 [SMILES: CC(C)CC(=O)N1CCCC[C@H]1COc1cccc(NS(N)(=O)=O)c1C#N]

Prepared as in Example 5a from (S)-2-amino-6-((1-(3-methylbutanoyl)piperidin-2-yl)methoxy)benzonitrile (Example 47b) (100% yield). MS 395 (MH+).

Example 47b (S)-2-amino-6-((1-(3-methylbutanoyl)piperidin-2-yl)methoxy)benzonitrile

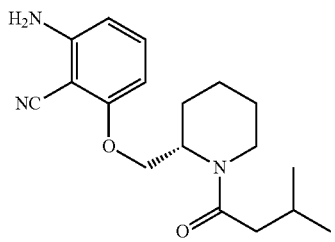

Prepared as in Example 2c from (S)-2-((1-(3-methylbutanoyl)piperidin-2-yl)methoxy)-6-nitrobenzonitrile (Example 47c) (96% yield). MS 316 (MH).

Example 47c (S)-2-((1-(3-methylbutanoyl)piperidin-2-yl)methoxy)-6-nitrobenzonitrile

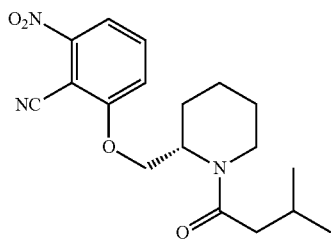 [SMILES: CC(C)CC(=O)N1CCCC[C@H]1COc1cccc([N+](=O)[O-])c1C#N]

Prepared as in Example 34d from (S)-2-nitro-6-(piperidin-2-ylmethoxy)benzonitrile hydrochloride (Example 47d) and isovaleryl chloride (40% yield). MS 346 (MH+).

Example 47d (S)-2-nitro-6-(piperidin-2-ylmethoxy)benzonitrile hydrochloride

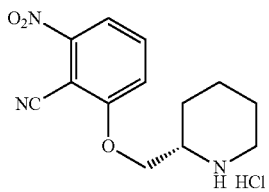 [SMILES: N#Cc1c(OC[C@@H]2CCCCN2)cccc1[N+](=O)[O-] ; Cl]

Prepared as in Example 1d from (S)-tert-butyl 2-((2-cyano-3-nitrophenoxy)methyl)piperidine-1-carboxylate (Example 47e). MS 262 (MH+—HCl).

Example 47e (S)-tert-butyl 2-((2-cyano-3-nitrophenoxy)methyl)piperidine-1-carboxylate

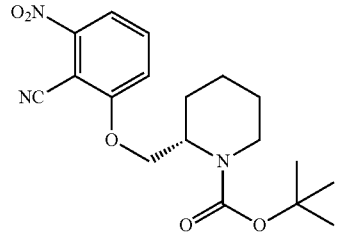

Prepared as in Example 1e from (S)-tert-butyl 2-(hydroxymethyl)piperidine-1-carboxylate (Example 47l) and 2,6-dinitrobenzonitrile (91% yield). MS 262 (MH+-boc).

Example 47f (S)-tert-butyl 2-(hydroxymethyl)piperidine-1-carboxylate

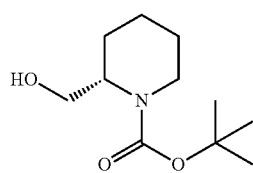

Prepared as in Example 15f from (S)-1-(tert-butoxycarbonyl)piperidine-2-carboxylic acid. MS116 (MH+-boc).

Example 48 sodium (S)-4-amino-5-((1-(3-methylbutanoyl)piperidin-3-yl)methoxy)benzo[c][1,2,6]thiadiazin-1-ide 2,2-dioxide

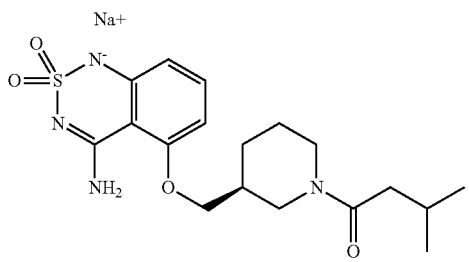 [SMILES: [Na+] ; CC(C)CC(=O)N1CCC[C@H](COc2cccc3c2C(N)=NS(=O)(=O)[N-]3)C1]

To a suspension of (S)-1-(3-(((4-amino-2,2-dioxido-1H-benzo[c][1,2,6]thiadiazin-5-yl)oxy)methyl)piperidin-1-yl)-3-methylbutan-1-one (2.0 g, 5.07 mmol) (Example 5) in water (25 mL), was added NaHCO$_3$ (425 mg, 5.07 mmol). The reaction was heated to reflux until complete dissolution of solid material occurred, and then concentrated under reduced pressure. The resulting residue was dissolved in water and lyophilized to give the title compound as a beige solid (2.1 g, 100%). $^1$H NMR (400 MHz, DMSO-d$_6$) δ 0.78-0.96 (m, 6H), 1.21-1.50 (m, 2H), 1.55-1.75 (m, 1H), 1.78-2.07 (m, 3H), 2.10-2.25 (m, 2H). 2.60-2.78 (m, 1H), 2.88-3.15 (m, 2H), 3.65-3.97 (m, 3H), 4.00-4.41 (m, 1H), 5.97 (t, 1H, J=8.0 Hz), 6.21 (d, 1H, J=8.8 Hz), 6.57 (br. s, 2H). 6.95 (d. 1H, J=8.0, 3.2 Hz). MS 395 (MH$^+$-Na).

Example 49

1-(3-(hydroxymethyl)piperidin-1-yl)-3-methylbutan-1-one

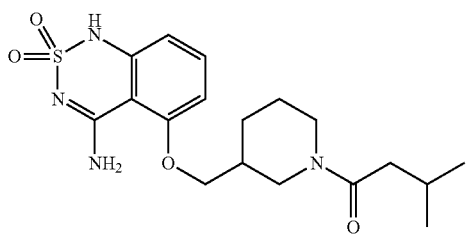 [SMILES: CC(C)CC(=O)N1CCCC(COc2cccc3c2C(N)=NS(=O)(=O)N3)C1]

Prepared as in Example 5 from 2-sulfamoylamino-6-((1-(3-methylbutanoyl)piperidin-3-yl)methoxy)benzonitrile (Example 49a) (89% yield). $^1$H NMR (400 MHz, DMSO-d$_6$, 80° C.) δ 0.88 (d, 6H, J=6.3 Hz), 1.40 (t, 2H, J=9.2, 9.2 Hz), 1.63-1.73 (m, 1H), 1.80-1.90 (m, 1H), 1.90-2.20 (m, 4H), 2.88-2.98 (m, 2H). 3.58-4.25 (m, 4H), 6.64 (dd, 1H, J=8.2, 1.1 Hz). 6.74 (d, 1H, J=8.4 Hz), 7.43 (t, 1H, J=8.2, 8.2 Hz), 7.79 (br s, 1H), 7.95 (br s, 1H). 10.68 (s, 1H). MS 395 (MH$^+$).

Example 49a 2-sulfamoylamino-6-((1-(3-methylbutanoyl)piperidin-3-yl)methoxy)benzonitrile

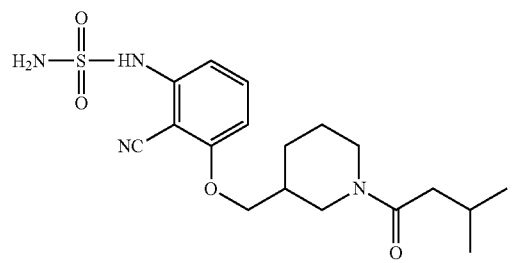 [SMILES: CC(C)CC(=O)N1CCCC(COc2cccc(NS(N)(=O)=O)c2C#N)C1]

Prepared as in Example 5a from 2-amino-6-((1-(3-methylbutanoyl)piperidin-3-yl)methoxy)benzonitrile (Example 49b) (98% yield). MS 395 (MH$^+$)

Example 49b 2-amino-6-((1-(3-methylbutanoyl)piperidin-3-yl)methoxy)benzonitrile

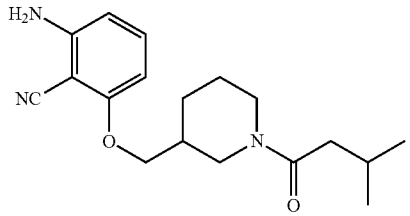 [SMILES: CC(C)CC(=O)N1CCCC(COc2cccc(N)c2C#N)C1]

Prepared as in Example 34b from 1-(3-(hydroxymethyl)piperidin-1-yl)-3-methylbutan-1-one (Example 49c). MS 316 (MH$^+$).

Example 49c 1-(3-(hydroxymethyl)piperidin-1-yl)-3-methylbutan-1-one

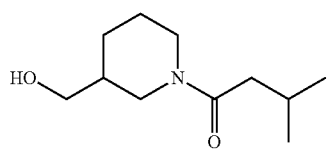

To a solution of piperidin-3-ylmethanol (10 g, 86.83 mmol) in water (25 mL), was added a solution of NaOH (13.89 g, 347.31 mmol) in water (25 mL) dropwise at 0° C. The mixture was stirred for 15 minutes, after which time, a solution of 3-methylbutanoyl chloride (20.94 g, 173.66 mmol) in THF (25 mL) was added dropwise with vigorous stirring. The reaction was slowly warmed to room temperature and, upon completion was diluted with Et$_2$O (500 mL)

was added with vigouous stirring. After 15 minutes, the phases were separated, and the aqueous phase was extracted with Et$_2$O (2×). The combined organic extracts were washed with brine, dried over Na$_2$SO$_4$, concentrated under reduced pressure and flash chromatographed on silica gel (0-100% EtOAc in hexanes) to give the title compound as a colorless oil (16.27 g, 94%). MS 200 (MH$^+$).

Example 50

(S)-5-(4-(3-(((4-amino-2,2-dioxido-1H-benzo[c][1,2,6]thiadiazin-5-yl)oxy)methyl)piperidin-1-yl)-2-methyl-4-oxobutan-2-yl)-2-methoxyphenyl ethanesulfonate

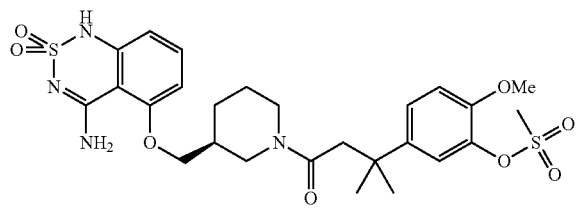 [SMILES: COc1ccc(C(C)(C)CC(=O)N2CCC[C@H](COc3cccc4c3C(N)=NS(=O)(=O)N4)C2)cc1OS(C)(=O)=O]

Prepared as in Example 2 from (S)-4-amino-5-(piperidin-3-ylmethoxy)-1H-benzo[c][1,2,6]thiadiazine 2,2-dioxide hydrochloride (Example 2a) and 3-(4-methoxy-3-((methylsulfonyl)oxy)phenyl)-3-methylbutanoic acid (Example 50a) (23% yield). $^1$H NMR (400 MHz, DMSO-d$_6$) δ 1.17-1.26 (m, 1H), 1.30-1.34 (m, 7H), 1.46-1.57 (m, 1H), 1.74-1.76 (m, 1H), 1.90 (brs, 1H), 2.56-2.93 (m, 4H), 3.28-3.29 (m, 3H), 3.49-3.61 (m, 1H), 3.68 (s, 1.5H), 3.77 (s, 1.5H), 3.89-4.03 (m, 3H), 6.58-6.63 (m, 1H), 6.69-6.75 (m, 1H), 6.98-7.05 (m, 1H), 7.13-7.28 (m, 2H), 7.44-7.46 (m, 1H), 7.72-7.74 (m, 1H), 8.33-8.38 (m, 1H). 10.95 (s, 1H). MS 595 (MH$^+$).

Example 50a 3-(4-methoxy-3-((methylsulfonyl)oxy)phenyl)-3-methylbutanoic acid

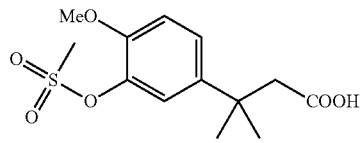 [SMILES: COc1ccc(C(C)(C)CC(=O)O)cc1OS(C)(=O)=O]

To a mixture of 2-methoxyphenyl methanesulfonate (Example 50b) (82 g, 406.4 mmol) and 3-methylbut-2-enoic acid (20.3 g, 203.2 mmol), was added concentrate sulfuric acid (11 mL, 96%, 206.3 mmol) at 0° C. The reaction mixture was stirred at 0° C. for 15 min, then heated to 70° C. and stirred under nitrogen overnight. Upon completion, the reaction was cooled to room temperature, quenched with ice water (500 mL) and extracted with ether (1×). The phases were separated, and the organic layer was washed with 2N NaOH (1×). The combined aqueous layers were acidified to pH 1 with 12N HCl at 0° C. and extracted with ether (1×). The organic layer was washed with brine, dried over Na$_2$SO$_4$, filtered and concentrated under reduced pressure to give the title compound as a red-brown oil (14.4 g, contained <20% 3-methylbut-2-enoic acid) $^1$H NMR (400 MHz, DMSO-d$_4$) δ 1.33 (s, 6H), 2.53 (s, 2H), 3.31 (s, 3H), 3.79 (s, 3H). 7.08-7.31 (m, 3H), 11.87 (s, 1H).

Example 50b 2-methoxyphenyl methanesulfonate

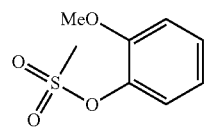

To a solution of 2-methoxyphenol (50 g, 402.8 mmol) and triethylamine (84.2 mL, 604.2 mmol) in anhydrous dichloromethane (300 mL), was added methanesulfonyl chloride (37.6 mL, 483.3 mmol) at 0° C. under nitrogen. The reaction mixture was stirred at 0° C. for 2 hours, quenched with ice water (250 mL) and transferred to a separatory funnel. The organic phase was washed with a solution of NaOH (8 g) in ice water (200 mL), brine, dried over Na$_2$SO$_4$, filtered and concentrated under reduced pressure to give the title compound as a colorless liquid (81.44 g, 100%). $^1$H NMR (400 MHz, DMSO-d$_6$) δ 3.32 (s, 3H), 3.83 (s, 3H), 6.96-7.0 (m, 1H), 7.18-7.2 (m, 1H), 7.27-7.33 (m, 2H).

Example 51

(S)-1-(3-(((4-amino-2,2-dioxido-1H-benzo[c][1,2,6]thiadiazin-5-yl)oxy)methyl)piperidin-1-yl)-3-(3-hydroxy-4-methoxyphenyl)-3-methylbutan-1-one

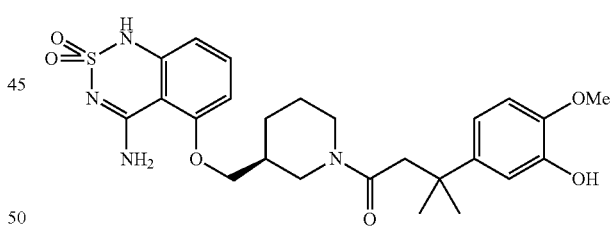

To a solution of (S)-5-(4-(3-(((4-amino-2,2-dioxido-1H-benzo[c][1,2,6]thiadiazin-5-yl)oxy)methyl)piperidin-1-yl)-2-methyl-4-oxobutan-2-yl)-2-methoxyphenyl methanesulfonate (200 mg, 0.34 mmol) (Example 50) in EtOH (20 mL) was added 2N aqueous NaOH (0.34 mL). The reaction mixture was stirred at 85° C. for 3 hours, cooled to 0° C. and neutralized 2N HCl. The solution was concentrated under reduced pressure and purified by preparative HPLC (10-90% acetonitrile in water) to give the title compound (78 mg, 45%). $^1$H NMR (400 MHz. DMSO-d$_6$) δ 1.17-1.32 (m, 8H), 1.43-1.64 (m, 2H), 1.74-1.8 (m, 1H), 2.52-2.67 (m, 2H), 2.77-2.83 (m, 0.5H), 3.51-3.54 (m, 0.5H). 3.65-3.68 (m, 4H), 3.73-3.84 (m, 2H), 4.1-4.18 (m, 1H), 5.9-5.94 (m, 1H), 6.15-

6.19 (m, 1H), 6.5 (brs, 1H), 6.66-6.78 (m, 3H), 6.89-6.95 (m, 1H), 8.71 (s, 1H). MS 517 (MH+).

Example 52

(S)-2-(1H-imidazol-1-yl)pyridin-4-yl)(3-(((4-amino-2,2-dioxido-1H-benzo[c][1,2,6]thiadiazin-5-yl)oxy)methyl)piperidin-1-yl)methanone

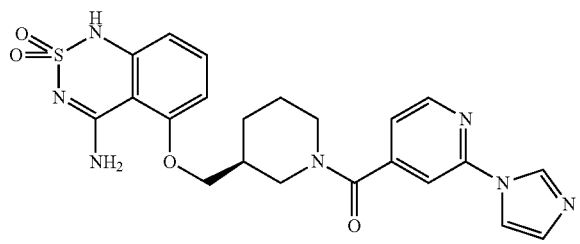 [SMILES: NC1=NS(=O)(=O)Nc2cccc(OC[C@H]3CCCN(C(=O)c4ccnc(-n5ccnc5)c4)C3)c21]

Prepared as in Example 2 from (S)-5-(piperidin-3-yl-methoxy)-1H-benzo[c][1,2,6]thiadiazin-4-amine-2,2-dioxide hydrochloride (Example 2a) and 2-(1H-imidazol-1-yl)isonicotinic acid (Example 52a) (42% yield). ¹H NMR (400 MHz, DMSO-d₆, 80° C.) δ 1.42-1.60 (m, 2H), 1.71 (m, 1H), 1.93 (m, 1H), 2.22 (m, 1H), 3.11 (m, 1H), 3.34-3.75 (m, 1H), 3.92-4.42 (m, 2H), 6.63 (m, 1H), 6.74 (br s, 1H), 7.11 (s, 1H), 7.29 (m, 1H), 7.42 (m, 1H), 7.52-8.28 (br s, 2H), 7.76 (m, 1H), 7.93 (m, 1H), 8.52 (m, 2H), 10.71 (br s, 1H). MS 482 (MH+).

Example 52a 2-(1H-imidazol-1-yl)isonicotinic acid

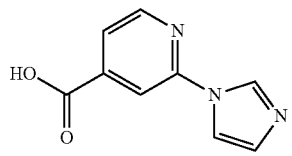 [SMILES: O=C(O)c1ccnc(-n2ccnc2)c1]

To a solution of 2-bromoisonicotinic acid (1.87 g. 9.26 mmol), 1H-imidazole (573 mg, 8.42 mmol) and Cs₂CO₃ (6.03 g, 18.5 mmol) in DMSO (18.6 mL), was added CuI (176 mg, 0.926 mmol). The mixture was heated to 125° C., stirred for 18 hours, cooled to room temperature, filtered and purified by preparative HPLC (10-90% acetonitrile in water) to give the title compound as a light pink solid (1.72 g, 98%). MS 190 (MH+).

Example 53

(R)-(2-(H-imidazol-1-yl)pyridin-4-yl)(2-(((4-amino-2,2-dioxido-1H-benzo[c][1,2,6]thiadiazin-5-yl)oxy)methyl)piperidin-1-yl)methanone

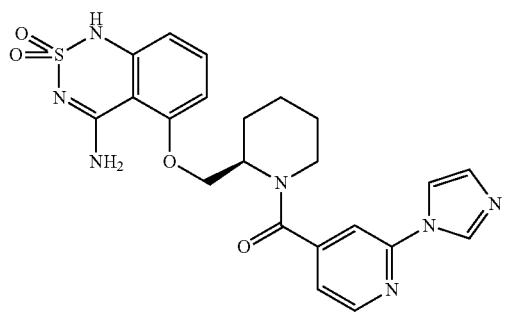 [SMILES: NC1=NS(=O)(=O)Nc2cccc(OC[C@H]3CCCCN3C(=O)c3ccnc(-n4ccnc4)c3)c21]

Prepared as in Example 15 from (R)-2-(((4-amino-2,2-dioxido-1H-benzo[c][1,2,6]thiadiazin-5-yl)oxy)methyl)piperidinium hydrochloride (Example 15a) and 2-(1H-imidazol-1-yl)isonicotinic acid (Example 52a) (22% yield). ¹H NMR (400 MHz, DMSO-d₆) δ 1.47-1.91 (m, 6H), 3.02 (m, 1H), 3.35 (m, 1H), 4.28 (dd 1H, J=10.4, 4.4 Hz), 4.65 (t, 1H, J=10.4 Hz), 5.24 (m, 1H), 6.63 (d. 1H, J=8.2 Hz), 6.90 (d, 1H, J=8.5 Hz). 7.31 (d. 1H, J=5.2 Hz), 7.48 (d, 1H, J=8.2 Hz), 7.77 (s, 1H). 7.84 (br s. 1H), 8.00 (s, 1H). 8.44 (br s, 1H), 8.52-8.59 (m, 2H), 10.95 (br s, 1H). MS 482 (MH+).

The compounds in Table A below were synthesized following the procedures described above.

TABLE A

| Compound No. | Compound | MS (MH+) |
|---|---|---|
| A-1 | ![structure] 1-(3-(((4-amino-2,2-dioxido-1H-benzo[c][1,2,6]thiadiazin-5-yl)oxy)methyl)piperidin-1-yl)butan-1-one | 381 |

TABLE A-continued

| Compound No. | Compound | MS (MH+) |
|---|---|---|
| A-2 | 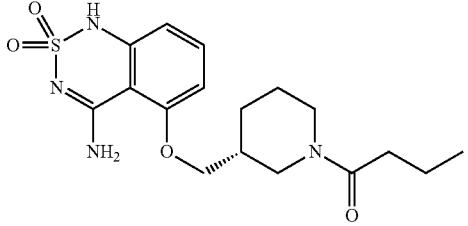 [SMILES: CCCC(=O)N1CCC[C@@H](COc2cccc3c2C(N)=NS(=O)(=O)N3)C1]<br>(R)-1-(3-(((4-amino-2,2-dioxido-1H-benzo[c][1,2,6]thiadiazin-5-yl)oxy)methyl)piperidin-1-yl)butan-1-one | 381 |
| A-3 | 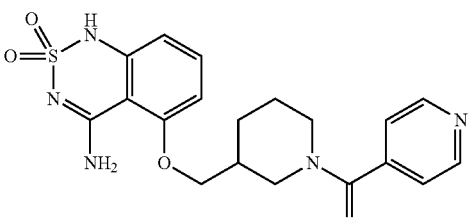<br>(3-(((4-amino-2,2-dioxido-1H-benzo[c][1,2,6]thiadiazin-5-yl)oxy)methyl)piperidin-1-yl)(pyridin-4-yl)methanone | 416 |
| A-4 | 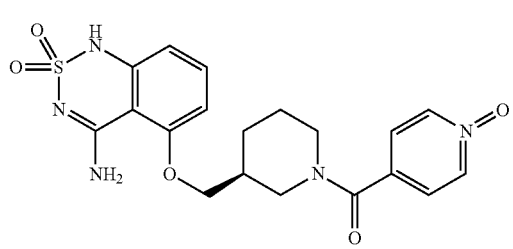 [SMILES: NC1=NS(=O)(=O)Nc2cccc(OC[C@H]3CCCN(C(=O)c4cc[n+]([O-])cc4)C3)c21]<br>(S)-4-(3-(((4-amino-2,2-dioxido-1H-benzo[c][1,2,6]thiadiazin-5-yl)oxy)methyl)piperidine-1-carbonyl)pyridine 1-oxide | 432 |
| A-5 | 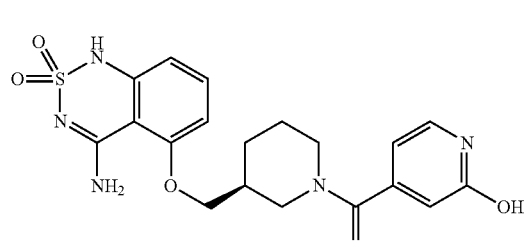<br>(S)-(3-(((4-amino-2,2-dioxido-1H-benzo[c][1,2,6]thiadiazin-5-yl)oxy)methyl)piperidin-1-yl)(2-hydroxypyridin-4-yl)methanone | 432 |

TABLE A-continued

| Compound No. | Compound | MS (MH+) |
|---|---|---|
| A-6 | (S)-(3-(((4-amino-2,2-dioxido-1H-benzo[c][1,2,6]thiadiazin-5-yl)oxy)methyl)piperidin-1-yl)(3-methylpyridin-4-yl)methanone | 430 |
| A-7 | (S)-(3-(((4-amino-2,2-dioxido-1H-benzo[c][1,2,6]thiadiazin-5-yl)oxy)methyl)piperidin-1-yl)(3,4-dihydroxyphenyl)methanone | 447 |
| A-8 | (S)-1-(3-(((4-amino-2,2-dioxido-1H-benzo[c][1,2,6]thiadiazin-5-yl)oxy)methyl)piperidin-1-yl)-2-methylpropan-1-one | 381 |
| A-9 | (S)-(3-(((4-amino-2,2-dioxido-1H-benzo[c][1,2,6]thiadiazin-5-yl)oxy)methyl)piperidin-1-yl)(cyclopropyl)methanone | 379 |

TABLE A-continued

| Compound No. | Compound | MS (MH+) |
|---|---|---|
| A-10 | 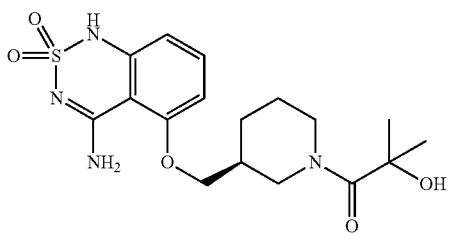 [SMILES: CC(C)(O)C(=O)N1CCC[C@H](COc2cccc3c2C(N)=NS(=O)(=O)N3)C1]<br>(S)-1-(3-(((4-amino-2,2-dioxido-1H-benzo[c][1,2,6]thiadiazin-5-yl)oxy)methyl)piperidin-1-yl)-2-hydroxy-2-methylpropan-1-one | 397 |
| A-11 | 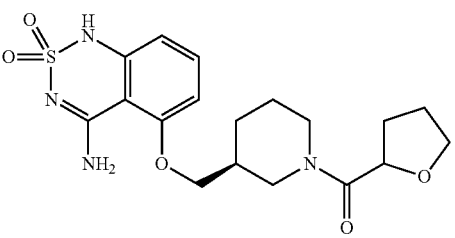<br>((S)-3-(((4-amino-2,2-dioxido-1H-benzo[c][1,2,6]thiadiazin-5-yl)oxy)methyl)piperidin-1-yl)(tetrahydrofuran-2-yl)methanone | 409 |
| A-12 | 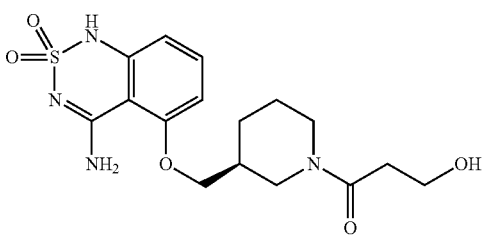 [SMILES: NC1=NS(=O)(=O)Nc2cccc(OC[C@H]3CCCN(C(=O)CCO)C3)c21]<br>(S)-1-(3-(((4-amino-2,2-dioxido-1H-benzo[c][1,2,6]thiadiazin-5-yl)oxy)methyl)piperidin-1-yl)-3-hydroxypropan-1-one | 383 |
| A-13 | 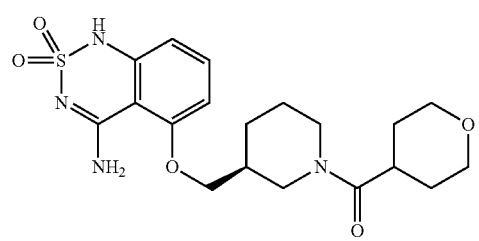 [SMILES: NC1=NS(=O)(=O)Nc2cccc(OC[C@H]3CCCN(C(=O)C4CCOCC4)C3)c21]<br>(S)-(3-(((4-amino-2,2-dioxido-1H-benzo[c][1,2,6]thiadiazin-5-yl)oxy)methyl)piperidin-1-yl)(tetrahydro-2H-pyran-4-yl)methanone | 423 |

TABLE A-continued

| Compound No. | Compound | MS (MH+) |
|---|---|---|
| A-14 | 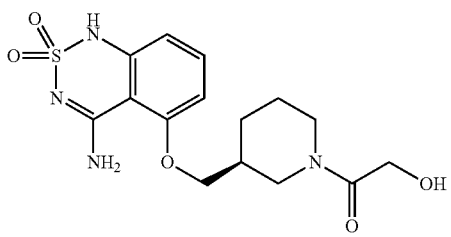 [SMILES: NC1=NS(=O)(=O)Nc2cccc(OC[C@H]3CCCN(C(=O)CO)C3)c21]<br>(S)-1-(3-(((4-amino-2,2-dioxido-1H-benzo[c][1,2,6]thiadiazin-5-yl)oxy)methyl)piperidin-1-yl)-2-hydroxyethanone | 369 |
| A-15 | 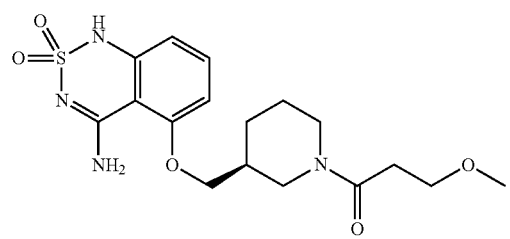 [SMILES: COCCC(=O)N1CCC[C@H](COc2cccc3c2C(N)=NS(=O)(=O)N3)C1]<br>(S)-1-(3-(((4-amino-2,2-dioxido-1H-benzo[c][1,2,6]thiadiazin-5-yl)oxy)methyl)piperidin-1-yl)-3-methoxy-propan-1-one | 397 |
| A-16 | 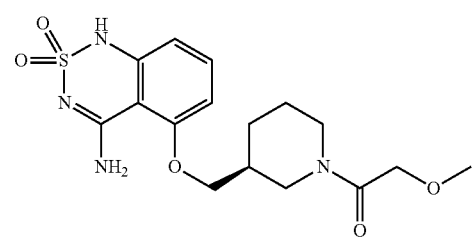 [SMILES: COCC(=O)N1CCC[C@H](COc2cccc3c2C(N)=NS(=O)(=O)N3)C1]<br>(S)-1-(3-(((4-amino-2,2-dioxido-1H-benzo[c][1,2,6]thiadiazin-5-yl)oxy)methyl)piperidin-1-yl)-2-methoxyethanone | 383 |
| A-17 | 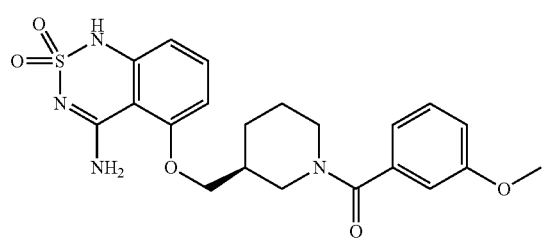 [SMILES: COc1cccc(C(=O)N2CCC[C@H](COc3cccc4c3C(N)=NS(=O)(=O)N4)C2)c1]<br>(S)-(3-(((4-amino-2,2-dioxido-1H-benzo[c][1,2,6]thiadiazin-5-yl)oxy)methyl)piperidin-1-yl)(3-methoxyphenyl)methanone | 445 |

TABLE A-continued

| Compound No. | Compound | MS (MH+) |
|---|---|---|
| A-18 | 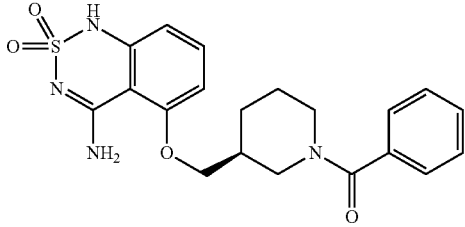 [SMILES: NC1=NS(=O)(=O)Nc2cccc(OC[C@H]3CCCN(C(=O)c4ccccc4)C3)c21]<br>(S)-(3-(((4-amino-2,2-dioxido-1H-benzo[c][1,2,6]thiadiazin-5-yl)oxy)methyl)piperidin-1-yl)(phenyl)methanone | 415 |
| A-19 | 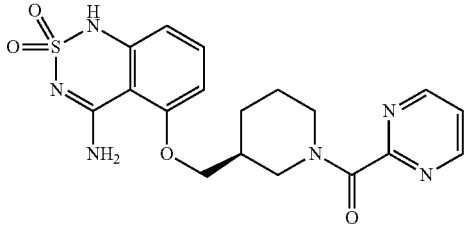 [SMILES: NC1=NS(=O)(=O)Nc2cccc(OC[C@H]3CCCN(C(=O)c4ncccn4)C3)c21]<br>(S)-(3-(((4-amino-2,2-dioxido-1H-benzo[c][1,2,6]thiadiazin-5-yl)oxy)methyl)piperidin-1-yl)(pyrimidin-2-yl)methanone | 417 |
| A-20 | 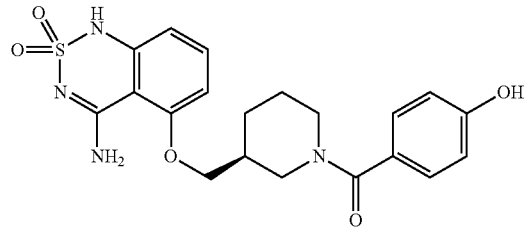 [SMILES: NC1=NS(=O)(=O)Nc2cccc(OC[C@H]3CCCN(C(=O)c4ccc(O)cc4)C3)c21]<br>(S)-(3-(((4-amino-2,2-dioxido-1H-benzo[c][1,2,6]thiadiazin-5-yl)oxy)methyl)piperidin-1-yl)(4-hydroxyphenyl)methanone | 431 |
| A-21 | 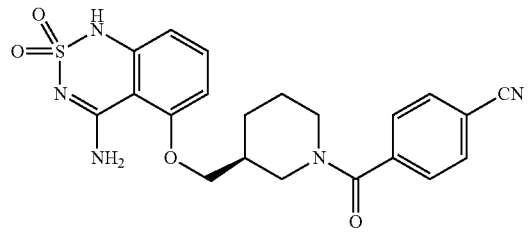 [SMILES: N#Cc1ccc(C(=O)N2CCC[C@H](COc3cccc4c3C(N)=NS(=O)(=O)N4)C2)cc1]<br>(S)-4-(3-(((4-amino-2,2-dioxido-1H-benzo[c][1,2,6]thiadiazin-5-yl)oxy)methyl)piperidine-1-carbonyl)benzonitrile | 440 |

TABLE A-continued

| Compound No. | Compound | MS (MH+) |
|---|---|---|
| A-22 | (S)-(3-(((4-amino-2,2-dioxido-1H-benzo[c][1,2,6]thiadiazin-5-yl)oxy)methyl)piperidin-1-yl)(pyrimidin-5-yl)methanone | 417 |
| A-23 | (S)-(3-(((4-amino-2,2-dioxido-1H-benzo[c][1,2,6]thiadiazin-5-yl)oxy)methyl)piperidin-1-yl)(2,3-dihydrobenzo[b][1,4]dioxin-6-yl)methanone | 473 |
| A-24 | 2-(((4-amino-2,2-dioxido-1H-benzo[c][1,2,6]thiadiazin-5-yl)oxy)methyl)-N-propylpiperidine-1-carboxamide | 396 |
| A-25 | 2-(((4-amino-2,2-dioxido-1H-benzo[c][1,2,6]thiadiazin-5-yl)oxy)methyl)-N-(tert-butyl)piperidine-1-carboxamide | 410 |

TABLE A-continued

| Compound No. | Compound | MS (MH+) |
|---|---|---|
| A-26 | (R)-2-(((4-amino-2,2-dioxido-1H-benzo[c][1,2,6]thiadiazin-5-yl)oxy)methyl)-N-ethylpiperidine-1-carboxamide | 382 |
| A-27 | (S)-2-(((4-amino-2,2-dioxido-1H-benzo[c][1,2,6]thiadiazin-5-yl)oxy)methyl)-N-ethylpiperidine-1-carboxamide | 382 |
| A-28 | 3-(((4-amino-2,2-dioxido-1H-benzo[c][1,2,6]thiadiazin-5-yl)oxy)methyl)-N-butylpiperidine-1-carboxamide | 410 |
| A-29 | 3-(((4-amino-2,2-dioxido-1H-benzo[c][1,2,6]thiadiazin-5-yl)oxy)methyl)-N-(tert-butyl)piperidine-1-carboxamide | 410 |

TABLE A-continued

| Compound No. | Compound | MS (MH+) |
|---|---|---|
| A-30 | (R)-(2-(((4-amino-2,2-dioxido-1H-benzo[c][1,2,6]thiadiazin-5-yl)oxy)methyl)piperidin-1-yl)(2,5-dihydroxyphenyl)methanone | 447 |
| A-31 | 1-(2-(((4-amino-2,2-dioxido-1H-benzo[c][1,2,6]thiadiazin-5-yl)oxy)methyl)piperidin-1-yl)butan-1-one | 381 |
| A-32 | (R)-1-(2-(((4-amino-2,2-dioxido-1H-benzo[c][1,2,6]thiadiazin-5-yl)oxy)methyl)piperidin-1-yl)butan-1-one | 381 |
| A-33 | (R)-1-(2-(((4-amino-2,2-dioxido-1H-benzo[c][1,2,6]thiadiazin-5-yl)oxy)methyl)piperidin-1-yl)ethanone | 353 |

TABLE A-continued
| Compound No. | Compound | MS (MH+) |
|---|---|---|
| A-34 | 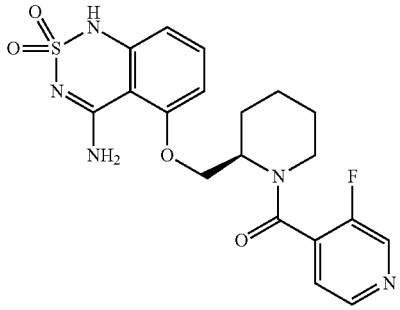(R)-(2-(((4-amino-2,2-dioxido-1H-benzo[c][1,2,6]thiadiazin-5-yl)oxy)methyl)piperidin-1-yl)(3-fluoropyridin-4-yl)methanone | 434 |
| A-35 | 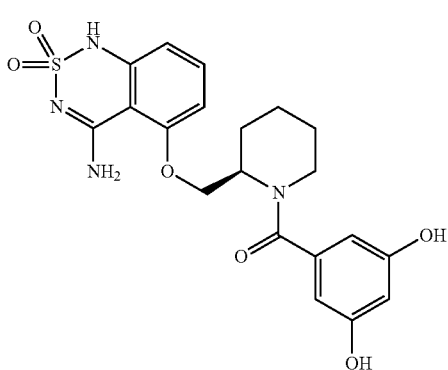 [SMILES: NC1=NS(=O)(=O)Nc2cccc(OC[C@H]3CCCCN3C(=O)c3cc(O)cc(O)c3)c21](R)-(2-(((4-amino-2,2-dioxido-1H-benzo[c][1,2,6]thiadiazin-5-yl)oxy)methyl)piperidin-1-yl)(3,5-dihydroxyphenyl)methanone | 447 |
| A-36 | 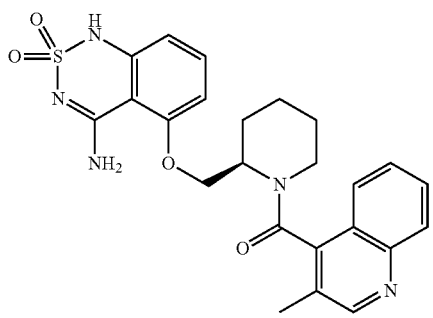 [SMILES: Cc1cnc2ccccc2c1C(=O)N1CCCC[C@@H]1COc1cccc2c1C(N)=NS(=O)(=O)N2](R)-(2-(((4-amino-2,2-dioxido-1H-benzo[c][1,2,6]thiadiazin-5-yl)oxy)methyl)piperidin-1-yl)(3-methylquinolin-4-yl)methanone | 480 |

TABLE A-continued

| Compound No. | Compound | MS (MH+) |
|---|---|---|
| A-37 | 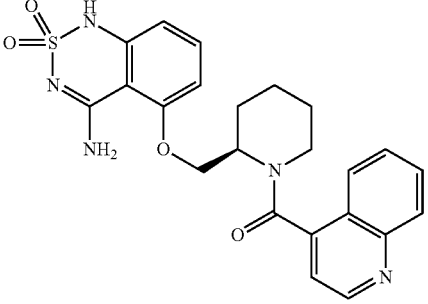 [SMILES: NC1=NS(=O)(=O)Nc2cccc(OC[C@H]3CCCCN3C(=O)c3ccnc4ccccc34)c21]<br>(R)-(2-(((4-amino-2,2-dioxido-1H-benzo[c][1,2,6]thiadiazin-5-yl)oxy)methyl)piperidin-1-yl)(quinolin-4-yl)methanone | 466 |
| A-38 | 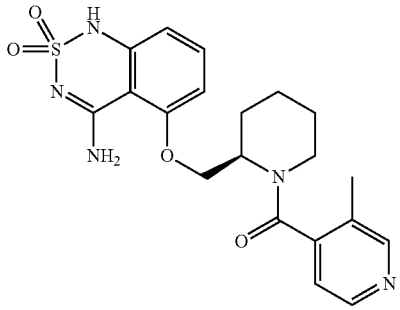 [SMILES: Cc1cnccc1C(=O)N1CCCC[C@@H]1COc1cccc2c1C(N)=NS(=O)(=O)N2]<br>(R)-(2-(((4-amino-2,2-dioxido-1H-benzo[c][1,2,6]thiadiazin-5-yl)oxy)methyl)piperidin-1-yl)(3-methylpyridin-4-yl)methanone | 430 |
| A-39 | 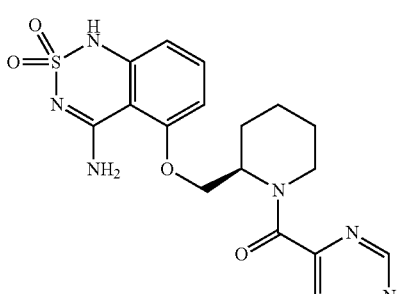<br>(R)-(2-(((4-amino-2,2-dioxido-1H-benzo[c][1,2,6]thiadiazin-5-yl)oxy)methyl)piperidin-1-yl)(pyrimidin-4-yl)methanone | 417 |
| A-40 | 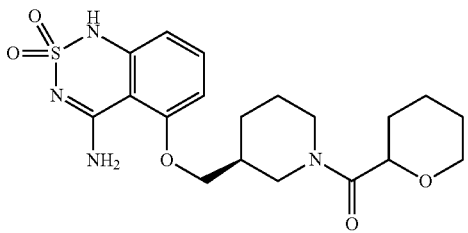 [SMILES: NC1=NS(=O)(=O)Nc2cccc(OC[C@H]3CCCN(C(=O)C4CCCCO4)C3)c21]<br>((S)-3-(((4-amino-2,2-dioxido-1H-benzo[c][1,2,6]thiadiazin-5-yl)oxy)methyl)piperidin-1-yl)(tetrahydro-2H-pyran-2-yl)methanone | 423 |

TABLE A-continued

| Compound No. | Compound | MS (MH+) |
|---|---|---|
| A-41 | (S)-1-(3-(((4-amino-2,2-dioxido-1H-benzo[c][1,2,6]thiadiazin-5-yl)oxy)methyl)piperidin-1-yl)ethanone | 953 |
| A-42 | ((S)-3-(((4-amino-2,2-dioxido-1H-benzo[c][1,2,6]thiadiazin-5-yl)oxy)methyl)piperidin-1-yl)(tetrahydrofuran-3-yl)methanone | 409 |
| A-43 | (S)-(3-(((4-amino-2,2-dioxido-1H-benzo[c][1,2,6]thiadiazin-5-yl)oxy)methyl)piperidin-1-yl)(2-methoxyphenyl)methanone | 445 |
| A-44 | (S)-(3-(((4-amino-2,2-dioxido-1H-benzo[c][1,2,6]thiadiazin-5-yl)oxy)methyl)piperidin-1-yl)(2,3-dihydrobenzo[b][1,4]dioxin-5-yl)methanone | 473 |

TABLE A-continued

| Compound No. | Compound | MS (MH+) |
|---|---|---|
| A-45 | (S)-(3-(((4-amino-2,2-dioxido-1H-benzo[c][1,2,6]thiadiazin-5-yl)oxy)methyl)piperidin-1-yl)(2-fluorophenyl)methanone | 433 |
| A-46 | (S)-(3-(((4-amino-2,2-dioxido-1H-benzo[c][1,2,6]thiadiazin-5-yl)oxy)methyl)piperidin-1-yl)(pyridin-2-yl)methanone | 416 |
| A-47 | (S)-3-(3-(((4-amino-2,2-dioxido-1H-benzo]c][1,2,6]thiadiazin-5-yl)oxy)methyl)piperidine-1-carbonyl)benzonitrile | 440 |
| A-48 | (S)-(3-(((4-amino-2,2-dioxido-1H-benzo[c][1,2,6]thiadiazin-5-yl)oxy)methyl)piperidin-1-yl)(2-fluoropyridin-4-yl)methanone | 434 |

TABLE A-continued

| Compound No. | Compound | MS (MH+) |
|---|---|---|
| A-49 | 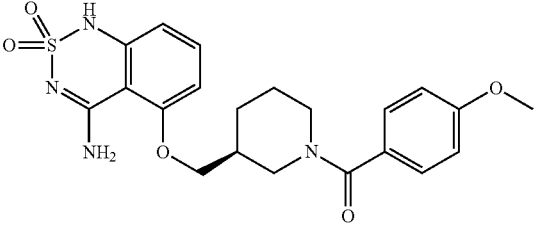 [SMILES: COc1ccc(C(=O)N2CCC[C@H](COc3cccc4c3C(N)=NS(=O)(=O)N4)C2)cc1]<br>(S)-(3-(((4-amino-2,2-dioxido-1H-benzo[c][1,2,6]thiadiazin-5-yl)oxy)methyl)piperidin-1-yl)(4-methoxyphenyl)methanone | 445 |
| A-50 | 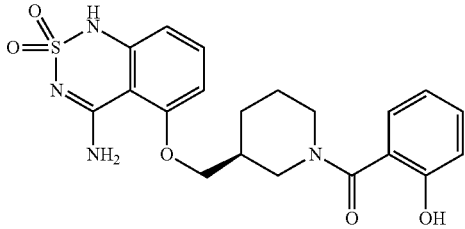 [SMILES: NC1=NS(=O)(=O)Nc2cccc(OC[C@H]3CCCN(C(=O)c4ccccc4O)C3)c21]<br>(S)-(3-(((4-amino-2,2-dioxido-1H-benzo[c][1,2,6]thiadiazin-5-yl)oxy)methyl)piperidin-1-yl)(2-hydroxyphenyl)methanone | 431 |
| A-51 | 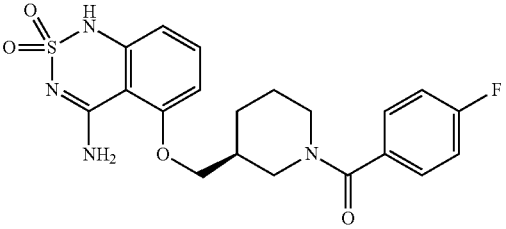 [SMILES: NC1=NS(=O)(=O)Nc2cccc(OC[C@H]3CCCN(C(=O)c4ccc(F)cc4)C3)c21]<br>(S)-(3-(((4-amino-2,2-dioxido-1H-benzo[c][1,2,6]thiadiazin-5-yl)oxy)methyl)piperidin-1-yl)(4-fluorophenyl)methanone | 433 |
| A-52 | 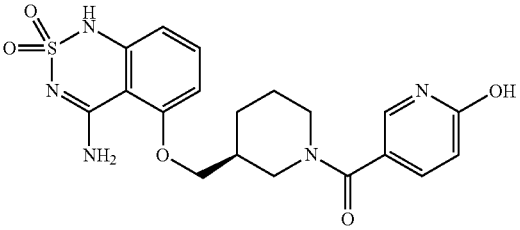<br>(S)-(3-(((4-amino-2,2-dioxido-1H-benzo[c][1,2,6]thiadiazin-5-yl)oxy)methyl)piperidin-1-yl)(6-hydroxypyridin-3-yl)methanone | 432 |

TABLE A-continued

| Compound No. | Compound | MS (MH+) |
|---|---|---|
| A-53 | 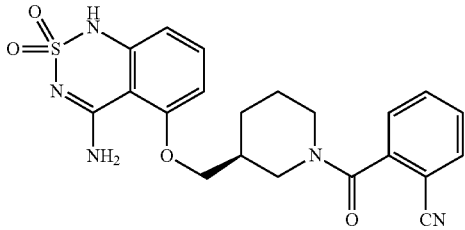 [SMILES: N#Cc1ccccc1C(=O)N1CCC[C@H](COc2cccc3c2C(N)=NS(=O)(=O)N3)C1]<br>(S)-2-(3-(((4-amino-2,2-dioxido-1H-benzo[c][1,2,6]thiadiazin-5-yl)oxy)methyl)piperidine-1 carbonyl)benzonitrile | 440 |
| A-54 | 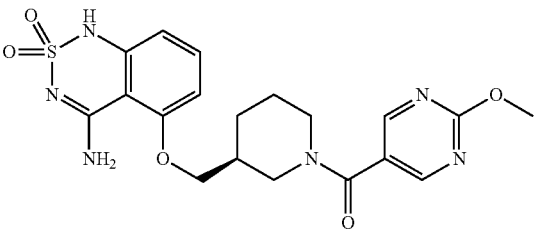<br>(S)-(3-(((4-amino-2,2-dioxido-1H-benzo[c][1,2,6]thiadiazin-5-yl)oxy)methyl)piperidin-1-yl)(2-methoxypyrimidin-5-yl)methanone | 447 |
| A-55 | 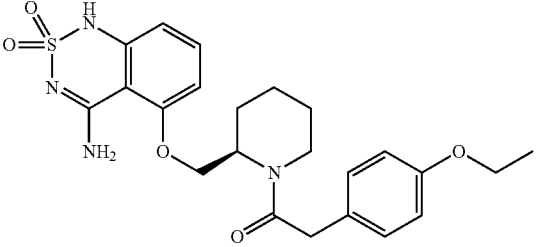 [SMILES: CCOc1ccc(CC(=O)N2CCCC[C@@H]2COc2cccc3c2C(N)=NS(=O)(=O)N3)cc1]<br>(R)-1-(2-(((4-amino-2,2-dioxido-1H-benzo[c][1,2,6]thiadiazin-5-yl)oxy)methyl)piperidin-1-yl)-2-(4-ethoxyphenyl)ethanone | 473 |
| A-56 | 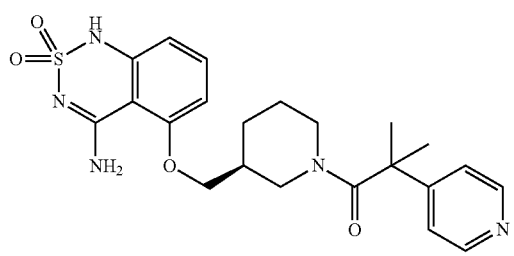 [SMILES: CC(C)(C(=O)N1CCC[C@H](COc2cccc3c2C(N)=NS(=O)(=O)N3)C1)c1ccncc1]<br>(S)-1-(3-(((4-amino-2,2-dioxido-1H-benzo[c][1,2,6]thiadiazin-5-yl)oxy)methyl)piperidin-1-yl)-2-methyl-2-(pyridin-4-yl)propan-1-one | 458 |

TABLE A-continued

| Compound No. | Compound | MS (MH+) |
|---|---|---|
| A-57 | 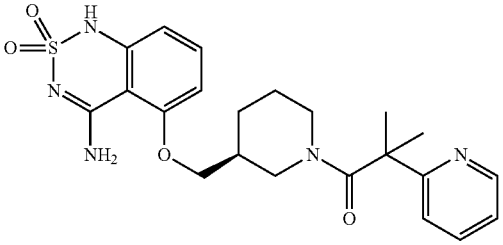 [SMILES: CC(C)(C(=O)N1CCC[C@H](COc2cccc3c2C(N)=NS(=O)(=O)N3)C1)c1ccccn1]<br>(S)-1-(3-(((4-amino-2,2-dioxido-1H-benzo[c][1,2,6]thiadiazin-5-yl)oxy)methyl)piperidin-1-yl)-2-methyl-2-(pyridin-2-yl)propan-1-one | 458 |
| A-58 | 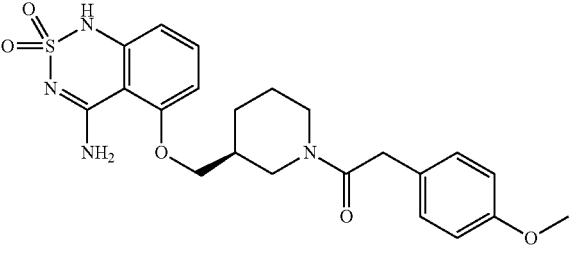 [SMILES: COc1ccc(CC(=O)N2CCC[C@H](COc3cccc4c3C(N)=NS(=O)(=O)N4)C2)cc1]<br>(S)-1-(3-(((4-amino-2,2-dioxido-1H-benzo[c][1,2,6]thiadiazin-5-yl)oxy)methyl)piperidin-1-yl)-2-(4-methoxyphenyl)ethanone | 459 |
| A-59 | 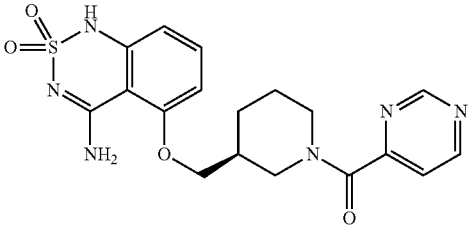<br>(S)-(3-(((4-amino-2,2-dioxido-1H-benzo[c][1,2,6]thiadiazin-5-yl)oxy)methyl)piperidin-1-yl)(pyrimidin-4-yl)methanone | 417 |
| A-60 | 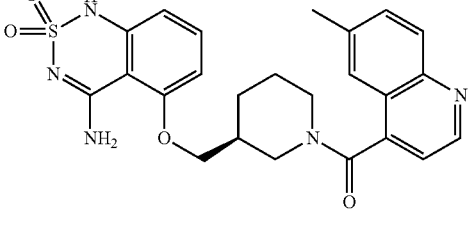<br>(S)-(3-(((4-amino-2,2-dioxido-1H-benzo[c][1,2,6]thiadiazin-5-yl)oxy)methyl)piperidin-1-yl)(6-methylquinolin-4-yl)methanone | 480 |

TABLE A-continued

| Compound No. | Compound | MS (MH+) |
|---|---|---|
| A-61 | (S)-(3-(((4-amino-2,2-dioxido-1H-benzo[c][1,2,6]thiadiazin-5-yl)oxy)methyl)piperidin-1-yl)(1-isopropyl-6-methyl-1H-pyrazolo[3,4-b]pyridin-4-yl)methanone | 512 |
| A-62 | (S)-(3-(((4-amino-2,2-dioxido-1H-benzo[c][1,2,6]thiadiazin-5-yl)oxy)methyl)piperidin-1-yl)(2-methylpyridin-3-yl)methanone | 430 |
| A-63 | (S)-(3-(((4-amino-2,2-dioxido-1H-benzo[c][1,2,6]thiadiazin-5-yl)oxy)methyl)piperidin-1-yl)(2-hydroxy-6-methylpyridin-4-yl)methanone | 446 |
| A-64 | (S)-(3-(((4-amino-2,2-dioxido-1H-benzo[c][1,2,6]thiadiazin-5-yl)oxy)methyl)piperidin-1-yl)(2,5-dihydroxyphenyl)methanone | 447 |

TABLE A-continued

| Compound No. | Compound | MS (MH+) |
|---|---|---|
| A-65 | (S)-1-(3-(((4-amino-2,2-dioxido-1H-benzo[c][1,2,6]thiadiazin-5-yl)oxy)methyl)piperidin-1-yl)-2-(pyridin-3-yl)ethanone | 430 |
| A-66 | (S)-(3-(((4-amino-2,2-dioxido-1H-benzo[c][1,2,6]thiadiazin-5-yl)oxy)methyl)piperidin-1-yl)(imidazo[1,2-a]pyridin-7-yl)methanone | 455 |
| A-67 | (S)-(3-(((4-amino-2,2-dioxido-1H-benzo[c][1,2,6]thiadiazin-5-yl)oxy)methyl)piperidin-1-yl)(3,5-dihydroxyphenyl)methanone | 447 |
| A-68 | (S)-(3-(((4-amino-2,2-dioxido-1H-benzo[c][1,2,6]thiadiazin-5-yl)oxy)methyl)piperidin-1-yl)(isoquinolin-1-yl)methanone | 466 |

TABLE A-continued

| Compound No. | Compound | MS (MH+) |
|---|---|---|
| A-69 | (S)-(3-(((4-amino-2,2-dioxido-1H-benzo[c][1,2,6]thiadiazin-5-yl)oxy)methyl)piperidin-1-yl)(6-hydroxy-2-methylquinolin-4-yl)methanone | 496 |
| A-70 | (S)-(3-(((4-amino-2,2-dioxido-1H-benzo[c][1,2,6]thiadiazin-5-yl)oxy)methyl)piperidin-1-yl)(2,6-dimethylquinolin-4-yl)methanone | 494 |
| A-71 | (S)-1-(3-(((4-amino-2,2-dioxido-1H-benzo[c][1,2,6]thiadiazin-5-yl)oxy)methyl)piperidin-1-yl)-3-(pyridin-3-yl)propan-1-one | 444 |
| A-72 | (S)-(3-(((4-amino-2,2-dioxido-1H-benzo[c][1,2,6]thiadiazin-5-yl)oxy)methyl)piperidin-1-yl)(2,4-dihydroxyphenyl)methanone | 447 |

TABLE A-continued

| Compound No. | Compound | MS (MH+) |
|---|---|---|
| A-73 | 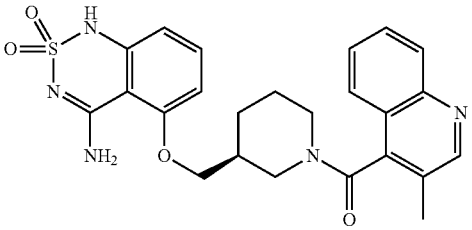 [SMILES: Cc1cnc2ccccc2c1C(=O)N1CCC[C@H](COc2cccc3c2C(N)=NS(=O)(=O)N3)C1]<br>(S)-(3-(((4-amino-2,2-dioxido-1H-benzo[c][1,2,6]thiadiazin-5-yl)oxy)methyl)piperidin-1-yl)(3-methylquinolin-4-yl)methanone | 480 |
| A-74 | 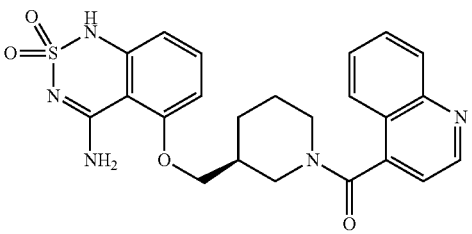 [SMILES: NC1=NS(=O)(=O)Nc2cccc(OC[C@H]3CCCN(C(=O)c4ccnc5ccccc45)C3)c21]<br>(S)-(3-(((4-amino-2,2-dioxido-1H-benzo[c][1,2,6]thiadiazin-5-yl)oxy)methyl)piperidin-1-yl)(quinolin-4-yl)methanone | 466 |
| A-75 | 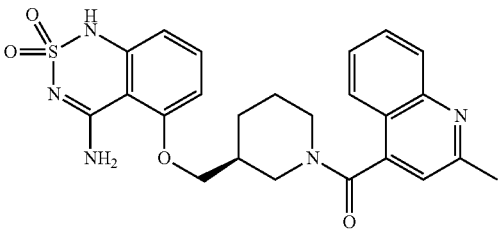 [SMILES: Cc1cc(C(=O)N2CCC[C@H](COc3cccc4c3C(N)=NS(=O)(=O)N4)C2)c2ccccc2n1]<br>(S)-(3-(((4-amino-2,2-dioxido-1H-benzo[c][1,2,6]thiadiazin-5-yl)oxy)methyl)piperidin-1-yl)(2-methylquinolin-4-yl)methanone | 480 |
| A-76 | 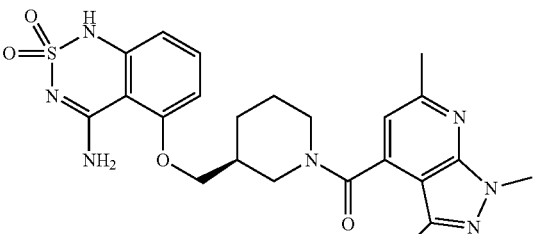<br>(S)-(3-(((4-amino-2,2-dioxido-1H-benzo[c][1,2,6]thiadiazin-5-yl)oxy)methyl)piperidin-1-yl)(1,3,6-trimethyl-1H-pyrazolo[3,4-b]pyridin-4-yl)methanone | 498 |

TABLE A-continued
| Compound No. | Compound | MS (MH+) |
|---|---|---|
| A-77 | 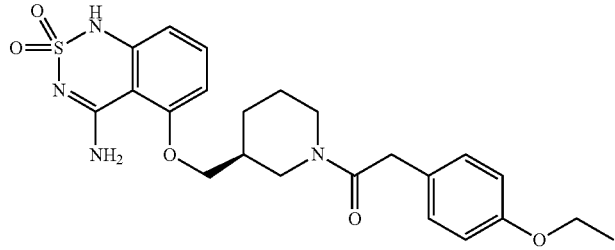 [SMILES: CCOc1ccc(CC(=O)N2CCC[C@H](COc3cccc4c3C(N)=NS(=O)(=O)N4)C2)cc1]<br>(S)-1-(3-(((4-amino-2,2-dioxido-1H-benzo[c][1,2,6]thiadiazin-5-yl)oxy)methyl)piperidin-1-yl)-2-(4-ethoxyphenyl)ethanone | 473 |
| A-78 | 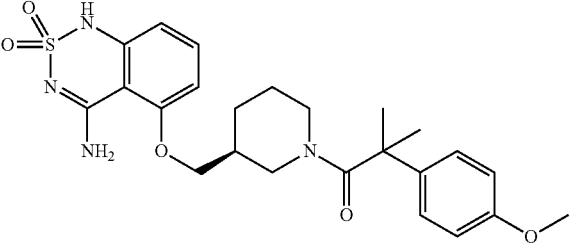 [SMILES: COc1ccc(C(C)(C)C(=O)N2CCC[C@H](COc3cccc4c3C(N)=NS(=O)(=O)N4)C2)cc1]<br>(S)-1-(3-(((4-amino-2,2-dioxido-1H-benzo[c][1,2,6]-thiadiazin-5-yl)oxy)methyl)piperidin-1-yl)-2-(4-methoxyphenyl)-2-methylpropan-1-one | 487 |
| A-79 | 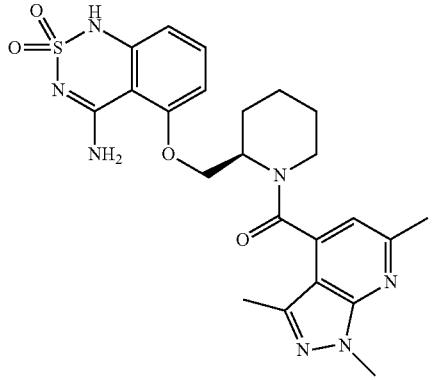 [SMILES: Cc1cc(C(=O)N2CCCC[C@@H]2COc2cccc3c2C(N)=NS(=O)(=O)N3)c2c(C)nn(C)c2n1]<br>(R)-(2-(((4-amino-2,2-dioxido-1H-benzo[c][1,2,6]thiadiazin-5-yl)oxy)methyl)piperidin-1-yl)(1,3,6-trimethyl-1H-pyrazolo[3,4-b]pyridin-4-yl)methanone | 498 |

TABLE A-continued

| Compound No. | Compound | MS (MH+) |
|---|---|---|
| A-80 | (R)-(2-(((4-amino-2,2-dioxido-1H-benzo[c][1,2,6]thiadiazin-5-yl)oxy)methyl)piperidin-1-yl)(1-isopropyl-6-methyl-1H-pyrazolo[3,4-b]pyridin-4-yl)methanone | 512 |
| A-81 | (S)-[1,1'-biphenyl]-3-yl(3-(((4-amino-2,2-dioxido-1H-benzo[c][1,2,6]thiadiazin-5-yl)oxy)methyl)piperidin-1-yl)methanone | 491 |
| A-82 | (S)-(3-(((4-amino-2,2-dioxido-1H-benzo[c][1,2,6]-thiadiazin-5-yl)oxy)methyl)piperidin-1-yl)(3-(pyridin-4-yl)phenyl)methanone | 492 |

TABLE A-continued

| Compound No. | Compound | MS (MH+) |
|---|---|---|
| A-83 | (S)-(3-(((4-amino-2,2-dioxido-1H-benzo[c][1,2,6]thiadiazin-5-yl)oxy)methyl)piperidin-1-yl)(3'-hydroxy-[1,1'-biphenyl]-3-yl)methanone | 507 |
| A-84 | (S)-(3-(1H-imidazol-1-yl)phenyl)(3-(((4-amino-2,2-dioxido-1H-benzo[c][1,2,6]thiadiazin-5-yl)oxy)methyl)piperidin-1-yl)methanone | 481 |
| A-85 | (S)-(3-(((4-amino-2,2-dioxido-1H-benzo[c][1,2,6]thiadiazin-5-yl)oxy)methyl)piperidin-1-yl)(2-(2-isopropyl-1H-imidazol-1-yl)pyridin-4-yl)methanone | 524 |
| A-86 | (S)-(3-(((4-amino-2,2-dioxido-1H-benzo[c][1,2,6]thiadiazin-5-yl)oxy)methyl)piperidin-1-yl)(2-phenylpyridin-4-yl)methanone | 492 |

TABLE A-continued

| Compound No. | Compound | MS (MH+) |
|---|---|---|
| A-87 | (S)-(3-(((4-amino-2,2-dioxido-1H-benzo[c][1,2,6]thiadiazin-5-yl)oxy)methyl)piperidin-1-yl)(2-(2-hydroxyphenyl)pyridin-4-yl)methanone | 508 |
| A-88 | (S)-(3-(((4-amino-2,2-dioxido-1H-benzo[c][1,2,6]thiadiazin-5-yl)oxy)methyl)piperidin-1-yl)(2-(4-fluorophenyl)pyridin-4-yl)methanone | 510 |
| A89 | (S)-(3-(((4-amino-2,2-dioxido-1H-benzo[c][1,2,6]thiadiazin-5-yl)oxy)methyl)piperidin-1-yl)(2-(3-fluorophenyl)pyridin-4-yl)methanone | 510 |
| A-90 | (S)-(3-(((4-amino-2,2-dioxido-1H-benzo[c][1,2,6]thiadiazin-5-yl)oxy)methyl)piperidin-1-yl)(2-(3-hydroxyphenyl)pyridin-4-yl)methanone | 508 |

TABLE A-continued

| Compound No. | Compound | MS (MH+) |
|---|---|---|
| A-91 | (S)-4-(3-(((4-amino-2,2-dioxido-1H-benzo[c][1,2,6]thiadiazin-5-yl)oxy)methyl)piperidine-1-carbonyl)picolinamide | 459 |
| A-92 | (S)-(3-(((4-amino-2,2-dioxido-1H-benzo[c][1,2,6]thiadiazin-5-yl)oxy)methyl)piperidin-1-yl)(2-ethylpyridin-4-yl)methanone | 444 |
| A-93 | (S)-(3-(((4-amino-2,2-dioxido-1H-benzo[c][1,2,6]-thiadiazin-5-yl)oxy)methyl)piperidin-1-yl)(2-isopropylpyridin-4-yl)methanone | 458 |
| A-94 | (S)-(3-(((4-amino-2,2-dioxido-1H-benzo[c][1,2,6]thiadiazin-5-yl)oxy)methyl)piperidin-1-yl)(2-diethylamino)pyridin-4-yl)methanone | 487 |

TABLE A-continued

| Compound No. | Compound | MS (MH+) |
|---|---|---|
| A-95 | 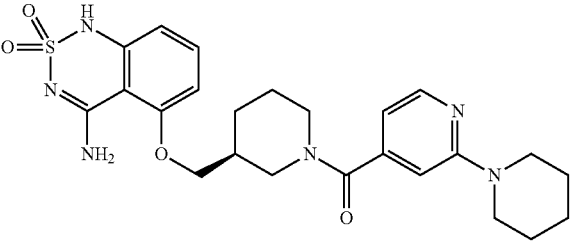 [SMILES: NC1=NS(=O)(=O)Nc2cccc(OC[C@H]3CCCN(C(=O)c4ccnc(N5CCCCC5)c4)C3)c21]<br>(S)-(3-(((4-amino-2,2-dioxido-1H-benzo[c][1,2,6]thiadiazin-5-yl)oxy)methyl)peridin-1-yl)(2-(piperidin-1-yl)pyridin-4-yl)methanone | 499 |
| A-96 | 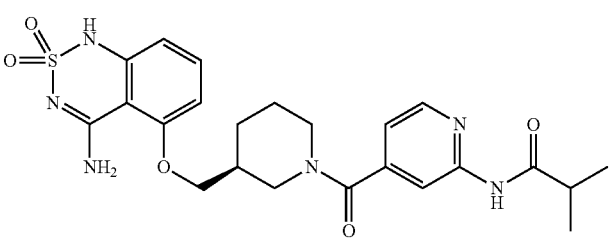 [SMILES: CC(C)C(=O)Nc1cc(C(=O)N2CCC[C@H](COc3cccc4c3C(N)=NS(=O)(=O)N4)C2)ccn1]<br>(S)-N-(4-(3-(((4-amino-2,2-dioxido-1H-benzo[c][1,2,6]thiadiazin-5-yl)oxy)methyl)piperidine-1-carbonyl)pyridin-2-yl)isobutyramide | 501 |
| A-97 | 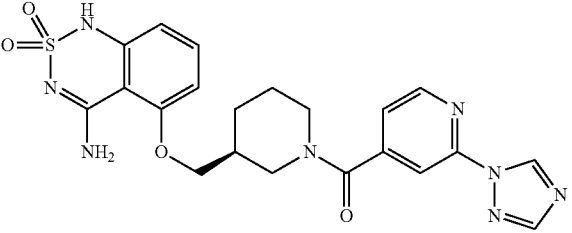 [SMILES: NC1=NS(=O)(=O)Nc2cccc(OC[C@H]3CCCN(C(=O)c4ccnc(-n5cncn5)c4)C3)c21]<br>(S)-(2-(1H-1,2,4-triazol-1-yl)pyridin-4-yl)(3-(((4-amino-2,2-dioxido-1H-benzo[c][1,2,6]thiadiazin-5-yl)oxy)methyl)piperidin-1-yl)methanone | 483 |
| A-98 | 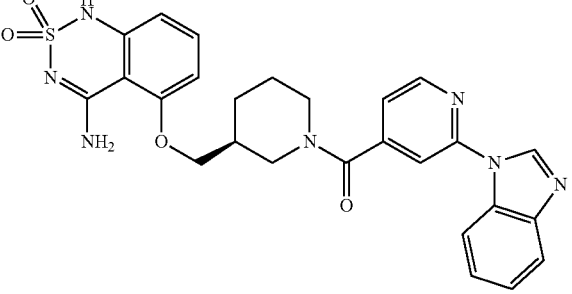<br>(S)-(2-(1H-benzo[d]imidazol-1-yl)pyridin-4-yl)(3-(((4-amino-2,2-dioxido-1H-benzo[c][1,2,6]thiadiazin-5-yl)oxy)methyl)piperidin-1-yl)methanone | 532 |

TABLE A-continued

| Compound No. | Compound | MS (MH+) |
|---|---|---|
| A-99 | (S)-(3-(((4-amino-2,2-dioxido-1H-benzo[c][1,2,6]thiadiazin-5-yl)oxy)methyl)piperidin-1-yl)(2-(2-methyl-1H-imidazol-1-yl)pyridin-4-yl)methanone | 496 |
| A-100 | 1-(3-(((4-amino-2,2-dioxido-1H-benzo[c][1,2,6]thiadiazin-5-yl)oxy)methyl)piperidin-1-yl)butan-1-one | 381 |
| A-101 | (R)-1-(3-(((4-amino-2,2-dioxido-1H-benzo[c][1,2,6]thiadiazin-5-yl)oxy)methyl)piperidin-1-yl)butan-1-one | 381 |
| A-102 | (3-(((4-amino-2,2-dioxido-1H-benzo[c][1,2,6]thiadiazin-5-yl)oxy)methyl)piperidin-1-yl)(pyridin-4-yl)methanone | 416 |

TABLE A-continued

| Compound No. | Compound | MS (MH+) |
|---|---|---|
| A-103 | (S)-4-(3-(((4-amino-2,2-dioxido-1H-benzo[c][1,2,6]thiadiazin-5-yl)oxy)methyl)piperidine-1-carbonyl)pyridine 1-oxide | 432 |
| A-104 | (S)-(3-(((4-amino-2,2-dioxido-1H-benzo[c][1,2,6]thiadiazin-5-yl)oxy)methyl)piperidin-1-yl)(2-hydroxypyridin-4-yl)methanone | 432 |
| A-105 | (S)-(3-(((4-amino-2,2-dioxido-1H-benzo[c][1,2,6]thiadiazin-5-yl)oxy)methyl)piperidin-1-yl)(3-methylpyridin-4-yl)methanone | 430 |
| A-106 | (S)-(3-(((4-amino-2,2-dioxido-1H-benzo[c][1,2,6]thiadiazin-5-yl)oxy)methyl)piperidin-1-yl)(3,4-dihydroxyphenyl)methanone | 447 |

| Compound No. | Compound | MS (MH+) |
|---|---|---|
| A-107 | 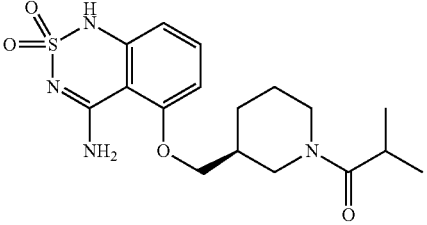 [SMILES: CC(C)C(=O)N1CCC[C@H](COc2cccc3c2C(N)=NS(=O)(=O)N3)C1]<br>(S)-1-(3-(((4-amino-2,2-dioxido-1H-benzo[c][1,2,6]thiadiazin-5-yl)oxy)methyl)piperidin-1-yl)-2-methylpropan-1-one | 381 |
| A-108 | 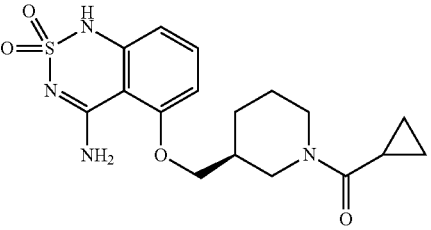 [SMILES: NC1=NS(=O)(=O)Nc2cccc(OC[C@H]3CCCN(C(=O)C4CC4)C3)c21]<br>(S)-(3-(((4-amino-2,2-dioxido-1H-benzo[c][1,2,6]thiadiazin-5-yl)oxy)methyl)piperidin-1-yl)(cyclopropyl)methanone | 379 |
| A-109 | 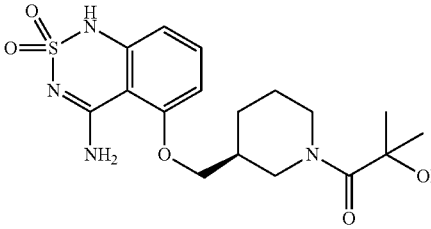<br>(S)-1-(3-(((4-amino-2,2-dioxido-1H-benzo[c][1,2,6]thiadiazin-5-yl)oxy)methyl)piperidin-1-yl)-2-hydroxy-2-methylpropan-1-one | 397 |
| A-110 | 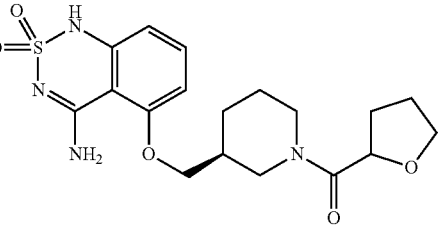<br>((S)-3-(((4-amino-2,2-dioxido-1H-benzo[c][1,2,6]thiadiazin-5-yl)oxy)methyl)piperidin-1-yl)(tetrahydrofuran-2-yl)methanone | 409 |

TABLE A-continued

| Compound No. | Compound | MS (MH+) |
|---|---|---|
| A-111 | 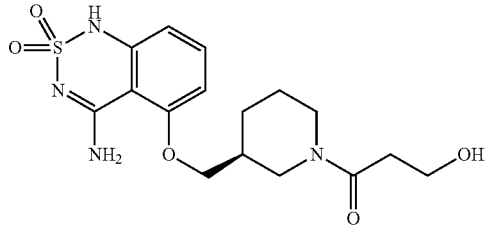 [SMILES: NC1=NS(=O)(=O)Nc2cccc(OC[C@H]3CCCN(C(=O)CCO)C3)c21]<br>(S)-1-(3-(((4-amino-2,2-dioxido-1H-benzo[c][1,2,6]thiadiazin-5-yl)oxy)methyl)piperidin-1-yl)-3-hydroxypropan-1-one | 383 |
| A-112 | 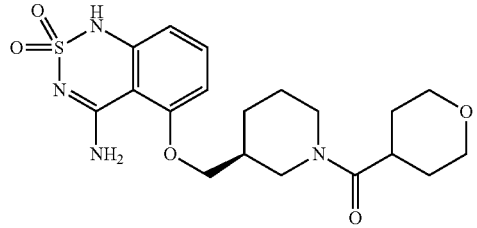 [SMILES: NC1=NS(=O)(=O)Nc2cccc(OC[C@H]3CCCN(C(=O)C4CCOCC4)C3)c21]<br>(S)-(3-(((4-amino-2,2-dioxido-1H-benzo[c][1,2,6]thiadiazin-5-yl)oxy)methyl)piperidin-1-yl)(tetrahydro-2H-pyran-4-yl)methanone | 423 |
| A-113 | 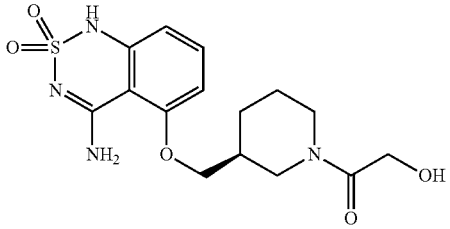 [SMILES: NC1=NS(=O)(=O)Nc2cccc(OC[C@H]3CCCN(C(=O)CO)C3)c21]<br>(S)-1-(3-(((4-amino-2,2-dioxido-1H-benzo[c][1,2,6]thiadiazin-5-yl)oxy)methyl)piperidin-1-yl)-2-hydroxyethanone | 369 |
| A-114 | 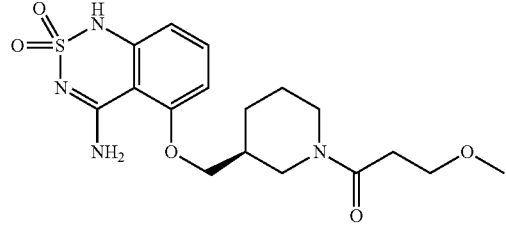 [SMILES: COCCC(=O)N1CCC[C@H](COc2cccc3c2C(N)=NS(=O)(=O)N3)C1]<br>(S)-1-(3-(((4-amino-2,2-dioxido-1H-benzo[c][1,2,6]thiadiazin-5-yl)oxy)methyl)piperidin-1-yl)-3-methoxypropan-1-one | 397 |

TABLE A-continued

| Compound No. | Compound | MS (MH+) |
|---|---|---|
| A-115 | (S)-1-(3-(((4-amino-2,2-dioxido-1H-benzo[c][1,2,6]thiadiazin-5-yl)oxy)methyl)piperidin-1-yl)-2-methoxyethanone | 383 |
| A-116 | (S)-(3-(((4-amino-2,2-dioxido-1H-benzo[c][1,2,6]thiadiazin-5-yl)oxy)methyl)piperidin-1-yl)(3-methoxyphenyl)methanone | 445 |
| A-117 | (S)-(3-(((4-amino-2,2-dioxido-1H-benzo[c][1,2,6]thiadiazin-5-yl)oxy)methyl)piperidin-1-yl)(phenyl)methanone | 415 |
| A-118 | (S)-(3-(((4-amino-2,2-dioxido-1H-benzo[c][1,2,6]thiadiazin-5-yl)oxy)methyl)piperidin-1-yl)(pyrimidin-2-yl)methanone | 417 |

TABLE A-continued

| Compound No. | Compound | MS (MH+) |
|---|---|---|
| A-119 | 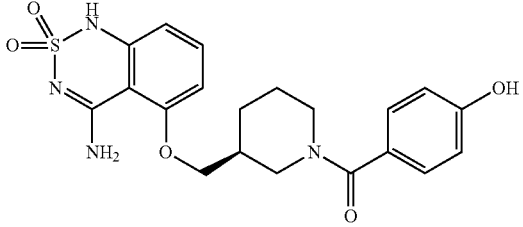 [SMILES: NC1=NS(=O)(=O)Nc2cccc(OC[C@H]3CCCN(C(=O)c4ccc(O)cc4)C3)c21]<br>(S)-(3-(((4-amino-2,2-dioxido-1H-benzo[c][1,2,6]thiadiazin-5-yl)oxy)methyl)piperidin-1-yl)(4-hydroxyphenyl)methanone | 431 |
| A-120 | 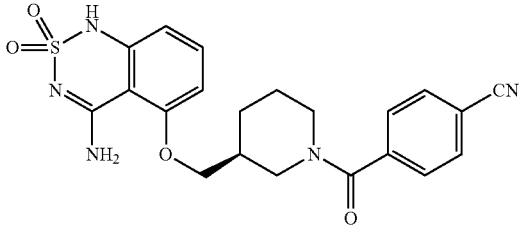 [SMILES: N#Cc1ccc(C(=O)N2CCC[C@H](COc3cccc4c3C(N)=NS(=O)(=O)N4)C2)cc1]<br>(S)-4-(3-(((4-amino-2,2-dioxido-1H-benzo[c][1,2,6]thiadiazin-5-yl)oxy)methyl)piperidine-1-carbonyl)benzonitrile | 440 |
| A-121 | 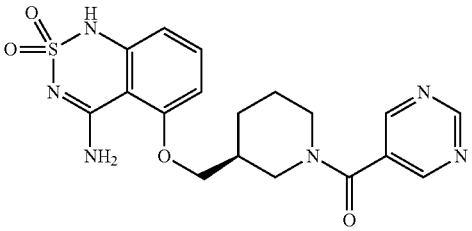 [SMILES: NC1=NS(=O)(=O)Nc2cccc(OC[C@H]3CCCN(C(=O)c4cncnc4)C3)c21]<br>(S)-(3-(((4-amino-2,2-dioxido-1H-benzo[c][1,2,6]thiadiazin-5-yl)oxy)methyl)piperidin-1-yl)(pyrimidin-5-yl)methanone | 417 |
| A-122 | 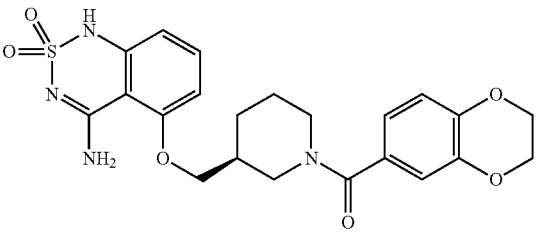 [SMILES: NC1=NS(=O)(=O)Nc2cccc(OC[C@H]3CCCN(C(=O)c4ccc5c(c4)OCCO5)C3)c21]<br>(S)-(3-(((4-amino-2,2-dioxido-1H-benzo[c][1,2,6]thiadiazin-5-yl)oxy)methyl)piperidin-1-yl)(2,3-dihydrobenzo[b][1,4]dioxin-6-yl)methanone | 473 |

| Compound No. | Compound | MS (MH+) |
|---|---|---|
| A-123 | 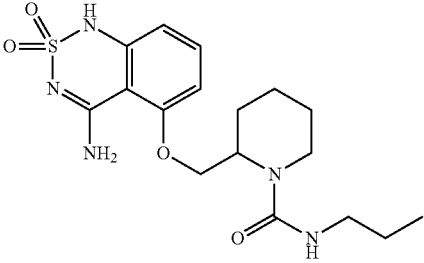 [SMILES: CCCNC(=O)N1CCCCC1COc1cccc2c1C(N)=NS(=O)(=O)N2]<br>2-(((4-amino-2,2-dioxido-1H-benzo[c][1,2,6]thiadiazin-5-yl)oxy)methyl)-N-propylpiperidine-1-carboxamide | 396 |
| A-124 | 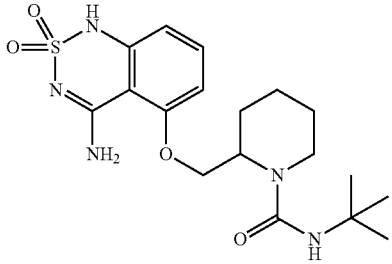 [SMILES: CC(C)(C)NC(=O)N1CCCCC1COc1cccc2c1C(N)=NS(=O)(=O)N2]<br>2-(((4-amino-2,2-dioxido-1H-benzo[c][1,2,6]thiadiazin-5-yl)oxy)methyl)-N-(tert-butyl)piperidine-1-carboxamide | 410 |
| A-125 | 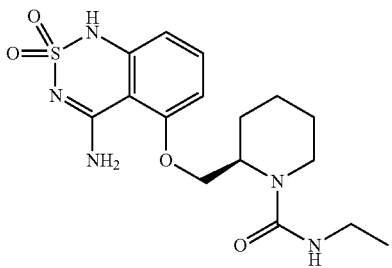 [SMILES: CCNC(=O)N1CCCC[C@@H]1COc1cccc2c1C(N)=NS(=O)(=O)N2]<br>(R)-2-(((4-amino-2,2-dioxido-1H-benzo[c][1,2,6]thiadiazin-5-yl)oxy)methyl)-N-ethylpiperidine-1-carboxamide | 382 |
| A-126 | 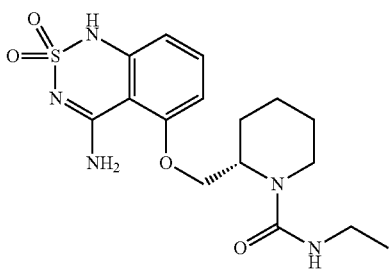<br>(S)-2-(((4-amino-2,2-dioxido-1H-benzo[c][1,2,6]thiadiazin-5-yl)oxy)methyl)-N-ethylpiperidine-1-carboxamide | 382 |

TABLE A-continued

| Compound No. | Compound | MS (MH+) |
|---|---|---|
| A-127 | 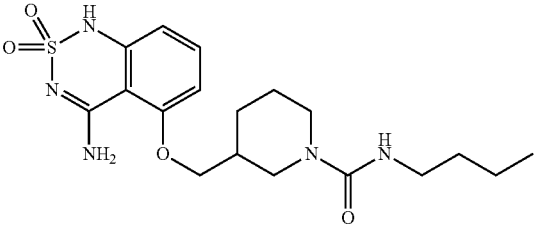 [SMILES: CCCCNC(=O)N1CCCC(COc2cccc3c2C(N)=NS(=O)(=O)N3)C1]<br>3-(((4-amino-2,2-dioxido-1H-benzo[c][1,2,6]thiadiazin-5-yl)oxy)methyl)-N-butylpiperidine-1-carboxamide | 410 |
| A-128 | 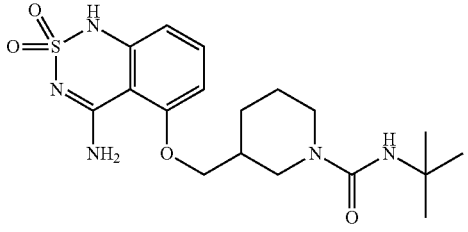 [SMILES: CC(C)(C)NC(=O)N1CCCC(COc2cccc3c2C(N)=NS(=O)(=O)N3)C1]<br>3-(((4-amino-2,2-dioxido-1H-benzo[c][1,2,6]thiadiazin-5-yl)oxy)methyl)-N-(tert-butyl)piperidine-1-carboxamide | 410 |
| A-129 | 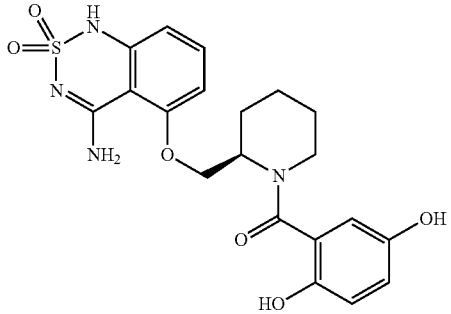 [SMILES: NC1=NS(=O)(=O)Nc2cccc(OC[C@H]3CCCCN3C(=O)c3cc(O)ccc3O)c21]<br>(R)-(2-(((4-amino-2,2-dioxido-1H-benzo[c][1,2,6]thiadiazin-5-yl)oxy)methyl)piperidin-1-yl)(2,5-dihydroxyphenyl)methanone | 447 |
| A-130 | 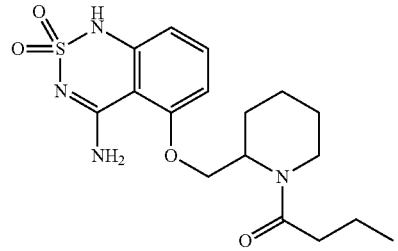 [SMILES: CCCC(=O)N1CCCCC1COc1cccc2c1C(N)=NS(=O)(=O)N2]<br>1-(2-(((4-amino-2,2-dioxido-1H-benzo[c][1,2,6]thiadiazin-5-yl)oxy)methyl)piperidin-1-yl)butan-1-one | 381 |

TABLE A-continued

| Compound No. | Compound | MS (MH+) |
|---|---|---|
| A-131 | 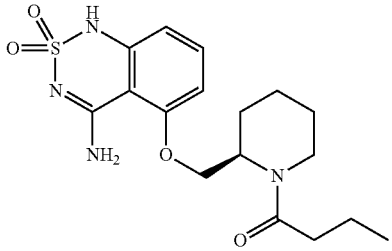 [SMILES: CCCC(=O)N1CCCC[C@@H]1COc1cccc2c1C(N)=NS(=O)(=O)N2]<br>(R)-1-(2-(((4-amino-2,2-dioxido-1H-benzo[c][1,2,6]thiadiazin-5-yl)oxy)methyl)piperidin-1-yl)butan-1-one | 381 |
| A-132 | 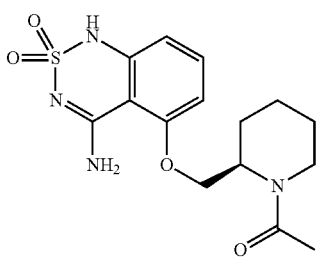 [SMILES: CC(=O)N1CCCC[C@@H]1COc1cccc2c1C(N)=NS(=O)(=O)N2]<br>(R)-1-(2-(((4-amino-2,2-dioxido-1H-benzo[c][1,2,6]thiadiazin-5-yl)oxy)methyl)piperidin-1-yl)ethanone | 353 |
| A-133 | 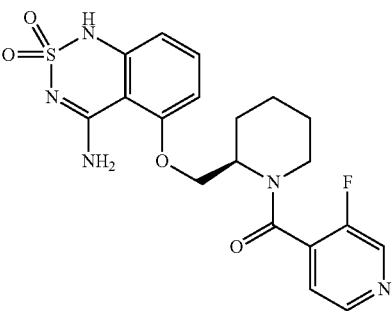<br>(R)-(2-(((4-amino-2,2-dioxido-1H-benzo[c][1,2,6]thiadiazin-5-yl)oxy)methyl)piperidin-1-yl)(3-fluoropyridin-4-yl)methanone | 434 |
| A-134 | 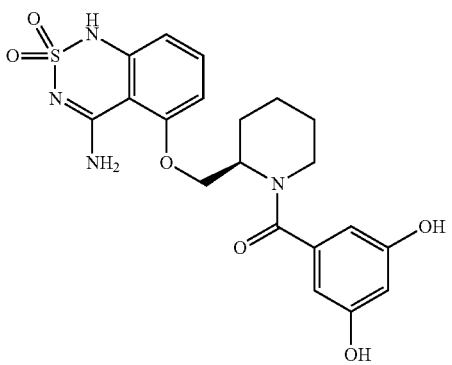 [SMILES: NC1=NS(=O)(=O)Nc2cccc(OC[C@H]3CCCCN3C(=O)c3cc(O)cc(O)c3)c21]<br>(R)-(2-(((4-amino-2,2-dioxido-1H-benzo[c][1,2,6]thiadiazin-5-yl)oxy)methyl)piperidin-1-yl)(3,5-dihydroxyphenyl)methanone | 447 |

TABLE A-continued
| Compound No. | Compound | MS (MH+) |
|---|---|---|
| A-135 | 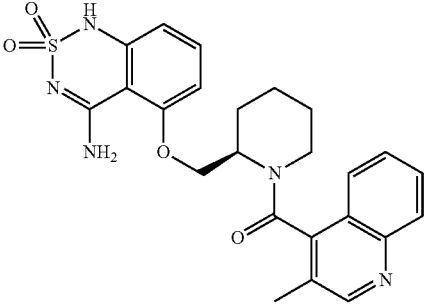 [SMILES: Cc1cnc2ccccc2c1C(=O)N1CCCC[C@@H]1COc1cccc2c1C(N)=NS(=O)(=O)N2]<br>(R)-(2-(((4-amino-2,2-dioxido-1H-benzo[c][1,2,6]thiadiazin-5-yl)oxy)methyl)piperidin-1-yl)(3-methylquinolin-4-yl)methanone | 480 |
| A-136 | 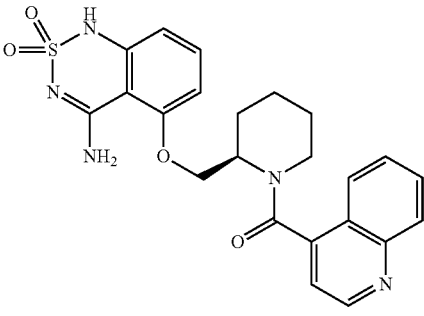 [SMILES: NC1=NS(=O)(=O)Nc2cccc(OC[C@H]3CCCCN3C(=O)c3ccnc4ccccc34)c21]<br>(R)-(2-(((4-amino-2,2-dioxido-1H-benzo[c][1,2,6]thiadiazin-5-yl)oxy)methyl)piperidin-1-yl)(quinolin-4-yl)methanone | 466 |
| A-137 | 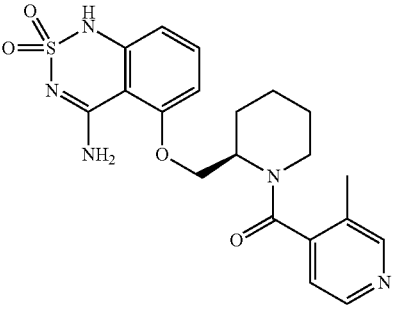<br>(R)-(2-(((4-amino-2,2-dioxido-1H-benzo[c][1,2,6]thiadiazin-5-yl)oxy)methyl)piperidin-1-yl)(3-methylpyridin-4-yl)methanone | 430 |

TABLE A-continued

| Compound No. | Compound | MS (MH+) |
|---|---|---|
| A-138 | 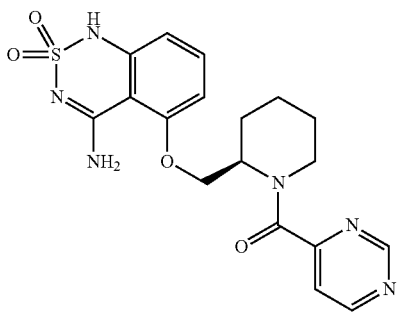<br>(R)-(2-(((4-amino-2,2-dioxido-1H-benzo[c][1,2,6]thiadiazin-5-yl)oxy)methyl)piperidin-1-yl)(pyrimidin-4-yl)methanone | 417 |

Biological Tests

The present compounds have been tested and shown sweet taste potentiating activities. Specifically, the present compounds have demonstrated activation of the T1R2/T1R3 receptor and enhancement of the activation of the T1R2/T1R3 receptor as well as sweet taste potentiating activities for sweetener, such as fructose. Compounds Q1, J2, K2, L2, B1, and F3 described in Experiment 1 and Experiment 2 below for the human taste tests are compounds selected from the compounds described throughout this document including Examples and compounds listed in Table A.

Experiment 1

Sweet Flavor and Sweet Flavor Potentiation Measurement Using Human Panelists Conducting a Paired Comparison Test Test samples containing experimental compounds are presented in pairs to the panelist and they are asked to determine which of the sample is sweeter. The present compounds showed sweet flavor potentiation in medium with a wide range of pH value, and this Experiment provided results for samples tested at pH of about 2.8 or 7.1. A group of 10-16 or more panelists participated in each test. Subjects refrained from eating or drinking (except water) for at least 1 hour prior to the test. Subjects rinsed with water several times to clean the mouth.

Taste tests were performed with sucrose or HFCS as the sweetener in the presence or absence of compound. A 0.2% stock solution of compound in water with sodium bicarbonate was prepared and then this stock solution was diluted in the final sample to achieve the targeted final concentration of compound. For the sample evaluated at pH 2.8 the pH of the solution is decreased to about pH 2.8 using citric acid. Taste samples were also prepared in a low sodium phosphate buffer (pH 7.1; "LSB") lacking sucrose or HFCS to evaluate the taste of the compound alone. Low sodium phosphate buffer consists of 0.3 mM KCl, 0.5 mM $Na_2HPO_4$, and 0.175 mM $KH_2PO_4$. Sample volumes are usually 20 ml.

In one paired comparison test, the panelist is presented with two different samples and asked to identify the sample which is sweeter. The samples within a paired comparison test are presented in a randomized, counterbalanced order. Panelists have up to a 1 minute delay between taste tests to clear the mouth of any tastes.

Binomial probability tables are used to determine the probability of the correct number of responses occurring for each test at alpha=0.05.

The results of human taste tests with Compound Q1 are found below. Table 1-a indicates that panelists perceived 6% sucrose+21 μM Compound Q1 as being not significantly different in sweetness than a solution of 12% sucrose at pH 7.1. Table 1-b indicates that panelists perceived 6% sucrose+7.8 μM Compound QI as being not significantly different in sweetness than a solution of 12% sucrose at pH 2.8. Table 2-a indicates that panelists perceived 6% High Fructose Corn Syrup+26.3 μM Compound QI as being not significantly different in sweetness than a solution of 9% High Fructose Corn Syrup at pH 7.1. Table 2-b indicates that panelists perceived 6% High Fructose Corn Syrup+7.8 μM Compound Q1 as being not significantly different in sweetness than a solution of 8% High Fructose Corn Syrup at pH 2.8. Table 3 indicates that 26.3 μM Compound Q1 alone is as sweet as a 1% sucrose solution.

TABLE 1-a

| Sample selected as sweeter by panelists, n = 30 (15 panelists × 2 reps), pH 7.1 | |
|---|---|
| Samples | Total |
| 12% Sucrose | 18 |
| 6% Sucrose + 21 μM Compound Q1 | 12 |
| Total | 30 |
| 12% Sucrose (p-value) | 0.362 |

TABLE 1-b

| Sample selected as sweeter by panelists, n = 42 (14 panelists × 3 reps), pH 2.8 | |
|---|---|
| Samples | Total |
| 12% Sucrose | 24 |
| 6% Sucrose + 7.9 μM Compound Q1 | 18 |
| Total | 42 |
| 12% Sucrose (p-value) | 0.441 |

TABLE 2-a

Sample selected as sweeter by panelists, n = 30 (15 panelists × 2 reps). pH 7.1

| Samples | Total |
| --- | --- |
| 9% High Fructose Corn Syrup | 16 |
| 6% High Fructose Corn Syrup + 26.3 µM Compound Q1 | 14 |
| Total | 30 |
| 9% High Fructose Corn Syrup (p-value) | 0.856 |

TABLE 2-b

Sample selected as sweeter by panelists, n = 42 (14 panelists × 3 reps). pH 2.8

| Samples | Total |
| --- | --- |
| 8% High Fructose Corn Syrup | 21 |
| 6% High Fructose Corn Syrup + 7.8 µM Compound Q1 | 21 |
| Total | 42 |
| 8% High Fructose Corn Syrup (p-value) | 0.878 |

TABLE 3

Sample selected as sweeter by panelists, n = 26 (13 panelists × 2 reps).

| Samples | Total |
| --- | --- |
| 1% Sucrose | 14 |
| LSB + 26.3 µM Compound Q1 | 12 |
| Total | 26 |
| 1% Sucrose (p-value) | 0.845 |

The results of human taste tests with Compound J2 are found below. Table 4-a indicates that panelists perceived 6% sucrose+12.7 µM Compound J2 as being not significantly different in sweetness than a solution of 12% sucrose at pH 7.1. Table 4-b indicates that panelists perceived 6% sucrose+12.7 µM Compound J2 as being not significantly different in sweetness than a solution of 12% sucrose at pH 2.8. Table 5-a indicates that panelists perceived 6% High Fructose Corn Syrup+20.4 µM Compound J2 as being not significantly different in sweetness than a solution of 9% High Fructose Corn Syrup at pH 7.1. Table 5-b indicates that panelists perceived 6% High Fructose Corn Syrup+12.7 µM Compound J2 as being not significantly different in sweetness than a solution of 9% High Fructose Corn Syrup at pH 2.8. Table 6 indicates that 20.4 µM Compound J2 alone is as sweet as a 1% sucrose solution.

TABLE 4-a

Sample selected as sweeter by panelists, n = 51 (17 panelists × 3 reps). pH 7.1

| Samples | Total |
| --- | --- |
| 12% Sucrose | 28 |
| 6% Sucrose + 12.7 µM Compound J2 | 23 |
| Total | 51 |
| 12% Sucrose (p-value) | 0.575 |

TABLE 4-b

Sample selected as sweeter by panelists, n = 45 (15 panelists × 3 reps). pH 2.8

| Samples | Total |
| --- | --- |
| 12% Sucrose | 20 |
| 6% Sucrose + 12.7 µM Compound J2 | 25 |
| Total | 45 |
| 12% Sucrose (p-value) | 0.551 |

TABLE 5-a

Sample selected as sweeter by panelists, n = 39 (13 panelists × 3 reps). pH 7.1

| Samples | Total |
| --- | --- |
| 9% High Fructose Corn Syrup | 21 |
| 6% High Fructose Corn Syrup + 20.4 µM Compound J2 | 18 |
| Total | 39 |
| 9% High Fructose Corn Syrup (p-value) | 0.749 |

TABLE 5-b

Sample selected as sweeter by panelists, n = 45 (13 panelists × 3 reps). pH 2.8

| Samples | Total |
| --- | --- |
| 9% High Fructose Corn Syrup | 26 |
| 6% High Fructose Corn Syrup + 12.7 µM Compound J2 | 19 |
| Total | 45 |
| 9% High Fructose Corn Syrup (p-value) | 0.391 |

TABLE 6

Sample selected as sweeter by panelists, n = 26 (13 panelists × 2 reps).

| Samples | Total |
| --- | --- |
| 1% Sucrose | 14 |
| LSB + 20.4 µM Compound J2 | 12 |
| Total | 26 |
| 1% Sucrose (p-value) | 0.845 |

The results of human taste tests with Compound K2 are found below. Table 7-a indicates that panelists perceived 6% sucrose+12.7 µM Compound $K_2$ as being not significantly different in sweetness than a solution of 12% sucrose at pH 7.1. Table 7-b indicates that panelists perceived 6% sucrose+12.7 µM Compound $K_2$ as being not significantly different in sweetness than a solution of 12% sucrose at pH 2.8. Table 8-a indicates that panelists perceived 6% High Fructose Corn Syrup+12.7 µM Compound K2 as being not significantly different in sweetness than a solution of 9% High Fructose Corn Syrup at pH 7.1. Table 8-b indicates that panelists perceived 6% High Fructose Corn Syrup+12.7 µM Compound K2 as being not significantly different in sweetness than a solution of 8% High Fructose Corn Syrup at pH 2.8. Table 9 indicates that 12.7 µM Compound K2 alone is as sweet as a 1% sucrose solution.

TABLE 7-a

Sample selected as sweeter by panelists, n = 36 (12 panelists × 3 reps). pH 7.1

| Samples | Total |
| --- | --- |
| 11% Sucrose | 20 |
| 6% Sucrose + 12.7 μM Compound K2 | 16 |
| Total | 36 |
| 11% Sucrose (p-value) | 0.681 |

TABLE 7-b

Sample selected as sweeter by panelists, n = 36 (18 panelists × 2 reps). pH 2.8

| Samples | Total |
| --- | --- |
| 12% Sucrose | 21 |
| 6% Sucrose + 7.6 μM Compound K2 | 15 |
| Total | 36 |
| 12% Sucrose (p-value) | 0.405 |

TABLE 8-a

Sample selected as sweeter by panelists, n = 33 (11 panelists × 3 reps). pH 7.1

| Samples | Total |
| --- | --- |
| 8% High Fructose Corn Syrup | 17 |
| 6% High Fructose Corn Syrup + 12.7 μM Compound K2 | 16 |
| Total | 33 |
| 8% High Fructose Corn Syrup (p-value) | >0.860 |

TABLE 8-b

Sample selected as sweeter by panelists, n = 51 (17 panelists × 3 reps). pH 2.8

| Samples | Total |
| --- | --- |
| 9% High Fructose Corn Syrup | 25 |
| 6% High Fructose Corn Syrup + 12.7 μM Compound K2 | 26 |
| Total | 51 |
| 9% High Fructose Corn Syrup (p-value) | 1.00 |

TABLE 9

Sample selected as sweeter by panelists, n = 51 (17 panelists × 2 reps).

| Samples | Total |
| --- | --- |
| 1% Sucrose | 29 |
| LSB + 12.7 μM Compound K2 | 22 |
| Total | 51 |
| 1% Sucrose (p-value) | 0.401 |

The results of human taste tests with Compound L2 are found below. Table 10 indicates that panelists perceived 6% sucrose+12.7 μM Compound L2 as being not significantly different in sweetness than a solution of 12% sucrose at pH 7.1. Table 11 indicates that panelists perceived 6% High Fructose Corn Syrup+12.7 μM Compound L2 as being not significantly different in sweetness than a solution of 9% High Fructose Corn Syrup at pH 2.8. Table 12 indicates that 12.7 μM Compound L2 alone is as sweet as a 1% sucrose solution.

TABLE 10

Sample selected as sweeter by panelists, n = 42 (14 panelists × 3 reps). pH 7.1

| Samples | Total |
| --- | --- |
| 12% Sucrose | 19 |
| 6% Sucrose + 12.7 μM Compound L2 | 23 |
| Total | 42 |
| 12% Sucrose (p-value) | 0.644 |

TABLE 11

Sample selected as sweeter by panelists, n = 36 (12 panelists × 3 reps). pH 2.8

| Samples | Total |
| --- | --- |
| 9% High Fructose Corn Syrup | 16 |
| 6% High Fructose Corn Syrup + 12.7 μM Compound L2 | 20 |
| Total | 36 |
| 9% High Fructose Corn Syrup (p-value) | 0.681 |

TABLE 12

Sample selected as sweeter by panelists, n = 36 (12 panelists × 3 reps).

| Samples | Total |
| --- | --- |
| 1% Sucrose | 19 |
| LSB + 12.7 μM Compound L2 | 17 |
| Total | 36 |
| 1% Sucrose (p-value) | 0.868 |

The results of human taste tests with Compound B1 are found below. Table 13 indicates that panelists perceived 6% sucrose+11.9 μM Compound B1 as being not significantly different in sweetness than a solution of 12% sucrose at pH 7.1. Table 14 indicates that panelists perceived 6% High Fructose Corn Syrup+11.9 μM Compound B1 as being not significantly different in sweetness than a solution of 9% High Fructose Corn Syrup at pH 2.8. Table 12 indicates that 11.9 μM Compound B1 alone is as sweet as a 1% sucrose solution.

TABLE 13

Sample selected as sweeter by panelists, n = 34 (17 panelists × 2 reps). pH 7.1

| Samples | Total |
| --- | --- |
| 12% Sucrose | 19 |
| 6% Sucrose + 11.9 μM Compound B1 | 15 |
| Total | 34 |
| 12% Sucrose (p-value) | 0.608 |

TABLE 14

Sample selected as sweeter by panelists, n = 34 (17 panelists × 2 reps). pH 2.8

| Samples | Total |
|---|---|
| 9% High Fructose Corn Syrup | 20 |
| 6% High Fructose Corn Syrup + 11.9 µM Compound B1 | 14 |
| Total | 34 |
| 9% High Fructose Corn Syrup (p-value) | 0.392 |

TABLE 15

Sample selected as sweeter by panelists, n = 45 (15 panelists × 3 reps).

| Samples | Total |
|---|---|
| 1% Sucrose | 19 |
| LSB + 11.9 µM Compound B1 | 26 |
| Total | 45 |
| 1% Sucrose (p-value) | 0.371 |

The results of human taste tests with Compound F3 are found below. Table 16 indicates that panelists perceived 6% sucrose+9.2 µM Compound F3 as being not significantly different in sweetness than a solution of 10% sucrose at pH 7.1. Table 17 indicates that panelists perceived 6% High Fructose Corn Syrup+9.2 µM Compound F3 as being not significantly different in sweetness than a solution of 9% High Fructose Corn Syrup at pH 2.8. Table 18 indicates that 9.2 µM Compound F3 alone is as sweet as a 1% sucrose solution.

TABLE 16

Sample selected as sweeter by panelists, n = 33 (11 panelists × 3 reps). pH 7.1

| Samples | Total |
|---|---|
| 10% Sucrose | 16 |
| 6% Sucrose + 9.2 µM Compound F3 | 17 |
| Total | 33 |
| 10% Sucrose (p-value) | >0.728 |

TABLE 17

Sample selected as sweeter by panelists, n = 51 (17 panelists × 3 reps). pH 2.8

| Samples | Total |
|---|---|
| 9% High Fructose Corn Syrup | 28 |
| 6% High Fructose Corn Syrup + 9.2 µM Compound F3 | 23 |
| Total | 51 |
| 9% High Fructose Corn Syrup (p-value) | 0.576 |

TABLE 18

Sample selected as sweeter by panelists, n = 30 (15 panelists × 2 reps).

| Samples | Total |
|---|---|
| 1% Sucrose | 16 |
| LSB + 9.2 µM Compound F3 | 14 |
| Total | 30 |
| 1% Sucrose (p-value) | 0.856 |

Experiment 2

Sweet Flavor and Sweet Flavor Potentiation Measurement in Product prototypes Using Human Panelists Exp 2-1

Sucrose Potentiation of Compound K2 in Iced Coffee

All samples were made in an Iced Coffee formulation consisting of Brewed Coffee, 2% milk, Sucrose and water. The samples were prepared using a 0.2% Compound stock made with 0.2% sodium bicarbonate and water. Tests samples are presented in pairs to the panelists and they are asked to determine which of the sample is sweeter.

In one paired comparison test, the panelist is presented with two different samples and asked to identify the sample which is sweeter. The samples within a paired comparison test are presented in a randomized, counterbalanced order. Panelists have up to a 1 minute delay between taste tests to clear the mouth of any tastes.

Binomial probability tables are used to determine the probability of the correct number of responses occurring for each test at alpha=0.05.

Table 19 indicates that panelists perceived 4% sucrose Iced Coffee+7.6 µM Compound K2 as being not significantly different in sweetness than a solution of 8% sucrose Iced Coffee.

TABLE 19

Sample selected as sweeter by panelists, n = 33 (11 panelists × 3 reps)

| Samples | Total |
|---|---|
| 8% Sucrose | 16 |
| 4% Sucrose + 7.6 µM Compound K2 | 17 |
| Total | 30 |
| 8% Sucrose (p-value) | >0.728 |

All publications and patent applications herein are incorporated by reference to the same extent as if each individual publication or patent application was specifically and individually indicated to be incorporated by reference.

The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. An ingestible composition comprising a compound having structural Formula (Ia):

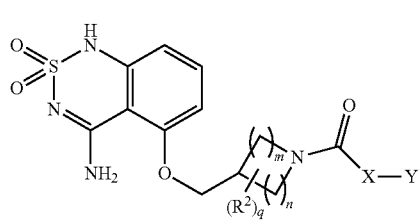

(Ia)

or a salt or solvate thereof, and an ingestibly acceptable excipient;
wherein in the compound of Formula (Ia),
in is 4, and n is 0; or m is 3, and n is 1; or m and n are both 2;
q is 0, 1, 2, or 3;
X is a covalent bond or —NR$^1$—;
R$^1$ is hydrogen or C1 to C6 alkyl;
Y is alkyl, substituted alkyl, heteroalkyl, substituted heteroalkyl, carbocyclyl, substituted carbocyclyl, heterocyclyl, substituted heterocyclyl, aryl, substituted aryl, heteroaryl, substituted heteroaryl, aralkyl, substituted aralkyl, heteroarylalkyl, or substituted heteroarylalkyl; and
each R$^2$ is independently selected from the group consisting of alkyl, heteroalkyl, halo, hydroxyl, alkoxy, amino, alkylamino, cyano, nitro, haloakl, carboxylic acid, amide, ester, acyl, thiol, alkylthio, and sulfonamide,
wherein the substituents are selected from the group consisting of —R$^a$, halo, —O$^-$, =O, —OR$^b$, —SR$^b$, —S$^-$, =S, —NR$^c$R$^c$, =NR$^b$, =N—OR$^b$, —CF$_3$, —CN, —OCN, —SCN, —S(O)$_2$R$^b$, —S(O)$_2$NR$^b$, —S(O)$_2$O$^-$, —S(O)$_2$OR$^b$, —OS(O)$_2$R$^b$, —OS(O) O$^-$, —OS(O)$_2$OR$^b$, —C(O)R$^b$ —C(S)R$^b$, —C(NR$^b$)R$^b$, —C(O)O$^-$, —C(O)OR$^b$, —C(S)OR$^b$, —C(O)NR$^c$NC$^c$, —C(NR$^b$)NR$^c$R$^c$, —OC(O)R$^b$, —OC(S)R$^b$, —OC(O) O$^-$, —OC(O)OR$^b$, —OC(S)OR$^b$, —NR$^b$C(O)R$^b$, —NR$^b$C(S)R$^b$, —NR$^b$C(O)O$^-$, —NR$^b$C(O)OR$^b$, —NR$^b$C(S)OR$^b$, —NR$^b$C(O)NR$^c$R$^c$, —NR$^b$C(NR$^b$)R$^b$ and —NR$^b$C(NR$^b$)NR$^c$R$^c$, where R$^a$ is selected from the group consisting of alkyl, cycloalkyl, heteroalkyl, cycloheteroalkyl, aryl, arylalkyl, heteroaryl and heteroarylalkyl; each R$^b$ is independently hydrogen or R$^a$; and each R$^c$ is independently R$^b$ or alternatively, the two R$^c$ s may be taken together with the nitrogen atom to which they are bonded form a 4-, 5-, 6- or 7-membered cycioheteroalkyl which may optionally include from 1 to 4 of the same or different additional heteroatoms selected from the group consisting of O, N and S.

2. The ingestible composition of claim 1, wherein in the compound of formula (Ia), X is NH.

3. The ingestible composition of claim 1, wherein in the compound of formula (Ia), X is a covalent bond.

4. The ingestible composition of claim 1, wherein the compound of Formula (Ia) is represented by structural Formula selected from the group consisting of:

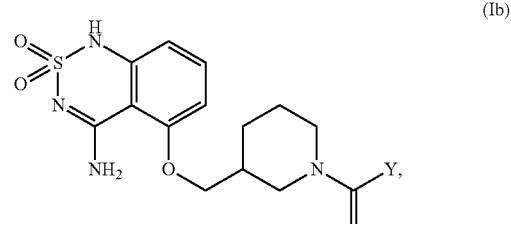

(Ib)

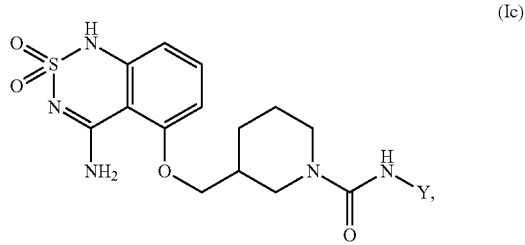

(Ic)

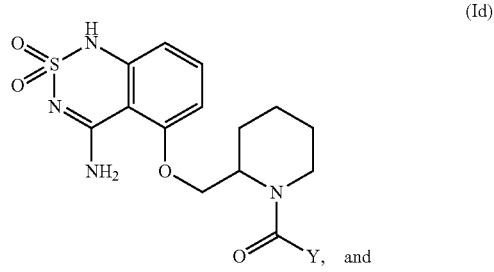

(Id)

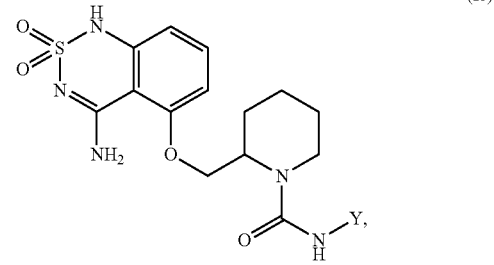

(Ie)

or a salt or solvate thereof;
wherein,
Y is alkyl, substituted alkyl, heteroalkyl, substituted heteroalkyl, carbocyclyl, substituted carbocyclyl, heterocyclyl, substituted heterocyclyl, aryl, substituted aryl, heteroaryl, substituted heteroaryl, aralkyl, substituted aralkyl, heteroarylalkyl, or substituted heteroaryialkyl.

5. The ingestible composition of claim 4, wherein in the compound of formula (Ib), Y is —(C1 to C3 alkylene)-aryl, —(C1 to C3 alkyiene)-substituted aryl, —(C1 to C3 alkylene)-heteroaryl or —(C1 to C3 alkylene)-substituted heteroaryl.

6. The ingestible composition of claim 4, wherein in the compound of formula (Ic), Y is C1 to C12 alkyl, substituted C1 to C12 alkyl, five or six-membered heteroaryl, substituted five or six-membered heteroaryl, —(C1 to C3 alkylene)-(five or six-membered heteroaryl), or —(C1 to C3 alkylene)-(substituted five or six-membered heteroaryl).

7. The ingestible composition of claim 4, wherein in the compound of formula (Ib), Y is C1 to C12 alkyl, substituted C1 to C12 alkyl, C1 to C12 heteroalkyl, or substituted C1 to C12 heteroalkyl.

8. The ingestible composition of claim 4, wherein in the compound of formula (Ib), Y is three to seven-membered cycloalkyl, substituted three to seven-membered cycloalkyl, five to seven-membered heterocyclyl, or substituted five to seven-membered heterocyclyl.

9. The ingestible composition of claim 4, wherein in the compound of formula (Ib), Y is phenyl, substituted phenyl, an optionally substituted five or six-membered monocyclic heteroaryl, or an optionally substituted ten to twelve-membered bicyclic heteroaryl.

10. The ingestible composition of claim 1, wherein the compound having Formula (Ia) is selected from the group consisting of

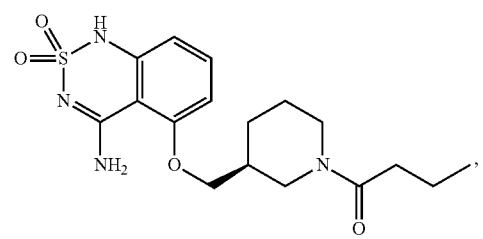

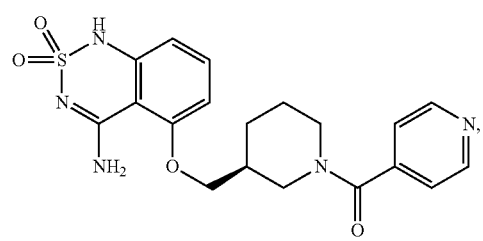

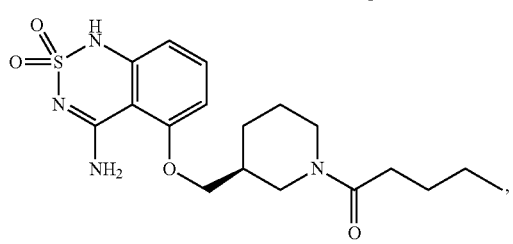

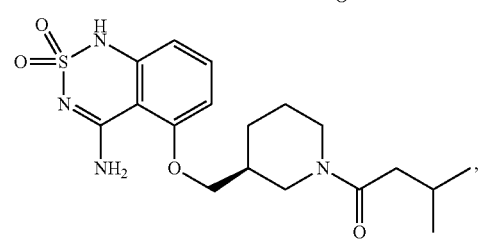

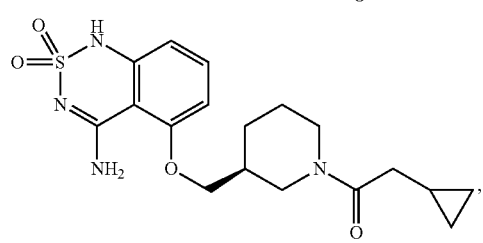

-continued

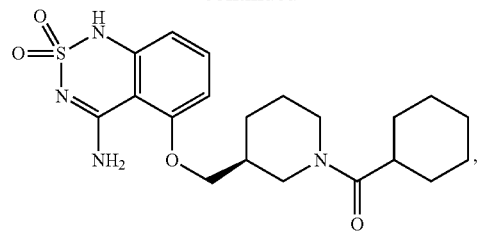

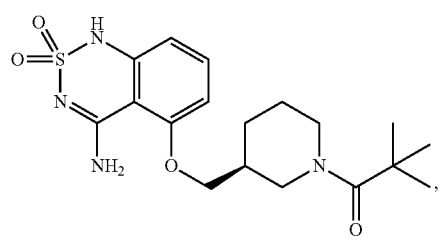

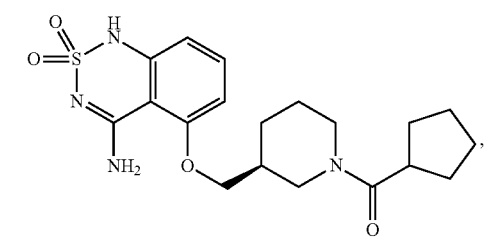

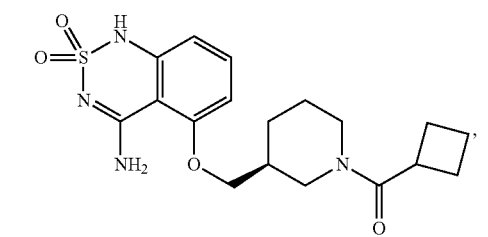

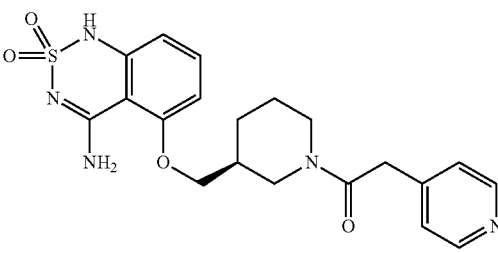

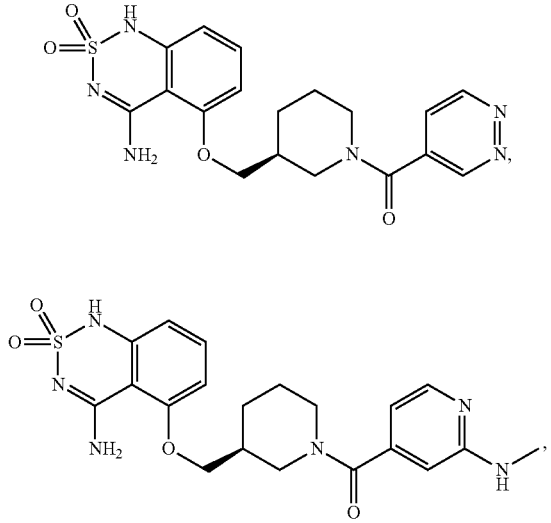

187
-continued
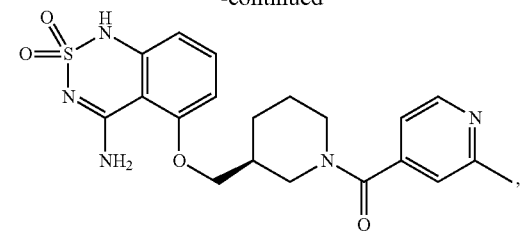
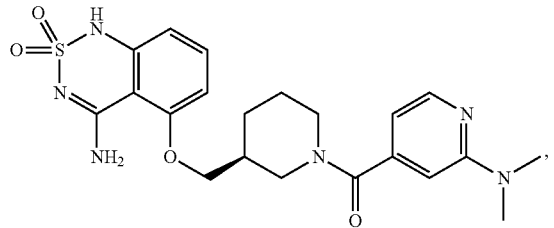
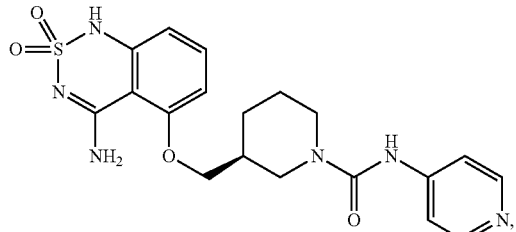
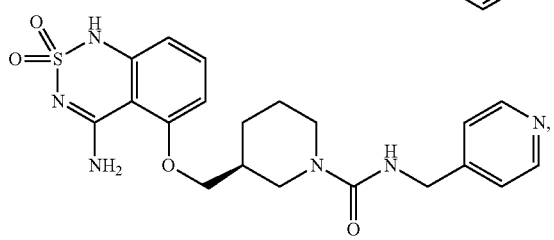
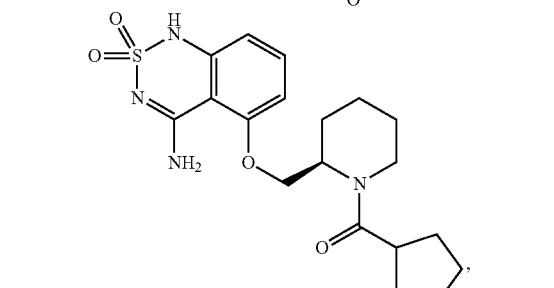
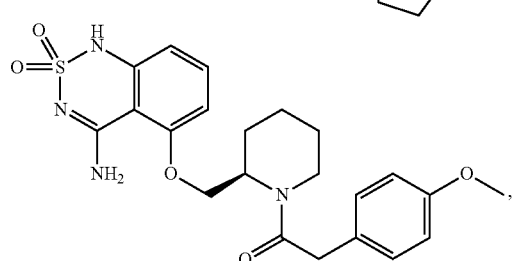
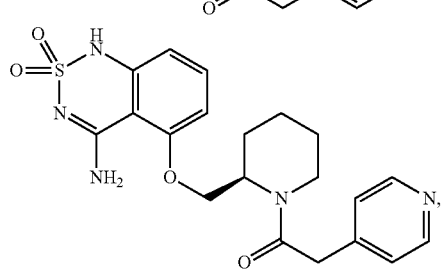
188
-continued
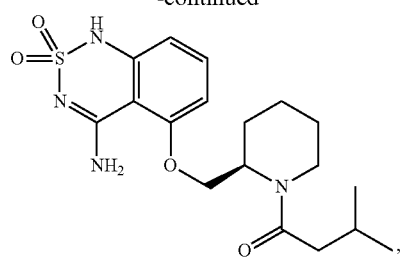
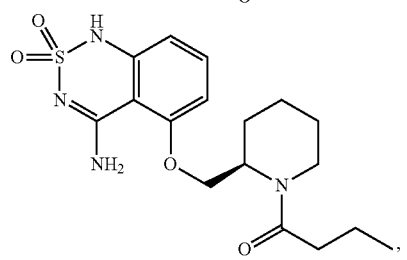
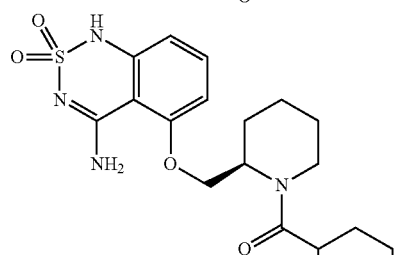
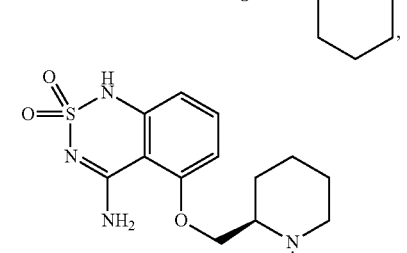
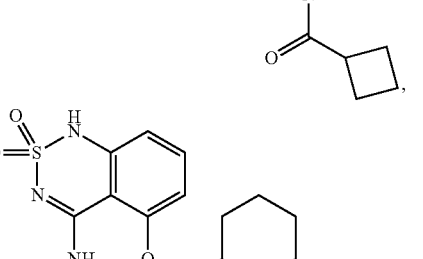
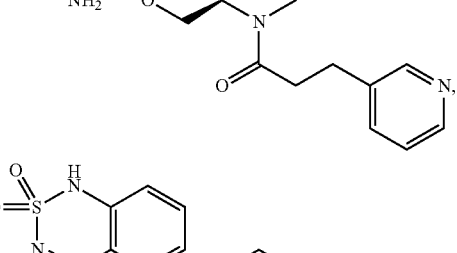
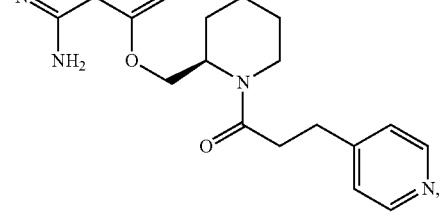

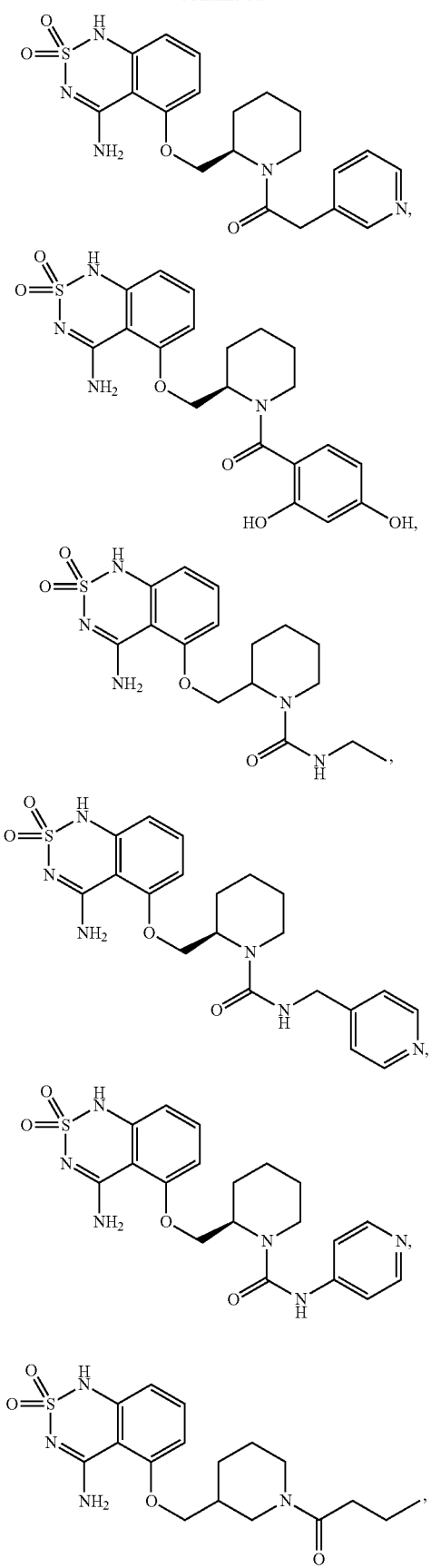

191
-continued
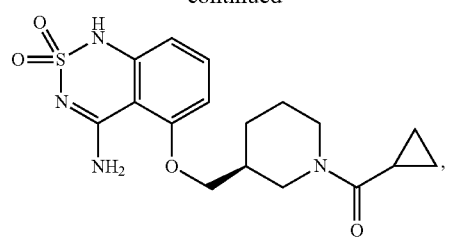
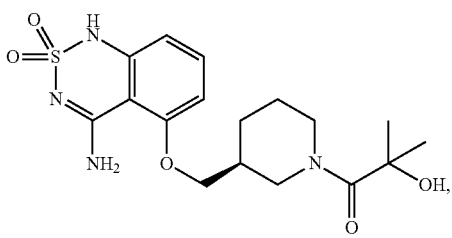
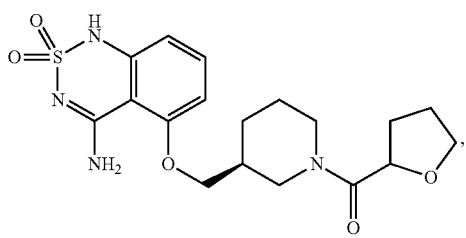
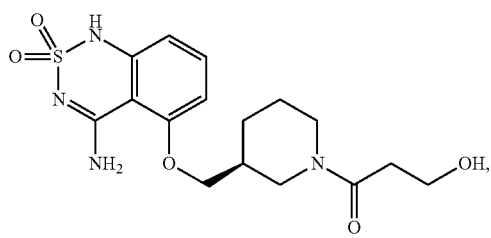
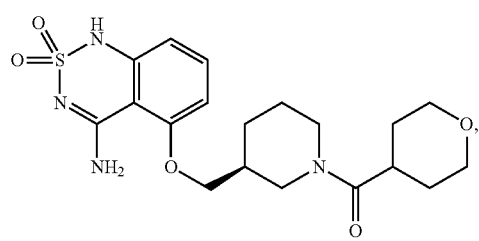
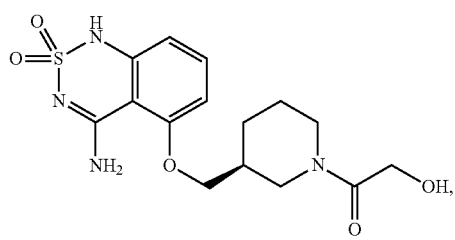
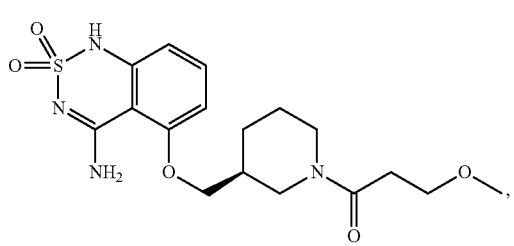
192
-continued
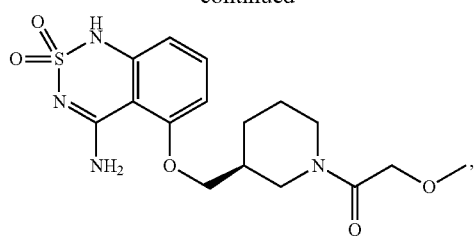
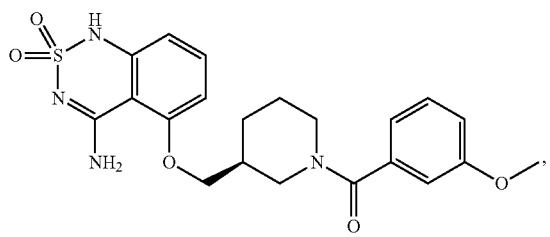
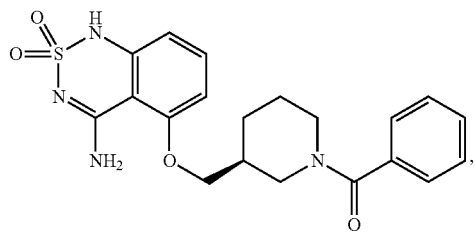
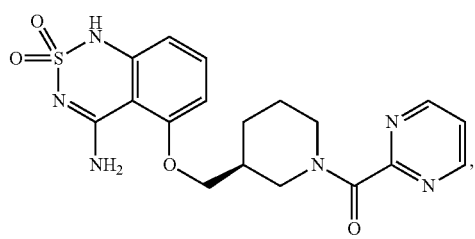
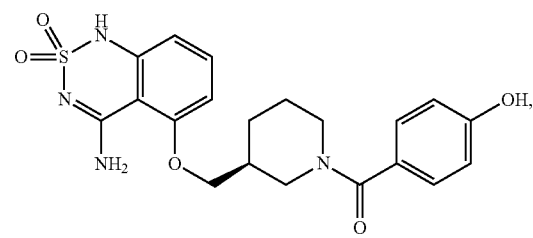
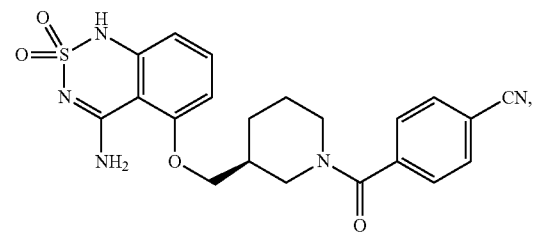
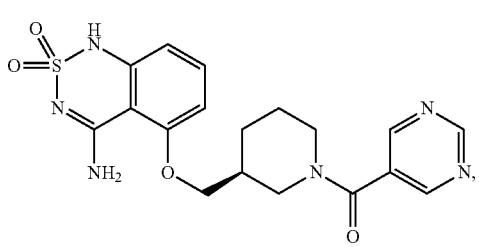

193
-continued
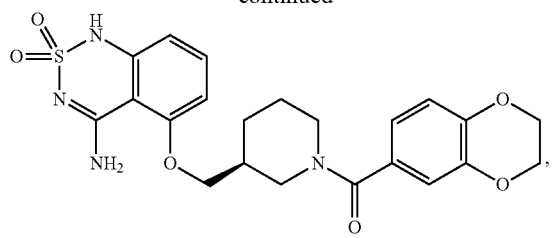
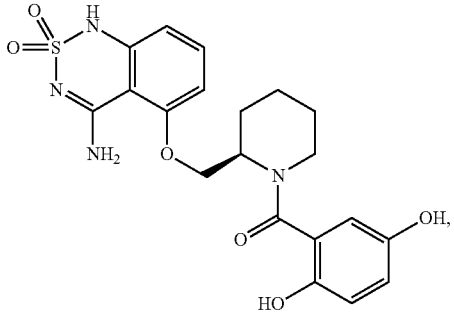
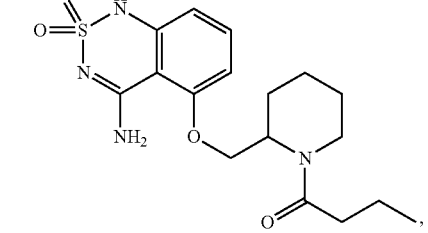
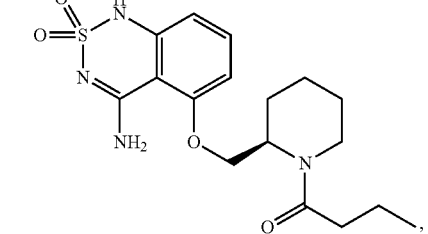
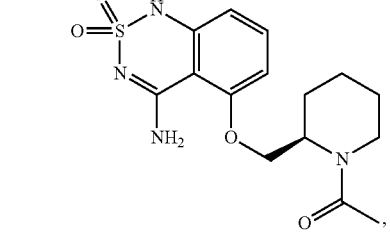
194
-continued
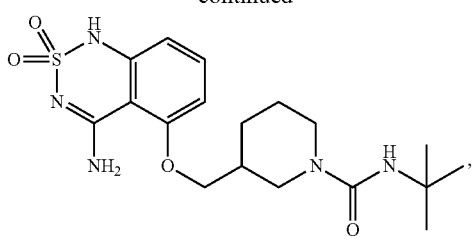
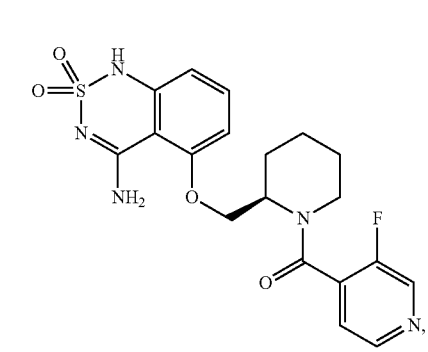

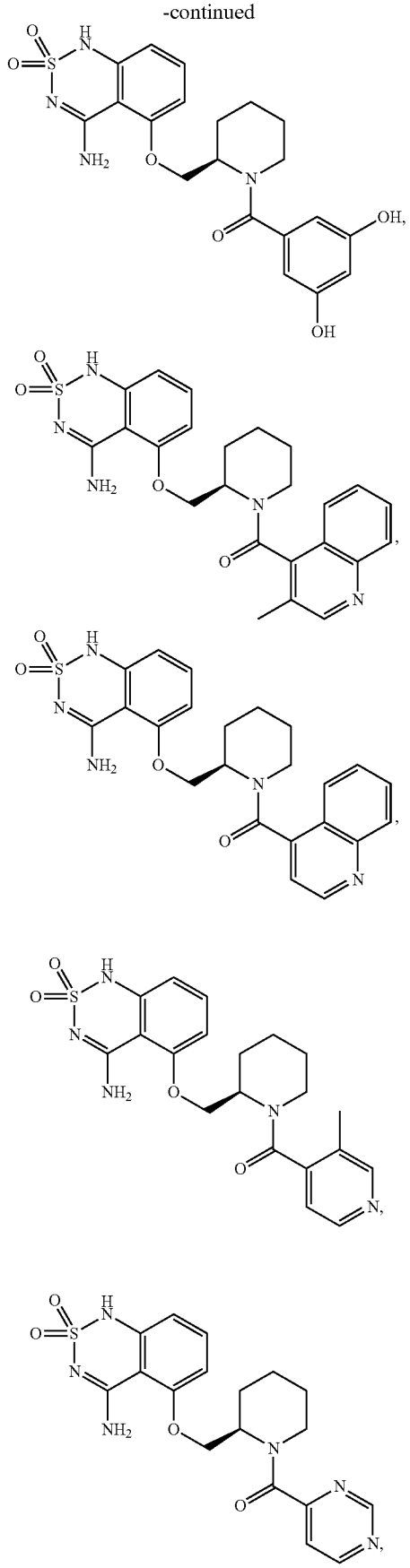
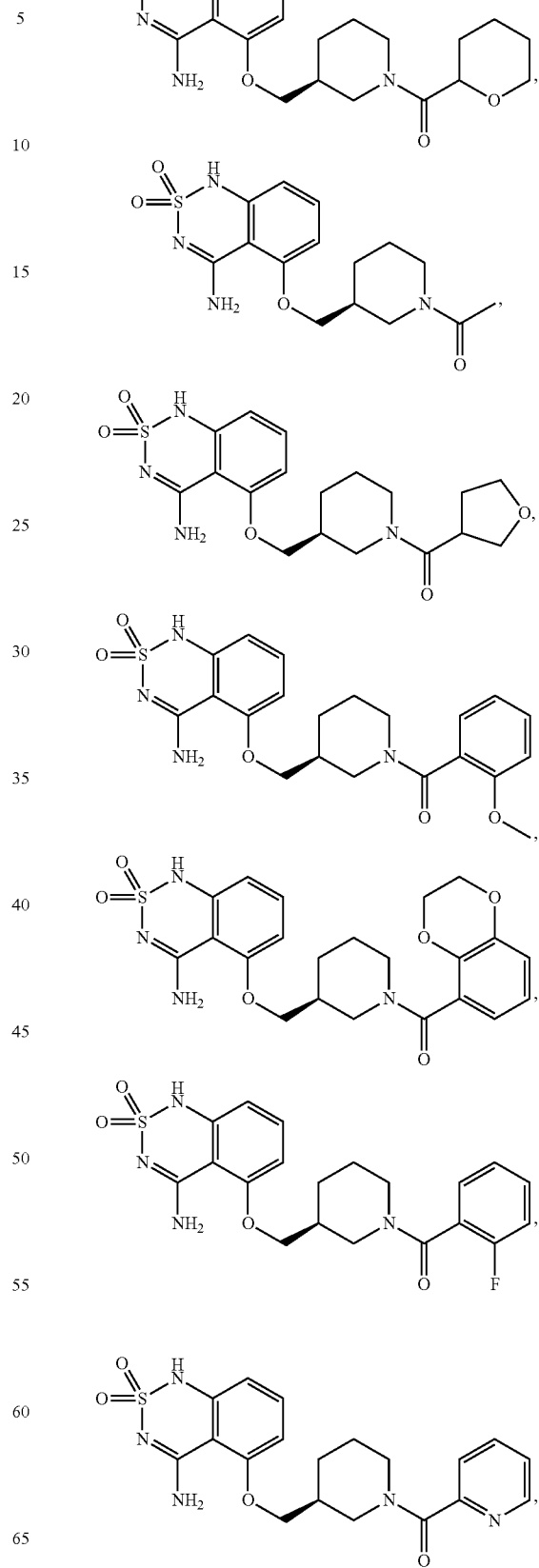

197
-continued
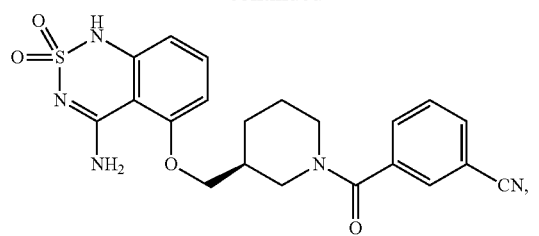
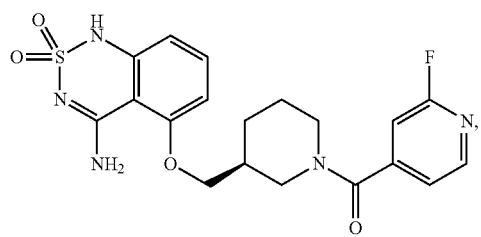
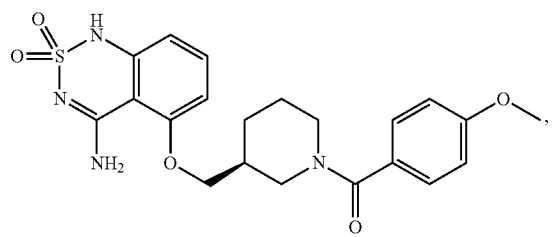
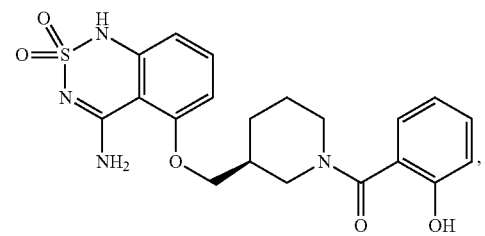
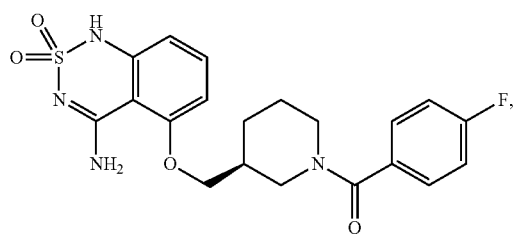
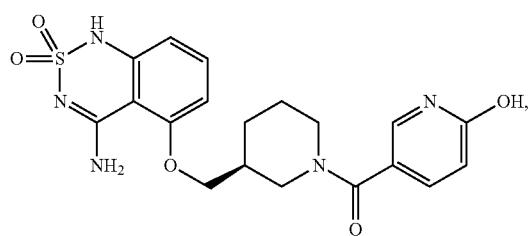
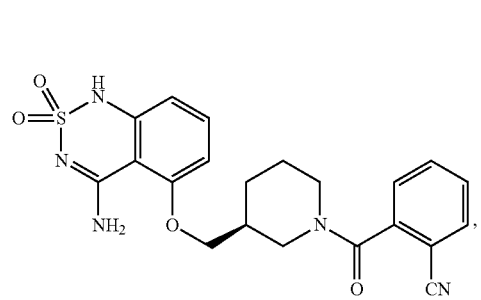
198
-continued
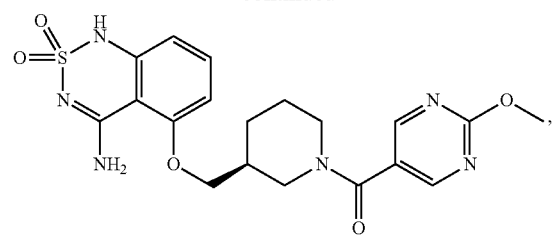
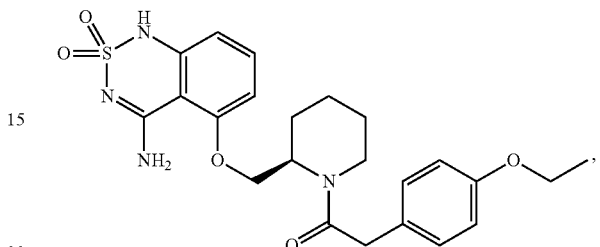
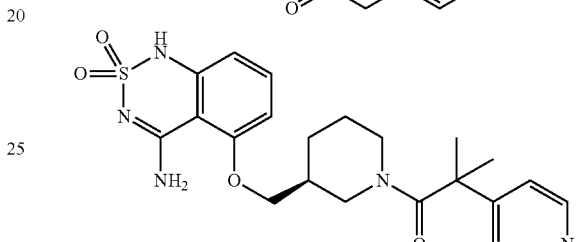
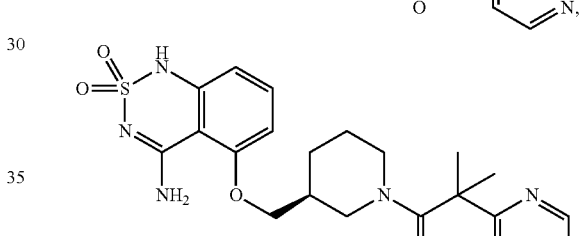
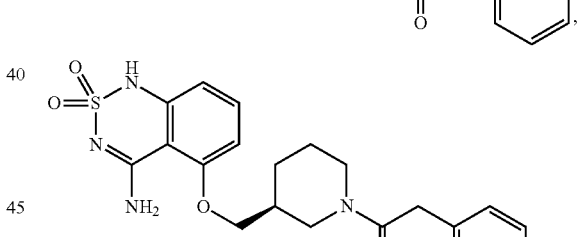
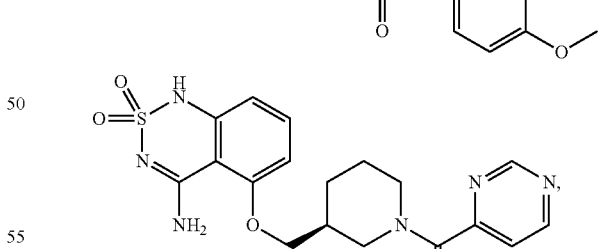
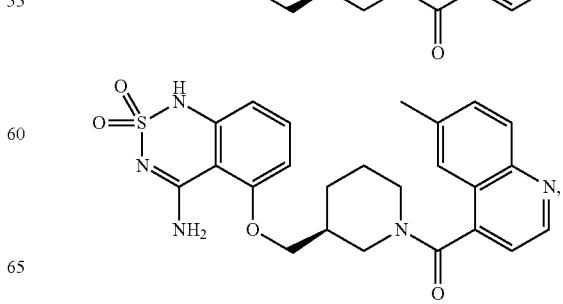

-continued
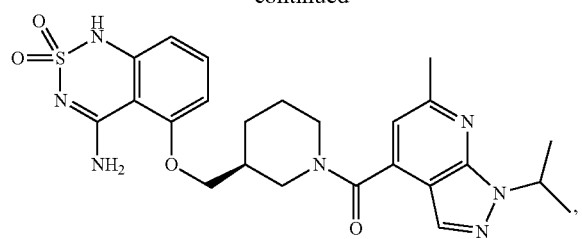
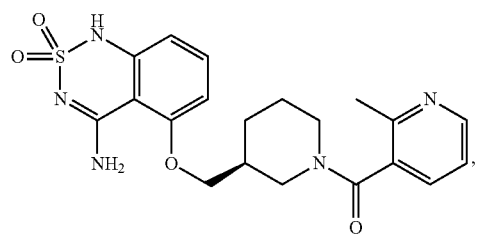
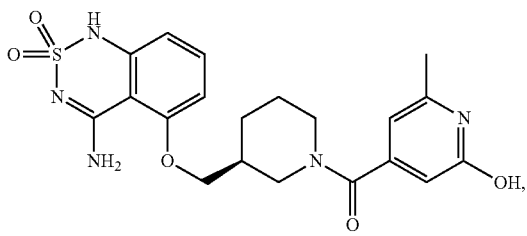
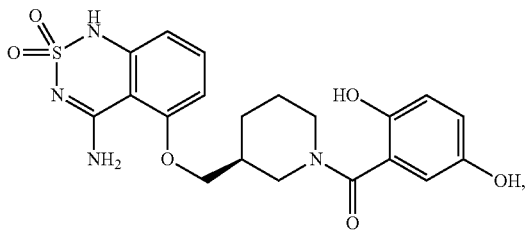
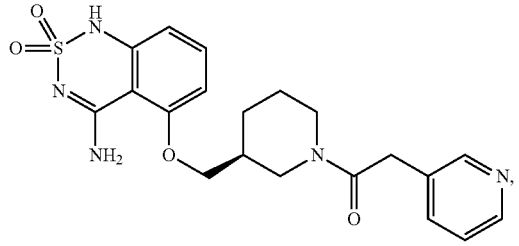
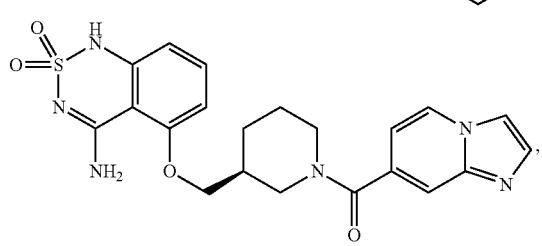
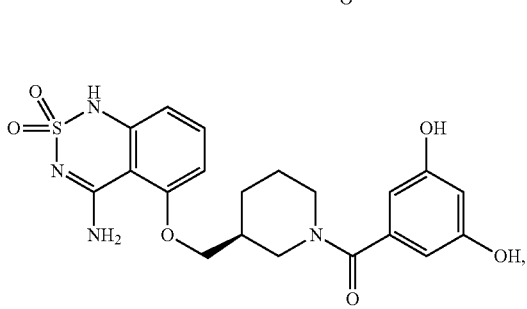
-continued
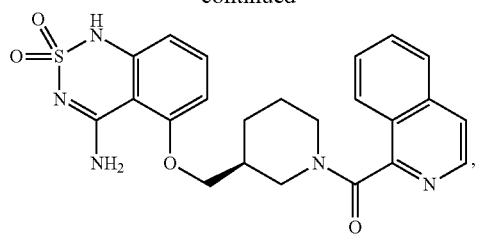
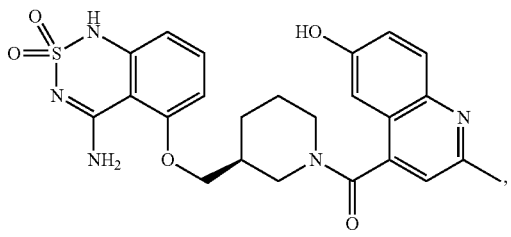
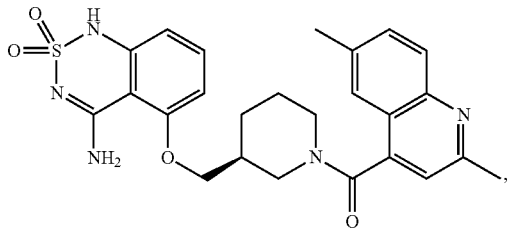
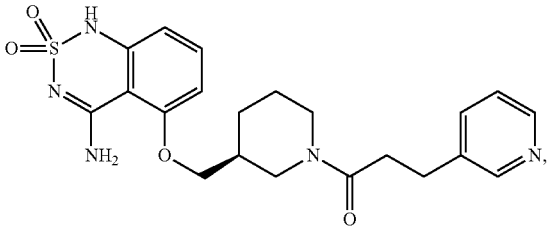
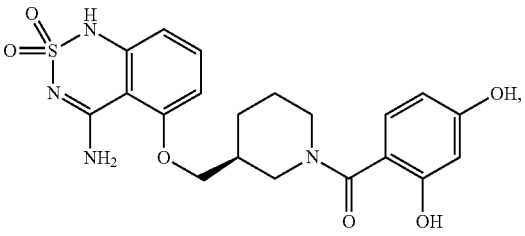
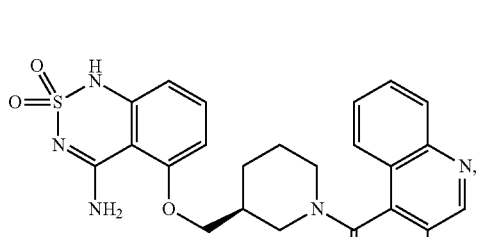
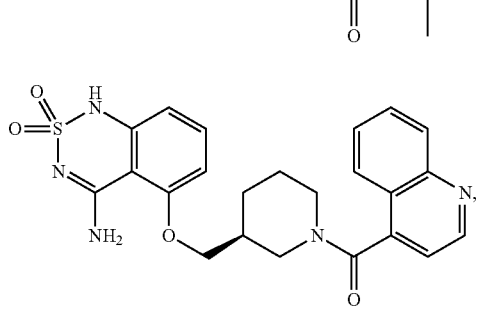

201
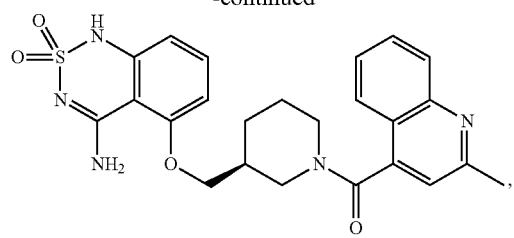
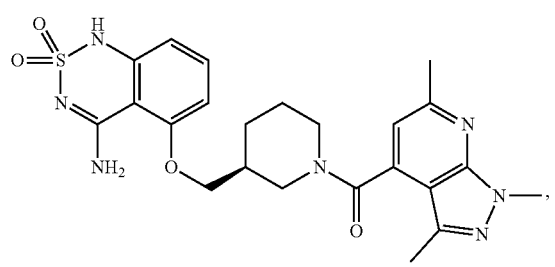
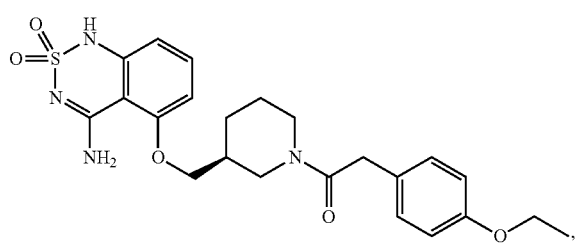
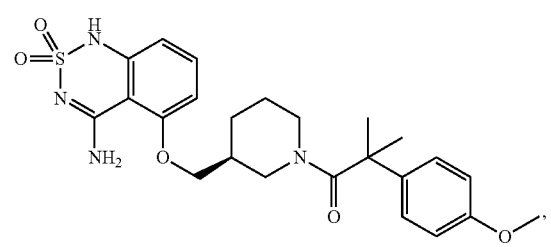
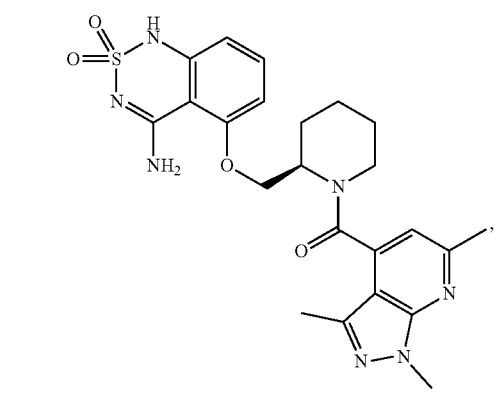
202
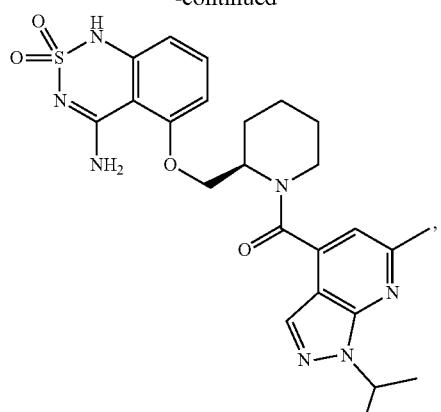
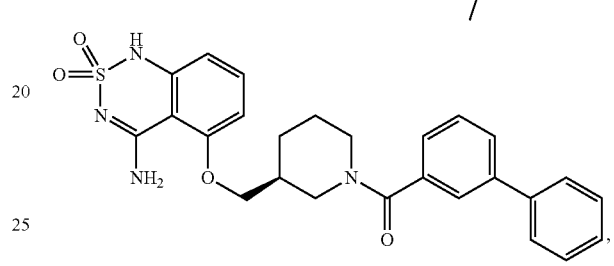
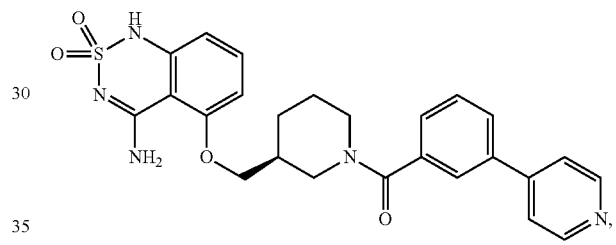
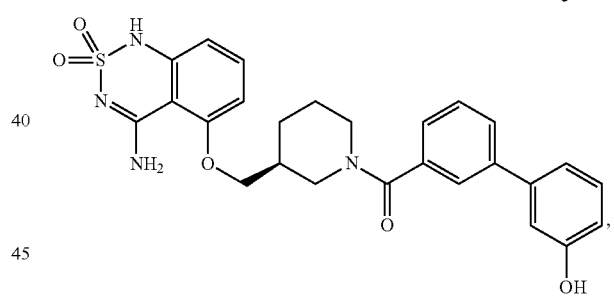
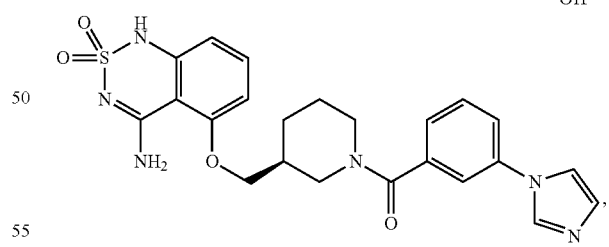
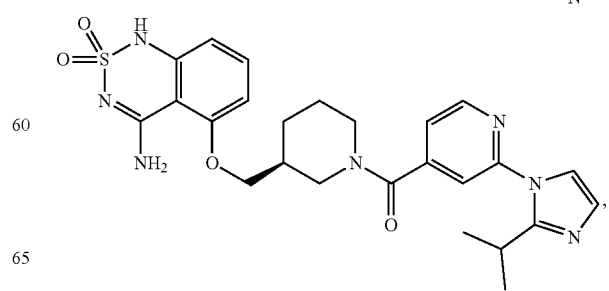

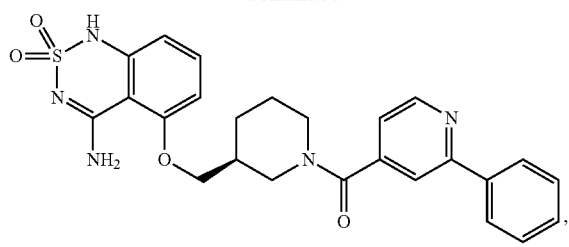,
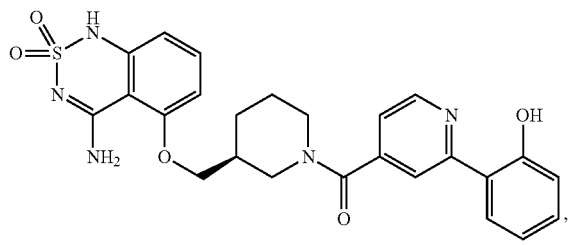,
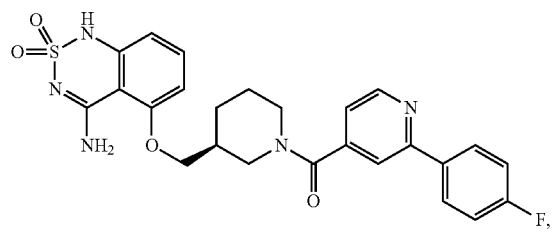,
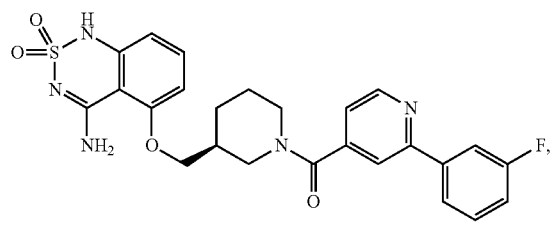,
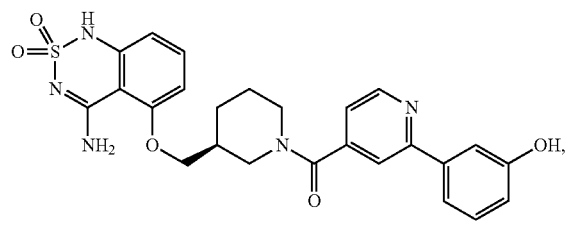,
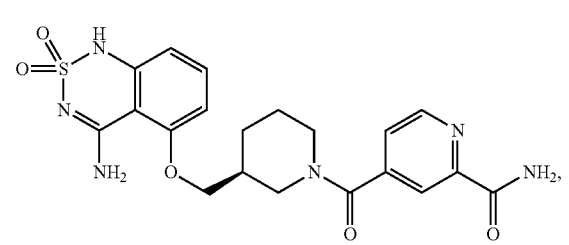,
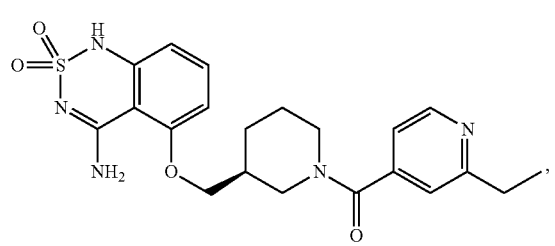,
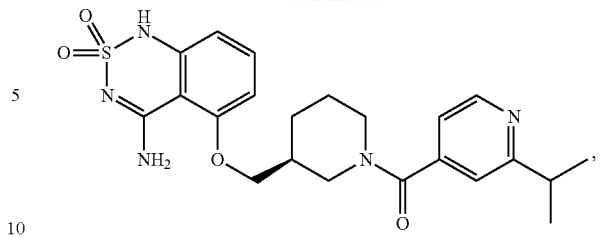,
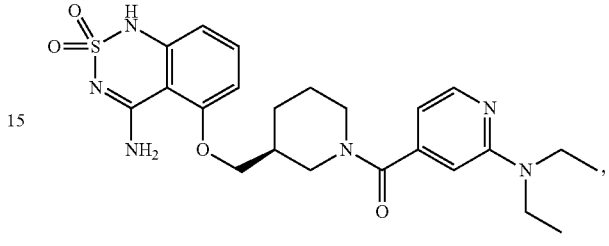,
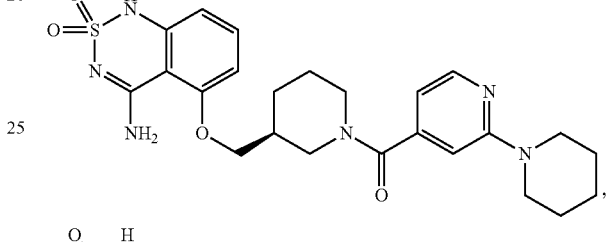,
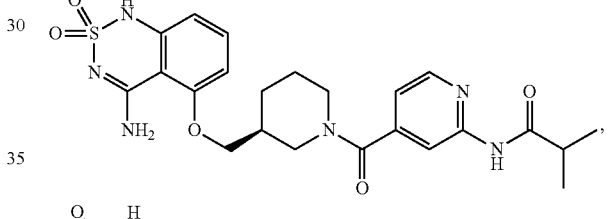,
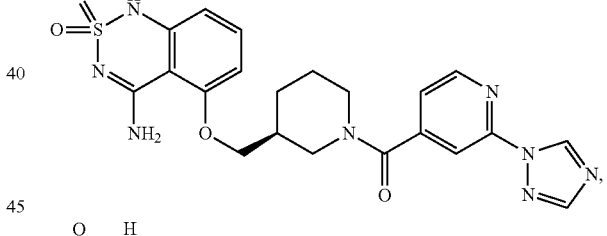,
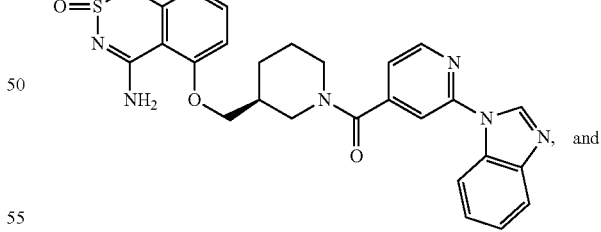 and
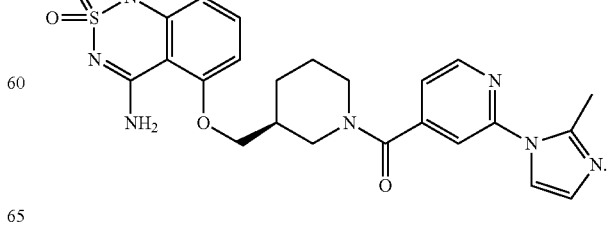
or a salt or solvate thereof.

11. The ingestible composition of claim 1, further comprising one or more sweeteners.

12. The ingestible composition of claim 11, wherein the sweetener is selected from the group consisting of sucrose, fructose, glucose, galactose, mannose, lactose, tagatose, maltose, high fructose corn syrup, D-tryptophan, glycine, erythritol, isomalt, lactitol, mannitol, sorbitol, xylitol, maltodextrin, maltitol, isomalt, hydrogenated glucose syrup (HGS), hydrogenated starch hydrolyzate (HSH), stevioside, rebaudioside A, other sweet Stevia-based glycosides, carrelame, other guanidine-based sweeteners, saccharin, acesulfatne-K, cyclamate, sucralose, alitame, mogroside, neotame, aspartame, other aspartame derivatives, and combinations thereof.

13. The ingestible composition of claim 1, which is a food or beverage product, a pharmaceutical composition, a nutritional product, a dietary supplement, over-the-counter medication, or oral care product.

14. The ingestible composition of claim 13, wherein the food or beverage product is for human or animal consumption.

15. The ingestible composition of claim 13, wherein the food or beverage product is selected from the group consisting of the Soup category; the Dried Processed Food category; the Beverage category; the Ready Meal category; the Canned or Preserved Food category; the Frozen Processed Food category; the Chilled Processed Food category; the Snack Food category; the Baked Goods category; the Confectionary category; the Dairy Product category; the Ice Cream category; the Meal Replacement category; the Pasta and Noodle category; the Sauces, Dressings, Condiments category; the Baby Food category; the Spreads category; sweet coatings, frostings, or glazes; and combinations thereof.

16. A method of increasing the sweet taste of a composition comprising contacting the composition with a compound having structural Formula (Ia):

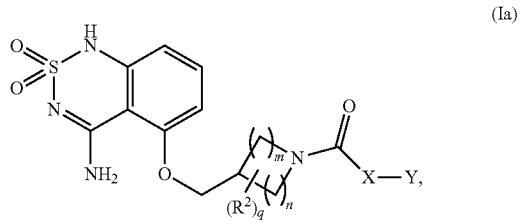

(Ia)

or a salt or solvate thereof;
wherein,
m is 4, and n is 0; or m is 3, and n is 1; or m and n are both 2;
q is 0, 1, 2, or 3;
X is a covalent bond or —NR$^1$—;
R$^1$ is hydrogen or C1 to C6 alkyl;
Y is alkyl, substituted alkyl, heteroalkyl, substituted heteroalkyl, carbocyclyl, substituted carbocyclyl, heterocyclyl, substituted heterocyclyl, aryl, substituted aryl, heteroaryl, substituted heteroaryl, aralkyl, substituted aralkyl, heteroarylalkyl, or substituted heteroarylalkyl; and
each R$^2$ is independently selected from the group consisting of alkyl, heteroalkyl, halo, hydroxyl, alkoxy, amino, alkylamino, cyano, nitro, haloalkyl, carboxylic acid, amide, ester, acyl, thiol, alkylthio, and sulfonamide, to form a modified composition,
wherein the substituents are selected from the group consisting of —R$^a$, halo, —O$^-$, =O, —OR$^b$, —SR$^b$, —S$^-$, =S, —NR$^c$R$^c$, =NR$^b$, =N—OR$^b$, —CF$_3$, —CN, —OCN, —SCN, —S(O)$_2$R$^b$, —S(O)$_2$NR$^b$, —S(O)$_2$O$^-$, —S(O)$_2$OR$^b$, —OS(O)$_2$R$^b$, —OS(O)$_2$O$^-$, —OS(O)$_2$OR$^b$, —C(O)R$^b$, —C(S)R$^b$, —C(NR$^b$)R$^b$, —C(O)O$^-$, —C(O)OR$^b$, —C(S)OR$^b$, —C(O)NR$^c$R$^c$, —C(NR$^b$)NR$^c$R$^c$, —OC(O)R$^b$, —OC(S)R$^b$, —OC(O)O$^-$, —OC(O)OR$^b$, —OC(S)OR$^b$, —NR$^b$C(O)R$^b$, —NR$^b$C(S)R$^b$, —NR$^b$C(O)O$^-$, —NR$^b$C(O)OR$^b$, —NR$^b$C(S)OR$^b$, —NR$^b$C(O)NR$^c$R$^c$, —NR$^b$C(NR$^b$)R$^b$ and —NR$^b$C(NR$^b$)NR$^c$ R$^c$, where R$^a$ is selected from the group consisting of alkyl, cycloalkyl, heteroalkyl, cycioheteroalkyl, aryl, arylalkyl, heteroaryl and heteroaryialkyl; each R$^b$ is independently hydrogen or R$^a$; and each R$^c$ is independently R$^b$ or alternatively, the two R$^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S.

17. A flavoring concentrate formulation comprising
i) as flavor modifying ingredient, a compound having structural Formula (Ia):

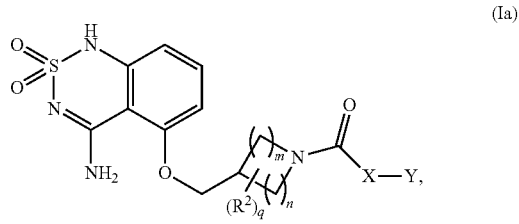

(Ia)

or a salt or solvate thereof;
wherein,
m is 4, and n is 0; or m is 3, and n is 1; or m and n are both 2;
q is 0, 1, 2, or 3;
X is a covalent bond or —NR$^1$—;
R$^1$ is hydrogen or C1 to C6 alkyl;
Y is alkyl, substituted alkyl, heteroalkyl, substituted heteroalkyl, carbocyclyl, substituted carbocyclyl, heterocyclyl, substituted heterocyclyl, aryl, substituted aryl, heteroaryl, substituted heteroaryl, aralkyl, substituted aralkyl, heteroarylalkyl, or substituted heteroarylalkyl; and
each R$^2$ is independently selected from the group consisting of alkyl, heteroalkyl, halo, hydroxyl, alkoxy, amino, alkylamino, cyano, nitro, haloalkyl, carboxylic acid, amide, ester, acyl, thiol, alkytthio, and sulfonamide,
wherein the substituents are selected from the group consisting of —R$^a$, halo, —O$^-$, =O, —OR$^b$, —SR$^b$;—S$^-$, =S, —NR$^c$R$^c$, =NR$^b$, =N—OR$^b$, —CF$_3$, —CN, —OCN, —SCN, —S(O)$_2$R$^b$, —S(O)$_2$NR$^b$, —S(O)$_2$O$^-$, —S(O)$_2$OR$^b$;    —OS(O)$_2$R$^b$,    —OS(O)$_2$O$^-$, —OS(O)$_2$OR$^b$, —C(O)R$^b$, —C(S)R$^b$, —C(NR$^b$)R$^b$, —C(O)O$^-$, —C(O)OR$^b$,—C(S)OR$^b$, —C(O)NR$^c$R$^c$, —C(NR$^b$)NR$^c$R$^c$, —OC(O)R$^b$, —OC(S)R$^b$, —OC(O)O$^-$, —OC(O)OR$^b$, —OC(S)OR$^b$, —NR$^b$C(O)R$^b$, —NR$^b$C(S)R$^b$, —NR$^b$C(O)O$^-$, —NR$^b$C(O)OR$^b$, —NR$^b$C(S)OR$^b$, —NR$^b$C(O)NR$^c$R$^c$, —NR$^b$C(NR$^b$)R$^b$ and —NR$^b$C(NR$^b$)NR$^c$ R$^c$, where R$^a$ is selected from the group consisting of alkyl, cycloalkyl, heteroalkyl, cycloheteroalkyl, aryl, arylalkyl, heteroaryl and heteroarylalkyl; each R$^b$ is independently hydrogen or R$^a$; and each R$^c$ is independently R$^b$ or alternatively, the two R[c]s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S;
ii) a carrierr; and
iii) optionally at least one adjuvant.

18. The flavoring concentrate formulation of claim 17, wherein X is NH in the compound of formula (Ia).

19. The flavoring concentrate formulation of claim 17, wherein X is a covalent bond in the compound of formula (Ia).

20. The flavoring concentrate formulation of claim 17, wherein the compound of Formula (Ia) is represented by structural Formula selected from the group consisting of:

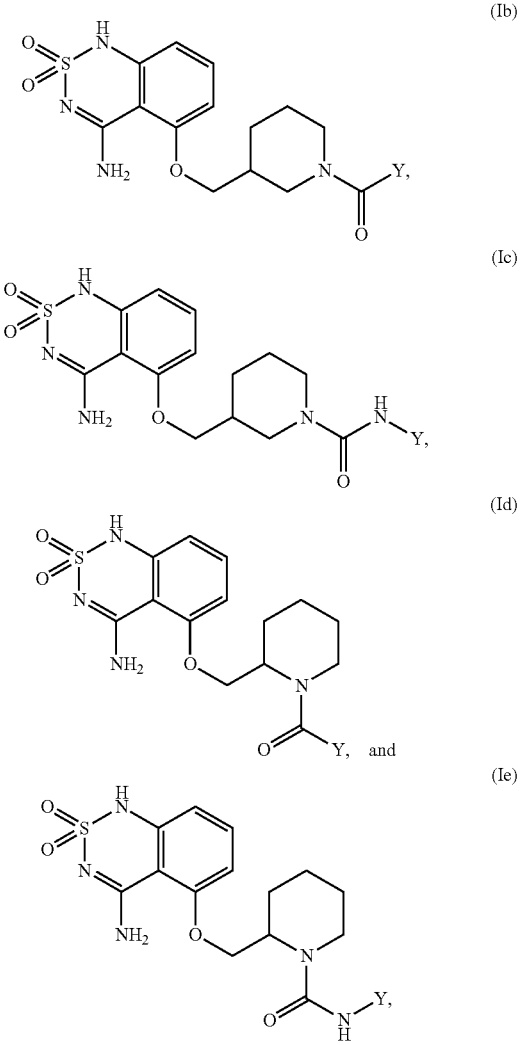

or a salt or solvate thereof;
wherein,
Y is alkyl, substituted alkyl, heteroalkyl, substituted heteroalkyl, carbocyclyl, substituted earboeyelyl, heterocyclyl, substituted heterocyclyl, aryl, substituted aryl, heteroaryl, substituted heteroalyi, aralkyl, substituted aralkyl, heteroaryl alkyl, or substituted heteroaryialkyl.

21. The flavoring concentrate formulation of claim 20, wherein in the compound of formula (Ib), Y is —(C1 to C3 alkylene)-aryl, —(C1 to C3 alkylene)-substituted aryl, —(C1to C3 alkylene)-heteroaryl or —(C1 to C3 alkylene)-substituted heteroaryl.

22. The flavoring concentrate formulation of claim 20, wherein in the compound of formula (Ic), Y is C1 to C12 alkyl, substituted C1 to C12 alkyl, five or six-membered heteroaryl, substituted five or six-membered heteroaryl, —(C1 to C3 alkylene)-(five or six-membered heteroaryl), or —(C1 to C3 alkylene)-(substituted five or six-membered heteroaryl).

23. The flavoring concentrate formulation of claim 20, wherein in the compound of formula (Ib), Y is C1 to C12 alkyl, substituted C1 to C12 alkyl, C1 to C12 heteroalkyl, or substituted C1 to C12 heteroalkyl.

24. The flavoring concentrate formulation of claim 20, wherein in the compound of formula (Ib), Y is three to seven-membered cycloalkyl, substituted three to seven-membered cycloakyl five to seven-membered heterocyclyl, or substituted five to seven-membered heterocyclyl.

25. The flavoring concentrate formulation of claim 20, wherein in the compound of formula (Ib), Y is phenyl, substituted phenyl, an optionally substituted five or six-membered monocyclic heteroaryl, or an optionally substituted ten to twelve-membered bicyclic heteroaryl.

26. The flavoring concentrate formulation of claim 20, wherein the compound having Formula (Ia) is selected from the group consisting of

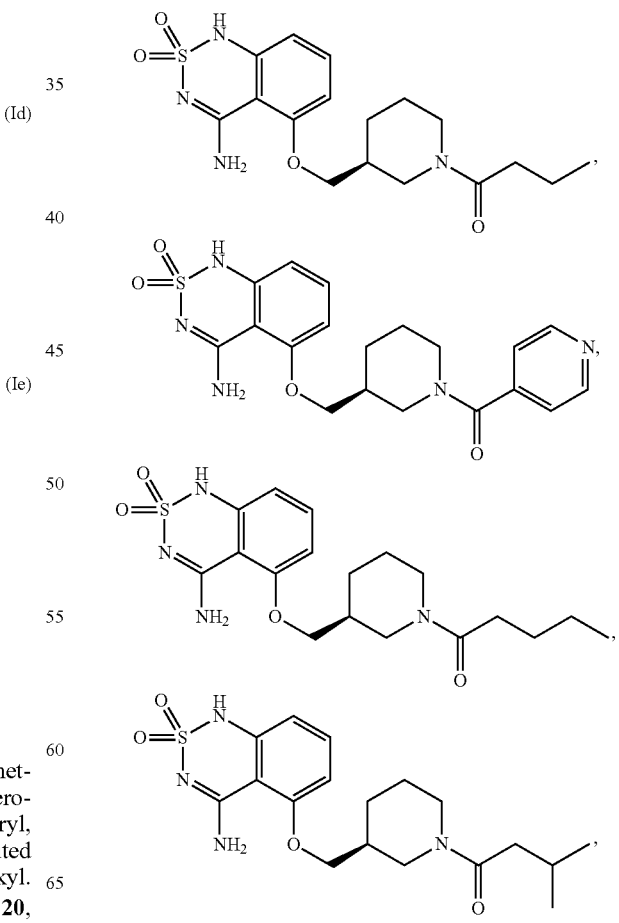

209
-continued
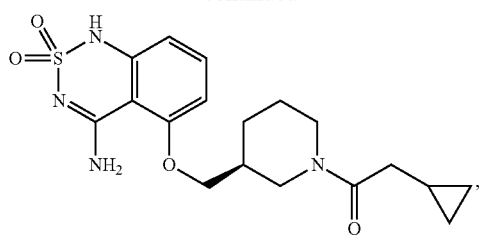
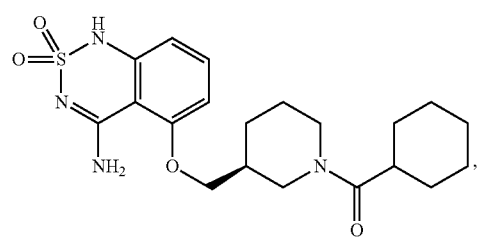
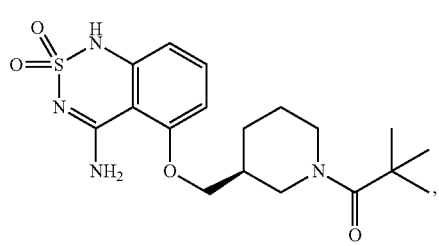
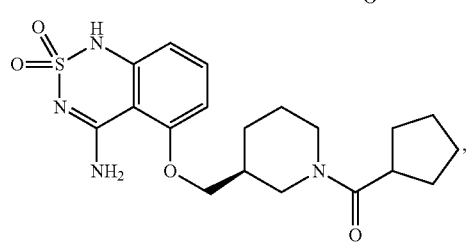
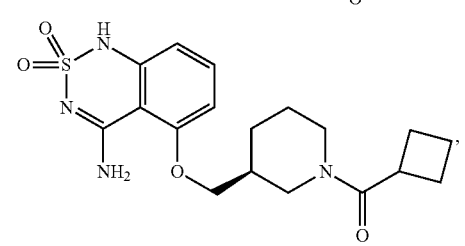
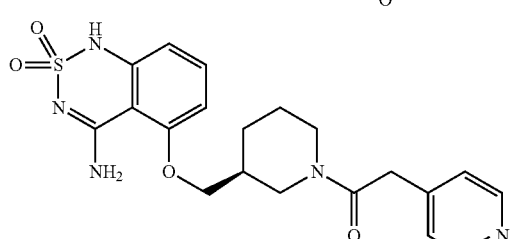
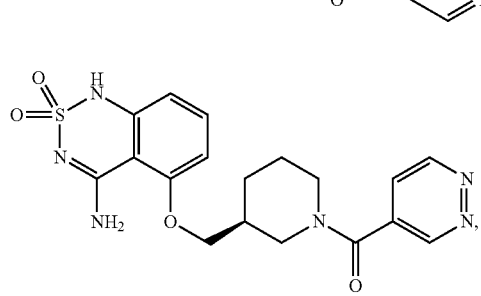
210
-continued
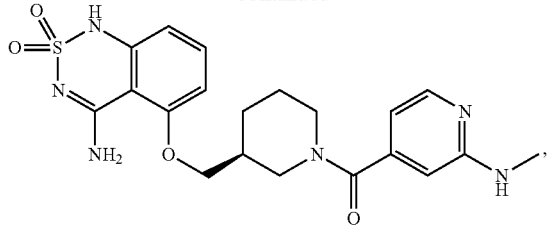
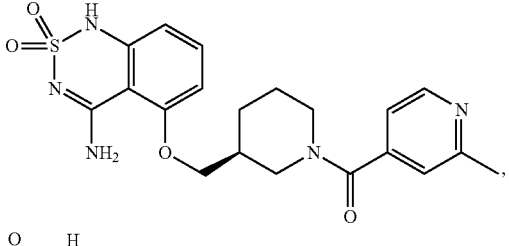
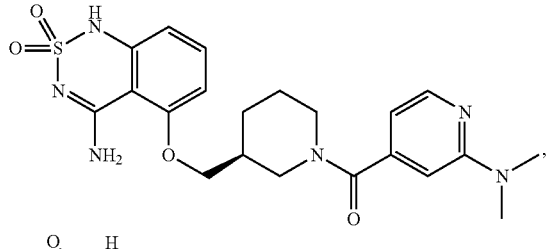
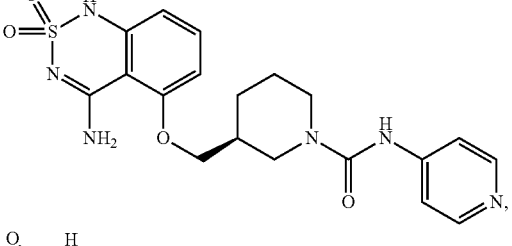
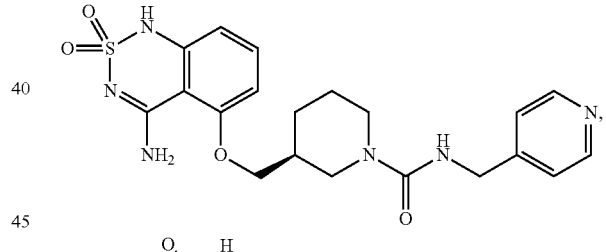
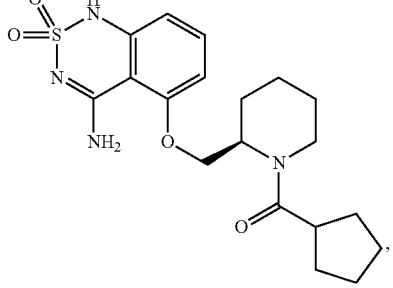
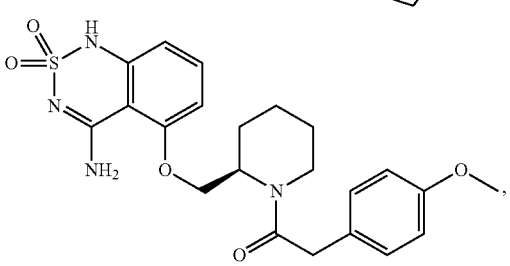

-continued
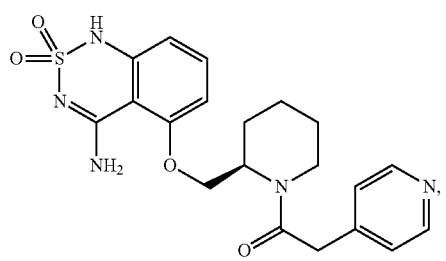
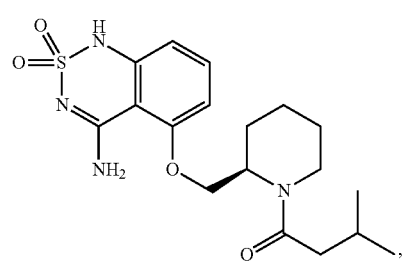
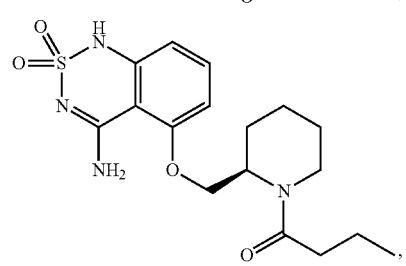
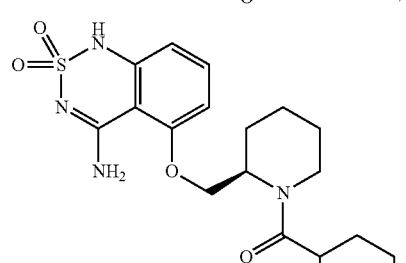
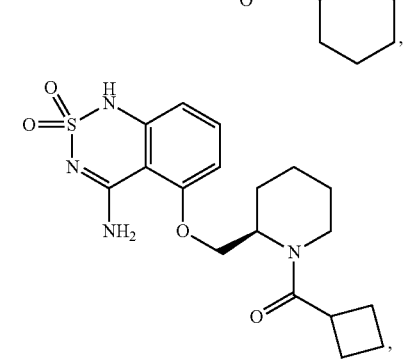
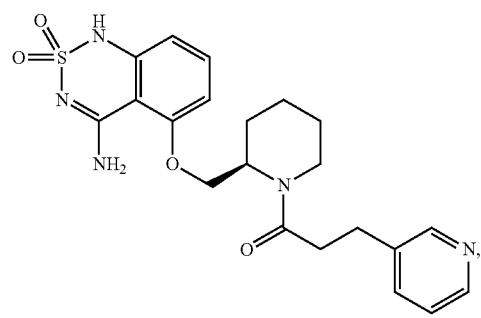
-continued
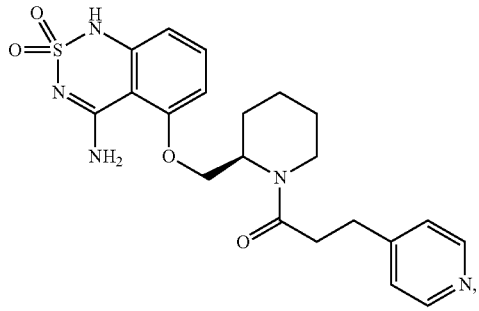
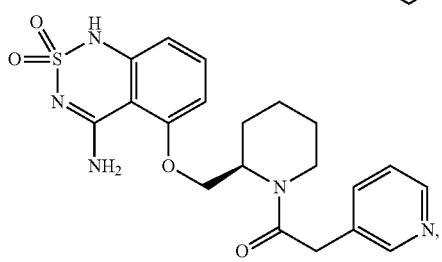
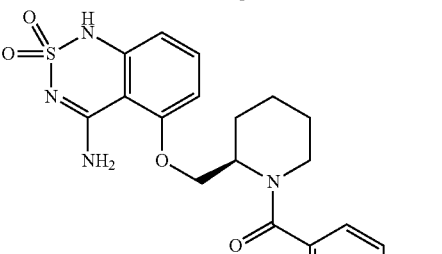
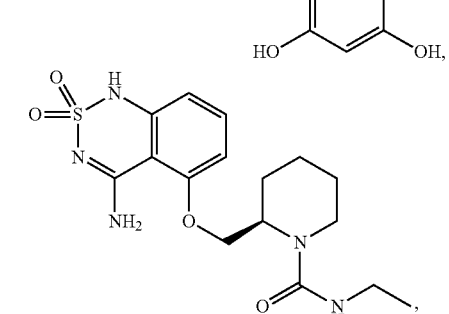
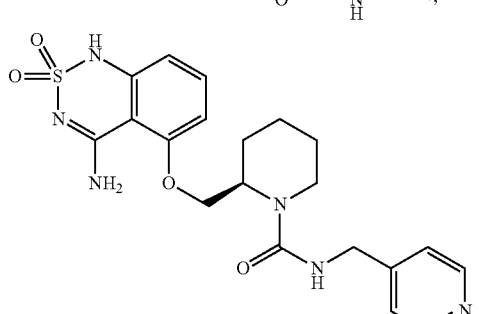
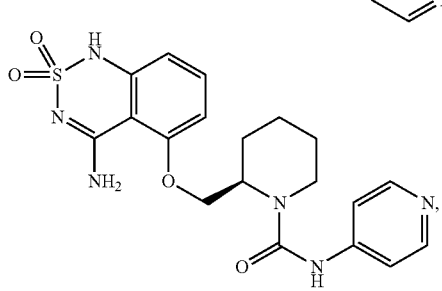

213
-continued
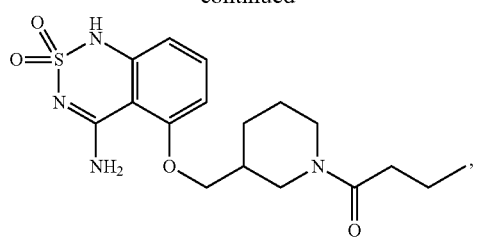
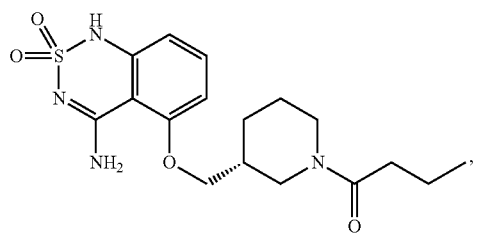
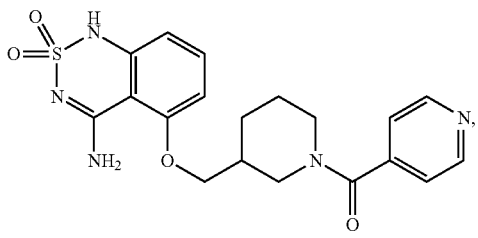
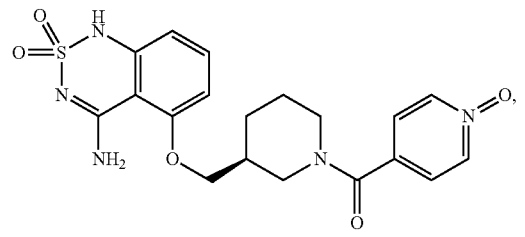
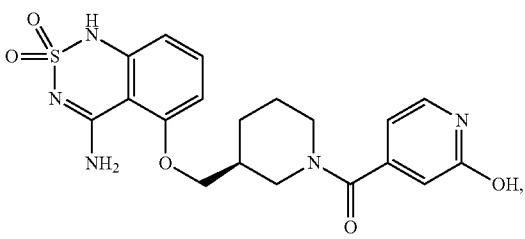
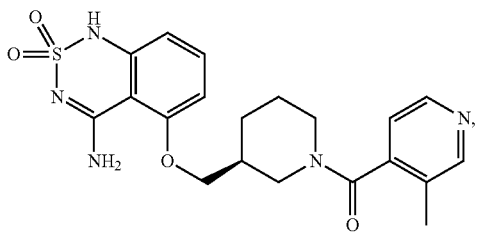
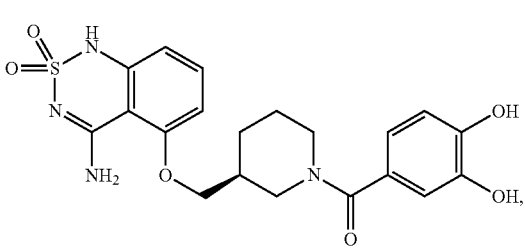
214
-continued
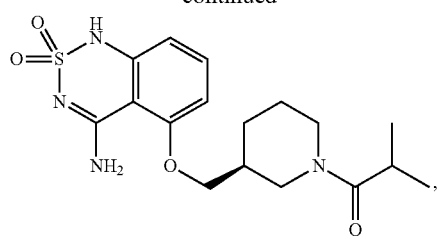
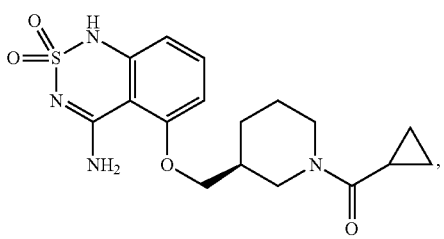
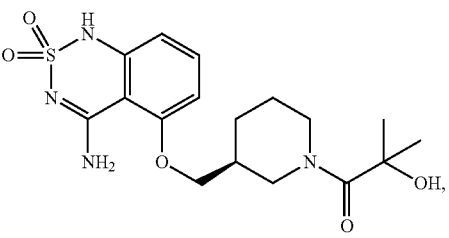
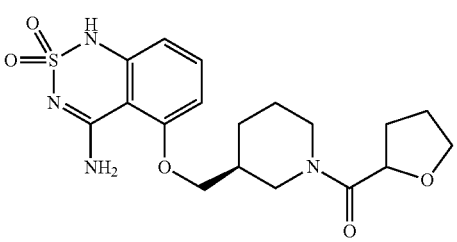
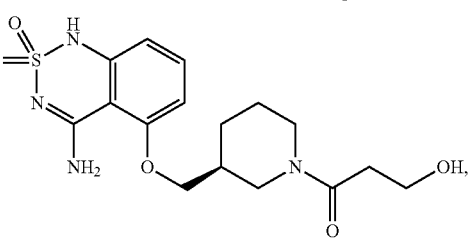
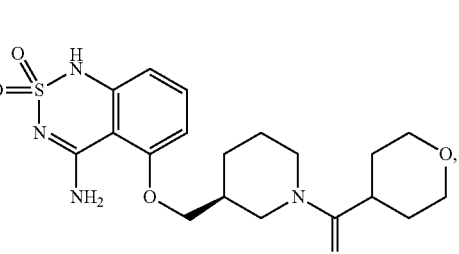
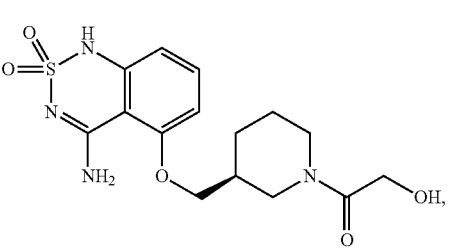

215
-continued
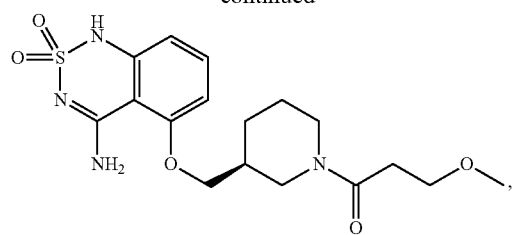
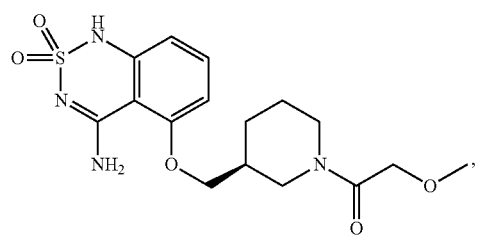
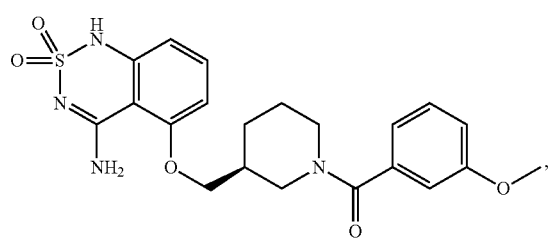
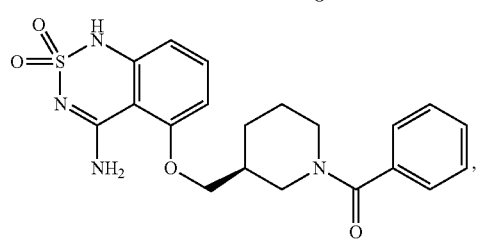
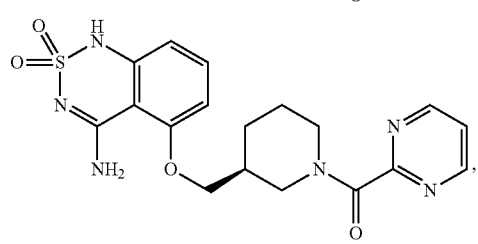
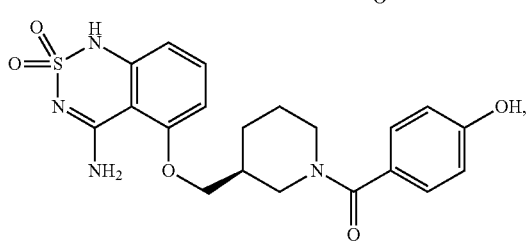
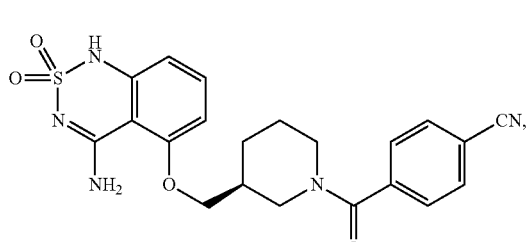
216
-continued
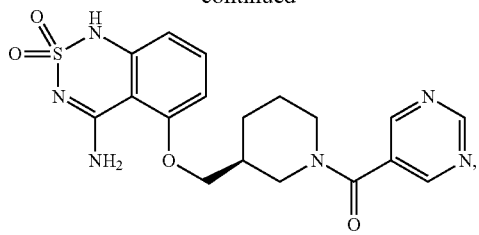
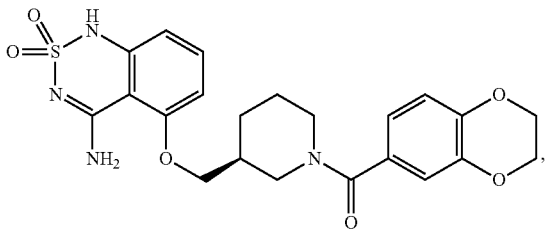
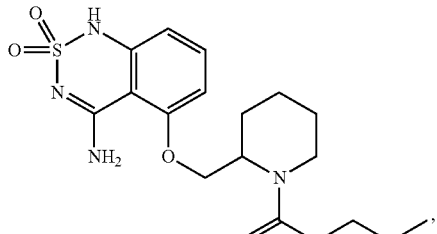
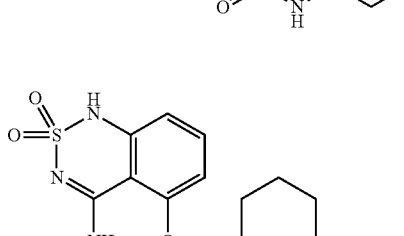
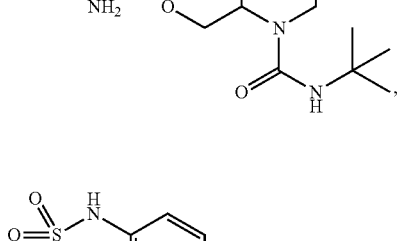
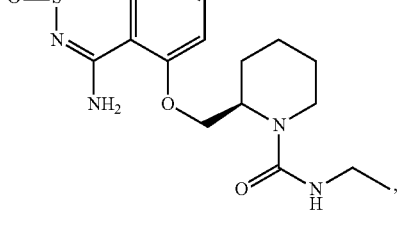
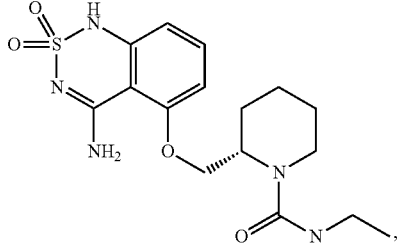

217
-continued
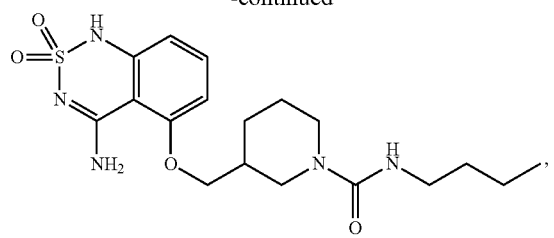
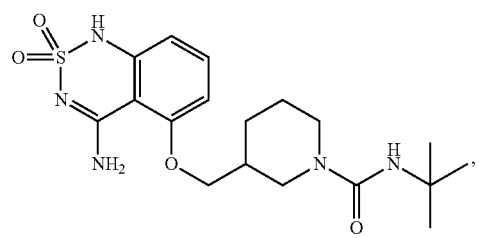
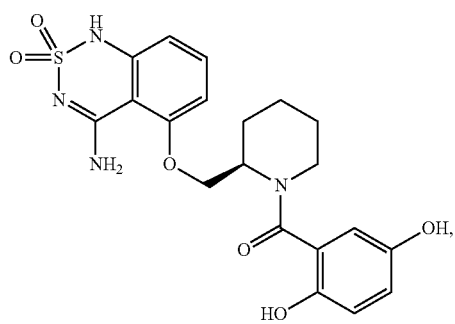
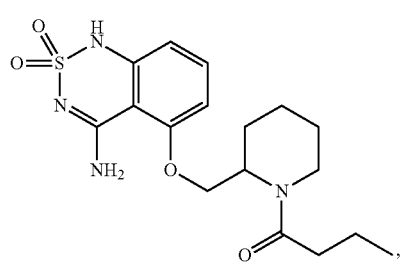
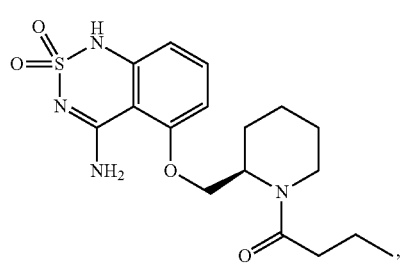
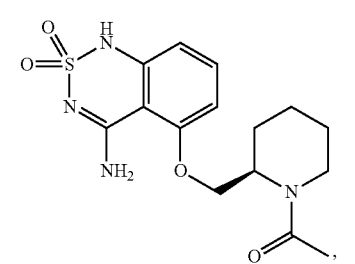
218
-continued
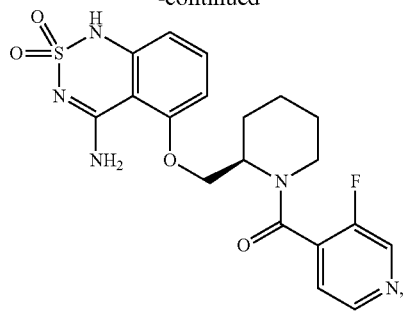
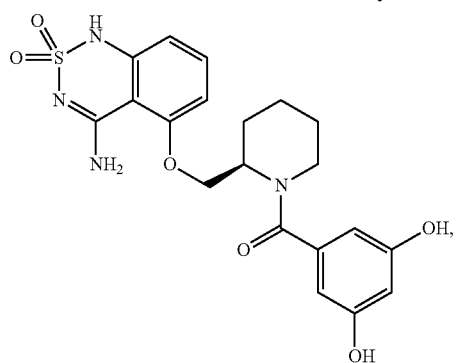
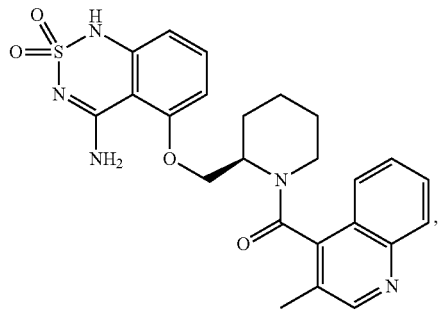
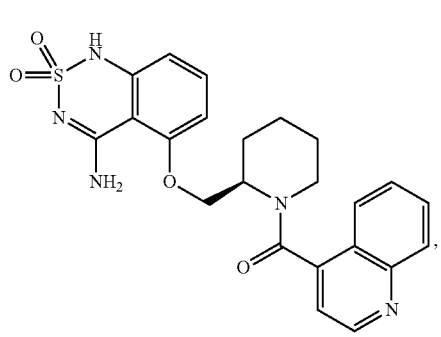
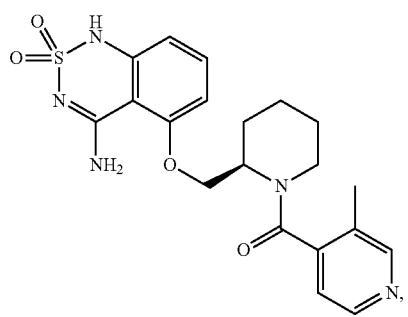

219
-continued
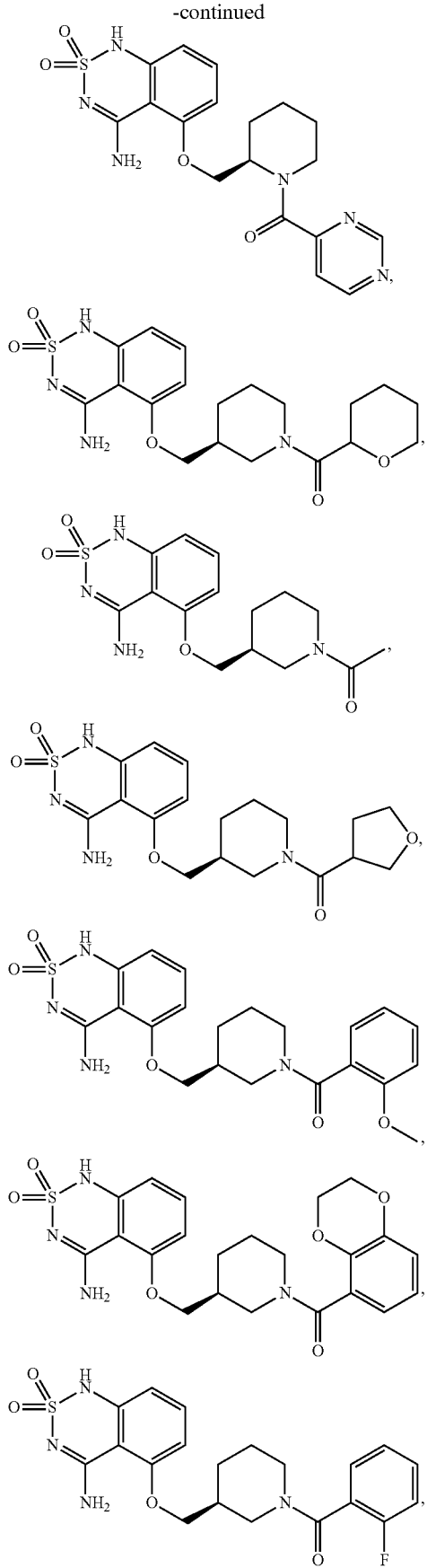
220
-continued
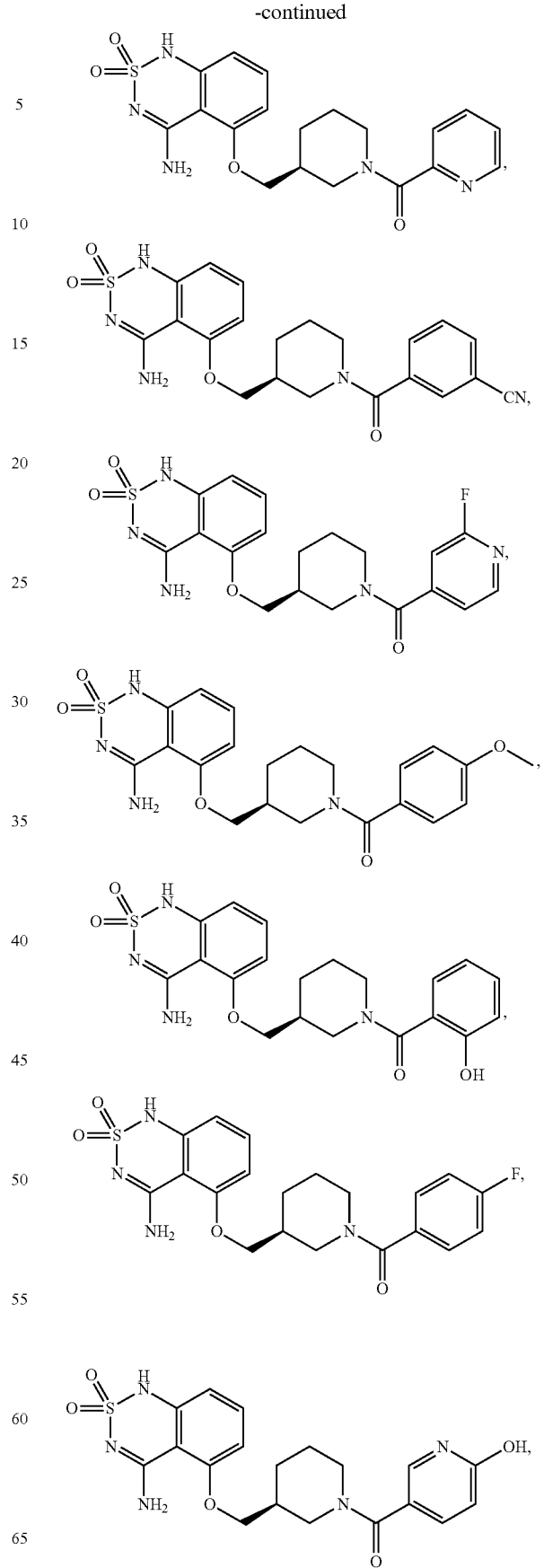

221
-continued
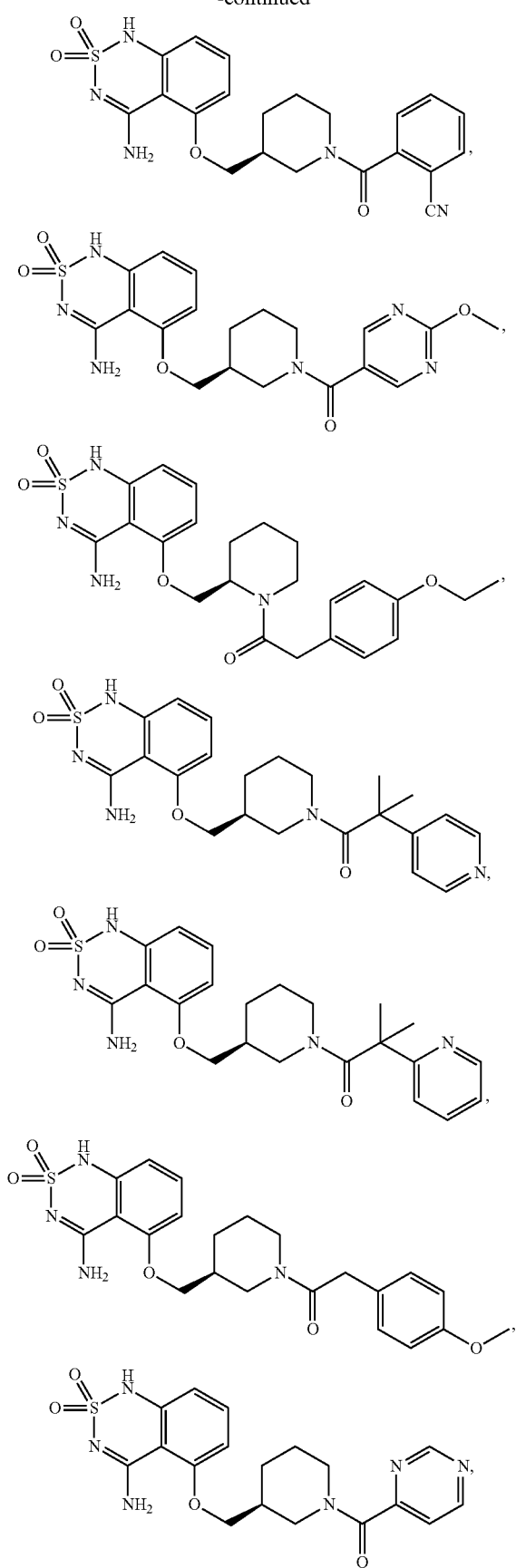
222
-continued
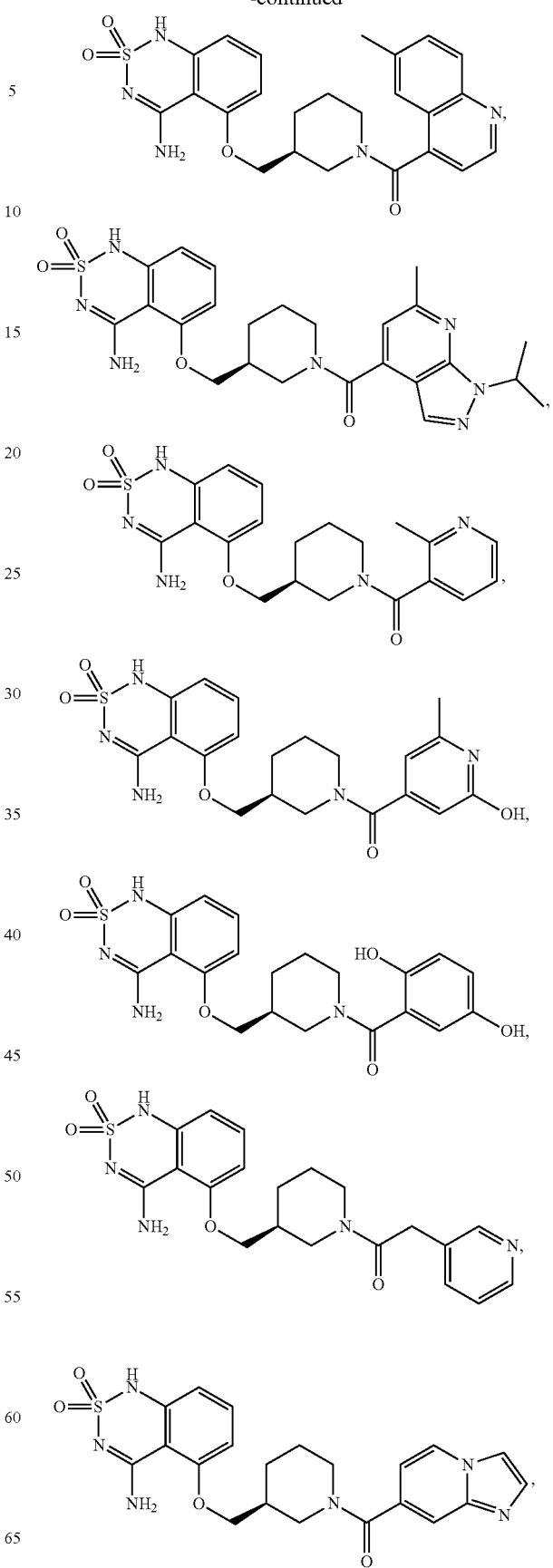

223
-continued
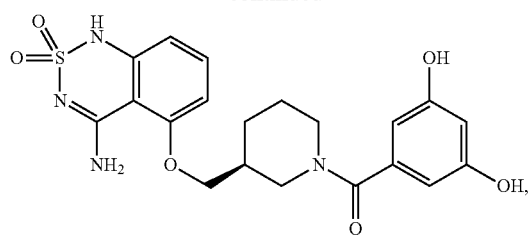
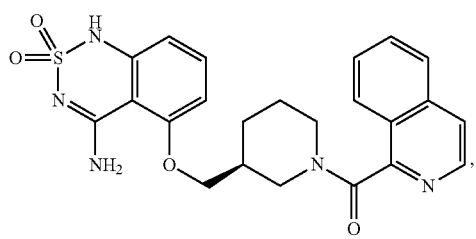
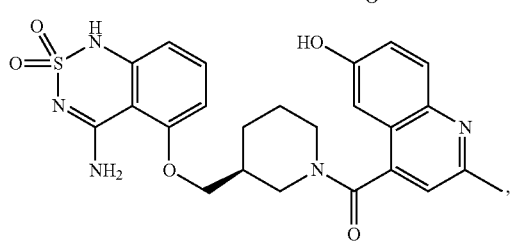
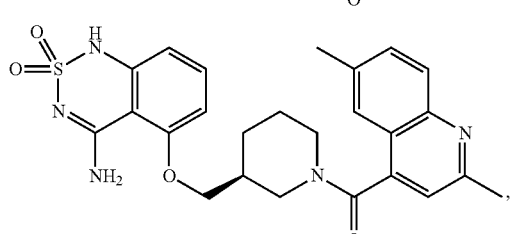
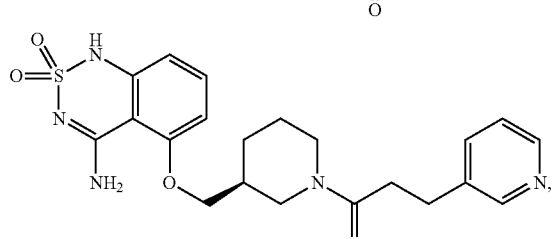
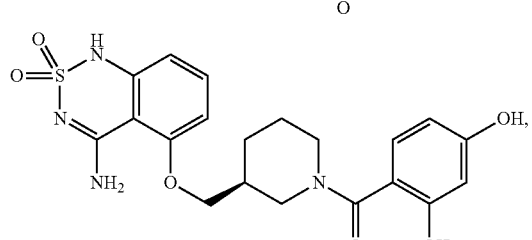
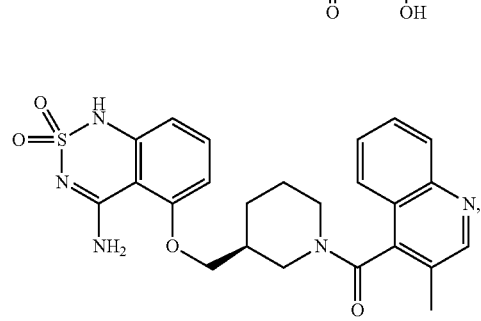
224
-continued
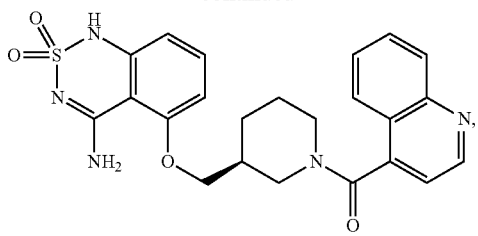
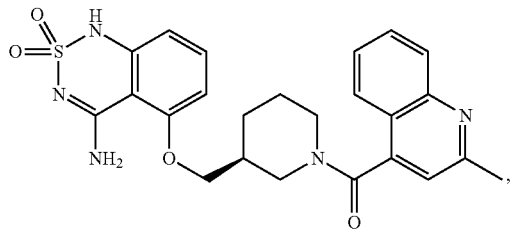
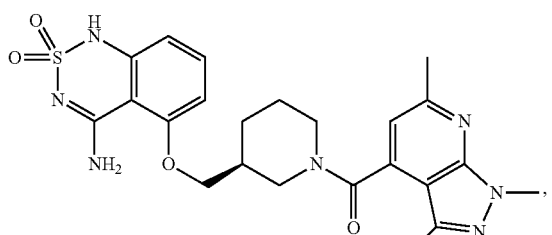
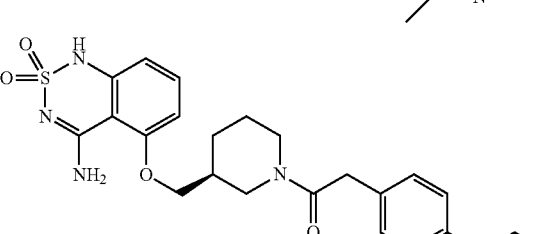
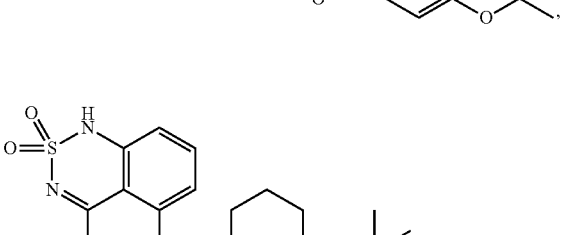
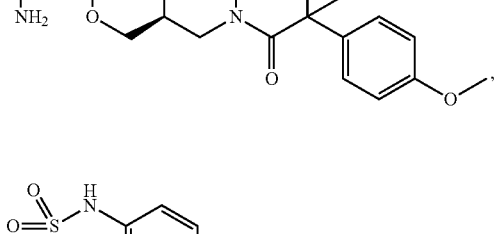
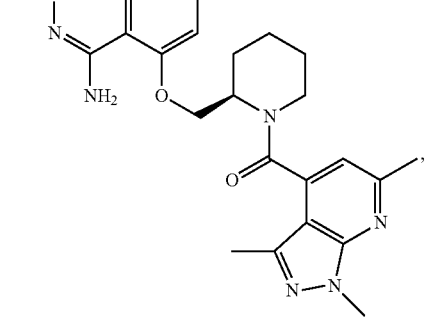

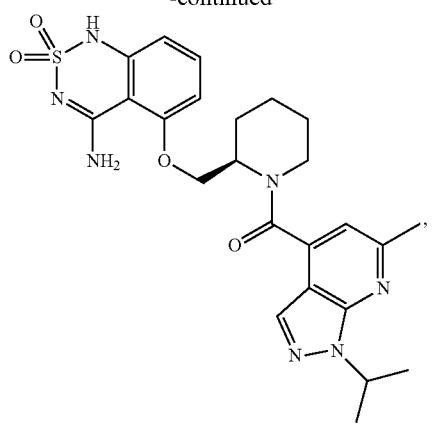
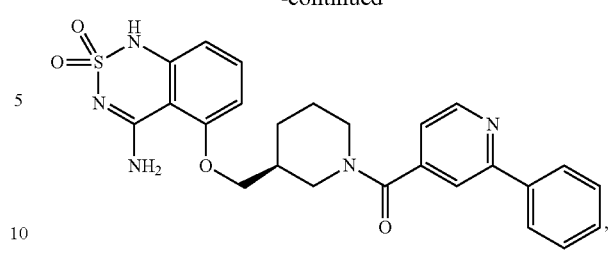
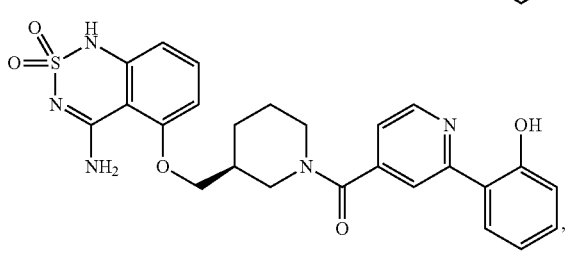
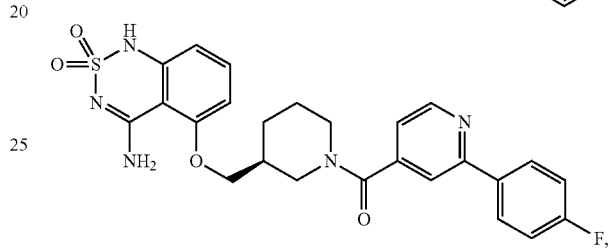
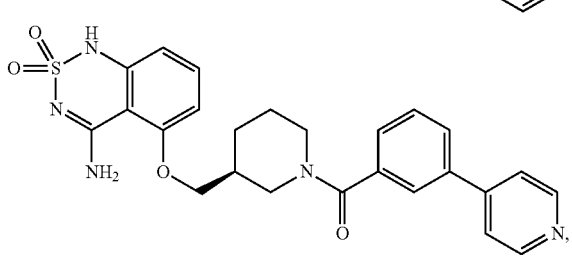
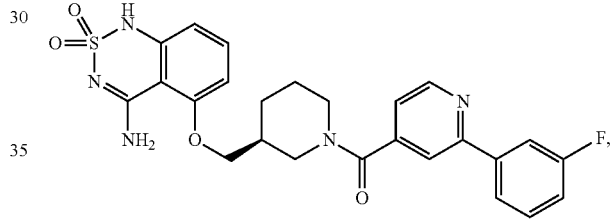
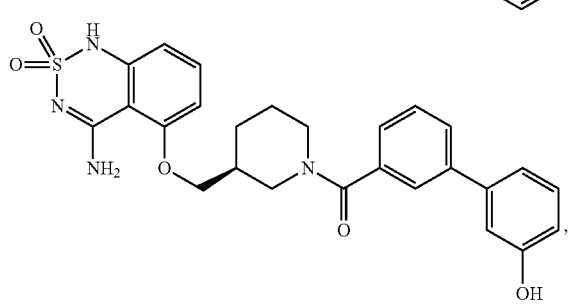
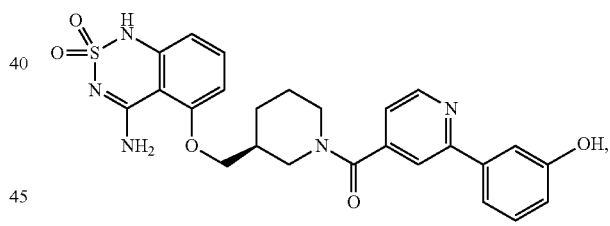
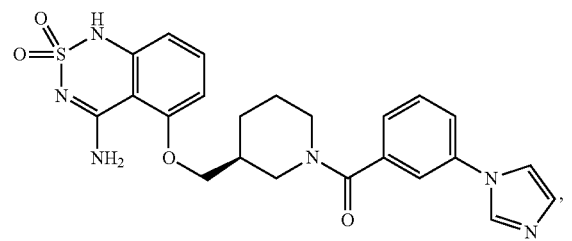
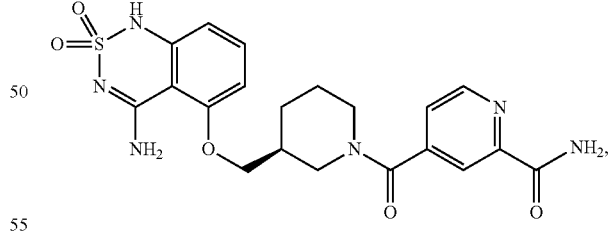
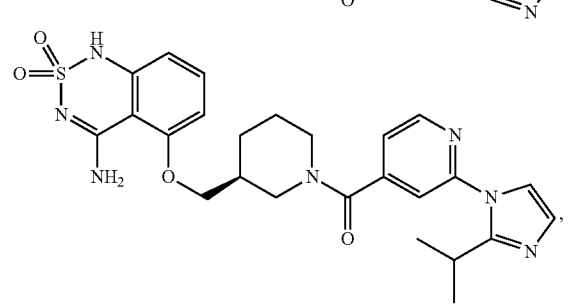
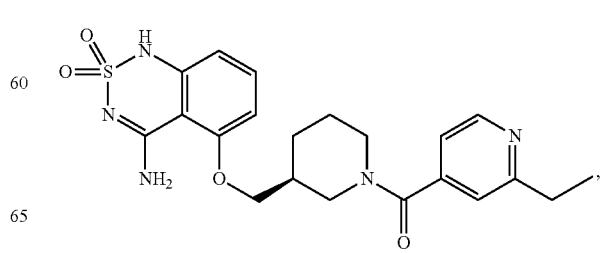

-continued

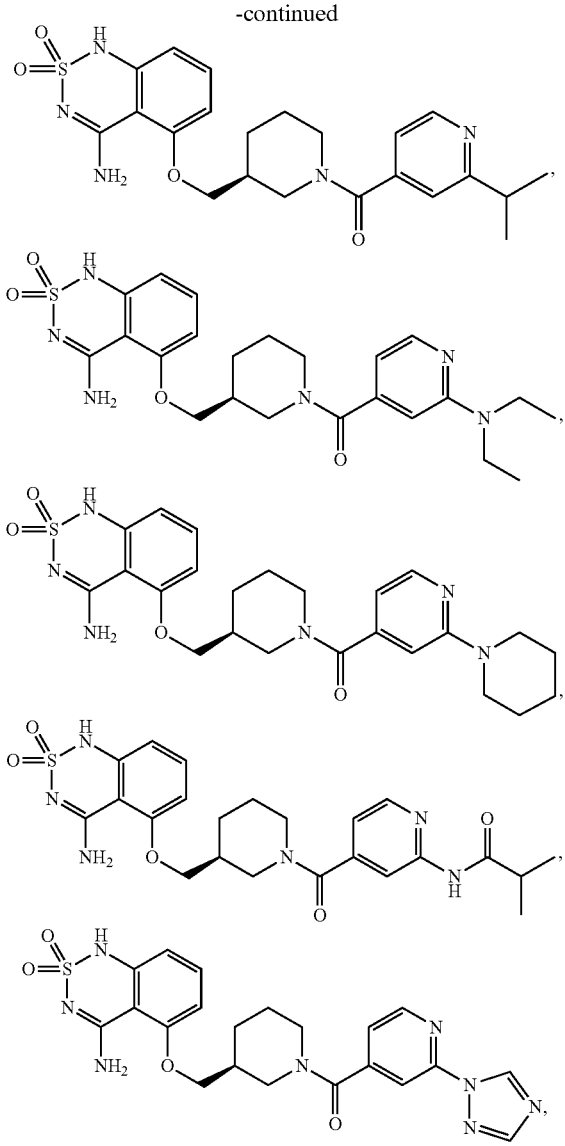

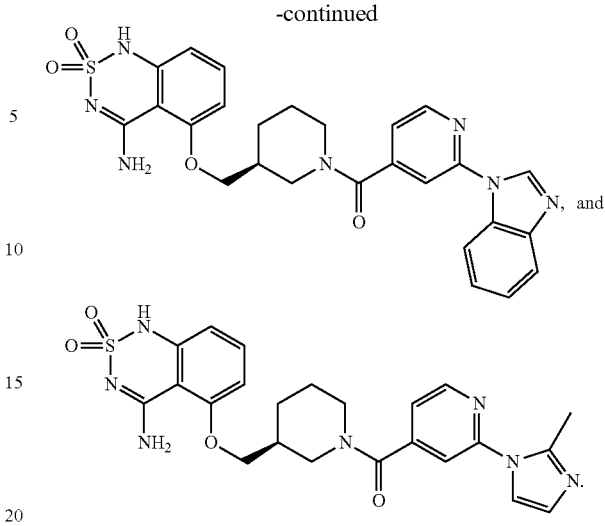

or a salt or solvate thereof.

27. The flavoring concentrate formulation of claim 17, wherein the at east one adjuvant comprises one or more flavoring agents.

28. The flavoring concentrate formulation of claim 17, wherein the at least one adjuvant comprises one or more sweeteners.

29. The flavoring concentrate formulation of any one of claims 17, 26, and 27, wherein the at least one adjuvant comprises one or more ingredients selected from the group consisting of a emulsifier, a stabilizer, an antimicrobial preservative, an antioxidant, vitamins, minerals, fats, starches, protein concentrates and isolates, salts, a freezing point depressant, nucleating agent, and combinations thereof.

30. The flavoring concentrate formulation of claim 17, which is in a form selected from the group consisting of liquid, solid, semi-solid, foamy material, paste, gel, cream, lotion, and combinations thereof.

31. The flavoring concentrate formulation of claim 17, wherein the compound having structural Formula (Ia) is in a concentration that is at least 2 times of the concentration in a ready-to-use composition.

* * * * *